United States Patent
Kastelein et al.

(10) Patent No.: US 12,122,839 B2
(45) Date of Patent: Oct. 22, 2024

(54) IFNGR BINDING SYNTHETIC CYTOKINES AND METHODS OF USE

(71) Applicant: Synthekine, Inc., Menlo Park, CA (US)

(72) Inventors: Robert Kastelein, Menlo Park, CA (US); Deepti Rokkam, Menlo Park, CA (US); Patrick J. Lupardus, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 0 days.

(21) Appl. No.: 18/006,484

(22) PCT Filed: Aug. 5, 2021

(86) PCT No.: PCT/US2021/044837
§ 371 (c)(1),
(2) Date: Jan. 23, 2023

(87) PCT Pub. No.: WO2022/032025
PCT Pub. Date: Feb. 10, 2022

(65) Prior Publication Data
US 2023/0272088 A1 Aug. 31, 2023

Related U.S. Application Data

(60) Provisional application No. 62/061,562, filed on Aug. 5, 2020, provisional application No. 63/078,745, filed on Sep. 15, 2020, provisional application No. 63/135,884, filed on Jan. 11, 2021.

(51) Int. Cl.
| | |
|---|---|
| C07K 16/28 | (2006.01) |
| A61K 39/00 | (2006.01) |
| A61P 37/02 | (2006.01) |
| C07K 14/715 | (2006.01) |
| C07K 16/46 | (2006.01) |
| C12N 15/63 | (2006.01) |
| C12N 15/86 | (2006.01) |

(52) U.S. Cl.
CPC .......... *C07K 16/2866* (2013.01); *A61P 37/02* (2018.01); *C07K 14/7155* (2013.01); *C07K 16/2803* (2013.01); *C07K 16/46* (2013.01); *C07K 16/468* (2013.01); *C12N 15/63* (2013.01); *C12N 15/86* (2013.01); *A61K 2039/505* (2013.01); *C07K 2317/22* (2013.01); *C07K 2317/24* (2013.01); *C07K 2317/31* (2013.01); *C07K 2317/33* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/567* (2013.01); *C07K 2317/569* (2013.01)

(58) Field of Classification Search
None
See application file for complete search history.

(56) References Cited

U.S. PATENT DOCUMENTS

| | | |
|---|---|---|
| 8,258,268 B2 | 9/2012 | Wu et al. |
| 8,921,528 B2 | 12/2014 | Holt et al. |
| 8,975,382 B2 | 3/2015 | Revets et al. |
| 9,334,331 B2 | 5/2016 | Igawa et al. |
| 10,421,807 B2 | 9/2019 | Gonzales et al. |
| 10,927,186 B2 | 2/2021 | Roobrouck et al. |
| 2006/0002935 A1 | 1/2006 | Brewis et al. |
| 2006/0024295 A1 | 2/2006 | Brunetta |
| 2009/0220511 A1 | 9/2009 | Kotenko et al. |
| 2010/0297127 A1 | 11/2010 | Ghilardi et al. |
| 2011/0028695 A1 | 2/2011 | Revets et al. |
| 2011/0053865 A1 | 3/2011 | Saunders et al. |
| 2011/0142831 A1 | 6/2011 | Cua et al. |
| 2011/0177081 A1 | 7/2011 | Thiry et al. |
| 2011/0250213 A1 | 10/2011 | Tso et al. |
| 2012/0201746 A1 | 8/2012 | Liu et al. |
| 2012/0225081 A1 | 9/2012 | Gschwind et al. |
| 2012/0316324 A1 | 12/2012 | Adams et al. |
| 2013/0189262 A1 | 7/2013 | Wong et al. |
| 2014/0065142 A1 | 3/2014 | Roschke et al. |
| 2014/0099708 A1 | 4/2014 | Carballido Herrera et al. |
| 2014/0154256 A1 | 6/2014 | Wu et al. |
| 2014/0170154 A1 | 6/2014 | Presta |
| 2014/0302038 A1 | 10/2014 | Dimasi et al. |
| 2015/0079088 A1 | 3/2015 | Lowman et al. |
| 2016/0046730 A1 | 2/2016 | Ghayur et al. |
| 2016/0251440 A1 | 9/2016 | Roobrouck et al. |
| 2017/0106051 A1 | 4/2017 | Oh et al. |
| 2017/0298149 A1 | 10/2017 | Baeuerle et al. |

(Continued)

FOREIGN PATENT DOCUMENTS

| | | |
|---|---|---|
| CN | 103396482 A | 11/2013 |
| CN | 111018985 A | 6/2019 |

(Continued)

OTHER PUBLICATIONS

Goel et al. Plasticity within the Antigen-Combining Site May Manifest as Molecular Mimicry in the Humoral Immune Response.1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
Maccallum et al. "Antibody-antigen interactions: contact analysis and binding site topography", Journal of Molecular Biology, 1996. vol. 262, pp. 732-745.*

(Continued)

*Primary Examiner* — Nora M Rooney
(74) *Attorney, Agent, or Firm* — Kilpatrick Townsend & Stockton LLP

(57) ABSTRACT

Provided herein are IFNGR binding molecules that bind to IFNGR1 and IFNGR2 and comprise an anti-IFNGR2 sdAb and an anti-IFNGR2 $V_HH$ antibody.

14 Claims, 4 Drawing Sheets

Specification includes a Sequence Listing.

(56) References Cited

U.S. PATENT DOCUMENTS

| | | |
|---|---|---|
| 2018/0362655 A1 | 12/2018 | Wang et al. |
| 2018/0362668 A1 | 12/2018 | Xu |
| 2019/0185562 A1 | 6/2019 | Gromada et al. |
| 2019/0315864 A1 | 10/2019 | Xu et al. |
| 2019/0352404 A1 | 11/2019 | Xu et al. |
| 2019/0382500 A1 | 12/2019 | Abujoub et al. |
| 2020/0055912 A1 | 2/2020 | Kley et al. |
| 2020/0071716 A1 | 3/2020 | Raab et al. |
| 2020/0087624 A1 | 3/2020 | Wood et al. |
| 2020/0148772 A1 | 5/2020 | Ting et al. |
| 2020/0157237 A1 | 5/2020 | Regev et al. |
| 2023/0137672 A1 | 5/2023 | Perna |

FOREIGN PATENT DOCUMENTS

| | | |
|---|---|---|
| CN | 111040035 A | 4/2020 |
| WO | 2008/011081 A2 | 1/2008 |
| WO | 2009/068631 A1 | 6/2009 |
| WO | 2010142551 A2 | 12/2010 |
| WO | 2011051327 A2 | 5/2011 |
| WO | 2013/006544 A1 | 1/2013 |
| WO | 2013/059299 A1 | 4/2013 |
| WO | 2015142675 A2 | 9/2015 |
| WO | 2016/097313 A1 | 6/2016 |
| WO | 2017/198212 A1 | 11/2017 |
| WO | 2018233624 A1 | 12/2018 |
| WO | 2019/129221 A1 | 7/2019 |
| WO | 2019242632 A1 | 12/2019 |
| WO | 2020052543 A1 | 3/2020 |
| WO | 2020094834 A1 | 5/2020 |
| WO | 2020094836 A1 | 5/2020 |
| WO | 2020/144164 A1 | 7/2020 |
| WO | 2020/187711 A1 | 9/2020 |
| WO | 2022031871 A1 | 2/2022 |
| WO | 2022055641 A1 | 3/2022 |

OTHER PUBLICATIONS

De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*

Kurucz et al. 'Current Animal Models of Bronchial Asthma.' Curr. Pharm. Des. 12:3175-3194, 2006.*

Mukherjee et al. 'Allergic Asthma: Influence of Genetic and Environmental Factors.' J. Biol. Chem. 286(38):32883-32889, 2011.*

Watzka, et al. "Guided selection of antibody fragments specific for human interferon γ receptor 1 from a human VH-and VL-gene repertoire." Immunotechnology 3, No. 4 (1998): 279-291.

International Search Report in PCT/US2021/044837, mailed Dec. 20, 2021, 11 pages.

Pingwara et al. IFN-λ Modulates the Migratory Capacity of Canine Mammary Tumor Cells via Regulation of the Expression of Matrix Metalloproteinases and Their Inhibitors. Cells. Apr. 23, 2021;10(5):999.

U.S. Appl. No. 18/019,042, filed Aug. 5, 2021, Kastelein, et al.

BioLegend, PE anti-mouse IL-23R Antibody, Catalog, Mar. 28, 2016, retrieved from the internet www.biolegend.com/en-us/global-elements/pdf-popup/pe-anti-mouse-il-23r-antibody-13084?filename=PE%20anti-mouse%20IL-23R%20Antibody.pdf&pdfgen=true.

Cairo, et al. "Control of multivalent interactions by binding epitope density." Journal of the American Chemical Society 124, No. 8 (2002): 1615-1619.

Crepaldi et al. Up-regulation of IL-1 0R1 expression is required to render human neutrophils fully responsive to IL-10. The Journal of Immunology. Aug. 15, 2001;167(4):2312-22.

De Weerd, et al. "The interferons and their receptors-distribution and regulation." Immunology and cell biology 90, No. 5 (2012): 483-491.

Delgoffe et al., "Interpreting mixed signals: the cell's cytokine conundrum," Current Opinion in Immunology, vol. 23(5), pp. 632-638, Retrieved from the internet, URL: https://www.ncbi.nlm.nih.gov/pmc/articles/PMC3190023/pdf/nihms315192.pdf, (Oct. 2011).

Donnelly et al.. The expanded family of class II cytokines that share the IL-1 0 receptor-2 (IL-1 0R2) chain. Journal of leukocyte biology. Aug. 2004;76(2):314-21.

Fan, et al. "Bispecific antibodies and their applications." Journal of hematology & oncology 8 (2015): 1-14.

Franke et al. Human and murine interleukin 23 receptors are novel substrates for a disintegrin and metalloproteases ADAM10 and ADAM17. Journal of Biological Chemistry. May 13, 2016;291(20):10551-61.

Fu et al. Comparison of Camelus Bactrianus VHH Sequences From Conventional and Heavy Chain Antibodies. Genbank Entry (online) National Center for Biotechnology Information, Sep. 21, 2013. Retried www.ncbi.nlm.nih.gov/nucleotide/KF179376.1, 1 page from the Internet.

Goel, et al. "Plasticity within the antigen-combining site may manifest as molecular mimicry in the humoral immune response." The Journal of Immunology 173, No. 12 (2004): 7358-7367.

Heldin, Carl-Henrik. "Dimerization of cell surface receptors in signal transduction." Cell 80, No. 2 (1995): 213-223.

Holliger, et al. ""Diabodies": small bivalent and bispecific antibody fragments." Proceedings of the National Academy of Sciences 90, No. 14 (1993): 6444-6448.

https://www.ncbi.nlm.nih.gov/gene/163702 (accessed from the internet Sep. 1, 2023).

International Patent Application No. PCT/US2021/044698, "International Search Report and Written Opinion", Feb. 1, 2022, 13 pages.

International Search Report in PCT/US2021 /044695, mailed Feb. 2, 2022, 14 pages.

International Search Report in PCT/US2021 /044802, mailed Feb. 3, 2022, 16 pages.

International Search Report in PCT/US2021 /044835, mailed Feb. 8, 2022, 17 pages.

International Search Report in PCT/US2021 /044855, mailed Dec. 16, 2021, 11 pages.

International Search Report in PCT/US2021/044575, mailed Feb. 2, 2022.

International Search Report in PCT/US2021/044576, mailed Jan. 12, 2022, 12 pages.

International Search Report in PCT/US2021/044674, mailed Jan. 19, 2022, 12 pages.

International Search Report in PCT/US2021/044730, mailed Jun. 21, 2022, 26 pages.

International Search Report in PCT/US2021/044734, mailed Feb. 2, 2022, 13 pages.

International Search Report in PCT/US2021/044803, mailed Jan. 26, 2022, 11 pages.

International Search Report in PCT/US2021/044834, mailed Feb. 2, 2022, 15 pages.

International Search Report in PCT/US2021/044841 mailed Dec. 17, 2021, 10 pages.

International Search Report in PCT/US2021/044850, mailed Jan. 6, 2022, 9 pages.

International Search Report in PCT/US2021/044853, mailed Dec. 17, 2021, ten pages.

ISA/USA; International Search Report and Written Opinion; PCT/US21/44610, mailed Jan. 5, 2022; 11 pgs.

Jiang et al. Regulation of interleukin-1 0 receptor ubiquitination and stability by beta-TrCP-containing ubiquitin E3 ligase. PloS one. Nov. 8, 2011;6(11):e27464.

Khan, et al. "Adjustable locks and flexible keys: plasticity of epitope-paratope interactions in germline antibodies." The Journal of Immunology 192, No. 11 (2014): 5398-5405.

Kontermann, Roland. "Dual targeting strategies with bispecific antibodies." In MAbs, vol. 4, No. 2, pp. 182-197. Taylor & Francis, 2012.

Lloyd, et al. "Modelling the human immune response: performance of a 1011 human antibody repertoire against a broad panel of therapeutically relevant antigens." Protein Engineering, Design & Selection 22, No. 3 (2009): 159-168.

(56) References Cited

OTHER PUBLICATIONS

Lo, et al. "Conformational epitope matching and prediction based on protein surface spiral features." BMC genomics 22, No. 2 (2021): 1-16.

Lundin, et al. "Production and partial characterization of mouse monoclonal antibodies recognizing common cytokine receptor gamma chain (ye) of human, mouse and primate origin Note." Apmis 109, No. 1 O (2001): 64 7-655.

Marks, et al. "How repertoire data are changing antibody science." Journal of Biological Chemistry 295, No. 29 (2020): 9823-9837.

Nie, et al. "Biology drives the discovery of bispecific antibodies as innovative therapeutics." Antibody therapeutics 3, No. 1 (2020): 18-62.

PCT/US21/44602, International Search Report and Written Opinion dated Feb. 2, 2022, 13 pages.

Saerens, et al. "Single-domain antibodies as building blocks for novel therapeutics." Current opinion in pharmacology 8, No. 5 (2008): 600-608.

Shahangain et al., VVH Against VEGF-RBD, Genbank entry (online) National Center for Biotechnology Information, May 12, 215, retrieved from the internet www.ncbi.nlm.nih.gov/protein/BAR73350. 1, 2 pages.

Shouval, et al. "Interleukin 1 O receptor signaling: master regulator of intestinal mucosal homeostasis in mice and humans." Advances in immunology 122 (2014): 177-210.

UniProtKB A0A066RQT8, UniProtKB Accession No. A0A066RQT8, Sep. 3, 2014, retrieved from internet www.uniprot.org/uniprot/A0A066RQT8.

Weidle et al., "The Intriguing Options of Multispecific Antibody Formats for treatment of Cancer," Cancer Genomics & Proteomics 10:1-18 (2013).

Wilton et al. sdAb-DB: the single domain antibody database. ACS Synthetic Biology. Nov. 16, 2018;7(11):2480-4.

Yoshinaga et al., J. Biochem 2008; 143:593-601 (Year: 2008).

"Anti-IFNGR2 Antibody Products", Available Online at: www.biocompare.com/pfu/110447/soids/22483/Antibodies/IFNGR2, 2023, 12 pages.

"IFNGR2 Interferon Gamma Receptor 2 [ *Homo sapiens* (human) ]", Available Online at: www.ncbi.nlm.nih.gov/gene/3460, Sep. 7, 2023, 7 pages.

"IFNGR2 Recombinant Rabbit Monoclonal Antibody (7)", Available Online at: www.thermofisher.com/antibody/product/IFNGR2-Antibody-clone-7-Recombinant-Monoclonal MA5-31154, 2023, 6 pages.

"Recombinant Anti-IFN Gamma Receptor Beta/AF-1 Antibody [epr8813] (ab171081)", Available Online At:https://www.abcam.com/products/primary-antibodies/ifn-gamma-receptor-betaaf-1-antibody-epr8813-ab17108, 2023, 3 pages.

Hoey et al., "Structure and Development of Single Domain Antibodies as Modules for Therapeutics and Diagnostics", Experimental Biology and Medicine, vol. 244, No. 17, Dec. 2019, pp. 1568-1576.

Watzka et al., "Guided Selection of Antibody Fragments Specific for Human Interferon Gamma Receptor 1 from a Human VH- and VL-Gene Repertoire", Immunotechnology, vol. 3, Issue 4, Jan. 1998, pp. 279-291.

* cited by examiner

IFNGR BINDING SYNTHETIC CYTOKINES AND METHODS OF USE

CROSS-REFERENCES TO RELATED APPLICATIONS

This application is a U.S. National Stage of PCT/US2021/044837, international filing date Aug. 5, 2021, which claims priority to U.S. Provisional Application No. 63/061,562, filed Aug. 5, 2020, U.S. Provisional Application No. 63/078,745, filed Sep. 15, 2020, and U.S. Provisional Application No. 63/135,884, filed Jan. 11, 2021, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Jan. 20, 2023, is named 1361726-Sequence-Listing.txt and is 254,805 bytes in size.

FIELD OF THE INVENTION

The present disclosure relates to biologically active molecules comprising single domain antibodies that specifically bind to the extracellular domains of the Interferon-γ R1 (IFNGR1) and the Interferon-γ R2 (IFNGR2), compositions comprising such single domain antibodies, and methods of use thereof.

BACKGROUND OF THE DISCLOSURE

Cytokine and growth-factor ligands typically signal through multimerization of cell surface receptors subunits. In some instance, cytokines act as multispecific (e.g., bispecific or trispecific) ligands which facilitate the association of such receptor subunits, bringing their intracellular domains into proximity such that intracellular signaling may occur. The nature of the cytokine determines which receptor subunits are associated to form the cytokine receptor complex. Cytokines thus act to bridge the individual receptor subunits into a receptor complex that results in intracellular signaling.

The intracellular domains of cytokine receptor subunits possess proline rich JAK binding domains which are typically located in the box1/box region of the intracellular domain of the cytokine receptor subunit near the interior surface of the cell membrane. Intracellular JAK kinases associate with JAK binding domains. When the intracellular domains receptor subunits are brought into proximity, typically by the binding of the cognate ligand for the receptor to the extracellular domains of the receptor subunits, the JAKs phosphorylate each other. Four Janus kinases have been identified in mammalian cells: JAK1, JAK2, JAK3 and TYK2. Ihle, et al. (1995) Nature 377(6550):591-4, 1995; O'Shea and Plenge (2012) *Immunity* 36(4):542-50. The phosphorylation of the JAK induces a conformational change in the JAK providing the ability to further phosphorylate other intracellular proteins which initiates a cascade that results in activation of multiple intracellular factors which transduce the intracellular signal associated with the receptor resulting intracellular responses such as gene transcription, frequently referred to as downstream signaling. In many instances, the proteins which are phosphorylated by the JAKs are members of the signal transducer and activator of transcription (STAT) protein family. Seven members of the mammalian STAT family have been identified to date: STAT1, STAT2, STAT3, STAT4, STAT5a STAT5b, and STAT6. Delgoffe, et al., (2011) Curr Opin Immunol. 23(5):632-8; Levy and Darnell (2002) Nat Rev Mol Cell Biol. 3(9):651-62 and Murray, (2007) J Immunol. 178(5):2623-9. The selective interplay of activated JAK and STAT proteins, collectively referred to a the JAK/STAT pathway, provide for a wide variety of intracellular responses observed in response to cytokine binding.

The human genome encodes for approximately forty different JAK/STAT cytokine receptors. In principle, approximately 1600 unique homodimeric and heterodimeric cytokine receptor pairs could be generated with the potential to signal through different JAK/TYK/STAT combinations (Bazan, Proc Natl Acad Sci USA. 87(18):6934-8, 1990; Huising et al., J Endocrinol. 189(1):1-25, 2006). However, as of the present knowledge, the human genome encodes for less than fifty different cytokine ligands (Bazan, Proc Natl Acad Sci USA. 87(18):6934-8, 1990; Huising et al., J Endocrinol. 189(1):1-25, 2006), limiting the scope of cytokine receptor complexes to those that can be assembled by the natural ligands. Given that interaction of the a cytokine ligand with the extracellular domains of the cytokine receptor subunits determines the composition of receptor subunits in a receptor complex and the intracellular JAK/TYK and RTK enzymes are degenerate, the number of cytokine and growth factor receptor dimer pairings that occur in nature represents only a fraction of the total number of signaling-competent receptor pairings theoretically allowed by the system.

Naturally occurring cytokine ligands mediate a wide variety of cellular response. In some instances, a heteromultimeric cytokine receptor is composed of one or more receptor subunits that is unique to the receptor complex, referred to as "proprietary" subunits, which interact with other receptor subunits that are shared by multiple cytokine receptors, frequently referred to as "common" receptor subunits. For example, the IL7 receptor is a heterodimeric receptor complex of the IL7Ra proprietary subunit and a CD132 subunit which is also referred to as the "common gamma" subunit as it is a shared receptor subunit of multiple cytokine receptor complexes including IL2, IL4, IL19, IL15 and IL21. The relative affinity and kinetic of the interaction of the cytokine for the ECDs of the receptor subunits and the stability of the complex formed in response to cytokine binding mediates the nature and intensity of the intracellular signaling. In some instances, the binding of the cytokine to a the proprietary subunit enhances the formation of the complete receptor where the affinity of the cytokine for the common subunit may be significantly lower when not associated with the proprietary subunit.

The nuances of the interplay between the cytokine ligand and the receptor subunits is a matter of significant scientific investigation. For example, many properties of naturally occurring cytokines suggest their potential utility in the treatment of human disease but such naturally occurring cytokines may also trigger adverse and undesirable effects. In many instances, the disease is associated with a particular cell type which expresses the receptor for the potentially therapeutic cytokine. However, the cytokine receptor is also expressed on other cell types not desired to be targeted for therapeutic intervention. The administration of the native ligand activates both cell types resulting result in undesirable side effects.

To attempt to generate cytokine analogs which provide selective activation of the desired cell types, a variety of engineered cytokine ligands (or components thereof) have been generated so as to selectively modulate their affinity for the extracellular domains of receptor subunits. These efforts have generated cytokine variants been shown to provide partial activity which results in uncoupling of the beneficial properties of the ligand from the undesired effects. See, e.g, Mendoza, et al. (2019) 567:56-60. However, the engineering of such selective cytokines ligand is based on selective modulation of individual amino acid residues at the interface of the ligand and the receptor. This protein engineering approach to modulation of cytokine receptor affinity requires a three dimensional, usually x-ray crystallographic, map of the interation of the receptor and the cytokine to identify the residues of the cytokine that interface with the receptor subunit. Additionally the effects of amino acid substitutions at these interface residues can be highly variable often requiring a significant amount of time consuming trial-and-error to identify the particular amino acid substitutions required to produce the desired activity profile. However, even once the engineered cytokine with the desired signaling profile is achieved, many proteins are highly sensitive to amino acid substitutions result in significant issues for recombinant expression, both in mammalian expression systems and procaryotic systems where such amino acid substitutions can affect protein refolding when expressed in inclusion bodies.

Interferon gamma is homodimer of two 17 kDa subunits. The IFN-γ receptor is tetramer comprising two ligand-binding IFNγR1 subunits which associated two signal-transducing IFNγR2 subunits. IFN-γ binding results in the oligomerization of the intracellular domains of IFNγR2 and activation of intracellular signaling vi JAK1 and JAK2. Phosphorylation of the intracellular domain of the IFNγR2 creates binding sites for STAT1 which is in turn phosphorylated which dimerize and translocate to the nucleus. The IFNγ signaling pathway results in a variety of biological responses primarily associated with host defense and immune surveillance. IFNγ results upregulation of the major histocompatibility complex (MHC) molecules as well as the upregulation MHC I and II antigen processing and presentation machinery.

IFN-γ is a major product of Th1-mediated immune response. Upregulation of cell surface MHC class I by IFN-γ is an essential element in the response to intracellular pathogens and tumor cells. IFN-γ acts as a cytotoxic CD8 T cell differentiation signal and is essential for CD8T cell proliferation. IFN-γ also upregulates cell surface MHC class II on antigen presenting cells and activates CD4 T cells. The central role of IFN-γ in the immune response can be illustrated by its involvement in more 290 genes related to cytokine and chemokine receptors, cell activation markers, cellular adhesion proteins, MHC proteins, proteasome formation, protein turnover, and signaling mediators and regulators.

As a result of the central role of IFNγ in the immune response, inhibition of IFNγ is associated with significant downregulation of immunity and mobility. IFNγR1 deficiency is a life-threatening autosomal recessive immune disorder and affected children frequently die of infection in the absence of bone marrow transplantation. Affected children invariably die of mycobacterial infection, unless bone marrow transplantation is undertaken. Even then, survivors are susceptible to severe infection from environmental factors.

Although monoclonal antibodies are the most widely used reagents for the detection and quantification of proteins, monoclonal antibodies are large molecules of about 150 kDa and it sometimes limits their use in assays with several reagents competing for close epitopes recognition. A unique class of immunoglobulin containing a heavy chain domain and lacking a light chain domain (commonly referred to as heavy chain" antibodies (HCAbs) is present in camelids, including dromedary camels, Bactrian camels, wild Bactrian camels, llamas, alpacas, vicunas, and guanacos as well as cartilaginous fishes such as sharks. The isolated variable domain region of HCAbs is known as a VHH (an abbreviation for "variable-heavy-heavy" reflecting their architecture) or Nanobody® (Ablynx). Single domain VHH antibodies possesses the advantage of small size (~12-14 kD), approximately one-tenth the molecular weight a conventional mammalian IgG class antibody) which facilitates the binding of these VHH molecules to antigenic determinants of the target which may be inaccessible to a conventional monoclonal IgG format (Ingram et al., 2018). Furthermore, VHH single domain antibodies are frequently characterized by high thermal stability facilitating pharmaceutical distribution to geographic areas where maintenance of the cold chain is difficult or impossible. These properties, particularly in combination with simple phage display discovery methods that do not require heavy/light chain pairing (as is the case with IgG antibodies) and simple manufacture (e.g., in bacterial expression systems) make VHH single domain antibodies useful in a variety of applications including the development of imaging and therapeutic agents. This disclosure provides molecules which provide the activity of cytokines, that may be readily generated and engineered for receptor affinity and do not have independent off-target activity.

SUMMARY OF THE DISCLOSURE

The present disclosure provides compositions useful in the pairing of cellular receptors to generate desirable effects useful in treatment of disease in mammalian subjects.

The present disclosure provides compositions comprising at least a first domain that specifically binds to a first receptor subunit and a second domain that specifically binds to a second receptor subunit, such that upon contacting with a cell expressing the first and second receptors, the composition causes the functional association of the first and second receptors, thereby triggering their interaction and resulting in downstream signaling. In some embodiments, the first and second receptors occur in proximity in response to the cognate ligand binding and are referred to herein as "natural" cytokine receptor pairs.

The present disclosure provides cytokine receptor binding molecules that are ligands for a cytokine receptor, the cytokine receptor binding molecule comprising:

(a) a first single domain antibody (sdAb) that specifically binds to the extracellular domain a first subunit of a cytokine receptor; and (b) a second single domain antibody that specifically binds to extracellular domain of a second subunit of cytokine receptor subunit;

wherein:

the first sdAb and second sdAb are in stable association;

the first and second subunits of the cytokine receptor are dimerized in response to contact with the cognate ligand for the cytokine receptor; and contacting a cell expressing the first and the second subunit of the cytokine receptor with an effective amount of the cytokine receptor binding molecule results in the intracellular domains of the first and second subunits of the cytokine receptors being brought into proximity and results in intraceullar signaling.

The present disclosure thus provides binding molecules that comprise a first domain that binds to IFNGR1 of the IFNGR receptor and a second domain that binds to IFNGR2 the IFNGR receptor, such that upon contacting with a cell expressing IFNGR1 the IFNGR receptor and IFNGR2 the IFNGR receptor, the IFNGR binding molecule causes the functional association of IFNGR1 and IFNGR2, thereby resulting in functional dimerization of the receptors and downstream signaling.

In one aspect, the disclosure provides an IFNG receptor (IFNGR) binding molecule that specifically binds to IFNGR1 and IFNGR2,
wherein the binding molecule causes the multimerization of IFNGR1 and IFNGR2 when bound to IFNGR1 and IFNGR2, and
wherein the binding molecule comprises a single-domain antibody (sdAb) that specifically binds to IFNGR1 and a sdAb that specifically binds to IFNGR2.

In some embodiments, the anti-IFNGR1 sdAb is a VHH antibody and/or the anti-IFNGR2 sdAb is a $V_H$H antibody.

In some embodiments, the anti-IFNGR1 sdAb and the anti-IFNGR2 sdAb are joined by a peptide linker.

In some embodiments, the peptide linker comprises between 1 and 50 amino acids.

In some embodiments, the peptide linker comprises a sequence of GGGS (SEQ ID NO:13).

In some embodiments, the anti-IFNGR1 sdAb comprises one or more CDRs in a row of Table 2, wherein each CDR independently comprises 0, 1, 2, or 3 amino acid changes, optionally conservative amino acid changes, relative to the sequence of Table 2.

In some embodiments, the anti-IFNGR2 sdAb comprises one or more CDRs in a row of Table 3, wherein each CDR independently comprises 0, 1, 2, or 3 amino acid changes, optionally conservative amino acid changes, relative to the sequence of Table 3.

In some embodiments, the IFNGR binding molecule comprises an anti-IFNGR1 sdAb comprising a CDR1, a CDR2, and a CDR3 in a row of Table 2 and an anti-IFNGR2 sdAb a CDR1, a CDR2, and a CDR3 in a row of Table 3.

In some embodiments, the binding molecule comprises an anti-IFNGR1 sdAb linked to the N-terminus of a linker and an anti-IFNGR2 sdAb linked to the C-terminus of the linker.

In some embodiments, the binding molecule comprises an anti-IFNGR2 sdAb linked to the N-terminus of a linker and an anti-IFNGR1 sdAb linked to the C-terminus of the linker.

In some embodiments, the anti-IFNGR1 sdAb comprises a sequence having at least 90% sequence identity to a sequence of Table 4.

In some embodiments, the anti-IFNGR1 sdAb comprises a sequence of Table 4.

In some embodiments, the anti-IFNGR2 sdAb comprises a sequence having at least 90% sequence identity to a sequence of Table 5.

In some embodiments, the anti-IFNGR2 sdAb comprises a sequence of Table 5.

In some embodiments,

In some embodiments, each of the anti-IFNGR1 sdAb comprises a sequence having at least 90% sequence identity to a sequence of Table 4 and the anti-IFNGR2 sdAb comprises a sequence having at least 90% sequence identity to a sequence of Table 5.

In another aspect, the disclosure provides an isolated nucleic acid encoding the IFNGR binding molecule disclosed herein. In some embodiments, the isolated nucleic acid comprises a sequence having at least 90% sequence identity to a sequence of Table 6 and the anti-IFNGR2 sdAb comprises a sequence having at least 90% sequence identity to a sequence of Table 7.

The disclosure further provides recombinant viral and non-viral expression vectors comprising a nucleic acid encoding the IFNGR binding molecules of the present disclosure or the CDRs of the IFNGR binding molecules of the present disclosure.

The disclosure further provides host cells comprising recombinant viral and non-viral expression vectors comprising a nucleic acid encoding the IFNGR binding molecules of the present disclosure or the CDRs of the IFNGR binding molecules of the present disclosure.

The disclosure further provides pharmaceutical formulations comprising the recombinant viral and non-viral expression vectors comprising a nucleic acid encoding the IFNGR1 binding molecules of the present disclosure and methods of use thereof in the treatment or prevention of diseases, disorders or conditions in a mammalian subject.

The disclosure further provides kits comprising the IFNGR1 binding molecules of the present disclosure.

In some embodiments, the IFNGR1 binding molecules of the present disclosure are useful to inhibit the activity of interferon gamma in vitro and/or in vivo. In some embodiments, the IFNGR1 binding molecules of the present disclosure are useful in the treatment of autoimmune diseases. The disclosure further provides methods of use of the foregoing in the treatment of an autoimmune disease in a subject, the method comprising administering to the subject a therapeutically effective amount IFNGR1 binding molecule of the present disclosure. In some IFNGR1 binding molecule of the present disclosure may be used alone or in combination with one or more supplementary therapeutic agents. In some embodiments, the diseases amenable to treatment are diseases, disorders or conditions associated with signaling from receptor comprising the IFNGR1. In some embodiments, the IFNGR1 binding molecules of the present disclosure are useful in the treatment of diseases associated with dysregulated T cell or B cell activity. In some embodiments, the IFNGR1 binding molecules of the present disclosure are useful in the treatment of autoimmune diseases. In some embodiments, the IFNGR1 binding molecule of the present disclosure is administered to a subject in a pharmaceutically acceptable formulation. In some embodiments, the IFNGR1 binding molecule of the present disclosure is administered by the administration to the subject of a composition comprising a recombinant viral or non-viral vector comprising a nucleic acid sequence encoding the IFNGR1 binding molecule of the present disclosure.

In some embodiments, the methods comprise administering one or more supplementary agents selected from the group consisting of a corticosteroid, a Janus kinase inhibitor, a calcineurin inhibitor, a mTor inhibitor, an IMDH inhibitor, a biologic, a vaccine, and a therapeutic antibody.

In some embodiments, the therapeutic antibody is an antibody that binds a protein selected from the group consisting of BLyS, CD11a, CD20, CD25, CD3, CD52, IgEIL12/IL23, IL17a, IL1β, IL4Rα, IL5, IL6R, integrin-α4β7, RANKL, TNFα, VEGF-A, and VLA-4.

In some embodiments, the disease, disorder, or condition is selected from viral infections, heliobacter pylori infection, HTLV, organ rejection, graft versus host disease, autoimmune thyroid disease, multiple sclerosis, allergy, asthma, neurodegenerative diseases including Alzheimer's disease, systemic lupus erythramatosis (SLE), autoinflammatory diseases, inflammatory bowel disease (IBD), Crohn's disease, diabetes, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter's syndrome, SEA Syndrome, psoriasis, psoriatic arthritis, dermatitis (eczema), exfoliative dermatitis or atopic dermatitis, pityriasis rubra pilaris, pityriasis rosacea, parapsoriasis, pityriasis lichenoides, lichen planus, lichen nitidus, ichthyosiform dermatosis, keratodermas, dermatosis, alopecia areata, pyoderma gangrenosum, vitiligo, pemphigoid, urticaria, prokeratosis, rheumatoid arthritis; seborrheic dermatitis, solar dermatitis; seborrheic keratosis, senile keratosis, actinic keratosis, photo-induced keratosis, keratosis follicularis; acne vulgaris; keloids; nevi; warts including verruca, condyloma or condyloma acuminatum, and human papilloma viral (HPV) infections.

The present disclosure provides binding molecules that are agonists of the IFNG receptor (IFNGR), the binding molecule comprising:
a first single domain antibody (sdAb) that specifically binds to the extracellular domain of IFNGR1 of the IFNG receptor (an "anti-IFNGR1 sdAb"), and
a second single domain antibody that specifically binds to the extracellular domain of IFNGR2 of the IFNG receptor (an "anti-IFNGR2 sdAb"),
wherein the anti-IFNGR1 sdAb and anti-IFNGR2 sdAb are stably associated and wherein contacting a cell expressing IFNGR1 and IFNGR2 with an effective amount of the binding molecule results in the dimerization of IFNGR1 and IFNGR2 and results in intraceullar signaling characteristic of the IFNGR when activated by its natural cognate ligand, IFNG. In some embodiments, one or both of the sdAbs is a an scFv. In some embodiments, one or both of the sdAbs is a VHH.

In some embodiments, one sdAb of the bivalent binding molecule is an scFv and the other sdAb is a VHH.

In some embodiments, the first and second sdAbs are covalently bound via a chemical linkage.

In some embodiments, the first and second sdAbs are provided as single continuous polypeptide.

In some embodiments, the first and second sdAbs are provided as single continuous polypeptide optionally comprising an intervening polypeptide linker between the amino acid sequences of the first and second sdAbs.

In some embodiments the bivalent binding molecule optionally comprising a linker, is optionally expressed as a fusion protein with an additional amino acid sequence. In some embodiments, the additional amino acid sequence is a purification handle such as a chelating peptide or an additional protein such as a subunit of an Fc molecule.

The disclosure also provides an expression vector comprising a nucleic acid encoding the bispecific binding molecule operably linked to one or more expression control sequences. The disclosure also provides an isolated host cell comprising the expression vector expression vector comprising a nucleic acid encoding the bispecific binding molecule operably linked to one or more expression control sequences functional in the host cell.

In another aspect, the disclosure provides a pharmaceutical composition comprising the IFNGR binding molecule described herein and a pharmaceutically acceptable carrier.

In another aspect, the disclosure provides a method of treating an autoimmune or inflammatory disease, disorder, or condition or a viral infection in a subject in need thereof, comprising administering to the subject a therapeutically effective amount of an IFNGR binding molecule described herein or a pharmaceutical composition described herein.

Several advantages flow from the binding molecules described herein. The natural ligand of the IFNGR, IFNG, causes IFNGR1 and IFNGR2 to come into proximity (i.e., in response to the binding of IFNG). However, when IFNG is used as a therapeutic in mammalian, particularly human, subjects, it may also trigger a number of adverse and undesirable effects by a variety of mechanisms including the presence of IFNGR1 and IFNGR2 on other cell types and the binding to IFNGR1 and IFNGR2 on the other cell types may result in undesirable effects and/or undesired signaling on cells expressing IFNGR1 and IFNGR2. The present disclosure is directed to methods and compositions that modulate the multiple effects of IFNGR1 and IFNGR2 binding so that desired therapeutic signaling occurs, particularly in a desired cellular or tissue subtype, while minimizing undesired activity and/or intracellular signaling.

In some embodiments, the IFNGR binding molecules described herein are partial agonists of the IFNGR. In some embodiments, the binding molecules described herein are designed such that the binding molecules are full agonists. In some embodiments, the binding molecules described herein are designed such that the binding molecules are super agonists.

In some embodiments, the binding molecules provide the maximal desired IFNG intracellular signaling from binding to IFNGR1 and IFNGR2 on the desired cell types, while providing significantly less IFNG signaling on other undesired cell types. This can be achieved, for example, by selection of binding molecules having differing affinities or causing different $E_{max}$ for IFNGR1 and IFNGR2 as compared to the affinity of IFNG for IFNGR1 and IFNGR2. Because different cell types respond to the binding of ligands to its cognate receptor with different sensitivity, by modulating the affinity of the dimeric ligand (or its individual binding moieties) for the IFNG receptor relative to wild-type IFNG binding facilitates the stimulation of desired activities while reducing undesired activities on non-target cells.

BRIEF DESCRIPTION OF THE FIGURES

FIG. 4, Panel B provides a schematic representations of a binding molecule the binding domains are single domain antibodies associated via transition metal coordinate covalent complex. As illustrated, the binding molecules comprises two polypeptide subunits: the first subunit comprising a first single domain antibody (1) is attached via a first linker (15) to a first chelating peptide (17) and second subunit comprising a second single domain antibody (3) is attached via a second linker (16) to a second chelating peptide (18), wherein the first chelating peptide (17) and second chelating peptide (18) form a coordinate covalent complex with a single transition metal ion ("M"). The transition metal ion may be in a kinetically labile or kinetically inert oxidation state.

DETAILED DESCRIPTION OF THE INVENTION

Figure 1:
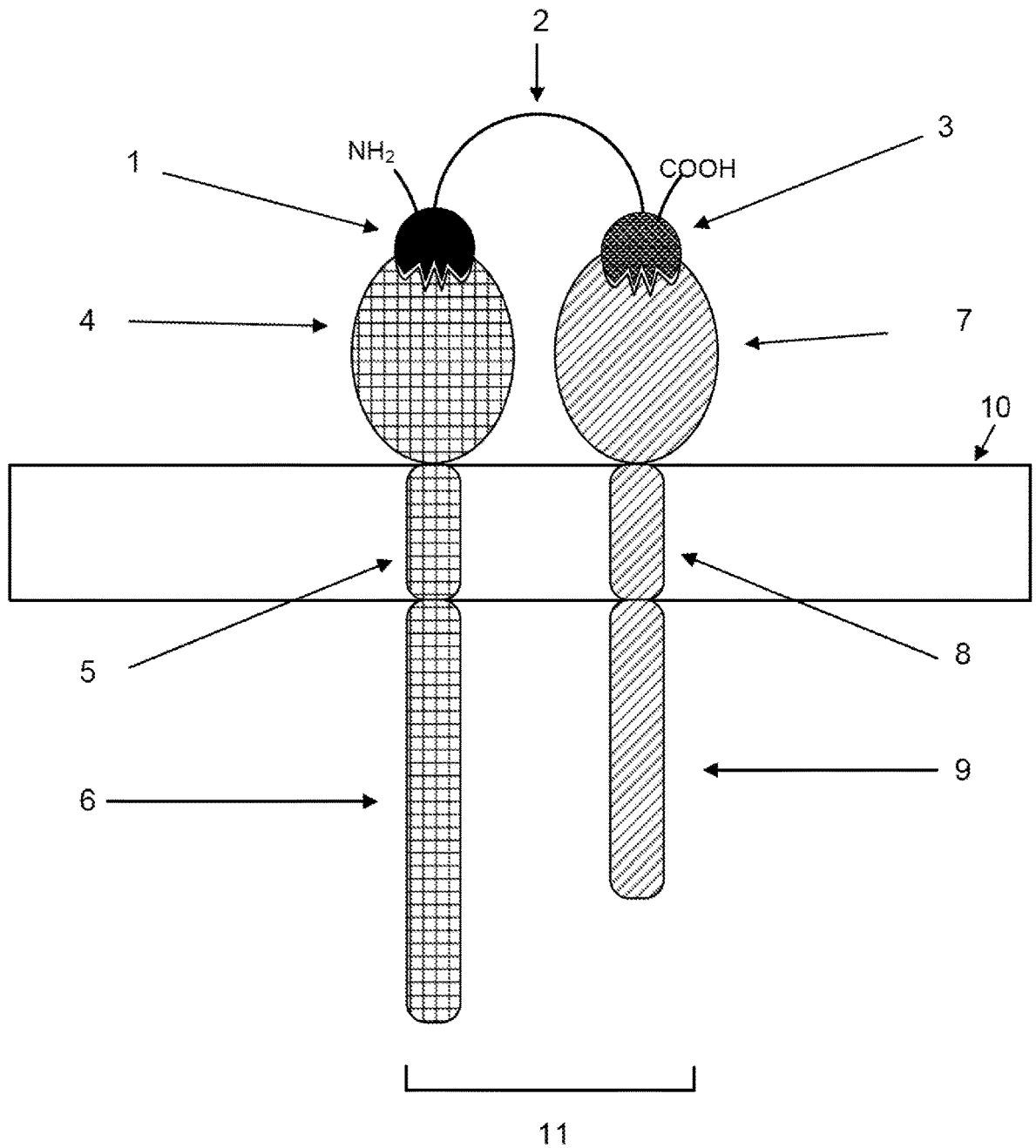
FIG. 1 of the attached drawings provides a schematic representation of one embodiment of the bivalent binding molecule of the present disclosure comprising a first single domain antibody (1) and a second single domain antibody (3) and a linker (2) depicted as interacting with a cell membrane (10) associated heterodimeric receptor comprising a first receptor subunit comprising an extracellular domain (4), and transmembrane domain (5) and an intracellular domain (6) interaction of a bivalent binding molecule and a second first receptor subunit comprising an extracellular domain (7), and transmembrane domain (8) and an intracellular domain (9) wherein the intracellular domain of the first receptor (6) and the intracellular domain of the second receptor (9) on of a bivalent binding molecule are within a proximal distance (11).
Figure 2:
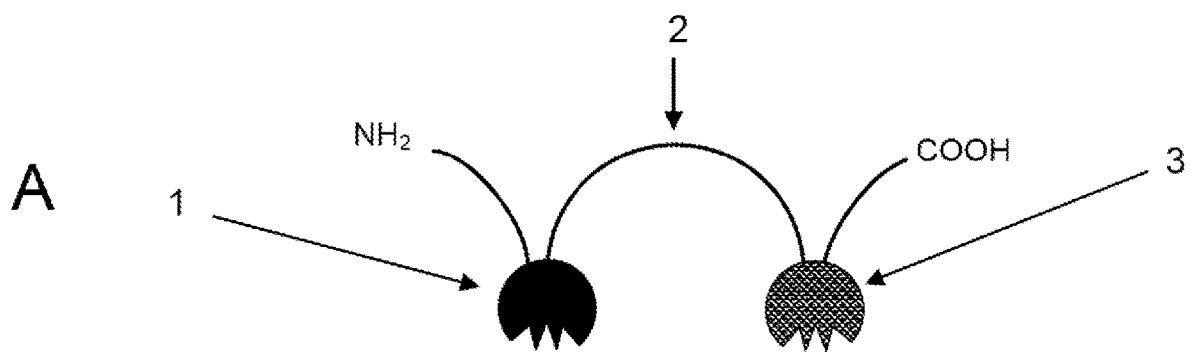
FIG. 2 of the attached drawings provides a schematic representation of two illustrative configurations of bivalent binding molecules of the present disclosure. Panel A provides a schematic representation of an illustrative single polypeptide chain bivalent binding molecule comprising, from amino to carboxy, a first single domain antibody (1) and a second single domain antibody (3) and a linker (2). Panel B provides a schematic representation of a bivalent binding molecule comprising a first single domain antibody (1) and a second single domain antibody (3) and a linker (2) and a knob-into-hole Fc domain, the Fc domain comprising a first subunit which is a Fc knob (13) and a second subunit which is a Fc hole (14) wherein the bivalent binding molecule is covalently linked to an Fc domain subunit_via a IgG hinge sequence (12).
Figure 2:
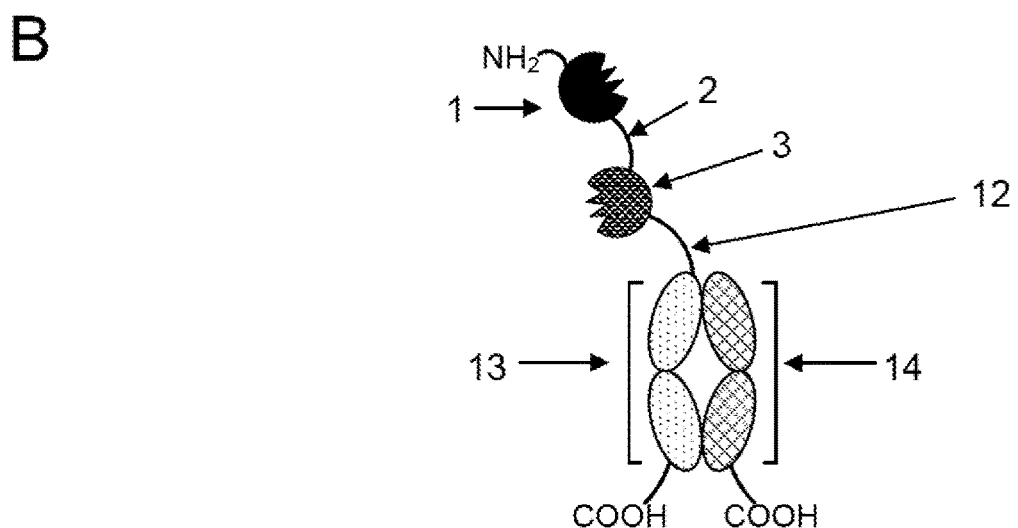
Figure 3:
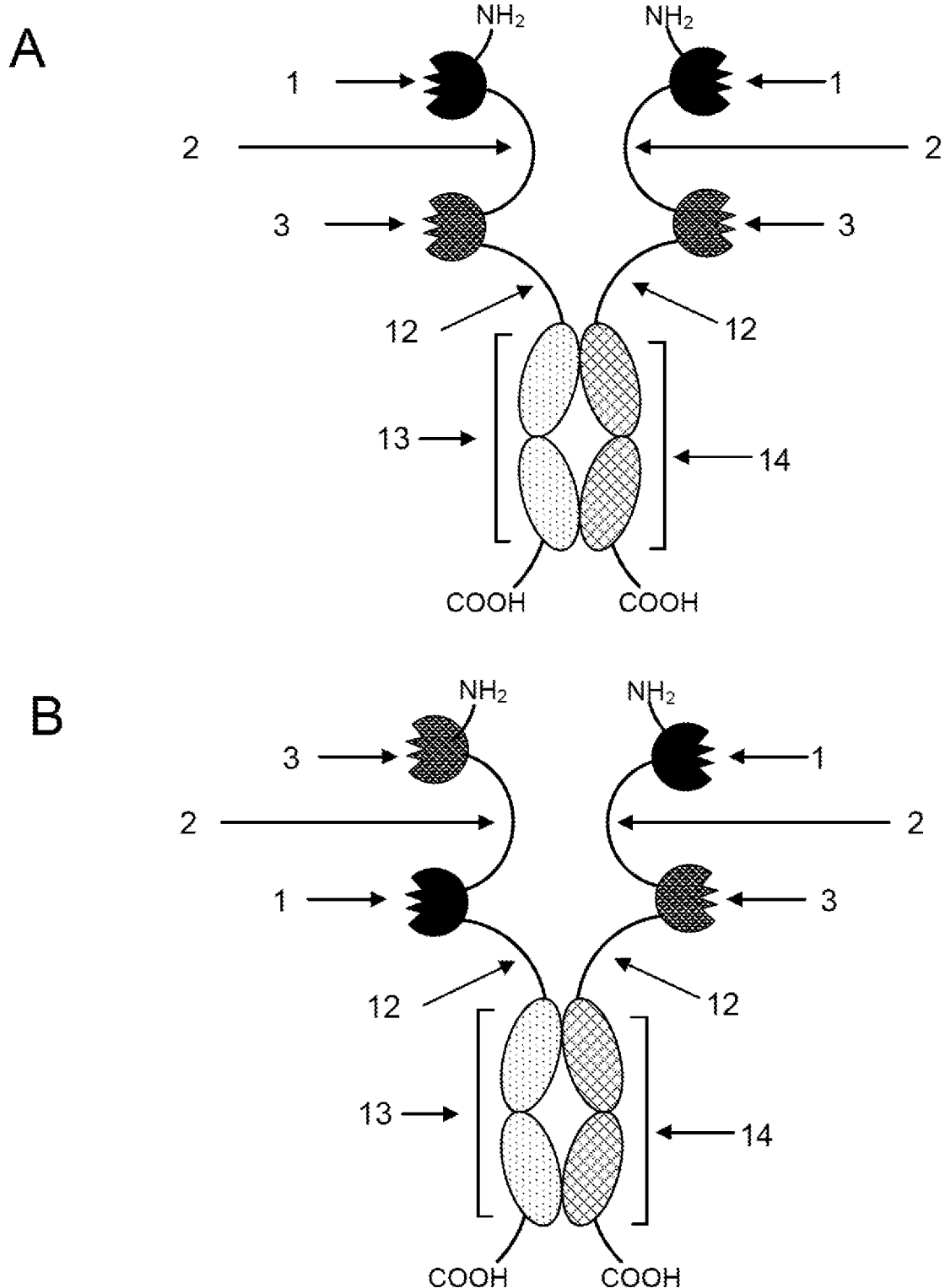
FIG. 3 of the attached drawings provides a schematic representations of two illustrative configurations of bivalent binding molecules of the present disclosure. Panel A provides a schematic representation of an illustrative bivalent binding molecule construct comprising two bivalent binding molecules each attached to a subunit of a knob-into-hole Fc domain, the construct comprising two polypeptide chains, the first polypeptide chain comprising, from amino to carboxy, a first single domain antibody (1), a linker (2) and a second single domain antibody (3), a IgG hinge sequence (12) and a Fc knob subunit (13) and a second polypeptide chain comprising, from amino to carboxy, a first single domain antibody (1), a linker (2) and a second single domain antibody (3), a IgG hinge sequence (12) and a Fc hole subunit (14) wherein the first and second polypeptides are in stable associate via the interaction of the knob-into-hole Fc domain. Panel B provides schematic representation of a an alternative arrangement of a bivalent binding molecule construct comprising two polypeptides a first polypeptide chain comprising, from amino to carboxy, a first single domain antibody (1), a linker (2) and a second single domain antibody (3), an IgG hinge sequence (12) and a Fc knob subunit (13) and a second polypeptide chain comprising, from amino to carboxy, a first second domain antibody (3), a linker (2) and a first single domain antibody (1), a IgG hinge sequence (12) and a Fc hole subunit (14), wherein the first and second polypeptides are in stable association via the interaction of the knob-into-hole Fc domain.

To facilitate the understanding of present disclosure, certain terms and phrases are defined below as well as throughout the specification. The definitions provided herein are non-limiting and should be read in view of the knowledge of one of skill in the art would know.

Before the present methods and compositions are described, it is to be understood that this invention is not limited to a particular method or composition described, as such may, of course, vary. It is also to be understood that the terminology used herein is for the purpose of describing embodiments only and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); AA or aa=amino acid(s); kb=kilobase(s); nt=nucleotide(s); pg=picogram; ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=once weekly; QM=once monthly; HPLC=high performance liquid chromatography; BW=body weight; U=unit; ns=not statistically significant; PBS=phosphate-buffered saline; PCR=polymerase chain reaction; HSA=human serum albumin; MSA=mouse serum albumin; DMEM Dulbeco's Modification of Eagle's Medium; EDTA=ethylenediaminetetraacetic acid.

It will be appreciated that throughout this disclosure reference is made to amino acids according to the single letter or three letter codes. For the reader's convenience, the single and three letter amino acid codes are provided in Table 1 below:

TABLE 1

Amino Acid Abbreviations

| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term "activity" is used with respect to a molecule to describe a property of the molecule with respect to a test system (e.g. an assay) or biological or chemical property (e.g. the degree of binding of the molecule to another molecule) or of a physical property of a material or cell (e.g. modification of cell membrane potential). Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a level of a biological activity per unit of agent tested such as [catalytic activity]/[mg protein], [immunological activity]/[mg protein], international units (IU) of activity, [STAT5 phosphorylation]/[mg protein], [T-cell proliferation]/[mg protein], plaque forming units (pfu), etc. As used herein, the term "proliferative activity" refers to an activity that promotes cell proliferation and replication.

Administer/Administration: The terms "administration" and "administer" are used interchangeably herein to refer the act of contacting a subject, including contacting a cell, tissue, organ, or biological fluid of the subject in vitro, in vivo or ex vivo with an agent (e.g. an ortholog, an IL2 ortholog, an engineered cell expressing an orthogonal receptor, an engineered cell expressing an orthogonal IL2 receptor, a CAR-T cell expressing an orthogonal IL2 receptor, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, inhalation and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the equilibrium dissociation constant ($K_D$), a ratio of the dissociation rate constant between the molecule and its target ($K_{off}$) and the association rate constant between the molecule and its target ($K_{on}$).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state, resulting in a biological response. The response mimics the effect of the endogenous activator of the receptor. The term "agonist" includes partial agonists, full agonists and superagonists. An agonist may be described as a "full agonist" when such agonist which leads to a substantially full biological response (i.e., the response associated with the naturally occurring ligand/receptor binding interaction) induced by receptor under study, or a partial agonist. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist. A "superagonist" is a type of agonist that is capable of producing a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway, or cell.

Antibody: As used herein, the term "antibody" refers collectively to: (a) glycosylated and non-glycosylated immunoglobulins (including but not limited to mammalian immunoglobulin classes IgG1, IgG2, IgG3 and IgG4) that specifically binds to target molecule and (b) immunoglobulin derivatives including but not limited to IgG(1-4)deltaC$_H$2, F(ab')$_2$, Fab, ScFv, V$_H$, V$_L$, tetrabodies, triabodies, diabodies, dsFv, F(ab')$_3$, scFv-Fc and (scFv)$_2$ that competes with the immunoglobulin from which it was derived for binding to the target molecule. The term antibody is not restricted to immunoglobulins derived from any particular mammalian species and includes murine, human, equine, and camelids antibodies (e.g., human antibodies). The term "antibody" encompasses antibodies isolatable from natural sources or from animals following immunization with an antigen and as well as engineered antibodies including monoclonal antibodies, bispecific antibodies, trispecific, chimeric antibodies, humanized antibodies, human antibodies, CDR-grafted, veneered, or deimmunized (e.g., to remove T-cell epitopes) antibodies. The term "human antibody" includes antibodies obtained from human beings as well as antibodies obtained from transgenic mammals comprising human immunoglobulin genes such that, upon stimulation with an antigen the transgenic animal produces antibodies comprising amino acid sequences characteristic of antibodies produced by human beings. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries.

Binding molecule: As used herein, the term "binding molecule" refers to a bivalent molecule that can bind to the extracellular domain of two cell surface receptors. In some embodiments, a binding molecule specifically binds to two different receptors (or domains or subunits thereof) such that the receptors (or domains or subunits) are maintained in proximity to each other such that the receptors (or domains or subunits), including domains thereof (e.g., intracellular domains) interact with each other and result in downstream signaling.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., J. Biol. Chem. 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs2 and 3 in the variable region of an antibody follows Kabat numbering or simply, "Kabat." The positioning of CDR1 in the variable region of an antibody follows a hybrid of Kabat and Chothia numbering schemes.

As used herein, a clonotype refers to a collection of binding molecules that originate from the same B-cell progenitor cell. The term "clonotype" is used to refer to a collection of antigen binding molecules that belong to the same germline family, have the same CDR3 lengths, and have 70% or greater homology in CDR3 sequence.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Effective Concentration (EC): As used herein, the terms "effective concentration" or its abbreviation "EC" are used interchangeably to refer to the concentration of an agent (e.g., an hIL2 mutein) in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term $E_{max}$ refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the $E_{max}$ of the biological observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect. The EC of a particular effective concentration of a test agent may be abbreviated with respect to the with respect to particular parameter and test system.

Extracellular Domain: As used herein the term "extracellular domain" or its abbreviation "ECD" refers to the portion of a cell surface protein (e.g. a cell surface receptor) which is outside of the plasma membrane of a cell. The term "ECD" may include the extra-cytoplasmic portion of a transmembrane protein or the extra-cytoplasmic portion of a cell surface (or membrane associated protein).

Identity: As used herein, the term "percent (%) sequence identity" or "substantially identical" used in the context of nucleic acids or polypeptides, refers to a sequence that has at least 50% sequence identity with a reference sequence. Alternatively, percent sequence identity can be any integer from 50% to 100%. In some embodiments, a sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined with BLAST using standard parameters, as described below. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. A comparison window includes reference to a segment of any one of the number of contiguous positions, e.g., a segment of at least 10 residues. In some embodiments, the comparison window has from 10 to 600 residues, e.g., about 10 to about 30 residues, about 10 to about 20 residues, about 50 to about 200 residues, or about 100 to about 150 residues, in which a sequence may be compared to a reference sequence of the same number of contiguous positions after the two sequences are optimally aligned. Algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=-2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)). The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference sequence if the smallest sum probability in a comparison of the test amino acid sequence to the reference amino acid sequence is less than about 0.01, more preferably less than about $10^{-5}$, and most preferably less than about $10^{-20}$.

Intracellular Signaling: As used herein, the terms "intracellular signaling" and "downstream signaling" are used interchangeably to refer to the to the cellular signaling process that is caused by the interaction of the intracellular domains (ICDs) of two or more cell surface receptors that are in proximity of each other. In receptor complexes via the JAK/STAT pathway, the association of the ICDS of the receptor subunits brings the JAK domains of the ICDs into proximity which initiates a phosphorylation cascade in which STAT molecules are phosphorylated and translocate to the nucleus associating with particular nucleic acid sequences resulting in the activation and expression of particular genes in the cell. The binding molecules of the present disclosure provide intraceullar signaling characteristic of the IFNGR receptor when activated by its natural cognate IFNG. To measure downstream signaling activity, a number of methods are available. For example, in some embodiments, one can measure JAK/STAT signaling by the presence of phosphorylated receptors and/or phosphorylated STATs. In other embodiments, the expression of one or more downstream genes, whose expression levels can be affected by the level of downstream signaling caused by the binding molecule, can also be measured.

Ligand: As used herein, the term "ligand" refers to a molecule that exhibits specific binding to a receptor and results in a change in the biological activity of the receptor so as to effect a change in the activity of the receptor to which it binds. In one embodiment, the term "ligand" refers to a molecule, or complex thereof, that can act as an agonist or antagonist of a receptor. As used herein, the term "ligand" encompasses natural and synthetic ligands. "Ligand" also encompasses small molecules, e.g., peptide mimetics of cytokines and peptide mimetics of antibodies. The complex of a ligand and receptor is termed a "ligand-receptor complex."

As used herein, the term "linker" refers to a linkage between two elements, e.g., protein domains. A linker can be a covalent bond or a peptide linker. The term "bond" refers to a chemical bond, e.g., an amide bond or a disulfide bond, or any kind of bond created from a chemical reaction, e.g., chemical conjugation. The term "peptide linker" refers to an amino acid or polypeptide that may be employed to link two protein domains to provide space and/or flexibility between the two protein domains.

Modulate: As used herein, the terms "modulate", "modulation" and the like refer to the ability of a test agent to affect a response, either positive or negative or directly or indirectly, in a system, including a biological system or biochemical pathway.

Multimerization: As used herein, the term "multimerization" refers to two or more cell surface receptors, or domains or subunits thereof, being brought in close proximity to each other such that the receptors, or domains or subunits thereof, can interact with each other and cause intracellular signaling.

N-Terminus: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. The terms "immediately N-terminal" or "immediately C-terminal" are used to refers to a position of a first amino acid residue relative to a second amino acid residue where the first and second amino acid residues are covalently bound to provide a contiguous amino acid sequence.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the Operably Linked: The term "operably linked" is used herein to refer to the relationship between nucleic acid sequences encoding differing functions when combined into a single nucleic acid sequence that, when introduced into a cell, provides a nucleic acid which is capable of effecting the transcription and/or translation of a particular nucleic acid sequence in a cell. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, certain genetic elements such as enhancers need not be contiguous with respect to the sequence to which they provide their effect.

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Clinically, partial agonists can be used to activate receptors to give a desired submaximal response when inadequate amounts of the endogenous ligand are present, or they can reduce the overstimulation of receptors when excess amounts of the endogenous ligand are present. The maximum response (Emax) produced by a partial agonist is called its intrinsic activity and may be expressed on a percentage scale where a full agonist produced a 100% response. A In some embodiments, the IFNGR binding molecule has a reduced $E_{max}$ compared to the $E_{max}$ caused by IFNG. $E_{max}$ reflects the maximum response level in a cell type that can be obtained by a ligand (e.g., a binding molecule described herein or the native cytokine (e.g., IFNG)). In some embodiments, the IFNGR binding molecule described herein has at least 1% (e.g., between 1% and 100%, between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ caused by IFNG. In other embodiments, the $E_{max}$ of the IFNGR binding molecule described herein is greater (e.g., at least 1%, 5%, 10%, 15%, 20%, 25%, 30%, 35%, 40%, 45%, or 50% greater) than the $E_{max}$ of the natural ligand, IFNG. In some embodiments, by varying the linker length of the IFNGR binding molecule, the $E_{max}$ of the IFNGR binding molecule can be changed. The IFNGR binding molecule can cause $E_{max}$ in the most desired cell types, and a reduced $E_{max}$ in other cell types.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; fusion proteins of immunologically active proteins (e.g. antigenic diphtheria or tetanus toxin fragments) and the like.

As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed due to genetic, experiential or environmental factors to having a particular disease, disorder or condition. In certain instances, the terms "prevent", "preventing", "prevention" are also used to refer to the slowing of the progression of a disease, disorder or condition from a present its state to a more deleterious state.

Proximity: As used herein, the term "proximity" refers to the spatial proximity or physical distance between two cell surface receptors, or domains or subunits thereof, after a binding molecule described herein binds to the two cell surface receptors, or domains or subunits thereof. In some embodiments, after the binding molecule binds to the cell surface receptors, or domains or subunits thereof, the spatial proximity between the cell surface receptors, or domains or subunits thereof, can be, e.g., less than about 500 angstroms, such as e.g., a distance of about 5 angstroms to about 500 angstroms. In some embodiments, the spatial proximity amounts to less than about 5 angstroms, less than about 20 angstroms, less than about 50 angstroms, less than about 75 angstroms, less than about 100 angstroms, less than about 150 angstroms, less than about 250 angstroms, less than about 300 angstroms, less than about 350 angstroms, less than about 400 angstroms, less than about 450 angstroms, or less than about 500 angstroms. In some embodiments, the spatial proximity amounts to less than about 100 angstroms. In some embodiments, the spatial proximity amounts to less than about 50 angstroms. In some embodiments, the spatial proximity amounts to less than about 20 angstroms. In some embodiments, the spatial proximity amounts to less than about 10 angstroms. In some embodiments, the spatial proximity ranges from about 10 to 100 angstroms, from about 50 to 150 angstroms, from about 100 to 200 angstroms, from about 150 to 250 angstroms, from about 200 to 300 angstroms, from about 250 to 350 angstroms, from about 300 to 400 angstroms, from about 350 to 450 angstroms, or about 400 to 500 angstroms. In some embodiments, the spatial proximity amounts to less than about 250 angstroms, alternatively less than about 200 angstroms, alternatively less than about 150 angstroms, alternatively less than about 120 angstroms, alternatively less than about 100 angstroms, alternatively less than about 80 angstroms, alternatively less than about 70 angstroms, or alternatively less than about 50 angstroms.

Receptor: As used herein, the term "receptor" refers to a polypeptide having a domain that specifically binds a ligand that binding of the ligand results in a change to at least one biological property of the polypeptide. In some embodiments, the receptor is a "soluble" receptor that is not associated with a cell surface. In some embodiments, the receptor is a cell surface receptor that comprises an extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of the ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface molecule having not associated with any intracellular signaling alone but upon ligand binding facilitates the formation of a multimeric complex that results in intracellular signaling.

Recombinant: As used herein, the term "recombinant" is used as an adjective to refer to the method by a polypeptide, nucleic acid, or cell that was modified using recombinant DNA technology. A recombinant protein is a protein produced using recombinant DNA technology and may be designated as such using the abbreviation of a lower case "r" (e.g., rhIL2) to denote the method by which the protein was produced. Similarly, a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors. In contrast, the terms "inhibition", "down-regulation" and the like refer to the opposite effects.

Single Domain Antibody (sdAb): The term "single-domain antibody" or "sdAbs," refers to an antibody having a single (only one) monomeric variable antibody domain. A sdAb is able to bind selectively to a specific antigen. A VHH antibody, further defined below, is an example of a sdAb.

Specifically Binds: As used herein the term "specifically binds" refers to the degree of affinity for which a first molecule exhibits with respect to a second molecule. In the context of binding pairs (e.g., ligand/receptor, antibody/antigen) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the antigen (or antigenic determinant (epitope) of a protein, antigen, ligand, or receptor) if the equilibrium dissociation constant ($K_D$) between antibody and the antigen is lesser than about $10^{-6}$ M, alternatively lesser than about $10^{-8}$ M, alternatively lesser than about $10^{-10}$ M, alternatively lesser than about $10^{-11}$ M, lesser than about $10^{-12}$ M as determined by, e.g., Scatchard analysis (Munsen, et al. (1980) Analyt. Biochem. 107:220-239). In one embodiment where the ligand is an ILR binding sdAb and the receptor comprises an ILR, the ILR binding sdAb specifically binds if the equilibrium dissociation constant ($K_D$) of the ILR binding sdAb/ILR ECD is lesser than about $10^{-5}$M, alternatively lesser than about $10^{-6}$ M, alternatively lesser than about $10^{-7}$M, alternatively lesser than about $10^{-8}$M, alternatively lesser than about $10^{-9}$ M, alternatively lesser than about $10^{-10}$ M, or alternatively lesser than about $10^{-11}$ M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8+, Biacore S200, Biacore T200 (GE Healthcare Bio-Sciences, 100 Results Way, Marlborough MA 01752). In some embodiments, the present disclosure provides molecules (e.g., ILR binding sdAbs) that specifically bind to the hILR. As used herein, the binding affinity of an ILR binding molecule for the ILR, the binding affinity may be determined and/or quantified by surface plasmon resonance ("SPR"). In evaluating binding affinity of an ILR binding molecule for the ILR, either member of the binding pair may be immobilized, and the other element of the binding pair be provided in the mobile phase. In some embodiments, the sensor chip on which the protein of interest is to be immobilized is conjugated with a substance to facilitate binding of the protein of interest such as nitrilotriacetic acid (NTA) derivatized surface plasmon resonance sensor chips (e.g., Sensor Chip NTA available from Cytiva Global Life Science Solutions USA LLC, Marlborough MA as catalog number BR100407), as anti-His tag antibodies (e.g. anti-histidine CM5 chips commercially available from Cytiva, Marlborough MA), protein A or biotin. Consequently, to evaluate binding, it is frequently necessary to modify the protein to provide for binding to the substance conjugated to the surface of the chip. For example, the one member of the binding pair to be evaluated by incorporation of a chelating peptide comprising poly-histidine sequence (e.g., 6xHis (SEQ ID NO: 307) or 8xHis (SEQ ID NO: 308)) for retention on a chip conjugated with NTA. In some embodiments, the ILR binding molecule may be immobilized on the chip and ILR (or ECD fragment thereof) be provided in the mobile phase. Alternatively, the ILR (or ECD fragment thereof) may be immobilized on the chip and the ILR binding molecule be provided in the mobile phase. In either circumstance, it should be noted that modifications of some proteins for immobilization on a coated SPR chip may interfere with the binding properties of one or both components of the binding pair to be evaluated by SPR. In such cases, it may be necessary to switch the mobile and bound elements of the binding pair or use a chip with a binding agent that facilitates non-interfering conjugation of the protein to be evaluated. Alternatively, when evaluating the binding affinity of ILR binding molecule for ILR using SPR, the ILR binding molecule may be derivatized by the C-terminal addition of a poly-His sequence (e.g., 6xHis (SEQ ID NO: 307) or 8xHis (SEQ ID NO: 308)) and immobilized on the NTA derivatized sensor chip and the ILR receptor subunit for which the ILR VHH's binding affinity is being evaluated is provided in the mobile phase. The means for incorporation of a poly-His sequence into the C-terminus of the ILR binding molecule produced by recombinant DNA technology is well known to those of skill in the relevant art of biotechnology. In some embodiments, the binding affinity of ILR binding molecule for an ILR comprises using SPR substantially in accordance with the teaching of the Examples.

Stably Associated: As used herein, the term "stably associated" or "in stable association with" are used to refer to the various means by which one molecule (e.g., a polypeptide) may be associated with another molecule over an extended period of time. The stable association of one molecule to another may be effected by a variety of means, including covalent bonding and non-covalent interactions. In some embodiments, stable association of two molecules may be effected by covalent bonds such as peptide bonds. In other embodiments, stable association of two molecules may be effected b non-covalent interactions. Examples of non-covalent interactions which may providea a stable association between two molecules include electrostatic interactions (e.g., hydrogen bonding, ionic bonding, halogen binding, dipole-dipole interactions, Van der Waals forces and π-effects including cation-π interactions, anion-π interactions and π-π interactions) and hydrophobilic/hydrophilic interactions. In some embodiments, the stable association of sdAbs of the bivalent binding molecules of the present disclosure may be effected by non-covalent interactions. In one embodiment, the non-covalent stable association of the sdAbs of the bivalent binding molecules may be achieved by conjugation of the sdAbs to "knob-into-hole" modified Fc monomers. An Fc "knob" monomer stably associates non-covalently with an Fc "hole" monomer. Conjugation of a first sdAb which specifically binds to the extracellular domain of a first subunit of a heterodimeric receptor to an "Fc knob" monomer and conjugation of an second sdAb which specifically binds to the extracellular domain of a second subunit of a heterodimeric receptor to an "Fc hole" monomer provides stable association of the first and second sdAbs.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially: As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher of a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Suffering From: As used herein, the term "suffering from" refers to a determination made by a physician with respect to a subject based on the available information accepted in the field for the identification of a disease, disorder or condition including but not limited to X-ray, CT-scans, conventional laboratory diagnostic tests (e.g., blood count), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

Therapeutically Effective Amount: As used herein, the term The phrase "therapeutically effective amount" is used in reference to the administration of an agent to a subject, either alone or as part of a pharmaceutical composition or treatment regimen, in a single dose or as part of a series of doses in an amount capable of having any detectable, positive effect on any symptom, aspect, or characteristic of a disease, disorder or condition when administered to the subject. The therapeutically effective amount can be ascertained by measuring relevant physiological effects, and it may be adjusted in connection with a dosing regimen and in response to diagnostic analysis of the subject's condition, and the like. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, modification of biomarker levels, increase in duration of survival, extended duration of progression free survival, extension of the time to progression, increased time to treatment failure, extended duration of event free survival, extension of time to next treatment, improvement objective response rate, improvement in the duration of response, and the like that that are relied upon by clinicians in the field for the assessment of an improvement in the condition of the subject in response to administration of an agent.

Treat: The terms "treat", "treating", treatment" and the like refer to a course of action (such as administering a binding molecule described herein, or a pharmaceutical composition comprising same) initiated with respect to a subject after a disease, disorder or condition, or a symptom thereof, has been diagnosed, observed, or the like in the subject so as to eliminate, reduce, suppress, mitigate, or ameliorate, either temporarily or permanently, at least one of the underlying causes of such disease, disorder, or condition afflicting a subject, or at least one of the symptoms associated with such disease, disorder, or condition. The treatment includes a course of action taken with respect to a subject suffering from a disease where the course of action results in the inhibition (e.g., arrests the development of the disease, disorder or condition or ameliorates one or more symptoms associated therewith) of the disease in the subject.

VHH: As used herein, the term "VHH" is a type of sdAb that has a single monomeric heavy chain variable antibody domain. Such antibodies can be found in or produced from Camelid mammals (e.g., camels, llamas) which are naturally devoid of light chains $V_HH$s can be obtained from immunization of camelids (including camels, llamas, and alpacas (see, e.g., Hamers-Casterman, et al. (1993) Nature 363:446-448) or by screening libraries (e.g., phage libraries) constructed in $V_HH$ frameworks. Antibodies having a given specificity may also be derived from non-mammalian sources such as $V_HH$s obtained from immunization of cartilaginous fishes including, but not limited to, sharks. In a particular embodiment, a $V_HH$ in a bispecific $V_HH^2$ binding molecule described herein binds to a receptor (e.g., the first receptor or the second receptor of the natural or non-natural receptor pairs) if the equilibrium dissociation constant between the $V_HH$ and the receptor is lesser than about $10^{-6}$ M, alternatively lesser than about $10^{-8}$ M, alternatively lesser than about $10^{-10}$ M, alternatively lesser than about $10^{-11}$ M, alternatively lesser than about $10^{-10}$ M, lesser than about $10^{-12}$ M as determined by, e.g., Scatchard analysis (Munsen, et al. 1980 Analyt. Biochem. 107:220-239). Standardized protocols for the generation of single domain antibodies from camelids are well known in the scientific literature. See, e.g., Vincke, et al (2012) Chapter 8 in *Methods in Molecular Biology*, Walker, J. editor (Humana Press, Totowa NJ). Specific binding may be assessed using techniques known in the art including but not limited to competition ELISA, BIACORE® assays and/or KINEXA® assays. In some embodiments, a $V_HH$ described herein can be humanized to contain human framework regions. Examples of human germlines that could be used to create humanized $V_HH$s include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

$V_HH^2$: As used herein, the term "$V_HH^2$" and "bispecific $V_HH^2$" and "VHH dimer" refers to are used interchangeably to refer to a subtype of the binding molecules of the present disclosure wherein the first and second sdAbs are both VHHs and first $V_HH$ binding to a first receptor, or domain or subunit thereof, and a second $V_HH$ binding to a second receptor, or domain or subunit thereof.

Wild Type: As used herein, the term "wild type" or "WT" or "native" is used to refer to an amino acid sequence or a nucleotide sequence that is found in nature and that has not been altered by the hand of man.

Cytokine Receptor Binding Molecules

General Description

The present disclosure provides disclosure provides cytokine receptor binding molecules that are ligands for a cytokine receptor, the cytokine receptor binding molecule comprising:
(a) a first single domain antibody (sdAb) that specifically binds to the extracellular domain a first subunit of a cytokine receptor; and
(b) a second single domain antibody that specifically binds to extracellular domain of a second subunit of cytokine receptor subunit;

wherein:
the first sdAb and second sdAb are in stable association;
the first and second subunits of the cytokine receptor are dimerized in response to contact with the cognate ligand for the cytokine receptor; and
contacting a cell expressing the first and the second subunits of the cytokine receptor with an effective amount of the cytokine receptor binding molecule results in the intracellular domains of the first and second subunits of the cytokine receptors being brought into proximity and results in intraceullar signaling.

Single Domain Antibody

The cytokine receptor binding molecules of the present disclosure comprise two or more single domain antibodies. The term "single domain antibody" (sdAb) as used herein refers an antibody fragment consisting of a monomeric variable antibody domain that is able to bind specifically to an antigen and compete for binding with the parent antibody from which it is derived. The term "single domain antibody" includes scFv and VHH molecules. In some embodiments, one or both of the sdAbs of the cytokine receptor binding molecule is a an scFv. In some embodiments, one or both of the sdAbs is a VHH. In some embodiments, one or both of the sdAbs is a scFv.

Single Domain Antibody Is A VHH

In some embodiments, one or more of the sdAb of the cytokine receptor binding molecules of the present disclosure is a VHH. As used herein, the term "VHH" refers to a single domain antibody derived from camelid antibody typically obtained from immunization of camelids (including camels, llamas and alpacas (see, e.g., Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks. A VHH is a type of single-domain antibody (sdAb) containing a single monomeric variable antibody domain. Like a full-length antibody, it is able to bind selectively to a specific antigen. The complementary determining regions (CDRs) of VHHs are within a single-domain polypeptide. VHHs can be engineered from heavy-chain antibodies found in camelids. An exemplary VHH has a molecular weight of approximately 12-15 kDa which is much smaller than traditional mammalian antibodies (150-160 kDa) composed of two heavy chains and two light chains. VHHs can be found in or produced from Camelidae mammals (e.g., camels, llamas, dromedary, alpaca, and guanaco) which are naturally devoid of light chains. Descriptions of sdAbs and VHHS can be found in, e.g., De Greve et al., *Curr Opin Biotechnol.* 61:96-101, 2019; Ciccarese, et al., *Front Genet.* 10:997, 2019; Chanier and Chames, *Antibodies* (*Basel*) 8(1), 2019; and De Vlieger et al., *Antibodies* (*Basel*) 8(1), 2018.

Engineered sdAbs.

The term single domain antibody includes engineered sdAbs including but not limited to chimeric sdAbs, CDR grafted sdAbs and humanized sdAbs.

In some embodiments, the one or more of the sdAbs for incorporation into the bivalent binding molecules of the present disclosure are CDR grafted. CDRs obtained from antibodies, heavy chain antibodies, and sdAbs derived therefrom may be grafted onto alternative frameworks as described in Saerens, et al. (2005) J. Mol Biol 352:597-607 to generate CDR-grafted sdAbs. Any framework region can be used with the CDRs as described herein.

In some embodiments, one or more of the sdAbs for incorporation into the bivalent binding molecules is a chimeric sdAb, in which the CDRs are derived from one species (e.g., camel) and the framework and/or constant regions are derived from another species (e.g., human or mouse). In specific embodiments, the framework regions are human or humanized sequences. Thus, bivalent binding molecules comprising one or more humanized sdAbs are considered within the scope of the present disclosure. The techniques for humanization of camelid single domain antibodies are well known in the art. See, e.g., Vincke, et al. (2009) *General Strategy to Humanize a Camelid Single-domain Antibody and Identification of a Universal Humanized Nanobody Scaffold* J. Biol. Chem. 284(5)3273-3284.

In some embodiments, a VHH described herein can be humanized to contain human framework regions. Examples of human germlines that could be used to create humanized VHHs include, but are not limited to, VH3-23 (e.g., UniProt ID: P01764), VH3-74 (e.g., UniProt ID: AOA0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

Stably Associated:

The present disclosure provides a synthetic cytokine receptor ligand comprising at least two binding domains, the synthetic ligand comprising a first binding domain that specifically binds to the extracellular domain of a first cytokine receptor subunit in stable association with a second binding domain that specifically binds to the extracellular domain of a second cytokine receptor subunit. As used herein, the term "stably associated" or "in stable association with" are used to refer to the various means by which one molecule (e.g., a polypeptide) may be thermodynamically and/or kinetically associated with another molecule. The stable association of one molecule to another may be achieved by a variety of means, including covalent bonding and non-covalent interactions.

Covalent Bonding

In some embodiments, stable association of two molecules may be effected by covalent bonds such as peptide bonds. In some embodiments, the covalent linkage between the first and second binding domains is a covalent bond between the C-terminus of the first binding domain and the N-terminus of the second binding domain.

In some embodiments, the first binding domain that specifically binds to the extracellular domain of a first cytokine receptor subunit in stable association with a second binding domain that specifically binds to the extracellular domain of a second cytokine receptor subunit are covalent bonded via a linker. In some embodiments, a linker joins the C-terminus of the first sdAb which binds to the ECD of the first receptor subunit of the cytokine receptor of the binding molecule to the N-terminus of the second sdAb which binds to the ECD of the second receptor subunit of the cytokine receptor. In some embodiments, a linker joins the C-terminus of the second sdAb which binds to the ECD of the second receptor subunit of the cytokine receptor of the binding molecule to the N-terminus of the first sdAb which binds to the ECD of the first receptor subunit of the cytokine receptor. Linkers may be selected from selected from the group including but not limited to peptide linkers or chemical linkers.

Peptide Linkers

In some embodiments, the stable association of the first and second domains may be achieved by covalent linkage of the C-terminus of the first binding domain and the N-terminus of the second binding domain via a peptide linker. A peptide linker can include between 1 and 50 amino acids (e.g., between 2 and 50, between 5 and 50, between 10 and 50, between 15 and 50, between 20 and 50, between 25 and 50, between 30 and 50, between 35 and 50, between 40 and 50, between 45 and 50, between 2 and 45, between 2 and 40, between 2 and 35, between 2 and 30, between 2 and 25, between 2 and 20, between 2 and 15, between 2 and 10, between 2 and 5 amino acids). Examples of flexible peptide linkers include glycine polymers (G)n, glycine-alanine polymers, alanine-serine polymers, glycine-serine polymers (for example, (GmSo)n (SEQ ID NO: 309), (GSGGS)n (SEQ ID NO: 310), (GmSoGm)n (SEQ ID NO: 311), (GmSoGm-SoGm)n (SEQ ID NO: 312), (GSGGSm)n (SEQ ID NO: 313), (GSGSmG)n (SEQ ID NO: 314) and (GGGSm)n (SEQ ID NO: 315), and combinations thereof, where m, n, and o are each independently selected from an integer of at least 1 to 20, e.g., 1-18, 216, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components. Exemplary flexible linkers include the linkers of but are not limited to the linkers provided in Table 16 as SEQ ID NOS; 462-484.

Chemical Linkers

In some embodiments, the covalent linkage of the first and second domains may be achieved by a chemical linker. Examples of chemical linkers include aryl acetylene, ethylene glycol oligomers containing 2-10 monomer units, diamines, diacids, amino acids, polymers such as PEG or combinations thereof.

Non-Covalent Bonding

In some embodiments, stable association of the first and second binding domains of the binding molecules may be effected by non-covalent interactions. Examples of non-covalent interactions which may providea a stable association between two molecules include electrostatic interactions (e.g., hydrogen bonding, ionic bonding, halogen binding, dipole-dipole interactions, Van der Waals forces and p-effects including cation-p interactions, anion-p interactions and p-p interactions) and hydrophobilic/hydrophilic interactions. In some embodiments, the stable association of sdAbs of the binding molecules of the present disclosure may be effected by non-covalent interactions. In one embodiment, the non-covalent stable association of a receptor binding molecules to a subunit of an Fc, domain optionally incorporating a linker between the receptor binding molecule and the Fc such as the IgG4 hinge domain. Alternatively, the receptor binding molecule or individual sdAbs of the binding molecules may be achieved by conjugation to a domain (or both domains) of the sdAbs to "knob-into-hole" modified Fc monomers.

Figure 4:
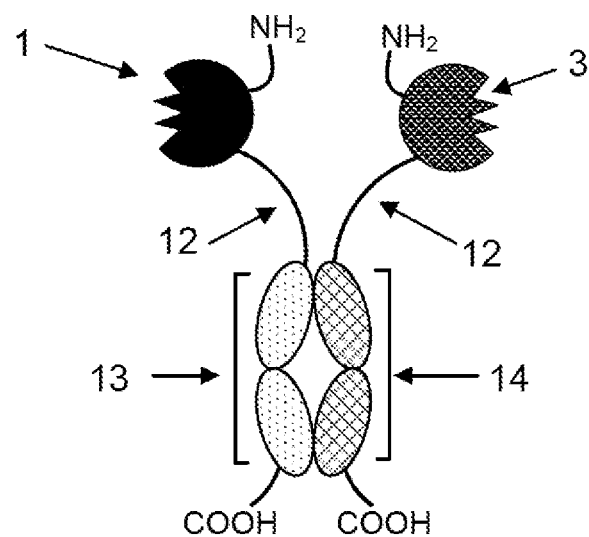
FIG. 4, Panel A provides alternative schematic representations of configurations of the bivalent binding molecules of the present disclosure where one single domain antibody is attached to each subunit of a knob-into-hole Fc domain comprising two polypeptides, the first polypeptide comprising from amino to carboxy, a first single domain antibody (1), an IgG hinge sequence (12) and a Fc knob subunit (13), the second polypeptide comprising from amino to carboxy, a second single domain antibody (3), an IgG hinge sequence (12) and a Fc hole subunit (13), wherein the first and second single domain antibodies are in stable associate via the interaction of the knob-into-hole Fc domain.
Figure 4:
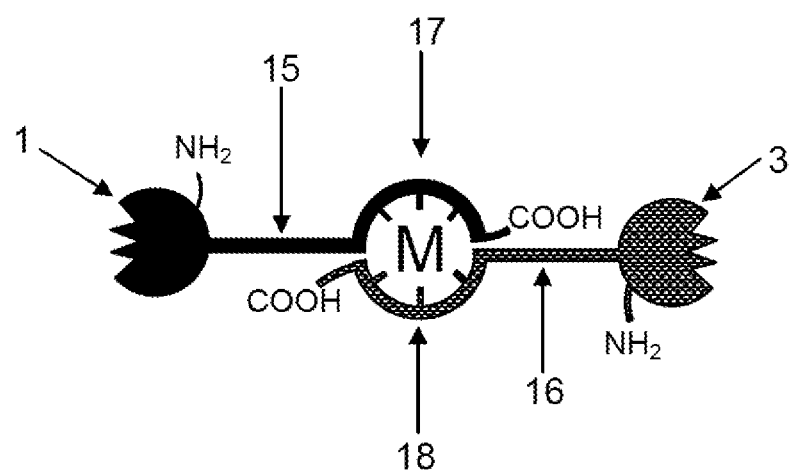

In one embodiment, the non-covalent stable association of the sdAbs of the binding molecules may be achieved by conjugation of the sdAbs to "knob-into-hole" modified Fc monomers. An Fc "knob" monomer stably associates non-covalently with an Fc "hole" monomer. Conjugation of a first sdAb which specifically binds to the extracellular domain of a first subunit of a heterodimeric receptor to an "Fc knob" monomer and conjugation of an second sdAb which specifically binds to the extracellular domain of a second subunit of a heterodimeric receptor to an "Fc hole" monomer provides stable association of the first and second sdAbs. The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 on one chain and Y349 on the second chain which results in a stabilizing disulfide bridge between the two antibody heavy chains in the Fc region (Carter, et al. (2001) Immunol Methods 248, 7-15). The knob-into-hole format is used to facilitate the expression of a first polypeptide (e.g., an IL27Rα binding sdAb) on a first Fc monomer with a "knob" modification and a second polypeptide on the second Fc monomer possessing a "hole" modification to facilitate the expression of heterodimeric polypeptide conjugates. A schematic illustration of this wherein each binding domain is be provided on separate subunits of a knob-into-hole Fc dimer such that the first and second binding domains are non-covalently linked via the non-covalent linkage of the knob and hole as illustrated in FIG. 4, Panel A of the attached drawings.

Coordinate Covalent Bonding

In some embodiments, stable association of the first and second binding domains of the binding molecules may be effected by a coordinate covalent linkage. The present disclosure provides examples of single domain antibodies comprising a chelating peptide. The chelating peptide results in a coordinate covalent linkage to a transition metal ion. In some embodiments, a transition metal ion is capable of forming a coordinate covalent linkage with two or more chelating peptides. Consequently, the first and second binding domains may each comprise a chelating peptide and a stable association of the binding domains by each subunit forming a coordinate covalent complex with a transition metal ion. In some embodiments, the transition metal ion is selected from vanadium, manganese, iron, iridium, osmium, rhenium platinum, palladium, cobalt, chromium or ruthenium. A schematic illustration of this configuration is provided in FIG. 4, Panel B of the attached drawings. It should be noted that in each of the configurations illustrated in FIG. 4, Panels A and B, the N-terminal domain of the single domain antibody is presented to the environment enabling facilitating enhanced exposure of the CDRs of the sdAb to the target cytokine receptor ECD. The formation of the coordinate covalent linkage between the is favored when the transition metal ion is in a kinetically labile oxidation state, for example Co(II), Cr(II), or Ru(III). Following complexation, the oxidation state of the transition metal may be changed (oxidized or reduced) to a kinetically inert oxidation state, for example Co(III), Cr(III), or Ru(II), provide a kinetically inert coordinate covalent complex. The formation of kinetically inert and kinetically labile coordinate covalent complexes between proteins comprising chelating peptides via a transition metal are described in more detail in Anderon, et al. U.S. Pat. No. 5,439,928 issued Aug. 8, 1995.

Modulation of Activity of Receptor Binding Molecules

In some embodiments, such as to achieve partial agonism or selective activation of particular cell types, the design of the cytokine receptor binding molecules of the present disclosure may be modulated by structural variations in the design of the receptor binding molecule. This variation in activity may be employed to modulated the binding and activity of the receptor binding molecule, for example to variations in chieve partial agonism, selective cell type activation or increased or decreased activity relative to the cognate ligand for the receptor. Examples of the means by which the modulation of the activity and/or specificity of the receptor binding molecule of the present disclosure include but are not limited to altering the sequential orientation of the sdAb, independently varying the of the binding affinity of the sdAbs with respect to each target, and modulating the distance between the sdAbs such as by employing linkers or varying lengths.

In some embodiments, the cytokine receptor binding protein has a reduced $E_{max}$ compared to the $E_{max}$ caused by the cognate ligand. $E_{max}$ reflects the maximum response level in a cell type that can be obtained by a ligand (e.g., a binding protein described herein or the cognate ligand (e.g., IFNG). In some embodiments, the IFNGR binding protein described herein has at least 1% (e.g., between 1% and 100%, between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ caused by hIFNG.

Modulation of Activity By Varying the Distance Between the sdAbs

In some embodiments, by modulating the distance between the sdAbs of receptor binding protein (e.g. by varying the linker length between the sdAbs), the $E_{max}$ of the binding protein can be modulated. The such variations in receptor binding protein geometry can exploited to increase activity in the most desired cell types (e.g., CD8+ T cells), while reducing activity in other cell types (e.g., macrophages). With respect to the IFNGR binding molecules, in some embodiments, the $E_{max}$ of the IFNGR binding protein on macrophages is between 1% and 100% (e.g., between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ the IFNGR binding protein on T cells (e.g., CD8+ T cells). In other embodiments, the $E_{max}$ of the IFNGR binding protein described herein is greater (e.g., at least 1%, 5%, 10%, 15%, 20%, 25%, 30%, 35%, 40%, 45%, or 50% greater) than the $E_{max}$ of the natural ligand, IFNG.

Sequential Orientation of sdAbs

When the cytokine receptor binding molecule of the present disclosure is expressed as a single polypeptide chain, the binding activity and/or specificity of the receptor binding molecule may be modulated by the order (N-terminal versus C-terminal) arrangements of the sdAbs in the polypeptide.

In some embodiments, the cytokine receptor binding molecule is a polypeptide IFNGR binding molecule and the activity and/or specificity of the IFNGR binding is modulated by the sequential arrangement of the IFNGR1 and IFNGR2 sdAbs in the polypeptide.

"Forward Orientation"

In some embodiments, the cytokine receptor binding molecule (e.g., an IFNGR binding molecule) comprises a polypeptide of the structure:

$H_2N$-[First Receptor Subunit sdAb]-$[L]_x$-[Second Receptor Subunit sdAb]-$[CP]_y$—COOH wherein and L is a polypeptide linker of 1-50 amino acids and x=0 or 1, and CP is a chelating peptide or a subunit of an Fc domain and y=0 or 1.

In one embodiment, the present disclosure provides a IFNGR binding molecule comprises a polypeptide of the structure:

$H_2N$-[IFNGR1sdAb]-$[L]_x$-[IFNGR2sdAb]-$[CP]_y$—COOH wherein and L is a polypeptide linker of 1-50 amino acids and x=0 or 1, and CP is a chelating peptide or a subunit of an Fc domain and y=0 or 1. This is referred to herein as the "forward orientation" of the IFNGR sdAbs of the IFNGR binding molecule.

"Reverse Orientation"

In some embodiments, the cytokine receptor binding molecule (e.g., an IFNGR binding molecule) comprises a polypeptide of the structure:

$H_2N$-[Second Receptor Subunit sdAb]-$[L]_x$-[First Receptor Subunit sdAb]-$[CP]_y$—COOH wherein and L is a polypeptide linker of 1-50 amino acids and x=0 or 1, and CP is a chelating peptide or a subunit of an Fc domain and y=0 or 1.

In some embodiments, the bivalent IFNGR binding molecule comprises a polypeptide of the structure:

$H_2N$-[IFNGR2sdAb]-$[L]_x$-[IFNGR1sdAb]-$[CP]_y$—COOH wherein and L is a polypeptide linker of 1-50 amino acids and x=0 or 1, and CP is a chelating peptide or a subunit of an Fc domain, and y=0 or 1.

Modulation of Activity Variation of The Binding Affinities of sdAbs

In some embodiments, the activity and/or specificity of the bivalent receptor binding molecule of the present disclosure may be modulated by independently varying the respective binding affinities of the first and second sdAbs for their respective receptor subunits.

It will be appreciated by one of skill in the art that the binding of the first sdAb of the bivalent binding molecule to the first receptor subunit ECD on the cell surface will enhance the probability of a binding interaction between the second sdAb of the bivalent binding molecule with the ECD of the second receptor subunit. This cooperative binding effect may result in a bivalent receptor binding molecule which has a very high affinity for the receptor and a very slow "off rate" from the receptor. Typical VHH single domain antibodies have an affinity for their targets of from about $10^{-5}$M to about $10^{-10}$M. In those instances such slow off-rate kinetics are desirable in the bivalent IFNGR binding molecules\, the selection of sdAbs having high affinities (about $10^{-7}$M to about $10^{-10}$M) for incorporation into the bivalent IFNGR binding molecule are favored.

Naturally occurring cytokine ligands for typically do not exhibit a similar affinity for each subunit of a heterodimeric receptor. Consequently, in designing a bivalent cytokine receptor binding molecule which is a mimetic of the cognate cytokine ligand as contemplated by some embodiments of the present disclosure, selection of sdAbs for the first and second receptor receptor subunit have an affinity similar to (e.g., having an affinity about 10 fold, alternatively about 20 fold, or alternatively about 50 fold higher or lower than) the cognate IFNG for the respective receptor subunit may be used.

In some embodiments, the bivalent receptor binding molecules of the present disclosure are partial agonists. As such, the activity of the binding molecule may be modulated by selecting sdAb which have greater or lesser affinity for either one or both of the receptor subunits relative to the cognate ligand. As some heterodimeric cytokine receptors are comprised of a "proprietary subunit" (i.e., a subunit which is not naturally a subunit of another multimeric receptor) and a second "common" subunit (such as IFNGR2) which is a shared component of multiple cytokine receptors), selectivity for the formation of such receptor may be enhanced by employing first sdAb which has a higher affinity for the proprietary receptor subunit and second sdAb which exhibits a lower affinity for the common receptor subunit. Additionally, the common receptor subunit may be expressed on a wider variety of cell types than the proprietary receptor subunit. In some embodiments wherein the receptor is a heterodimeric receptor comprising a proprietary subunit and a common subunit, the first sdAb of the bivalent IFNGR binding molecule exhibits a significantly greater (more than 10 times greater, alternatively more than 100 times greater, alternatively more than 1000 times greater) affinity for the proprietary receptor than the second sdAb of the bivalent IFNGR binding molecule for the common receptor subunit. In one embodiment, the present disclosure provides a bivalent IFNGR binding molecule wherein the affinity of the IFNGR1 sdAb has an affinity of more than 10 times greater, alternatively more than 100 times greater, alternatively more than 1000 times greater than the affinity for the IFNGR2 sdAb common receptor subunit.

With respect to the IFNGR binding molecules of the present disclosure, in some embodiments, the affinity of the IFNGR1 sdAb of the IFNGR binding molecule for the IFNGR1 ECD is at least about 2 fold, alternatively at least about 5 fold, alternatively at least about 5 fold, alternatively at least about 10 fold, alternatively at least about 50 fold, alternatively at least about 100 fold, alternatively at least about 200 fold, alternatively at least about 500 fold, or alternatively at least about 1000 fold greater than the binding affinity of IFNGR2 sdAb of the IFNGR binding molecule molecule for the IFNGR2 ECD. In some embodiments, the affinity of the IFNGR2 sdAb of the IFNGR binding molecule for the IFNGR2 ECD is at least about 2 fold, alternatively at least about 5 fold, alternatively at least about 5 fold, alternatively at least about 10 fold, alternatively at least about 50 fold, alternatively at least about 100 fold, alternatively at least about 200 fold, alternatively at least about 500 fold, or alternatively at least about 1000 fold greater than the binding affinity of IFNGR1 sdAb of the IFNGR binding molecule for the IFNGR1 ECD.

Cross Reactivity:

In some instances, due to sequence or structural similarities between the extracellular domains of IFNGR1 receptors from various mammalian species, immunization with an antigen derived from a IFNGR1 of a first mammalian species (e.g., the hIFNGR1-ECD) may provide antibodies which specifically bind to IFNGR1 receptors of one or more additional mammalian species. Such antibodies are termed "cross reactive." For example, immunization of a camelid with a human derived antigen (e.g., the hIFNGR1-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IFNGR1 VHH" or "hIFNGR1 VHH" merely denotes that the species of the IFNGR1 antigen used for immunization of the camelid from which the VHH was derived was the human IFNGR1 (e.g., the hIFNGR1 ECD, SEQ ID NO:2) but should not be understood as limiting with respect to the specific binding affinity of the VHH for IFNGR1 molecules of other mammalian species. Similarly, the use of the term "mouse IFNGR1 VHH" or "mIFNGR1 VHH" merely denotes that the species of the IFNGR1 antigen used for immunization of the camelid from which the VHH was derived was the murine IFNGR1 (e.g., the mIFNGR1 ECD, SEQ ID NO: 4) but should not be understood as limiting with respect to the specific binding affinity of the VHH for IFNGR1 molecules of other mammalian species.

The hIFNGR1 VHHs of Table 4 were evaluated for cross-reactivity with the mIFNGR1 by flow cytometry and were found to bind both the extracellular domain of hIFNGR1 (SEQ ID NO. 2) and the extracellular domain of mIFNGR1 (SEQ ID NO. 4). Consequently, the VHHs provided in Table 4 may be used in both murine and human applications avoiding the necessity of a surrogate anti-mIFNGR1 for anti-hIFNGR1 for in vivo models of efficacy, such as a mouse model of a human disease state.

In some instances, due to sequence or structural similarities between the extracellular domains of IFNGR2 receptors from various mammalian species, immunization with an antigen derived from a IFNGR2 of a first mammalian species (e.g., the hIFNGR2-ECD) may provide antibodies which specifically bind to IFNGR2 receptors of one or more additional mammalian species. Such antibodies are termed "cross reactive." For example, immunization of a camelid with a human derived antigen (e.g., the hIFNGR2-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IFNGR2 VHH" or "hIFNGR2 VHH" merely denotes that the species of the IFNGR2 antigen used for immunization of the camelid from which the VHH was derived was the human IFNGR2 (e.g., the hIFNGR2 ECD, SEQ ID NO:6) but should not be understood as limiting with respect to the specific binding affinity of the VHH for IFNGR2 molecules of other mammalian species. Similarly, the use of the term "mouse IFNGR2 VHH" or "mIFNGR2 VHH" merely denotes that the species of the IFNGR2 antigen used for immunization of the camelid from which the VHH was derived was the murine IFNGR2 (e.g., the mIFNGR2 ECD, SEQ ID NO:8) but should not be understood as limiting with respect to the specific binding affinity of the VHH for IFNGR2 molecules of other mammalian species.

The hIFNGR2 VHHs of Table 5 were evaluated for cross-reactivity with the mIFNGR2 by flow cytometry and were found to bind both the extracellular domain of hIFNGR2 (SEQ ID NO. 6) and the extracellular domain of mIFNGR2 (SEQ ID NO. 8). Consequently, the VHHs provided in Table 5 may be used in both murine and human applications avoiding the necessity of a surrogate anti-mIFNGR2 for anti-hIFNGR2 for in vivo models of efficacy, such as a mouse model of a human disease state.

I. Interferon Gamma Receptor Binding Molecules

In one embodiment, the present disclosure provides an IFNG receptor binding molecule that is a ligand for the IFNGR, the IFNGR binding molecule comprising:
 a first single domain antibody (sdAb) that specifically binds to the extracellular domain of IFNGR1 subunit of the IFNGR (an "anti-IFNGR1 sdAb"), and
 a second single domain antibody that specifically binds to extracellular domain IFNGR2 subunit of the IFNGR ((an "anti-IFNGR2 sdAb"),
wherein:
 the first sdAb and second sdAb are in stable association;
 the IFNGR1 and IFNGR2 subunits of the IFNGR are dimerized in response to contact with the IFNGR binding molecule; and
 contacting a cell expressing the IFNGR1 and IFNGR2 with an effective amount of the IFNGR binding molecule results in the intracellular domains of IFNGR1 and IFNGR2 being brought into proximity and intracellular signaling.

In some embodiments, one or both of the sdAbs is a an scFv. In some embodiments, one or both of the sdAbs is a VHH.

As used herein, the term "IFNGR receptor" or "IFNGR" refers to a heterodimeric receptor formed by subunits IFNGR1 and IFNGR2 when associated with the cognate IFNG.

The amino acid sequence of the mature form (less the signal peptide) of human IFNGR1 is provided as SEQ ID NO: _____. The human sequence of IFNGR1 is listed as UniProt ID NO. P15260.

The amino acid sequence of the mature form (less the signal peptide) of human IFNGR2 is provided as SEQ ID NO: _____. The human sequence of IFNGR2 is listed as UniProt ID NO. P38484.

The IFNG receptor (IFNGR) includes IFNGR1 subunit (IFNGR1) and IFNGR2 subunit (IFNGR2). Provided herein is an IFNGR binding molecule that specifically binds to IFNGR1 and IFNGR2. In some embodiments, the IFNGR binding molecule binds to a mammalian cell expressing both IFNGR1 and IFNGR2. In some embodiments, the IFNGR binding molecule can be a bispecific $V_HH^2$ as described below.

IFNG: the Cognate Ligand for the IFNG Receptor

The cognate ligand for the IFNG receptor is the cytokine IFNG. IFNG is a homodimeric polypeptide which is an agonist of the IFNGR. Human IFNG is a non-covalently linked homodimeric protein comprising two identical subunits. The canonical amino acid sequence of one subunit of the homodimeric mature human IFNG is provided below (UniProt Reference No: P01579).

(SEQ ID NO: 9)
MKYTSYILAFQLCIVLGSLGCYCQDPYVKEAENLKKYFNAGHSDVADNGT

LFLGILKNWKEESDRKIMQSQIVSFYFKLFKNFKDDQSIQKSVETIKEDM

NVKFFNSNKKKRDDFEKLTNYSVTDLNVQRKAIHELIQVMAELSPAAKTG

KRKRSQMLFRGRRASQ

The murine IFNG is a dimeric molecule comprised of two identical proteins. The amino acid sequence of one subunit of the homodimeric mature murine IFNG is provided below (UniProt Reference No: P01580).

(SEQ ID NO: 10)
MNATHCILALQLFLMAVSGCYCHGTVIESLESLNNYFNSSGIDVEEKSLF

LDIWRNWQKDGDMKILQSQIISFYLRLFEVLKDNQAISNNISVIESHLIT

TFFSNSKAKKDAFMSIAKFEVNNPQVQRQAFNELIRVVHQLLPESSLRKR

KRSRC

IFNgamma Receptor (IFNGR)

The present disclosure relates to synthetic mimetics of the naturally occurring IFNG which are agonists of the IFNGR. The IFNGR is a heterodimeric protein complex of IFNGR1 and IFNGR2. The binding of the IFNG results in dimerization IFNGR1 and IFNGR2 and intracellular signaling in cells expressing IFNGR1 and IFNGR2 characteristic of the binding of the naturally occurring IFNG for the IFNGR. In some embodiments, the IFNGR is the human IFNGR and the IFNG is the human IFNG. In some embodiments the IFNGR is the murine IFNGR and the IFNG is the murine IFNG. As used herein, the terms "IFNG receptor receptor" and "IFNG receptor" and "IFNGR" are used interchangeably to refer to a heterodimeric complex comprising IFNGR1 and IFNGR2. The term IFNGR includes IFNG receptors of any mammal including but not limited to human beings, dogs, cats, mice, monkeys, cows, and pigs.

IFNG Receptor Subunit IFNGR1

The present disclosure provides sdAbs that specifically bind to the extracellular domain of the IFNGR1 and IFNGR binding molecules comprising such sdAbs. In some embodiments, the IFNGR1 binding molecules of the present disclosure specifically bind to the extracellular domain of the IFNGR1.

Human IFNGR1

The human IFNGR1 is expressed as a 489 amino acid pre-protein comprising a 17 amino acid signal sequence which is post-translationally removed to render a 427 amino acid mature protein. The amino acid sequence of human IFNGR1 is provided as SEQ ID NO: 1. The extracellular domain of the human hIFNGR1 (hIFNGR1-ECD) is a 228 amino acid polypeptide corresponding to amino acids 18-245 of the human IFNGR1 preprotein and possesses the amino acid sequence of SEQID NO: 2

The murine form IFNGR1 is expressed as a 477 amino acid pre-protein comprising a 25 amino acid signal sequence which is post-translationally removed to render a 452 amino acid mature protein. The amino acid sequence of murine IFNGR1 is provided as SEQ ID NO: 3

The extracellular domain of the murine mIFNGR1 (mIFNGR1-ECD) is a 229 amino acid polypeptide corresponding to amino acids 26-254 of the mIFNGR1 preprotein and possesses the amino acid sequence of SEQID NO: 4. {suggest to delete this section as redundant over below}

In one embodiment, the IFNGR1 binding molecules of the present disclosure specifically bind to the extracellular domain of the human IFNGR1 receptor subunit (hIFNGR1). hIFNGR1 is expressed as a 489 amino acid precursor comprising a 17 amino acid N-terminal signal sequence which is post-translationally cleaved to provide a 472 amino acid mature protein. The canonical full-length acid hIFNGR1 precursor (including the signal peptide) is a 489 amino acid polypeptide having the amino acid sequence:

(SEQ ID NO: 1)
MALLFLLPLVMQGVSRAEMGTADLGPSSVPTPTNVTIESYNMNPIVYWEY

QIMPQVPVFTVEVKNYGVKNSEWIDACINISHHYCNISDHVGDPSNSLWV

RVKARVGQKESAYAKSEEFAVCRDGKIGPPKLDIRKEEKQIMIDIFHPSV

FVNGDEQEVDYDPETTCYIRVYNVYVRMNGSEIQYKILTQKEDDCDEIQC

QLAIPVSSLNSQYCVSAEGVLHVWGVTTEKSKEVCITIFNSSIKGSLWIP

VVAALLLFLVLSLVFICFYIKKINPLKEKSIILPKSLISVVRSATLETKP

ESKYVSLITSYQPFSLEKEVVCEEPLSPATVPGMHTEDNPGKVEHTEELS

SITEVVTTEENIPDVVPGSHLTPIERESSSPLSSNQSEPGSIALNSYHSR

NCSESDHSRNGFDTDSSCLESHSSLSDSEFPPNNKGEIKTEGQELITVIK

APTSFGYDKPHVLVDLLVDDSGKESLIGYRPTEDSKEFS

For purposes of the present disclosure, the numbering of amino acid residues of the human IFNGR1 polypeptides as described herein is made in accordance with the numbering of this canonical sequence (UniProt Reference No P15260, SEQ ID NO:1). Amino acids 1-17 of SEQ ID NO:1 are identified as the signal peptide of hIFNGR1, amino acids 18-245 of SEQ ID NO:1 are identified as the extracellular domain, amino acids 246-266 of SEQ ID NO:1 are identified as the transmembrane domain, and amino acids 267-489 of SEQ ID NO:1 are identified as the intracellular domain.

To generate sdAbs against the human IFNGR1, immunization may be performed with the extracellular domain of the hIFNGR1. In some embodiments, when using the ECD of hIFNGR1 as an immunogen, the hIFNGR1 ECD may be provided as part of a fusion protein. The extracellular domain of hIFNGR1 is a 228 amino acid polypeptide of the sequence:

(SEQ ID NO: 2)
EMGTADLGPSSVPTPTNVTIESYNMNPIVYWEYQIMPQVPVFTVEVKNYG

VKNSEWIDACINISHHYCNISDHVGDPSNSLWVRVKARVGQKESAYAKSE

EFAVCRDGKIGPPKLDIRKEEKQIMIDIFHPSVFVNGDEQEVDYDPETTC

YIRVYNVYVRMNGSEIQYKILTQKEDDCDEIQCQLAIPVSSLNSQYCVSA

EGVLHVWGVTTEKSKEVCITIFNSSIKG.

Mouse IFNGR1

In one embodiment, the IFNGR1 binding molecules of the present disclosure specifically bind to the extracellular domain of the mouse or murine IFNGR1 receptor subunit (mIFNGR1). mIFNGR1 is expressed as a 477 amino acid precursor comprising a 25 amino acid N-terminal signal sequence which is post-translationally cleaved to provide a 452 amino acid mature protein. The canonical full-length acid mIFNGR1 precursor (including the 25 amino acid signal peptide) is a 477 amino acid polypeptide having the amino acid sequence:

(SEQ ID NO: 3)
MGPQAAAGRMILLVVLMLSAKVGSGALTSTEDPEPPSVPVPTNVLIKSYN

LNPVVCWEYQNMSQTPIFTVQVKVYSGSWTDSCTNISDHCCNIYEQIMYP

DVSAWARVKAKVGQKESDYARSKEFLMCLKGKVGPPGLEIRRKKEEQLSV

LVFHPEVVVNGESQGTMFGDGSTCYTFDYTVYVEHNRSGEILHTKHTVEK

EECNETLCELNISVSTLDSRYCISVDGISSFWQVRTEKSKDVCIPPFHDD

RKDSIWILVVAPLTVFTVVILVFAYWYTKKNSFKRKSIMLPKSLLSVVKS

ATLETKPESKYSLVTPHQPAVLESETVICEEPLSTVTAPDSPEAAEQEEL

SKETKALEAGGSTSAMTPDSPPTPTQRRSFSLLSSNQSGPCSLTAYHSRN

GSDSGLVGSGSSISDLESLPNNNSETKMAEHDPPPVRKAPMASGYDKPHM

LVDVLVDVGGKESLMGYRLTGEAQELS

For purposes of the present disclosure, the numbering of amino acid residues of the mIFNGR1 polypeptides as described herein is made in accordance with the numbering of this canonical sequence (UniProt Reference No. P15261, SEQ ID NO: 3). Amino acids 1-25 of SEQ ID NO:3 are identified as the signal peptide of mIFNGR1, amino acids 26-254 of SEQ ID NO:3 are identified as the extracellular domain, amino acids 255-275 of SEQ ID NO:3 are identified as the transmembrane domain, and amino acids 276-477 of SEQ ID NO:3 are identified as the intracellular domain.

To generate sdAbs against the mouse IFNGR1, immunization may be performed with the extracellular domain of the mIFNGR1. In some embodiments, when using the ECD of mIFNGR1 as an immunogen, the mIFNGR1 ECD may be provided as part of a fusion protein. The extracellular domain of the mIFNGR1 receptor is a 229 amino acid polypeptide of the sequence:

(SEQ ID NO: 4)
ALTSTEDPEPPSVPVPTNVLIKSYNLNPVVCWEYQNMSQTPIFTVQVKVY

SGSWTDSCTNISDHCCNIYEQIMYPDVSAWARVKAKVGQKESDYARSKEF

LMCLKGKVGPPGLEIRRKKEEQLSVLVFHPEVVVNGESQGTMFGDGSTCY

TFDYTVYVEHNRSGEILHTKHTVEKEECNETLCELNISVSTLDSRYCISV

DGISSFWQVRTEKSKDVCIPPFHDDRKDS

Generation and Evaluation of IFNGR1 Single Domain Antibodies

A series of IFNGR1 sdAbs were generated in substantial accordance with the teaching of Examples 1-4 herein. Briefly, a camel was immunization with the extracellular domain (amino acids 18-245) of hIFNGR1 (UNIPROT Ref: P15260). _A synthetic DNA sequence encoding the antigen was inserted into the pFUSE_hIgG1_Fc2 vector (Generay Biotechnology) and transfected into the HEK293F mammalian cell host cell for expression. The antigen is expressed as an Fc fusion protein which is purified using Protein A chromatography. A series of VHHs was generated in response to this procedure and are provided as in Table 4.

Exemplary IFNGR1 Single Domain Antibodies

Table 2 provides CDRs useful in the preparation of IFNGR1 sdAbs for incorporation into the binding molecules of the present disclosure. In some embodiments, the IFNGR1 sdAbs are generated in response to immunization with the extracellular domain of the hIFNGR1 and specifically bind to the ECD of hIFNGR1. In some embodiments, the IFNGR1 sdAb is a single domain antibody comprising: a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR1s in Table 2; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR2s in Table 2; and a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one the CDR3s in Table 2.

In some embodiments, the IFNGR1 sdAb comprises a VHH amino acid sequence having at least 90% (e.g., 91%, 92%, 93%, 94%, 95%, 96%, 97%, 98%, 99%, or 100%) sequence identity to a sequence of any one the of IFNGR1 sdAb s provided in Table 4. In certain embodiments, the binding molecule comprises a sequence that is substantially identical to a sequence of any one of the sequences listed in a row of Table 4. In certain embodiments, the binding molecule comprises a sequence that is identical to a sequence of any one of the sequences listed in a row of Table 4.

In another aspect, the disclosure provides an isolated nucleic acid encoding an IFNGR1 sdAb described herein. Tables 6 provides DNA sequences encoding the IFNGR1 sdAbs of Table 4. In certain embodiments, the present disclosure provides an isolated nucleic acid comprising a sequence having at least 90% (e.g., 91%, 92%, 93%, 94%, 95%, 96%, 97%, 98%, 99%, or 100%) sequence identity to a DNA sequence of Table 6. In certain embodiments, the present disclosure provides an isolated nucleic acid comprising a DNA sequence that is substantially identical to a DNA sequence of Table 6. In certain embodiments, the present disclosure provides an isolated nucleic acid comprising a DNA sequence that is identical to a DNA sequence of Table 6.

The present disclosure provides sdAbs that specifically bind to the extracellular domain of the IFNGR2 and IFNGR binding molecules comprising such sdAbs. In some embodiments, the IFNGR2 binding molecules of the present disclosure specifically bind to the extracellular domain of the IFNGR2.

Human IFNGR2

In one embodiment, the IFNGR2 binding molecules of the present disclosure specifically bind to the extracellular domain of the human IFNGR2 receptor subunit (hIFNGR2). hIFNGR2 is expressed as a 337 amino acid precursor comprising a 21 amino acid N-terminal signal sequence which is post-translationally cleaved to provide a 316 amino acid mature protein. The canonical full-length acid hIFNGR2 precursor (including the signal peptide) is a 337 amino acid polypeptide having the amino acid sequence:

```
                                              (SEQ ID NO: 5)
MRPTLLWSLLLLLGVFAAAAAAPPDPLSQLPAPQHPKIRLYNAEQVLSWE

PVALSNSTRPVVYQVQFKYTDSKWFTADIMSIGVNCTQITATECDFTAAS

PSAGFPMDFNVTLRLRAELGALHSAWVTMPWFQHYRNVTVGPPENIEVTP

GEGSLIIRFSSPFDIADTSTAFFCYYVHYWEKGGIQQVKGPFRSNSISLD

NLKPSRVYCLQVQAQLLWNKSNIFRVGHLSNISCYETMADASTELQQVIL

ISVGTFSLLSVLAGACFFLVLKYRGLIKYWFHTPPSIPLQIEEYLKDPTQ

PILEALDKDSSPKDDVWDSVSIISFPEKEQEDVLQTL
```

For purposes of the present disclosure, the numbering of amino acid residues of the human IFNGR2 polypeptides as described herein is made in accordance with the numbering of this canonical sequence (UniProt Reference No. P38484, SEQ ID NO:5). Amino acids 1-21 of SEQ ID NO:5 are identified as the signal peptide of hIFNGR2, amino acids 22-247 of SEQ ID NO:1 are identified as the extracellular domain, amino acids 248-268 of SEQ ID NO:5 are identified as the transmembrane domain, and amino acids 269-337 of SEQ ID NO:5 are identified as the intracellular domain.

To generate sdAbs against the human IFNGR2 (hIFNGR2), immunization may be performed with the extracellular domain of hIFNGR2. In some embodiments, when using the ECD of hIFNGR2 as an immunogen, the hIFNGR2 ECD may be provided as part of a fusion protein. The extracellular domain of hIFNGR2 is a 220 amino acid polypeptide of the following sequence:

```
                                              (SEQ ID NO: 6)
SQLPAPQHPKIRLYNAEQVLSWEPVALSNSTRPVVYQVQFKYTDSKWFTA

DIMSIGVNCTQITATECDFTAASPSAGFPMDFNVTLRLRAELGALHSAWV

TMPWFQHYRNVTVGPPENIEVTPGEGSLIIRFSSPFDIADTSTAFFCYYV

HYWEKGGIQQVKGPFRSNSISLDNLKPSRVYCLQVQAQLLWNKSNIFRVG

HLSNISCYETMADASTELQQ.
```

Mouse IFNGR2

In one embodiment, the IFNGR2 binding molecules of the present disclosure specifically bind to the extracellular domain of the mouse or murine IFNGR2 receptor subunit (mIFNGR2). mIFNGR2 is expressed as a 332 amino acid precursor comprising a 19 amino acid N-terminal signal sequence which is post-translationally cleaved to provide a 313 amino acid mature protein. The canonical full-length acid mIFNGR2 precursor (including the 19 amino acid signal peptide) is a 332 amino acid polypeptide having the amino acid sequence:

```
                                              (SEQ ID NO: 7)
MRPLPLWLPSLLLCGLGAAASSPDSFSQLAAPLNPRLHLYNDEQILTWEP

SPSSNDPRPVVYQVEYSFIDGSWHRLLEPNCTDITETKCDLTGGGRLKLF

PHPFTVFLRVRAKRGNLTSKWVGLEPFQHYENVTVGPPKNISVTPGKGSL

VIHFSPPFDVFHGATFQYLVHYWEKSETQQEQVEGPFKSNSIVLGNLKPY

RVYCLQTEAQLILKNKKIRPHGLLSNVSCHETTANASARLQQVILIPLGI

FALLLGLTGACFTLFLKYQSRVKYWFQAPPNIPEQIEEYLKDPDQFILEV

LDKDGSPKEDSWDSVSIISSPEKERDDVLQTP
```

For purposes of the present disclosure, the numbering of amino acid residues of the mIFNGR2 polypeptides as described herein is made in accordance with the numbering of this canonical sequence (UniProt Reference No. Q63953, SEQ ID NO:7). Amino acids 1-19 of SEQ ID NO:7 are identified as the signal peptide of mIFNGR2, amino acids 20-243 of SEQ ID NO:7 are identified as the extracellular domain, amino acids 244-266 of SEQ ID NO:7 are identified as the transmembrane domain, and amino acids 267-332 of SEQ ID NO:7 are identified as the intracellular domain.

To generate sdAbs against the mouse IFNGR2, immunization may be performed with the extracellular domain of the mIFNGR2. In some embodiments, when using the ECD of mIFNGR2 as an immunogen, the mIFNGR2 ECD may be provided as part of a fusion protein. The extracellular domain of the mIFNGR2 receptor is a 229 amino acid polypeptide of the following sequence:

(SEQ ID NO: 8)
ASSPDSFSQLAAPLNPRLHLYNDEQILTWEPSPSSNDPRPVVYQVEYSFI

DGSWHRLLEPNCTDITETKCDLTGGGRLKLFPHPFTVFLRVRAKRGNLTS

KWVGLEPFQHYENVTVGPPKNISVTPGKGSLVIHFSPPFDVFHGATFQYL

VHYWEKSETQQEQVEGPFKSNSIVLGNLKPYRVYCLQTEAQLILKNKKIR

PHGLLSNVSCHETTANASARLQQV

Generation and Evaluation of IFNGR2 Single Domain Antibodies

A series of IFNGR2 sdAbs were generated in substantial accordance with the teaching of Examples 1-4 herein. Briefly, a camel was immunization with the extracellular domain (amino acids 22-247) of hIFNGR2 (UNIPROT Ref: P38484). _A synthetic DNA sequence encoding the antigen was inserted into the pFUSE_hIgGi_Fc2 vector (Generay Biotechnology) and transfected into the HEK293F mammalian cell host cell for expression. The antigen is expressed as an Fc fusion protein which is purified using Protein A chromatography. A series of VHHs was generated in response to this procedure and are provided as in Table 5.

Exemplary IFNGR2 Single Domain Antibodies

Table 3 provides CDRs useful in the preparation of IFNGR2 sdAbs for incorporation into the binding molecules of the present disclosure. In some embodiments, the IFNGR2 sdAbs are generated in response to immunization with the extracellular domain and specifically bind to the ECD of hIFNGR2. In some embodiments, the IFNGR2 sdAb is a single domain antibody comprising: a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR1s in Table 3; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR2s in Table 3; and a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one the CDR3s in Table 3.

In some embodiments, the IFNGR2 sdAb comprises a VHH amino acid sequence having at least 90% (e.g., 91%, 92%, 93%, 94%, 95%, 96%, 97%, 98%, 99%, or 100%) sequence identity to a sequence of any one the of IFNGR2 sdAb s provided in Table 5. In certain embodiments, the binding molecule comprises a sequence that is substantially identical to a sequence of any one of the sequences listed in a row of Table 5. In certain embodiments, the binding molecule comprises a sequence that is identical to a sequence of any one of the sequences listed in a row of Table 5.

In another aspect, the disclosure provides an isolated nucleic acid encoding an IFNGR2 sdAb described herein. Table 7 provides DNA sequences encoding the IFNGR2 sdAbs of Table 5. In certain embodiments, the present disclosure provides an isolated nucleic acid comprising a sequence having at least 90% (e.g., 91%, 92%, 93%, 94%, 95%, 96%, 97%, 98%, 99%, or 100%) sequence identity to a DNA sequence of Table 7. In certain embodiments, the present disclosure provides an isolated nucleic acid comprising a DNA sequence that is substantially identical to a DNA sequence of Table 7. In certain embodiments, the present disclosure provides an isolated nucleic acid comprising a DNA sequence that is identical to a DNA sequence of Table 7.

Exemplary IFNG Receptor Binding Proteins

In some embodiments, the IFNGR binding molecules of the present invention are polypeptides of the following formula [#1]:

$$H2N\text{-}(IFNG\ VHH\#1)\text{-}(L1)_a\text{-}(IFNG\ VHH\#2)\text{-}(L2)_b\text{-}(CP)_c\text{—}COOH \qquad [\#1]$$

wherein: "-" represents a covalent bond; L1 and L2 are linkers; CP is a chelating peptide; a, b, and c are independently selected from the integers 0 or 1; "$H_2N$" denotes the amino terminus; and "COOH" denotes the carboxy terminus.

Arrangements of IFNGR1 and IFNGR2 sdAbs in the IFNGR Binding Molecule:

As previously discussed, the orientation of the sdAbs of the IFNGR binding molecule may be used to optimize desired characteristics of the molecules. The orientation of the sdAbs of the IFNGR binding molecule mayIFNGR binding molecule may possess one of a variety of different structures, for example as illustrated in FIGS. 2, 3 and 4 of the attached drawings as provided formulaically below:

$$H_2N\text{-}[IFNGR1sdAb]\text{-}[L1]_x\text{-}[IFNGR2sdAb]\text{-}[L2]_y\text{-}[CP]_z\text{—}COOH; \qquad (a)$$

$$H_2N\text{-}[IFNGR2sdAb]\text{-}[L1]_x\text{-}[IFNGR1sdAb]\text{-}[L2]_y\text{-}[CP]_z\text{—}COOH; \qquad (b)$$

$$H_2N\text{-}[IFNGR1sdAb]\text{-}[L1]_x\text{-}[IFNGR2sdAb]\text{-}[L2]_y\text{-}[Fc]_z\text{—}COOH; \qquad (c)$$

$$H_2N\text{-}[IFNGR2sdAb]\text{-}[L1]_x\text{-}[IFNGR1sdAb]]\text{-}[L2]_y\text{-}[Fc]_z\text{—}COOH; \qquad (d)$$

wherein and L1 and L2 are independently selected polypeptide linkers of 1-50 amino acids and x=0 or 1, y=0 or 1; and CP is a chelating peptide; "Fc" is a monomeric Fc domain and y=0 or 1; non-covalent complexes of the structure:

$$[H_2N\text{-}[IFNGR1sdAb]\text{-}[L1]_x\text{-}Fc1\text{-}COOH:H_2N\text{-}[IFNGR2sdAb]\text{-}[L2]_y\text{-}Fc2\text{-}COOH]; \qquad (e)$$

wherein and L1 and L2 are independently selected polypeptide linkers of 1-50 amino acids and x=0 or 1, y=0 or 1; and CP is a chelating peptide; "Fc1" is a monomeric Fc domain "Fc2" is a monomeric Fc domain wherein Fc1 and Fc2 form a stable non-covalent association, and y=0 or 1; and coordinate covalent complexes of the structure $$H_2N\text{-}[IFNGR1sdAb]\text{-}[L1]_x\text{-}(CP1)\text{-}M\text{-}(CP2)\text{-}(L2)[IFNGR2sdAb]\text{-}NH_2 \qquad (f)$$

wherein and L1 and L2 are independently selected polypeptide linkers of 1-50 amino acids and x and y are independently selected from 0 or 1; and CP1 is a first chelating peptide; CP2 is a second chelating peptide; and M is a transition metal ion.

Sequential Orientations of IFNGR1 and IFNGR2 sdAbs in Single Polypeptide IFNGR Binding Molecules When the IFNGR binding molecule comprises and IFNGR1 sdAb and IFNGR2 sdAb sequences in a single polypeptide, the IFNGR1 sdAb and IFNGR2 sdAb sequences may be arranged wherein the IFNGR1 sdAb is N-terminal relative to the IFNGR2 sdAb (termed herein as the "forward configuration") or IFNGR2 sdAb is N-terminal relative to the IFNGR1 sdAb (termed herein as the "reverse configuration").

IFNGR Binding Molecules in "Forward" Configuration:

In some embodiments, the IFNGR binding molecule comprises a polypeptide of the structure of the formula [#1] wherein the N-terminal VHH of the above formula [#1] (i.e., IFNG VHH #1) is an anti-IFNGR1 VHH and the C-terminal VHH (i.e., IFNG VHH #2) is an anti-IFNGR2 VHH ("forward orientation") wherein L is a polypeptide linker of 1-50 amino acids and x=0 or 1, and CP is a chelating peptide or a subunit of an Fc domain and y=0 or 1. In some embodiments, the disclosure provides an IFNGR binding molecule of the "forward" configuration wherein the IFNGR binding molecule comprises a polyptide from amino to carboxy terminus:
- (a) an anti-IFNGR1 sdAb comprising:
  - a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR1s in Table 2;
  - a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR2s in Table 2; and
  - a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR3s in Table 2;
- (b) polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and
- (c) an anti-IFNGR2 sdAb comprising:
  - a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR1s in Table 3;
  - a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR2s in Table 3; and
  - a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR3s in Table 3.

In some embodiments, the IFNGR binding molecule of the "forward" configuration comprises an anti-IFNGR1 sdAb comprising a CDR1, a CDR2, and a CDR3 listed in a row of Table 2 and an anti-IFNGR2 sdAb comprising a CDR1, a CDR2, and a CDR3 listed in a row of Table 3.

In some embodiments, the IFNGR binding molecule of the "forward" configuration comprises an anti-IFNGR1 sdAb comprising a CDR1, a CDR2, and a CDR3 listed in a row of Table 2 and an anti-IFNGR2 sdAb comprising a CDR1, a CDR2, and a CDR3 listed in a row of Table 3, including any combination thereof.

In some embodiments, IFNGR binding molecule of the "forward" configuration comprises a polyptide from amino to carboxy terminus:
- (a) an IFNGR1 sdAb comprising an amino acid sequence having at least 90% (e.g., 91%, 92%, 93%, 94%, 95%, 96%, 97%, 98%, 99%, or 100%) sequence identity to a sequence of any one of the VHH sequences in Table 4;
- (b) polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and
- (c) an IFNGR2 sdAb comprising a sequence having at least 90% (e.g., 91%, 92%, 93%, 94%, 95%, 96%, 97%, 98%, 99%, or 100%) sequence identity to a sequence of any one of the VHH sequences in Table 5.

In some embodiments, the anti-IFNGR1 sdAb of the bivalent IFNGR binding molecule comprises a sequence having at least 90% (e.g., 91%, 92%, 93%, 94%, 95%, 96%, 97%, 98%, 99%, or 100%) sequence identity to a sequence of any one the of anti-IFNGR1 sdAbs provided in Table 4. In some embodiments, the anti-IFNGR2 sdAb of the bivalent IFNGR binding molecule comprises a sequence having at least 90% (e.g., 91%, 92%, 93%, 94%, 95%, 96%, 97%, 98%, 99%, or 100%) sequence identity to a sequence of any one the of anti-IFNGR2 sdAbs provided in Table 5.

In some embodiments, the bivalent IFNGR binding molecule comprises an amino acid sequence having at least 90% (e.g., 91%, 92%, 93%, 94%, 95%, 96%, 97%, 98%, 99%, or 100%) identity to a sequence listed in a row of Table 4 and an amino acid sequence having at least 90% (e.g., 91%, 92%, 93%, 94%, 95%, 96%, 97%, 98%, 99%, or 100%) identity to a sequence listed in a row of Table 5.

In some embodiments, the bivalent IFNGR binding molecule comprises an anti-IFNGR1 sdAb in combination with an anti-IFNGR2 sdAb. In some embodiments, the bivalent IFNGR binding molecule comprises an anti-IFNGR1 sdAb comprising an amino acid sequence having at least 90% (e.g., 91%, 92%, 93%, 94%, 95%, 96%, 97%, 98%, 99%, or 100%) identity to a sequence listed in a row of Table 4 in combination with an anti-IFNGR2 sdAb comprising an amino acid sequence having at least 90% (e.g., 91%, 92%, 93%, 94%, 95%, 96%, 97%, 98%, 99%, or 100%) identity to a sequence listed in a row of Table 5. {Rich, should we consider including language like above?}

In certain embodiments, the binding molecule comprises an anti-IFNGR1 sdAb amino acid sequence that is substantially identical to a sequence of any one of the sequences listed in a row of Table 4 and an anti-IFNGR2 sdAb amino acid sequence that is substantially identical to a sequence of any one of the sequences listed in a row of Table 5.

IFNGR Binding Molecules in "Reverse" Configuration

In some embodiments, the IFNGR binding molecule comprises a polypeptide of the structure of the formula [#1] wherein the N-terminal VHH of the above formula [#1] (i.e., IFNGR1 VHH #1) is an anti-IFNGR1 VHH and the C-terminal VHH (i.e., IFNGR2 VHH #2) is an anti-IFNGR2 VHH ("forward orientation") wherein and L is a polypeptide linker of 1-50 amino acids and x=0 or 1, and CP is a chelating peptide or a subunit of an Fc domain and y=0 or 1. In some embodiments, the disclosure provides an IFNGR binding molecule of the "reverse" configuration wherein the IFNGR binding molecule comprises a polyptide from amino to carboxy terminus:

(a) an IFNGR2 sdAb comprising:
   a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR1s in Table 3;
   a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR2s in Table 3; and
   a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR3s in Table 3;
(b) a polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and
(c) an IFNGR1 sdAb comprising:
   a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of the CDR1s in Table 2;
   a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149 and 152; and
   a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150 and 153.

In some embodiments, the disclosure provides an IFNGR binding molecule of the "reverse" configuration wherein the IFNGR binding molecule comprises a polyptide from amino to carboxy terminus:
(a) and IFNGR2 sdAb comprising a VHH sequence having at least 90% (e.g., 91%, 92%, 93%, 94%, 95%, 96%, 97%, 98%, 99%, or 100%) sequence identity to a sequence in Table 5;
(b) a polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and
(c) an IFNGR1 sdAb of comprising an amino acid sequence having at least 90% (e.g., 91%, 92%, 93%, 94%, 95%, 96%, 97%, 98%, 99%, or 100%) sequence identity to a sequence in Table 4.

In some embodiments, the IFNGR binding molecule molecule of the "reverse" configuration comprises an anti-IFNGR2 sdAb comprising a CDR1, a CDR2, and a CDR3 listed in a row of Table 3 and an anti-IFNGR1 sdAb comprising a CDR1, a CDR2, and a CDR3 listed in a row of Table 2, including any combination thereof.

In some embodiments, the bivalent IFNGR binding molecule comprises an anti-IFNGR2 sdAb comprising a CDR1, a CDR2, and a CDR3 listed in a row of Table 3 and an anti-IFNGR1 sdAb comprising a CDR1, a CDR2, and a CDR3 as listed in a row of Table 2.

In some embodiments, the anti-IFNGR2 sdAb of the bivalent IFNGR binding molecule comprises a sequence having at least 90% (e.g., 91%, 92%, 93%, 94%, 95%, 96%, 97%, 98%, 99%, or 100%) sequence identity to a sequence of any one the of anti-IFNGR2 sdAbs provided in Table 5. In some embodiments, the anti-IFNGR1 sdAb of the bivalent IFNGR binding molecule comprises a sequence having at least 90% (e.g., 91%, 92%, 93%, 94%, 95%, 96%, 97%, 98%, 99%, or 100%) sequence identity to a sequence of any one the of anti-IFNGR1 sdAbs provided in Table 4.

In some embodiments, in either the forward or reverse configuration, the bivalent IFNGR binding molecule comprises an anti-IFNGR2 sdAb in combination with an anti-IFNGR1 sdAb. In some embodiments, the bivalent IFNGR binding molecule comprises an anti-IFNGR2 sdAb comprising an amino acid sequence having at least 90% (e.g., 91%, 92%, 93%, 94%, 95%, 96%, 97%, 98%, 99%, or 100%) identity to a sequence listed in a row of Table 5 in combination with an anti-IFNGR1 sdAb comprising an amino acid sequence having at least 90% (e.g., 91%, 92%, 93%, 94%, 95%, 96%, 97%, 98%, 99%, or 100%) identity to a sequence listed in a row of Table 4.

In particular embodiments, each of the anti-IFNGR2 sdAb and the anti-IFNGR1 sdAb comprises a sequence having at least 90% (e.g., 91%, 92%, 93%, 94%, 95%, 96%, 97%, 98%, 99%, or 100%) identity to a sequence listed in a row of Tables 5 and Table 4, respectively.

In certain embodiments, the binding molecule comprises an anti-IFNGR2 sdAb amino acid sequence that is substantially identical to a sequence of any one of the sequences listed in a row of Table 5 and an anti-IFNGR1 sdAb amino acid sequence that is substantially identical to a sequence of any one of the sequences listed in a row of Table 4.

II. Linkers

A linker can be used to join the anti-IFNGR1 sdAb and the anti-IFNGR1 sdAb antibody. A linker is a linkage between two linker is a linkage between the two sdAbs in the binding molecule, e.g., protein domains. For example, a linker can simply be a covalent bond or a peptide linker. In some embodiments, the sdAbs in a binding molecule are joined directly (i.e., via a covalent bond). In a bispecific $V_HH^2$ binding molecule described herein, a linker is a linkage between the two $V_H$Hs in the binding molecule. A In some embodiments, the linker is a peptide linker. A peptide linker can include between 1 and 50 amino acids (e.g., between 2 and 50, between 5 and 50, between 10 and 50, between 15 and 50, between 20 and 50, between 25 and 50, between 30 and 50, between 35 and 50, between 40 and 50, between 45 and 50, between 2 and 45, between 2 and 40, between 2 and 35, between 2 and 30, between 2 and 25, between 2 and 20, between 2 and 15, between 2 and 10, between 2 and 5 amino acids).

Examples of flexible linkers include glycine polymers (G)n, glycine-alanine polymers, alanine-serine polymers, glycine-serine polymers (for example, (GmSo)n (SEQ ID NO: 309), (GSGGS)n (SEQ ID NO: 310), (GmSoGm)n (SEQ ID NO: 311), (GmSoGmSoGm)n (SEQ ID NO: 312), (GSGGSm)n (SEQ ID NO: 313), (GSGSmG)n (SEQ ID NO: 314), (GGS)nG (SEQ ID NO: 316) and (GGGSm)n (SEQ ID NO: 315), and combinations thereof, where m, n, and o are each independently selected from an integer of at least 1 to 20, e.g., 1-18, 216, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components Exemplary flexible linkers include, but are not limited to GGGS (SEQ ID NO:13), GGGGS (SEQ ID NO: 14), GGSG (SEQ ID NO: 15), GGSGG (SEQ ID NO: 16), GSGSG (SEQ ID NO: 17), GSGGG (SEQ ID NO: 18), GGGSG (SEQ ID NO: 19) and GSSSG (SEQ ID NO: 20). In yet other embodiments, a peptide linker can contain 4 to 20 amino acids including motifs of GGSG (SEQ ID NO:15), e.g., GGSGGGSG (SEQ ID NO:21), GGSGGGSGGGSG (SEQ ID NO:22), GGSGGGSGGGSGGGSG (SEQ ID NO:23), or GGSGGGSGGGSGGGSGGGSG (SEQ ID NO:24). In other embodiments, a peptide linker can contain motifs of GGSG (SEQ ID NO:15), e.g., GGSGGGSG (SEQ ID NO:21), GGSGGGSGGGSG (SEQ ID NO:22), GGSGGGSGGGSGGGSG (SEQ ID NO:23), or GGSGGGSGGGSGGGSGGGSG (SEQ ID NO:24)

A linker can also be a chemical linker, such as a synthetic polymer, e.g., a polyethylene glycol (PEG) polymer.

The length of the linker between two sdAb in a binding molecule can be used to modulate the proximity of the two sdAb of the binding molecule. By varying the length of the linker, the overall size and length of the binding molecule can be tailored to bind to specific cell receptors or domains or subunits thereof. For example, if the binding molecule is designed to bind to two receptors or domains or subunits thereof that are located close to each other on the same cell, then a short linker can be used. In another example, if the binding molecule is designed to bind to two receptors or domains or subunits there of that are located on two different cells, then a long linker can be used.

In some embodiments, a linker joins the C-terminus of the anti-IFNGR1 sdAb in the binding molecule to the N-terminus of the anti-IFNGR2 sdAb in the binding molecule. In other embodiments, a linker joins the C-terminus of the anti-IFNGR2 sdAb in the binding molecule to the N-terminus of the anti-IFNGR1 sdAb in the binding molecule.

Modulation of sdAb Binding Affinity:

In some embodiments, the activity and/or specificity of the bivalent IFNGR binding molecule of the present disclosure may be modulated by the respective binding affinities of the sdAbs for their respective receptor subunits.

It will be appreciated by one of skill in the art that the binding of the first sdAb of the bivalent IFNGR binding molecule to the first receptor subunit ECD on the cell surface will enhance the probability of a binding interaction between the second sdAb of the bivalent IFNGR binding molecule with the ECD of the second receptor subunit. This cooperative binding effect may result in a bivalent IFNGR binding molecule which has a very high affinity for the receptor and a very slow "off rate" from the receptor. Typical VHH single domain antibodies have an affinity for their targets of from about $10^{-5}$M to about $10^{-10}$M. In those instances such slow off-rate kinetics are desirable in the bivalent IFNGR binding molecule, the selection of sdAbs having high affinities (about $10^{-7}$M to about $10^{-10}$M) for incorporation into the bivalent IFNGR binding molecule are favored.

Naturally occurring cytokine ligands for typically do not exhibit a similar affinity for each subunit of a heterodimeric receptor. Consequently, in designing a bivalent IFNGR binding molecule which is a mimetic of the cognate cytokine IFNG as contemplated by some embodiments of the present disclosure, selection of sdAbs for the first and second IFNGR receptor subunit have an affinity similar to (e.g., having an affinity about 10 fold, alternatively about 20 fold, or alternatively about 50 fold higher or lower than) the cognate IFNG for the respective receptor subunit may be used.

In some embodiments, the bivalent IFNGR binding molecules of the present disclosure are partial agonists of the IFNGR receptor. As such, the activity of the bivalent binding molecule may be modulated by selecting sdAb which have greater or lesser affinity for either one or both of the IFNGR receptor subunits. As some heterodimeric cytokine receptors are comprised of a "proprietary subunit" (i.e., a subunit which is not naturally a subunit of another multimeric receptor) and a second "common" subunit (such as CD132) which is a shared component of multiple cytokine receptors), selectivity for the formation of such receptor may be enhanced by employing first sdAb which has a higher affinity for the proprietary receptor subunit and second sdAB which exhibits a lower affinity for the common receptor subunit. Additionally, the common receptor subunit may be expressed on a wider variety of cell types than the proprietary receptor subunit. In some embodiments wherein the receptor is a heterodimeric receptor comprising a proprietary subunit and a common subunit, the first sdAb of the bivalent IFNGR binding molecule exhibits a significantly greater (more than 10 times greater, alternatively more than 100 times greater, alternatively more than 1000 times greater) affinity for the proprietary receptor than the second sdAb of the bivalent IFNGR binding molecule for the common receptor subunit. In one embodiment, the present disclosure provides a bivalent IFNGR binding molecule wherein the affinity of the anti-IFNGR1 sdAb of has an affinity of more than 10 times greater, alternatively more than 100 times greater, alternatively more than 1000 times greater) affinity anti-IFNGR2 sdAb common receptor subunit.

III. Modifications to Extend Duration of Action In Vivo

The IFNGR bivalent binding molecule described herein can be modified to provide for an extended lifetime in vivo and/or extended duration of action in a subject. In some embodiments, the binding molecule can be conjugated to carrier molecules to provide desired pharmacological properties such as an extended half-life. In some embodiments, the binding molecule can be covalently linked to the Fc domain of IgG, albumin, or other molecules to extend its half-life, e.g., by pegylation, glycosylation, and the like as known in the art. In some embodiments, the IFNGR bivalent binding molecule modified to provide an extended duration of action in a mammalian subject has a half-life in a mammalian of greater than 4 hours, alternatively greater than 5 hours, alternatively greater than 6 hours, alternatively greater than 7 hours, alternatively greater than 8 hours, alternatively greater than 9 hours, alternatively greater than 10 hours, alternatively greater than 12 hours, alternatively greater than 18 hours, alternatively greater than 24 hours, alternatively greater than 2 days, alternatively greater than 3 days, alternatively greater than 4 days, alternatively greater than 5 days, alternatively greater than 6 days, alternatively greater than 7 days, alternatively greater than 10 days, alternatively greater than 14 days, alternatively greater than 21 days, or alternatively greater than 30 days.

Modifications of the IFNGR bivalent binding molecule to provide an extended duration of action in a mammalian subject include (but are not limited to);

conjugation of the IFNGR bivalent binding molecule to one or more carrier molecules, conjugation IFNGR bivalent binding molecule to protein carriers molecules, optionally in the form of a fusion protein with additional polypeptide sequences (e.g., IFNGR bivalent binding molecule-Fc fusions) and conjugation to polymers, (e.g. water soluble polymers to provide a PEGylated IFNGR bivalent binding molecule).

It should be noted that the more than one type of modification that provides for an extended duration of action in a mammalian subject may be employed with respect to a given IFNGR bivalent binding molecule. For example, IFNGR bivalent binding molecule of the present disclosure may comprise both amino acid substitutions that provide for an extended duration of action as well as conjugation to a carrier molecule such as a polyethylene glycol (PEG) molecule.

Protein Carrier Molecules:

Examples of protein carrier molecules which may be covalently attached to the IFNGR bivalent binding molecule to provide an extended duration of action in vivo include, but are not limited to albumins, antibodies and antibody fragments such and Fc domains of IgG molecules.

Fc Fusions:

In some embodiments, the IFNGR bivalent binding molecule is conjugated to a functional domain of an Fc-fusion chimeric polypeptide molecule. Fc fusion conjugates have been shown to increase the systemic half-life of biopharmaceuticals, and thus the biopharmaceutical product can require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates. The "Fc region" useful in the preparation of Fc fusions can be a naturally occurring or synthetic polypeptide that is homologous to an IgG C-terminal domain produced by digestion of IgG with papain. IgG Fc has a molecular weight of approximately 50 kDa. The binding molecule described herein can be conjugated to the entire Fc region, or a smaller portion that retains the ability to extend the circulating half-life of a chimeric polypeptide of which it is a part. In addition, full-length or fragmented Fc regions can be variants of the wild-type molecule. In a typical presentation, each monomer of the dimeric Fc can carry a heterologous polypeptide, the heterologous polypeptides being the same or different.

Illustrative examples of Fc formats useful for IFNGR bivalent binding molecules of the present disclosure are provided schematically in FIGS. 1-4 of the attached drawings.

Linkage of Bivalent Binding Molecule to Fc

As indicated, the linkage of the IFNGR bivalent binding molecule to the Fc subunit may incorporate a linker molecule as described below between the bivalent sdAb and Fc subunit. In some embodiments, the IFNGR bivalent binding molecule is expressed as a fusion protein with the Fc domain incorporating an amino acid sequence of a hinge region of an IgG antibody. The Fc domains engineered in accordance with the foregoing may be derived from IgG1, IgG2, IgG3 and IgG4 mammalian IgG species. In some embodiments, the Fc domains may be derived from human IgG1, IgG2, IgG3 and IgG4 IgG species. In some embodiments, the hinge region is the hinge region of an IgG1. In one particular embodiment, the IFNGR bivalent binding is linked to an Fc domain using an human IgG1 hinge domain.

Knob-Into-Hole Fc Format

In some embodiments, when the IFNGR bivalent binding molecule described herein is to be administered in the format of an Fc fusion, particularly in those situations when the polypeptide chains conjugated to each subunit of the Fc dimer are different, the Fc fusion may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob"), and ii) in the CH3 domain of a second heavy chain, an amino acid residue is replaced with an amino acid residue having a smaller side chain (e.g., alanine or threonine), thereby generating a cavity ("hole") at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fc region (Carter, et al. (2001) Immunol Methods 248, 7-15).

The knob-into-hole format is used to facilitate the expression of a first polypeptide on a first Fc monomer with a "knob" modification and a second polypeptide on the second Fc monomer possessing a "hole" modification to facilitate the expression of heterodimeric polypeptide conjugates. One embodiment of an IFNGR binding molecule wherein the IFNGR1 sdAb and IFNGR2 sdAb are in stable, non-covalent association is wherein each sdAb of the IFNGR binding molecule is covalently bonded, optionally including a linker, to each subunit of the knob-into-hole Fc dimer as illustrated in FIG. 4, Panel A of the attached drawings.

Albumin Carrier Molecules

In some embodiments, the IFNGR bivalent binding molecule conjugated to an is albumin molecule (e.g., human serum albumin) which is known in the art to facilitate extended exposure in vivo. In one embodiment of the invention, the IFNGR bivalent binding molecule is conjugated to albumin via chemical linkage or expressed as a fusion protein with an albumin molecule referred to herein as an IFNGR bivalent binding molecule albumin fusion." The term "albumin" as used in the context αβhIL2 mutein albumin fusions include albumins such as human serum albumin (HSA), cyno serum albumin, and bovine serum albumin (BSA). In some embodiments, the HSA the HSA comprises a C34S or K573P amino acid substitution relative to the wild-type HSA sequence According to the present disclosure, albumin can be conjugated to a IFNGR bivalent binding molecule at the carboxyl terminus, the amino terminus, both the carboxyl and amino termini, and internally (see, e.g., U.S. Pat. Nos. 5,876,969 and 7,056,701). In the HAS IFNGR bivalent binding molecule contemplated by the present disclosure, various forms of albumin can be used, such as albumin secretion pre-sequences and variants thereof, albumin fragments and variants thereof, and HSA variants. Such forms generally possess one or more desired albumin activities. In additional embodiments, the present disclosure involves fusion proteins comprising a IFNGR bivalent binding molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. As an alternative to chemical linkage between the IFNGR bivalent binding molecule and the albumin molecule the IFNGR bivalent binding molecule-albumin complex may be provided as a fusion protein comprising an albumin polypeptide sequence and an IFNGR bivalent binding molecule recombinantly expressed in a host cell as a single polypeptide chain, optionally comprising a linker molecule between the albumin and IFNGR bivalent binding molecule. Such fusion proteins may be readily prepared through recombinant technology to those of ordinary skill in the art. Nucleic acid sequences encoding such fusion proteins may be ordered from any of a variety of commercial sources. The nucleic acid sequence encoding the fusion protein is incorporated into an expression vector operably linked to one or more expression control elements, the vector introduced into a suitable host cell and the fusion protein solated from the host cell culture by techniques well known in the art.

Polymeric Carriers

In some embodiments, extended in vivo duration of action of the IFNGR bivalent binding molecule may be achieved by conjugation to one or more polymeric carrier molecules such as XTEN polymers or water soluble polymers.

XTEN Conjugates

The IFNGR bivalent binding molecule may further comprise an XTEN polymer. The XTEN polymer may be is conjugated (either chemically or as a fusion protein) the αβhIL2 mutein provides extended duration of akin to PEGylation and may be produced as a recombinant fusion protein in *E. coli*. XTEN polymers suitable for use in conjunction with the IFNGR bivalent binding molecule of the present disclosure are provided in Podust, et al. (2016) "*Extension of in vivo half-life of biologically active molecules by XTEN protein polymers*", J Controlled Release 240:52-66 and Haeckel et al. (2016) "XTEN as *Biological Alternative to PEGylation Allows Complete Expression of a Protease-Activatable Killin-Based Cytostatic*" PLOS ONE|DOI: 10.1371/journal.pone.0157193 Jun. 13, 2016. The XTEN polymer may fusion protein may incorporate a protease sensitive cleavage site between the XTEN polypeptide and the hIL2 mutein such as an MMP-2 cleavage site.

Water Soluble Polymers

In some embodiments, the IFNGR bivalent binding molecule can be conjugated to one or more water-soluble polymers. Examples of water soluble polymers useful in the practice of the present disclosure include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol), polysaccharides), poly-alpha-hydroxy acid), polyvinyl alcohol (PVA), polyphosphazene, polyoxazolines (POZ), poly(N-acryloylmorpholine), or a combination thereof.

In some embodiments, IFNGR bivalent binding molecule can be conjugated to one or more polyethylene glycol molecules or "PEGylated." Although the method or site of PEG attachment to the binding molecule may vary, in certain embodiments the PEGylation does not alter, or only minimally alters, the activity of the binding molecule.

PEGs suitable for conjugation to a polypeptide sequence are generally soluble in water at room temperature, and have the general formula $$R(O-CH_2-CH_2)_nO-R,$$

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

In some embodiments, selective PEGylation of the IFNGR bivalent binding molecule, for example, by the incorporation of non-natural amino acids having side chains to facilitate selective PEG conjugation, may be employed. Specific PEGylation sites can be chosen such that PEGylation of the binding molecule does not affect its binding to the target receptors.

In some instances, the sequences of IFNGR bivalent binding molecules provided in Tables 4 and 5 of the present disclosure possess an N-terminal glutamine ("1Q") residue. N-terminal glutamine residues have been observed to spontaneously cyclize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IFNGR binding molecules of the present disclosure, particularly when aldehyde chemistry is to be employed, the IFNGR binding molecules possessing an amino acid at position 1 (e.g., 1Q) are substituted at position 1 with an alternative amino acid or are deleted at position 1 (e.g., des-1Q). In some embodiments, the IFNGR binding molecules of the present disclosure comprise an amino acid substitution selected from the group Q1E and Q1D.

In certain embodiments, the increase in half-life is greater than any decrease in biological activity. PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure.

A molecular weight of the PEG used in the present disclosure is not restricted to any particular range. The PEG component of the binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa, or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, or alternatively about 30,000 to about 40,000 daltons. In one embodiment of the disclosure, the PEG is a 40kD branched PEG comprising two 20 kD arms.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbonst Two widely used first generation activated monomethoxy PEGs (mPEGs) are succinimdyl carbonate PEG (SC-PEG; see, e.g., Zalipsky, et al. (1992) Biotechnol. Appl. Biochem 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

Pegylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General PEGylation strategies known in the art can be applied herein.

The PEG can be bound to a binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the binding molecules is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin et al., PCT International Application No. PCT/US2018/045257 filed Aug. 3, 2018 and published Feb. 7, 2019 as International Publication Number WO 2019/028419A1.

The PEG conjugated to the polypeptide sequence can be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF), a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NIHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

In some embodiments, a linker can used to join the IFNGR bivalent binding molecule and the PEG molecule. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Examples of flexible linkers are described in Section IV. Further, a multimer (e.g., 1, 2, 3, 4, 5, 6, 7, 8, 9, 10, 10-20, 20-30, or 30-50) of these linker sequences may be linked together to provide flexible linkers that may be used to conjugate two molecules. Alternative to a polypeptide linker, the linker can be a chemical linker, e.g., a PEG-aldehyde linker. In some embodiments, the binding molecule is acetylated at the N-terminus by enzymatic reaction with N-terminal acetyltransferase and, for example, acetyl CoA. Alternatively, or in addition to N-terminal acetylation, the binding molecule can be acetylated at one or more lysine residues, e.g., by enzymatic reaction with a lysine acetyltransferase. See, for example Choudhary et al. (2009) Science 325 (5942):834-840.

Fatty Acid Carriers

In some embodiments an IFNGR bivalent binding molecule having an extended duration of action in a mammalian subject and useful in the practice of the present disclosure is achieved by covalent attachment of the IFNGR bivalent binding molecule to a fatty acid molecule as described in Resh (2016) Progress in Lipid Research 63: 120-131. Examples of fatty acids that may be conjugated include myristate, palmitate and palmitoleic acid. Myristoylate is typically linked to an N-terminal glycine but lysines may also be myristoylated. Palmitoylation is typically achieved by enzymatic modification of free cysteine —SH groups such as DHHC proteins catalyze S-palmitoylation. Palmitoleylation of serine and threonine residues is typically achieved enzymatically using PORCN enzymes. In some embodiments, the IFNGR bivalent binding molecule is acetylated at the N-terminus by enzymatic reaction with N-terminal acetyltransferase and, for example, acetyl CoA. Alternatively, or in addition to N-terminal acetylation, the IFNGR bivalent binding molecule is acetylated at one or more lysine residues, e.g., by enzymatic reaction with a lysine acetyltransferase. See, for example Choudhary et al. (2009) Science 325 (5942):834L2 ortho840.

Modifications to Provide Additional Functions

In some embodiments, embodiment, the IFNGR bivalent binding molecule may comprise a functional domain of a chimeric polypeptide. IFNGR bivalent binding molecule fusion proteins of the present disclosure may be readily produced by recombinant DNA methodology by techniques known in the art by constructing a recombinant vector comprising a nucleic acid sequence comprising a nucleic acid sequence encoding the IFNGR bivalent binding molecule in frame with a nucleic acid sequence encoding the fusion partner either at the N-terminus or C-terminus of the IFNGR bivalent binding molecule, the sequence optionally further comprising a nucleic acid sequence in frame encoding a linker or spacer polypeptide.

FLAG Tags

In other embodiments, the IFNGR bivalent binding molecule can be modified to include an additional polypeptide sequence that functions as an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the binding molecule further comprises a C-terminal c-myc epitope tag.

Chelating Peptides

In some embodiments, the IFNGR bivalent binding molecule (including fusion proteins of the IFNGR bivalent binding molecule) of the present disclosure are may be covalently bonded via a peptide bond to one or more transition metal chelating polypeptide sequences. The association of the IFNGR bivalent binding molecule with chelating peptide provides multiple utilities including: the purification of the IFNGR bivalent binding molecule using immobilized metal affinity chromatography (IMAC) as described in Smith, et al. U.S. Pat. No. 4,569,794 issued Feb. 11, 1986; immobilization of the IFNGR bivalent binding molecule on nitrilotriacetic acid (NTA) modified surface plasmon resonance sensor chips (e.g., Sensor Chip NTA available from Cytiva Global Life Science Solutions USA LLC, Marlborough MA as catalog number BR100407) as described in Nieba, et al. (1997) Analytical Biochemistry 252(2):217-228, or to form kinetically inert or kinetically labile complexes between the IFNGR bivalent binding molecule and a transition metal ion as described in Anderson, et al. (U.S. Pat. No. 5,439,829 issued Aug. 8, 1995 and Hale, J. E (1996) Analytical Biochemistry 231(1):46-49. Examples of transition metal chelating polypeptides useful in the practice of the present disclosure are described in Smith, et al. supra and Dobeli, et al. U.S. Pat. No. 5,320,663 issued May 10, 1995 the entire teachings of which are hereby incorporated by reference. Particular transition metal chelating polypeptides useful in the practice of the present disclosure are peptides comprising 3-6 contiguous histidine residues (SEQ ID NO: 317) such as a six-histidine peptide $(His)_6$ (SEQ ID NO: 307) and are frequently referred to in the art as "His-tags." In some embodiments, a purification handle is a polypeptide having the sequence Ala-Ser-His-His-His-His-His-His ("ASH6") (SEQ ID NO: 305) or Gly-Ser-His-His-His-His-His-His-His-His ("GSH8") (SEQ ID NO: 306).

Targeting Moieties:

In some embodiments, IFNGR bivalent binding molecule is conjugated to molecule which provides ("targeting domain") to facilitate selective binding to particular cell type or tissue expressing a cell surface molecule that specifically binds to such targeting domain, optionally incorporating a linker molecule of from 1-40 (alternatively 2-20, alternatively 5-20, alternatively 10-20) amino acids between IFNGR bivalent binding molecule sequence and the sequence of the targeting domain of the fusion protein.

In other embodiments, a chimeric polypeptide including a IFNGR bivalent binding molecule and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

In some embodiments, the targeting moiety is an antibody that specifically binds to at least one cell surface molecule associated with a tumor cell (i.e. at least one tumor antigen) wherein the cell surface molecule associated with a tumor cell is selected from the group consisting of GD2, BCMA, CD19, CD33, CD38, CD70, GD2, IL3Rα2, CD19, mesothelin, Her2, EpCam, Muc1, ROR1, CD133, CEA, EGR-FRVIII, PSCA, GPC3, Pan-ErbB and FAP.

Recombinant Production

Alternatively, the IFNGR binding molecules of the present disclosure are produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide.

Construction of Nucleic Acid Sequences Encoding the IFNGR Binding Molecule

In some embodiments, the IFNGR binding molecule is produced by recombinant methods using a nucleic acid sequence encoding the IFNGR binding molecule (or fusion protein comprising the IFNGR binding molecule). The nucleic acid sequence encoding the desired αβhIFNGR binding molecule can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the IFNGR binding molecule (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the IFNGR binding molecule may be obtained from various commercial sources that provide custom made nucleic acid sequences. Amino acid sequence variants of the IFNGR binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion is made to arrive at the final construct, provided that the final construct possesses the desired biological activity as defined herein.

Methods for constructing a DNA sequence encoding a IFNGR binding molecule and expressing those sequences in a suitably transformed host include, but are not limited to, using a PCR-assisted mutagenesis technique. Mutations that consist of deletions or additions of amino acid residues to a IFNGR binding molecule can also be made with standard recombinant techniques. In the event of a deletion or addition, the nucleic acid molecule encoding a IFNGR binding molecule is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A IFNGR binding molecule of the present disclosure may be produced recombinantly not only directly, but also as a fusion polypeptide with a heterologous polypeptide, e.g. a signal sequence or other polypeptide having a specific cleavage site at the N-terminus or C-terminus of the mature IFNGR binding molecule. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. The inclusion of a signal sequence depends on whether it is desired to secrete the IFNGR binding molecule from the recombinant cells in which it is made. If the chosen cells are prokaryotic, it generally is preferred that the DNA sequence not encode a signal sequence. When the recombinant host cell is a yeast cell such as *Saccharomyces cerevisiae*, the alpha mating factor secretion signal sequence may be employed to achieve extracellular secretion of the IFNGR binding molecule into the culture medium as described in Singh, U.S. Pat. No. 7,198,919 B1 issued Apr. 3, 2007.

In the event the IFNGR binding molecule to be expressed is to be expressed as a chimera (e.g., a fusion protein comprising a IFNGR binding molecule and a heterologous polypeptide sequence), the chimeric protein can be encoded by a hybrid nucleic acid molecule comprising a first sequence that encodes all or part of the IFNGR binding molecule and a second sequence that encodes all or part of the heterologous polypeptide. For example, subject IFNGR binding molecules described herein may be fused to a hexa-/octa-histidine (SEQ ID NOS 307-308, respectively) tag to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the IFNGR binding molecule. For example, the N-terminus may be linked to a targeting domain and the C-terminus linked to a hexa-histidine tag (SEQ ID NO: 307) purification handle.

The complete amino acid sequence of the polypeptide (or fusion/chimera) to be expressed can be used to construct a back-translated gene. A DNA oligomer containing a nucleotide sequence coding a IFNGR binding molecule can be synthesized. For example, several small oligonucleotides coding for portions of the desired polypeptide can be synthesized and then ligated. The individual oligonucleotides typically contain 5' or 3' overhangs for complementary assembly.

Codon Optimization:

In some embodiments, the nucleic acid sequence encoding the IFNGR binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g. Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Expression Vectors:

Once assembled (by synthesis, site-directed mutagenesis or another method), the nucleic acid sequence encoding an a IFNGR binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors.

To facilitate efficient expression of the recombinant polypeptide, the nucleic acid sequence encoding the polypeptide sequence to be expressed is operably linked to transcriptional and translational regulatory control sequences that are functional in the chosen expression host.

Selectable Marker:

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Regulatory Control Sequences:

Expression vectors for a IFNGR binding molecules of the present disclosure contain a regulatory sequence that is recognized by the host organism and is operably linked to nucleic acid sequence encoding the IFNGR binding molecule. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject a IFNGR binding molecule, particularly as regards potential secondary structures.

Promoters:

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Enhancers:

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context.

Proper assembly of the expression vector can be confirmed by nucleotide sequencing, restriction mapping, and expression of a biologically active polypeptide in a suitable host.

Host Cells:

The present disclosure further provides prokaryotic or eukaryotic cells that contain and express a nucleic acid molecule that encodes a IFNGR binding molecule. A cell of the present disclosure is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this invention, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant IFNGR binding molecule can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerenvisiae* include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The IFNGR binding molecule may be produced in a prokaryotic host, such as the bacterium *E. coli*, or in a eukaryotic host, such as an insect cell (e.g., an Sf21 cell), or mammalian cells (e.g., COS cells, NH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, a IFNGR binding molecule obtained will be glycosylated or unglycosylated depending on the host organism used to produce the mutein. If bacteria are chosen as the host then the a IFNGR binding molecule produced will be unglycosylated. Eukaryotic cells, on the other hand, will typically result in glycosylation of the IFNGR binding molecule.

In some embodiments, it is possible that an amino acid sequence (particularly a CDR sequence) of an sdAb to be incorporated into a bivalent IFNGR binding molecule may contain a glycosylation motif, particularly an N-linked glycosylation motif of the sequence Asn-X-Ser (N—X—S) or Asn-X-Thr (N—X-T), wherein X is any amino acid except for proline. In such instances, it is desirable to eliminate such N-linked glycosylation motifs by modifying the sequence of the N-linked glycosylation motif to prevent glycosylation. In some embodiments, the N-linked glycosylation motif is disrupted by the incorporation of conservative amino acid substitution of the Asn (N) residue of the N-linked glycosylation motif.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection:

The expression constructs of the can be introduced into host cells to thereby produce a IFNGR binding molecule disclosed herein. The expression vector comprising a nucleic acid sequence encoding IFNGR binding molecule is introduced into the prokaryotic or eukaryotic host cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals. To facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture:

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins:

Recombinantly produced IFNGR binding molecule polypeptides can be recovered from the culture medium as a secreted polypeptide if a secretion leader sequence is employed. Alternatively, the IFNGR binding molecule polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Various purification steps are known in the art and find use, e.g. affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g. gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

A recombinantly IFNGR binding molecule by the transformed host can be purified according to any suitable method. Recombinant IFNGR binding molecules can be isolated from inclusion bodies generated in *E. coli*, or from conditioned medium from either mammalian or yeast cultures producing a given mutein using cation exchange, gel filtration, and or reverse phase liquid chromatography. The substantially purified forms of the recombinant a IFNGR binding molecule can be purified from the expression system using routine biochemical procedures, and can be used, e.g., as therapeutic agents, as described herein.

In some embodiments, where the IFNGR binding molecule is expressed with a purification tag as discussed above, this purification handle may be used for isolation of the IFNGR binding molecule from the cell lysate or cell medium. Where the purification tag is a chelating peptide, methods for the isolation of such molecules using immobilized metal affinity chromatography are well known in the art. See, e.g., Smith, et al. U.S. Pat. No. 4,569,794.

The biological activity of the IFNGR binding molecules recovered can be assayed for activating by any suitable method known in the art and may be evaluated as substantially purified forms or as part of the cell lysate or cell medium when secretion leader sequences are employed for expression.

Pharmaceutical Formulations

In some embodiments, the subject IFNGR binding molecule (and/or nucleic acids encoding the IFNGR binding molecule or recombinant cells incorporating a nucleic acid sequence and modified to express the IFNGR binding molecule) can be incorporated into compositions, including pharmaceutical compositions. Such compositions typically include the polypeptide or nucleic acid molecule and a pharmaceutically acceptable carrier. A pharmaceutical composition is formulated to be compatible with its intended route of administration and is compatible with the therapeutic use for which the IFNGR binding molecule is to be administered to the subject in need of treatment or prophyaxis.

Carriers:

Carriers include a sterile diluent such as water for injection, saline solution, fixed oils, polyethylene glycols, glycerine, propylene glycol or other synthetic solvents. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. For intravenous administration, suitable carriers include physiological saline, bacteriostatic water, Cremophor EL™ (BASF, Parsippany, N.J.) or phosphate buffered saline (PBS).

Buffers:

The term buffers includes buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5).

Dispersions:

Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Preservatives:

The pharmaceutical formulations for parenteral administration to a subject should be sterile and should be fluid to facilitate easy syringability. It should be stable under the conditions of manufacture and storage and are preserved against the contamination. Prevention of the action of microorganisms can be achieved by various antibacterial and antifungal agents, for example, agents such as benzyl alcohol or methyl parabens; antioxidants such as ascorbic acid or sodium bisulfite; chelating agents such as ethylenediaminetetraacetic acid, parabens, chlorobutanol, phenol, ascorbic acid, thimerosal, and the like. Sterile solutions can be prepared by incorporating the active compound in the required amount in an appropriate solvent with one or a combination of ingredients enumerated above, as required, followed by filtered sterilization.

Tonicity Agents:

In many cases, it will be preferable to include isotonic agents, for example, sugars, polyalcohols such as mannitol, sorbitol, sodium chloride in the composition.

Routes of Administration:

In some embodiments of the therapeutic methods of the present disclosure involve the administration of a pharmaceutical formulation comprising a IFNGR binding molecule (and/or nucleic acids encoding the IFNGR binding molecule or recombinantly modified host cells expressing the IFNGR binding molecule) to a subject in need of treatment. The pharmaceutical formulation comprising a IFNGR binding molecules of the present disclosure may be administered to a subject in need of treatment or prophyaxis by a variety of routes of administration, including parenteral administration, oral, topical, or inhalation routes.

Parenteral Administration:

In some embodiments, the methods of the present disclosure involve the parenteral administration of a pharmaceutical formulation comprising a IFNGR binding molecule (and/or nucleic acids encoding the IFNGR binding molecule or recombinantly modified host cells expressing the IFNGR binding molecule) to a subject in need of treatment. Examples of parenteral routes of administration include, for example, intravenous, intradermal, subcutaneous, transdermal (topical), transmucosal, and rectal administration. Parenteral formulations comprise solutions or suspensions used for parenteral application can include vehicles the carriers and buffers. Pharmaceutical formulations for parenteral administration include sterile aqueous solutions (where water soluble) or dispersions and sterile powders for the extemporaneous preparation of sterile injectable solutions or dispersion. The parenteral preparation can be enclosed in ampoules, disposable syringes or multiple dose vials made of glass or plastic. In one embodiment, the formulation is provided in a prefilled syringe for parenteral administration.

Oral Administration:

In some embodiments, the methods of the present disclosure involve the oral administration of a pharmaceutical formulation comprising a IFNGR binding molecule (and/or nucleic acids encoding the IFNGR binding molecule or recombinantly modified host cells expressing the IFNGR binding molecule) to a subject in need of treatment. Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

Inhalation Formulations:

In some embodiments, the methods of the present disclosure involve the inhaled administration of a pharmaceutical formulation comprising a IFNGR binding molecule (and/or nucleic acids encoding the IFNGR binding molecule or recombinantly modified host cells expressing the IFNGR binding molecule) to a subject in need of treatment. In the event of administration by inhalation, subject IFNGR binding molecules, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Mucosal and Transdermal Formulations:

In some embodiments, the methods of the present disclosure involve the mucosal or transdermal administration of a pharmaceutical formulation comprising a IFNGR binding molecule (and/or nucleic acids encoding the IFNGR binding molecule or recombinantly modified host cells expressing the IFNGR binding molecule) to a subject in need of treatment. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories (e.g., with conventional suppository bases such as cocoa butter and other glycerides) or retention enemas for rectal delivery. For transdermal administration, the active compounds are formulated into ointments, salves, gels, or creams as generally known in the art and may incorporate permeation enhancers such as ethanol or lanolin.

Extended Release and Depot Formulations:

In some embodiments of the method of the present disclosure, the IFNGR binding molecule is administered to a subject in need of treatment in a formulation to provide extended release of the IFNGR binding molecule agent. Examples of extended release formulations of the injectable compositions can be brought about by including in the composition an agent which delays absorption, for example, aluminum monostearate and gelatin. In one embodiment, the subject IFNGR binding molecules or nucleic acids are prepared with carriers that will protect the IFNGR binding molecules against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Administration of Nucleic Acids Encoding the IFNGR Binding Molecule:

In some embodiments of the method of the present disclosure, delivery of the IFNGR binding molecule to a subject in need of treatment is achieved by the administration of a nucleic acid encoding the IFNGR binding molecule. Methods for the administration nucleic acid encoding the IFNGR binding molecule to a subject is achieved by transfection or infection using methods known in the art, including but not limited to the methods described in McCaffrey et al. (Nature (2002) 418:6893), Xia et al. (Nature Biotechnol. (2002) 20:1006-1010), or Putnam (Am. J. Health Syst. Pharm. (1996) 53: 151-160 erratum at Am. J. Health Syst. Pharm. (1996) 53:325). In some embodiments, the IFNGR binding molecule is administered to a subject by the administration of a pharmaceutically acceptable formulation of recombinant expression vector comprising a nucleic acid sequence encoding the IFNGR binding molecule operably linked to one or more expression control sequences operable in a mammalian subject. In some embodiments, the expression control sequence may be selected that is operable in a limited range of cell types (or single cell type) to facilitate the selective expression of the IFNGR binding molecule in a particular target cell type. In one embodiment, the recombinant expression vector is a viral vector. In some embodiments, the recombinant vector is a recombinant viral vector. In some embodiments the recombinant viral vector is a recombinant adenoassociated virus (rAAV) or recombinant adenovirus (rAd), in particular a replication deficient adenovirus derived from human adenovirus serotypes 3 and/or 5. In some embodiments, the replication deficient adenovirus has one or more modifications to the E1 region which interfere with the ability of the virus to initiate the cell cycle and/or apoptotic pathways in a human cell. The replication deficient adenoviral vector may optionally comprise deletions in the E3 domain. In some embodiments the adenovirus is a replication competent adenovirus. In some embodiments the adenovirus is a replication competent recombinant virus engineered to selectively replicate in the target cell type.

In some embodiments, particularly for administration of IFNGR binding molecules to the subject, particular for treatment of diseases of the intestinal tract or bacterial infections in a subject, the nucleic acid encoding the IFNGR binding molecule may be delivered to the subject by the administration of a recombinantly modified bacteriophage vector encoding the IFNGR binding molecule. As used herein, the terms "procaryotic virus," "bacteriophage" and "phage" are used interchangeably hereinto describe any of a variety of bacterial viruses that infect and replicate within a bacterium. Bacteriophage selectively infect procaryotic cells, restricting the expression of the IFNGR binding molecule to procaryotic cells in the subject while avoiding expression in mammalian cells. A wide variety of bacteriophages capable of selection a broad range of bacterial cells have been identified and characterized extensively in the scientific literature. In some embodiments, the phage is modified to remove adjacent motifs (PAM). Elimination of the of Cas9 sequences from the phage genome reduces ability of the Cas9 endonuclease of the target procaryotic cell to neutralize the invading phage encoding the IFNGR binding molecule.

Administration of Recombinantly Modified Cells Expressing the IFNGR Binding Molecule:

In some embodiments of the method of the present disclosure, delivery of the IFNGR binding molecule to a subject in need of treatment is achieved by the administration of recombinant host cells modified to express the IFNGR binding molecule may be administered in the therapeutic and prophylactic applications described herein. In some embodiments, the recombinant host cells are mammalian cells, e.g., human cells.

In some embodiments, the nucleic acid sequence encoding the IFNGR binding molecule (or vectors comprising same) may be maintained extrachromosomally in the recombinantly modified host cell for administration. In other embodiments, the nucleic acid sequence encoding the IFNGR binding molecule may be incorporated into the genome of the host cell to be administered using at least one endonuclease to facilitate incorporate insertion of a nucleic acid sequence into the genomic sequence of the cell. As used herein, the term "endonuclease" is used to refer to a wild-type or variant enzyme capable of catalyzing the cleavage of bonds between nucleic acids within a DNA or RNA molecule, preferably a DNA molecule. Endonucleases are referred to as "rare-cutting" endonucleases when such endonucleases have a polynucleotide recognition site greater than about 12 base pairs (bp) in length, more preferably of 14-55 bp. Rare-cutting endonucleases can be used for inactivating genes at a locus or to integrate transgenes by homologous recombination (HR) i.e. by inducing DNA double-strand breaks (DSBs) at a locus and insertion of exogenous DNA at this locus by gene repair mechanism. Examples of rare-cutting endonucleases include homing endonucleases (Grizot, et al (2009) Nucleic Acids Research 37(16):5405-5419), chimeric Zinc-Finger nucleases (ZFN) resulting from the fusion of engineered zinc-finger domains (Porteus M and Carroll D., *Gene targeting using zinc finger nucleases* (2005) Nature Biotechnology 23(3):967-973, a TALEN-nuclease, a Cas9 endonuclease from CRISPR system as or a modified restriction endonuclease to extended sequence specificity (Eisenschmidt, et al. 2005; 33(22): 7039-7047).

In some embodiments, particularly for administration of IFNGR binding molecules to the intestinal tract, the IFNGR binding molecule may be delivered to the subject by a recombinantly modified procaryotic cell (e.g., *Lactobacillus lacti*). The use of engineered procaryotic cells for the delivery of recombinant proteins to the intestinal tract are known in the art. See, e.g. Lin, et al. (2017) Microb Cell Fact 16:148. In some embodiments, the engineered bacterial cell expressing the IFNGR binding molecule may be administered orally, typically in aqueous suspension, or rectally (e.g. enema).

Therapeutic Applications

The present disclosure further provides methods of treating a subject suffering from a disease disorder or condition by the administration of a therapeutically effective amount of an IFNGR binding molecule (or nucleic acid encoding an IFNGR binding molecule including recombinant viruses encoding the IFNGR binding molecule) of the present disclosure.

Use In Combination With Supplementary Agents:

In some embodiments of the therapeutic uses of the compositions of the present disclosure, the administration of a therapeutically effective amount of an IFNGR binding molecule (or nucleic acid encoding an IFNGR binding molecule including recombinant viruses encoding the IFNGR binding molecule) are administered in combination with one or more additional active agents ("supplementary agents").

As used herein, the term "in combination with" when used in reference to the administration of multiple agents to a subject refers to the administration of a first agent at least one additional (i.e., second, third, fourth, fifth, etc.) agent to a subject. For purposes of the present invention, one agent (e.g., IFNGR binding molecule) is considered to be administered in combination with a second agent (e.g. a therapeutic autoimmune antibody such as Humira®) if the biological effect resulting from the administration of the first agent persists in the subject at the time of administration of the second agent such that the therapeutic effects of the first agent and second agent overlap. For example, the therapeutic antibodies are sometimes administered by IV infusion every two weeks while the IFNGR binding molecules of the present disclosure may be administered more frequently, e.g. daily, BID, or weekly. However, the administration of the first agent (e.g. entaercept) provides a therapeutic effect over an extended time and the administration of the second agent (e.g. an IFNGR binding molecule) provides its therapeutic effect while the therapeutic effect of the first agent remains ongoing such that the second agent is considered to be administered in combination with the first agent, even though the first agent may have been administered at a point in time significantly distant (e.g. days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IFNGR binding molecule and the supplementary agent(s) are administered or applied sequentially, e.g., where one agent is administered prior to one or more other agents. In other embodiments, the IFNGR binding molecule and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Supplementary agents may administered or introduced separately, for example, formulated separately for separate administration (e.g., as may be provided in a kit) and/or therapies that can be administered or introduced in combination with the IFNGR binding molecules.

Methods of Use

Inhibition of IFNGR Receptor Activity

In one embodiment, the present disclosure provides a method of modulating the activity of cells expressing the IFNGR by the administration of a composition comprising IFNGR binding molecule to a subject in an amount sufficient to interfere with the activity of receptors comprising the of IFNGR. The present disclosure further provides a method of modulating the activity of cells expressing the IFNGR in a mixed population of cells comprising contacting said population of cells, in vivo and/or ex vivo, with a IFNGR binding molecule or complex of the present disclosure to in an amount sufficient to interfere with the activity of receptors comprising the IFNGR.

Isolation, Enrichment or Depletion of IFNGR+ Cells From a Biological Sample

In one embodiment, the present disclosure provides a method of use of the IFNGR binding molecules of the present disclosure useful in a process for in the isolation, enrichment or depletion of IFNGR+ cells from a biological sample comprising IFNGR+ cells. The biological sample may comprise cells of blood origin such as PBMC, T cells, B cells of cell culture origin or of tissue origin such as brain or bone marrow. Processes suitable for the isolation, enrichment or depletion of IFNGR+ cells comprise centrifugation, filtration, magnetic cell sorting and fluorescent cell sorting by techniques well known in the art. The present disclosure further provides a method for the treatment of a subject suffering from a disease, disorder or condition by the administration of a therapeutically effective amount of a cell product enriched or depleted of IFNGR+ cells through the use of a IFNGR binding molecule as described herein.

In one embodiment, the sorting procedure employs a IFNGR binding molecule comprising a fluorescent label for use in FACS isolation or depletion of IFNGR+ cells from a sample. The fluorescent label may be attached to the sdAb of the IFNGR binding molecule directly (e.g., by chemical conjugation optionally employing a linker) or indirectly (e.g., by biotinylation of the sdAb and binding of the biotinylated antibody to a streptavidin fluorochrome conjugate). Such fluorescently labelled IFNGR+ cells may be separated from a mixed cell population using conventional FACS technology.

In an alternative embodiment, the selection procedure employs IFNGR binding molecules of the present disclosure (e.g., a IFNGR binding VHH) conjugated to magnetic particles which provide magnetic labeling of the IFNGR+ cells for use in magnetic cell separation procedures. In one embodiment the method comprises: (a) conjugation of one or more IFNGR binding molecule of the present disclosure (e.g., a IFNGR binding VHH) to a magnetic particle; (b) creating a mixture by contacting the biological sample with a quantity of the magnetic particles conjugated to IFNGR binding molecule; (c) subjecting to a magnetic field such that the magnetically labelled IFNGR+ cells are retained; (d) removing the non-magnetically labelled cells from the mixture; and (e) removal of the magnetic field enabling isolation of the IFNGR+ cells.

The cell selection procedure (e.g., FACS or magnetic separation) results in two products: (a) a population of cells depleted of IFNGR+ cells and (b) a population of cells enriched for IFNGR+ cells. Each of these populations may be further processed by convention procedures to identify particular IFNGR+ or IFNGR− cell subsets which may be useful in research, diagnostic or clinical applications. For example, isolation of specific IFNGR+ T cell subsets that also express one or more of CD4, CD8, CD19, CD25, and CD62L, further iterations of the using one or more antibodies that specifically bind to CD4, CD8, CD19, CD25, and CD62L antigens respectively by FACS or magnetic field separation by techniques well known in the art.

In one embodiment of the IFNGR binding molecule a humanized antibody or fragment thereof as disclosed herein may be used for depletion of IFNGR-expressing cells from a biological sample comprising IFNGR-expressing cells such peripheral blood or lymphoid tissue which may optionally be further processed for further isolation of IFNGR+ naïve T cell subsets, isolation human IFNGR+ memory T cells from a population of CD4+ or CD8+ cells, or isolation of human IFNGR+naïve T cells from presorted CD4+ or CD8+ cells by depletion of IFNGR+ cells. In one embodiment, the IFNGR binding molecule provides a method of generating a population of cells enriched for naïve Tregs from a biological sample, the method comprising depleting IFNGR+ cells using a IFNGR binding molecule of the present disclosure as described above, optionally further comprising the steps of depleting CD8+ and/or CD19+ cells. The IFNGR+ depleted cell population may optionally be further expanded in vitro for particular cell types to in the preparation of a cell product comprising a therapeutically effective amount of the IFNGR+ depleted cell product which may be administered to a subject suffering from a disease, disorder or condition.

The IFNGR+ enriched cell population may optionally be further expanded in vitro to in the preparation of a cell product comprising a therapeutically effective amount of the IFNGR+ cells.

Inflammatory and Autoimmune Disorders

Disorders amenable to treatment with an IFNGR binding molecule (including pharmaceutically acceptable formulations comprising an IFNGR binding molecules and/or the nucleic acid molecules that encode them including recombinant viruses encoding such an IFNGR binding molecules) of the present disclosure include inflammatory or autoimmune diseases including but not limited to, organ rejection, graft versus host disease, autoimmune thyroid disease, multiple sclerosis, allergy, asthma, neurodegenerative diseases including Alzheimer's disease, systemic lupus erythramatosis (SLE), autoinflammatory diseases, inflammatory bowel disease (IBD), Crohn's disease, diabetes including Type 1 or type 2 diabetes, inflammation, autoimmune disease, atopic diseases, paraneoplastic autoimmune diseases, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity Enthesopathy Arthropathy Syndrome), juvenile dermatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter's syndrome, SEA Syndrome (Seronegativity, Enthesopathy, Arthropathy Syndrome).

Other examples of proliferative and/or differentiative disorders amenable to treatment with IFNGR binding molecules (including pharmaceutically acceptable formulations comprising IFNGR binding molecules and/or the nucleic acid molecules that encode them including recombinant viruses encoding such IFNGR binding molecules) of the present disclosure include, but are not limited to, skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of inflammatory or autoimmune skin disorders include psoriasis, psoriatic arthritis, dermatitis (eczema), for example, exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

The compositions of the present disclosure (including pharmaceutically acceptable formulations comprising IFNGR binding molecules and/or the nucleic acid molecules that encode them including recombinant viruses encoding such IFNGR binding molecules) can also be administered to a patient who is suffering from (or may suffer from) psoriasis or psoriatic disorders. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, plaque psoriasis, moderate to severe plaque psoriasis, psoriasis vulgaris, eruptive psoriasis, psoriatic erythroderma, generalized pustular psoriasis, annular pustular psoriasis, or localized pustular psoriasis.

Combination with Supplementary Therapeutic Agents

The present disclosure provides for the use of the IFNGR binding molecules of the present disclosure in combination with one or more additional active agents ("supplementary agents"). Such further combinations are referred to interchangeably as "supplementary combinations" or "supplementary combination therapy" and those therapeutic agents that are used in combination with IFNGR binding molecules of the present disclosure are referred to as "supplementary agents." As used herein, the term "supplementary agents" includes agents that can be administered or introduced separately, for example, formulated separately for separate administration (e.g., as may be provided in a kit) and/or therapies that can be administered or introduced in combination with the IFNGR binding molecules.

As used herein, the term "in combination with" when used in reference to the administration of multiple agents to a subject refers to the administration of a first agent at least one additional (i.e. second, third, fourth, fifth, etc.) agent to a subject. For purposes of the present invention, one agent (e.g., IFNGR binding molecule) is considered to be administered in combination with a second agent (e.g., a modulator of an immune checkpoint pathway) if the biological effect resulting from the administration of the first agent persists in the subject at the time of administration of the second agent such that the therapeutic effects of the first agent and second agent overlap. For example, the PD1 immune checkpoint inhibitors (e.g., nivolumab or pembrolizumab) are typically administered by IV infusion every two weeks or every three weeks while the IFNGR binding molecules of the present disclosure are typically administered more frequently, e.g., daily, BID, or weekly. However, the administration of the first agent (e.g., pembrolizumab) provides a therapeutic effect over an extended time and the administration of the second agent (e.g., an IFNGR binding molecule) provides its therapeutic effect while the therapeutic effect of the first agent remains ongoing such that the second agent is considered to be administered in combination with the first agent, even though the first agent may have been administered at a point in time significantly distant (e.g., days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IFNGR binding molecule and the supplementary agent(s) are administered or applied sequentially, e.g., where one agent is administered prior to one or more other agents. In other embodiments, the IFNGR binding molecule and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Supplemental Agents Useful in the Treatment of Inflammatory or Autoimmune Disorders In some embodiments, the method further comprises administering of the IFNGR binding molecule of the present disclosure in combination with one or more supplementary agents selected from the group consisting of a corticosteroid, a Janus kinase inhibitor, a calcineurin inhibitor, a mTor inhibitor, an IMDH inhibitor, a biologic, a vaccine, and a therapeutic antibody. In certain embodiments, the therapeutic antibody is an antibody that binds a protein selected from the group consisting of BLyS, CD11a, CD20, CD25, CD3, CD52, IgEIL12/IL23, IL17a, IL1ß, IL4Rα, IL5, IL6R, integrin-α4β7, RANKL, TNFα, VEGF-A, and VLA-4.

In some embodiments, the supplementary agent is one or more agents selected from the group consisting of corticosteroids (including but not limited to prednisone, budesonide, prednilisone), Janus kinase inhibitors (including but not limited to tofacitinib (Xeljanz®), calcineurin inhibitors (including but not limited to cyclosporine and tacrolimus), mTor inhibitors (including but not limited to sirolimus and everolimus), IMDH inhibitors (including but not limited to azathioprine, leflunomide and mycophenolate), biologics such as abatcept (Orencia®) or etanercept (Enbrel®), and therapeutic antibodies.

Examples of therapeutic antibodies that may be administered as supplementary agents in combination with the IFNGR binding molecules of the present disclosure in the treatment of autoimmune disease include but are not limited to anti-CD25 antibodies (e.g. daclizumab and basiliximab), anti-VLA-4 antibodies (e.g. natalizumab), anti-CD52 antibodies (e.g. alemtuzumab), anti-CD20 antibodies (e.g. rituximab, ocrelizumab), anti-TNF antibodies (e.g. infliximab, and adalimumab), anti-IL6R antibodies (e.g. tocilizumab), anti-TNFα antibodies (e.g. adalimumab (Humira®), golimumab, and infliximab), anti-integrin-α4β7 antibodies (e.g. vedolizumab), anti-IL17a antibodies (e.g. brodalumab or secukinumab), anti-IL4Rα antibodies (e.g. dupilumab), anti-RANKL antibodies, IL6R antibodies, anti-IL1ß antibodies (e.g. canakinumab), anti-CD11a antibodies (e.g. efalizumab), anti-CD3 antibodies (e.g. muramonab), anti-IL5 antibodies (e.g. mepolizumab, reslizumab), anti-BLyS antibodies (e.g. belimumab); and anti-IL12/IL23 antibodies (e.g ustekinumab).

Many therapeutic antibodies have been approved for clinical use against autoimmune disease. Examples of antibodies approved by the United States Food and Drug Administration (FDA) for use in the treatment of autoimmune diseases in a subject suffering therefrom that may be administered as supplementary agents in combination with the IFNGR binding molecules of the present disclosure (and optionally additional supplementary agents) for the treatment of the indicated autoimmune disease are provided in Table 8 below:

TABLE 8

Antibodies Useful as Supplmentary Agents In the Treatment of Autoimmune and Inflammatory Disease

| Name | Target | Therapeutic Indication |
|---|---|---|
| efalizumab | CD11a | Psoriasis |
| belimumab | BLyS | Systemic lupus erythematosus |
| ocrelizumab | CD20 | Multiple sclerosis |
| rituximab | CD20 | Multiple sclerosis |
| basiliximab | CD25 | Transplantation rejection |
| daclizumab | CD25 | Transplantation rejection |
| muromonab | CD3 | Transplantation rejection |
| alemtuzumab | CD52 | Multiple sclerosis |
| omalizumab | IgE | Asthma |
| ustekinumab | IL12/IL23 | Plaque psoriasis |
| brodalumab | IL17a | Psoriasis, psoriatic arthritis, ankylosing spondylitis |

TABLE 8-continued

Antibodies Useful as Supplmentary Agents In the Treatment of Autoimmune and Inflammatory Disease

| Name | Target | Therapeutic Indication |
|---|---|---|
| secukinumab | IL17a | Psoriasis, psoriatic arthritis, ankylosing spondylitis |
| ixekizumab | IL17a | Psoriasis, psoriatic arthritis, ankylosing spondylitis |
| canakinumab | IL1β | Cryopyrin-associated periodic syndrome, tumor necrosis factor receptor associated periodic syndrome, hyperimmunoglobulin D syndrome, mevalonate kinase deficiency, familial Mediterranean fever, rheumatoid arthritis |
| dupilumab | IL4Rα | Asthma, dermatitis |
| mepolizumab | IL5 | Asthma |
| reslizumab | IL5 | Asthma |
| tocilizumab | IL6R | Rheumatoid arthritis |
| vedolizumab | Integrin-α4β7 | Ulcerative colitis, Crohn's disease |
| denosumab | RANKL | Osteoporosis |
| certolizumab | TNFa | Chron's disease, rheumatoid arthritis |
| golimumab | TNFa | Rheumatoid arthritis, psoriatic arthritis, ankylosing spondylitis |
| adalimumab | TNFα | Rheumatoid arthritis, juvenile idiopathic arthritis, psoriatic arthritis, ankylosing spondylitis, Crohn's disease, plaque psoriasis |
| infliximab | TNFα | Crohn's disease, ulcerative colitis, rheumatoid arthritis, ankylosing spondylitis, psoriatic arthritis, plaque psoriasis |
| ranibizumab | VEGF-A | Neovascular age-related macular degeneration, macular edema |
| natalizumab | VLA-4 | Multiple sclerosis, relapsing rultiple sclerosis, Crohn's disease |

The foregoing antibodies of Table 8 useful as supplementary agents in the practice of the methods of the present disclosure may be administered alone or in the form of any antibody drug conjugate (ADC) comprising the antibody, linker, and one or more drugs (e.g. 1, 2, 3, 4, 5, 6, 7, or 8 drugs) or in modified form (e.g. PEGylated).

Prophylactic Applications

In some embodiments where the IFNGR binding molecule is used in prophylaxis of disease, the supplementary agent may be a vaccine. The IFNGR binding molecule of the present invention may be administered to a subject in combination with vaccines as an adjuvant to enhance the immune response to the vaccine in accordance with the teaching of Doyle, et al U.S. Pat. No. 5,800,819 issued Sep. 1, 1998. Examples of vaccines that may be combined with the IFNGR binding molecule of the present invention include are HSV vaccines, *Bordetella pertussis, Escherichia coli* vaccines, pneumococcal vaccines including multivalent pneumococcal vaccines such as Prevnar® 13, diptheria, tetanus and pertussis vaccines (including combination vaccines such as Pediatrix®) and Pentacel®), varicella vaccines, *Haemophilus influenzae* type B vaccines, human papilloma virus vaccines such as Garasil®, polio vaccines, Leptospirosis vaccines, combination respiratory vaccine, *Moraxella* vaccines, and attenuated live or killed virus vaccine products such as bovine respiratory disease vaccine (RSV), multivalent human influenza vaccines such as Fluzone® and Quadravlent Fluzone®), feline leukemia vaccine, transmissible gastroenteritis vaccine, COVID-19 vaccine, and rabies vaccine.

EXAMPLES

The following examples are put forth so as to provide those of ordinary skill in the art with a complete disclosure and description of how to make and use the present IFNGR binding molecule, and are not intended to limit the scope of what the inventors regard as their IFNGR binding molecule nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for. Variations of the particularly described procedures employed may become apparent to individuals or skill in the art and it is expected that those skilled artisans may employ such variations as appropriate. Accordingly, it is intended that the IFNGR binding molecule be practiced otherwise than as specifically described herein, and that the invention includes all modifications and equivalents of the subject matter recited in the claims appended hereto as permitted by applicable law.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or seC=second(s); min=minute(s); h or hr=hour(s); aa=amino acid(s); kb=kilobase(s); nt=nucleotide(s); pg=picogram; ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-hydroxysuccinimide; HSA=human serum albumin; MSA=mouse serum albumin; DMEM=Dulbeco's Modification of Eagle's Medium; GC=genome copy; EDTA=ethylenediaminetetraacetic acid; PBMCs=primary peripheral blood mononuclear cells; FBS=fetal bovine serum; FCS=fetal calf serum; HEPES=4-(2-hydroxyethyl)-1piperazineethanesulfonic acid; LPS=lipopolysaccharide; ATCC=American Type Culture Collection.

Example 1. Immunization Protocol

The VHH was obtained by immunization of a llama with the extracellular domains of the hIFNGR1 and hIFNGR2 as the antigens. A synthetic DNA sequence encoding the antigen was inserted into the pExSyn2.0 vector and transfected into the HEK293F mammalian cell host cell for expression. The antigen is expressed as a his tagged fusion protein which is purified using immobilized metal affinity chromatography. The antigen was diluted with 1×PBS (antigen total about 1 mg). The quality was estimated by SDS-PAGE to ensure the purity was sufficient (>90%) for immunization. The llama was acclimated at the facility for at least 7 days. At the start of the immunization protocol, 100 mL of blood was drawn to be used as a pre-bleed followed by boost with 150 to 500 ug of protein. Additional boosts were performed on days 14, 28, 42, and 56. 350 ml of blood was collected on day 63 for construction of the yeast sdAb library.

Example 2. Phage Library Construction 350 ml of blood sample was collected from the llama seven days following the last injection in the immunization protocol. RNA was extracted from blood and transcribed to cDNA. The approximately 900 bp reverse transcribed sequences encoding the VH—CH1-hinge-CH2-CH3 constructs were isolated from the approximately desired 700 bp fragments encoding the VHH-hinge-CH2-CH3 species. The purified approximately 700 bp fragments were amplified by nested PCR. The amplified fragments were inserted into a NheI/BamHI digested pGAL 414 yeast display vector such that the sequence encoding the VHH was fused to the C-term of Aga2 with an N-term HA and C-term Myc tag. Yeast cells were transformed with digested vector and amplified insert. Transformants were enriched in SD-SCAA media lacking tryptophan and uracil and stored at 4 C till further use.

Example 3: Isolation of Antigen Specific VHHs sdAb were expressed on the surface of yeast (*S. cervisiae* ATCC strain EBY100) using standard protocols. Yeast were grown overnight at 30° C. in synthetic selective media SD-SCAA, then induced again overnight at 20° C. in SG-SCAA. SdAb expressing yeast were incubated with Alexa647 conjugated IFNGR1 or IFNGR2 from 30 minutes to 2 hours. Antigen binding yeast were sorted using a Sony sorter (SH800). After 3 rounds of selection, yeast cells were plated onto SD-SCAA plates lacking tryptophan and uracil. 192 colonies were picked from each campaign and grown overnight in 96 well plates at 30° C. in synthetic selective media SD-SCAA, then induced again overnight at 20° C. in SG-SCAA.

Example 4: Identification of Antibodies Exhibiting Specific Binding to IFNGR

Binding of individual VHH to human and murine antigen was tested by flow cytometry. Briefly, 2E5 yeast cells expressing a single sdAb clone were added to each well of a 96 well plate. The first plate was incubated with 100 nM of human antigen conjugated to Alexa647 whereas the second plate was incubated with 100 nM of murine antigen conjugated to Alexa647. Yeast cells were washed 3 times with PBS containing 1% bovine serum albumin. Yeast cells were analyzed using flow cytometry and clones showing a mean fluorescence intensity of greater than 1000 were considered as binding molecules. Specificity of sdAbs was confirmed by incubating yeast cells with a irrelevant protein conjugated to Alexa647. Positive clones were sequenced, and sequences analyzed to identify unique clonotypes.

The hIFNGR1 VHHs of Table 4 were evaluated for cross-reactivity with the mIFNGR1 by flow cytometry and were found to bind both the extracellular domain of hIFNGR1 (SEQ ID NO:2). and the extracellular domain of mIFNGR1 (SEQ ID NO:4). Consequently, the VHHs provided in Table 4 may be used in both murine and human applications avoiding the necessity of a surrogate anti-mIFNGR1 for anti-hIFNGR1 for in vivo models of efficacy, such as a mouse model of a human disease state.

The hIFNGR2 VHHs of Table 5 (SEQ ID NOS: 2-33) were evaluated for cross-reactivity with the mIFNGR2 by flow cytometry and were found to bind both the extracellular domain of hIFNGR2 (SEQ ID NO. 6) and the extracellular domain of mIFNGR2 (SEQ ID NO. 8). Consequently, the VHHs provided in Table 5 may be used in both murine and human applications avoiding the necessity of a surrogate anti-mIFNGR2 for anti-hIFNGR2 for in vivo models of efficacy, such as a mouse model of a human disease state.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

Tables

TABLE 2 anti-IFNGR1 sdAb CDRs HUMAN

| Name | CDR1 | SEQ ID NO: | CDR2 | SEQ ID NO: | CDR3 | SEQ ID NO: |
|---|---|---|---|---|---|---|
| DR903 | RIASDYTRG | 25. | AIIRSVGDSYYADSVKG | 49. | GGHLYYGSRWRYPASYDY | 73. |
| DR904 | SILSINTMG | 26. | AISSGGSTNYADSVKG | 50. | DRAYY | 74. |
| DR905 | RTFTGYAMG | 27. | VITWSGATTYYSASVKG | 51. | RIRDGVSPENPNEYGY | 75. |
| DR906 | STFSTYVMG | 28. | AISRSGGTTTYADSVKG | 52. | RAGPAIGRTANDYHS | 76. |
| DR907 | RTFSNYAMG | 29. | AINWNIGSTYYADSVKG | 53. | VWPTGRLRVDSEYDY | 77. |
| DR908 | RTFTSLAMG | 30. | AISRSGGSTDYADSVKG | 54. | RDYSTLQYYNEYEYSD | 78. |
| DR909 | RTFGTSFGALSMG | 31. | AITRNTGRTFYADSVKD | 55. | TNSYDDLRRSYAYNY | 79. |
| DR910 | RTFSSYAMA | 32. | AISILGGSADYEDSVQG | 56. | RRPAPSDSYWSSTSYAY | 80. |
| DR911 | RSFSTYAMA | 33. | AITVGGGSTYYVDSVKG | 57. | RDYRRRSYAPEAEQYDY | 81. |
| DR912 | RTFSSYAMA | 34. | AITVSGASTYYADSVKG | 58. | GGPGTIFPDYDY | 82. |
| DR913 | RTFSSYAMG | 35. | AISSWSGGSTYYADSVKG | 59. | GDYYSDYFKYDNEN | 83. |
| DR914 | RAFSNSAMA | 36. | AISRGGGSTDYADSVKG | 60. | RYYSGRYYESLEYDY | 84. |
| DR915 | RTLHNFAMA | 37. | AISKGGGSADYADSVKG | 61. | NDLASYSDSSYTSTSRYDY | 85. |
| DR916 | RPRTTYAMG | 38. | AISKAGGSTYVADSAKG | 62. | RAGFAAQIFEYDY | 86. |
| DR917 | RTFSGYNMG | 39. | AIAWAGSRTYYTDSVKG | 63. | HDETYYRLDRVDLYTH | 87. |
| DR918 | LTDSTYGMA | 40. | AISRAGGSADHADSVKG | 64. | GRSYSSPYDYFNALAYSY | 88. |
| DR919 | RTLSTYAMG | 41. | AISWRSGNTYYADSVKG | 65. | NEVATMSGPHDH | 89 |
| DR920 | RSFANYAMG | 42. | AISRGGGSTWYADSVKG | 66. | RSYSGSYTYSFGEYDY | 90. |
| DR921 | RTFTFSTHNMG | 43. | GIMWTSRASYADSVKG | 67. | AWYGNSGASYDY | 91. |
| DR922 | SITSINTMG | 44. | AITSGGSTNYADSVKG | 68. | DSMYF | 92. |
| DR923 | RTFMTYAMG | 45. | AISWSSGSTYYADSVKG | 69. | SSIATMYGPNDY | 93. |
| DR924 | RTFSRYAMG | 46. | TISRSGGTTSYANSVKG | 70. | RDGPAMGVFGSDYDY | 94. |
| DR925 | RTFSRYAMG | 47. | AISIGGGSADYADTVKG | 71. | RTPRPSSSYFTPQDYEY | 95. |

TABLE 2-continued anti-IFNGR1 sdAb CDRs HUMAN

| Name | CDR1 | SEQ ID NO: | CDR2 | SEQ ID NO: | CDR3 | SEQ ID NO: |
|---|---|---|---|---|---|---|
| DR926 | RTFSRYAMN | 48. | AISWSSGNTYVADSVKG | 72. | TTIATMSDENTY | 96. |

TABLE 3 anti-IFNGR2 sdAb CDRs Human

| Name | CDR1 | SEQ ID NO: | CDR2 | SEQ ID NO: | CDR3 | SEQ ID NO: |
|---|---|---|---|---|---|---|
| DR927 | RTFTSYAMN | 97. | AISWSSGNTYVADSVKG | 129. | TTIATMSDEYTY | 161. |
| DR928 | RTFSNYRMG | 98. | AISRGGGTTLYADSVKG | 130. | GDFSTTWDEYNY | 162. |
| DR929 | RTFSSYAMG | 99. | AISRGGGSTDYADSVKG | 131. | RAYSGRYYQFLEYDY | 163. |
| DR930 | RTFSSYAVA | 100. | ALSRGGGSAYYTDSVKG | 132. | RNYDGTYYQENQYNY | 164. |
| DR931 | RTFSTYAMG | 101. | AISVNGGSTYYADSVTG | 133. | RRPYPGSDFLTWASYDY | 165. |
| DR932 | RTFSYTTIG | 102. | VISAGGGSRDYADALKG | 134. | RRNTDTYTTTGDYDY | 166. |
| DR933 | GTISSLAMG | 103. | AISWSGRSTYYVDSVKG | 135. | GEDGHSEYDY | 167. |
| DR934 | RSFANYAMG | 104. | AISRGGGSTWYADSVKG | 136. | RSYSGSYTYSFGEYDY | 168. |
| DR935 | RAFSTYALG | 105. | AISRGGGSTDYADSVKG | 137. | RSYSSSYYYSQYEYDY | 169. |
| DR936 | RTFSSVAMA | 106. | AISSGGGSTDYADSVKG | 138. | RDYSSRRYYQSRYEYDL | 170. |
| DR937 | RTFRSYSMG | 107. | AISWYSGTTYYADPVKG | 139. | NEIATMESSNDY | 171. |
| DR938 | RPRTTYAMG | 108. | AISKAGGSTYVADSAKG | 140. | RAGFAAQIFEYDY | 172. |
| DR939 | RTFGTYAMG | 109. | SIDRDGSMSYYADSVKG | 141. | SRRAVISLQTVDY | 173. |
| DR940 | RTFSNYAMG | 110. | AISWYSGNTYYADSVKG | 142. | NQIATMISVGDY | 174. |
| DR941 | SIFRLNLMG | 111. | HVGTTGNTAYADSVKG | 143. | DRWGQFS | 175. |
| DR942 | RTFTGYAMG | 112. | VITWSGATTYYSASVKG | 144. | RIRDGVSPENPNEYGY | 176 |
| DR943 | RTVGYGMA | 113. | AITWSGTSTYYPDSVKG | 145. | GSRRVGVDVGGYDY | 177. |
| DR944 | RTFTFSTHNMG | 114. | GIMWTSRASYADSVKG | 146. | AWYGNSGASYDY | 178. |
| DR945 | RTFSGYNMG | 115. | AIAWAGSRTYYTDSVKG | 147. | HDETYYRLDRVDLYTH | 179. |
| DR946 | PFTRYAMG | 116. | AISWSSGNTYYVDSVKG | 148. | NEVATMSGPDDY | 180. |

TABLE 3-continued anti-IFNGR2 sdAb CDRs Human

| Name | CDR1 | SEQ ID NO: | CDR2 | SEQ ID NO: | CDR3 | SEQ ID NO: |
|---|---|---|---|---|---|---|
| DR947 | GSFGRYTMG | 117. | VISWSGTNTYYADSVKG | 149. | RETYYSHWDERMEYDY | 181. |
| DR948 | SIDSSYYVS | 118. | AINWGDSRTAYADSVKG | 150. | RIGLGGPVVAAPTRYPY | 182. |
| DR949 | SILRFNVMS | 119. | VITSGGSTNYADSVKG | 151. | DESGQYY | 183. |
| DR950 | LTTSSAALA | 120. | TITSGGGSTYYADSVKG | 152. | RFYSTTYYYREHEYSD | 184. |
| DR951 | RTFGTSFGSLSMG | 121. | AISRNIGRTYYADSVKD | 153. | TNSYDDLRRSYAYDY | 185. |
| DR952 | RTFSSLAMA | 122. | AISRSGGSTDYADSVKG | 154. | RDYSTLQYYNEYEYSD | 186. |
| DR953 | PTFSTYAMA | 123. | AITQSGRTTYYEDSVKG | 155. | RDLWSDSPDDWRIYSF | 187. |
| DR954 | RTLHNFAMA | 124. | AISKGGGSADYADSVKG | 156. | NDLASYSDSSYTSTSRYDY | 188. |
| DR955 | RTFSSYAMA | 125. | AISILGGSADYEDSVQG | 157. | RRPAPSDSYWSSTSYAY | 189. |
| DR956 | RTFSSLAMA | 126. | ATTILGGSADYGDPVKG | 158. | RRPAPSDNYWSPASYAY | 190. |
| DR957 | RTFSSYAMA | 127. | AITVSGASTYYADSVKG | 159. | GGPGTIFPDYDY | 191. |
| DR958 | RTFSGYNMG | 128. | AINWIGGATYYADSVKG | 160. | YSEKFYSGKDYYTRDYDY | 192. |

TABLE 4 anti-IFNGR1 sdAb VHH AMINO ACID SEQUENCE HUMAN

| Name | Sequence | SEQ ID NO: |
|---|---|---|
| DR903 | EVQLVESGGGLVQAGGSLRLSCAASGRIASDYTRGWFRQAPGKEREFVAAIIRSVGDSYYADSVKGRFTISIDNAENTVYLQMNSLKPEDTAVYYCAVGGHLYYGSRWRYPASYDYWGQGTQVTVSS | 193. |
| DR904 | EVQLVESGGGLVQAGGSLRLSCEASESILSINTMGWFRQAPGKQRELVAAISSGGSTNYADSVKGRFTISRDNAKNTVYLQMNSLKPEDTAVYYCDADRAYYKGQGTQVTVSS | 194. |
| DR905 | EVQLVESGGGLVQAGGSLRLSCVASGRTFTGYAMGWFRQAPGKEREFVAVITWSGATTYYSASVKGRFTLSRDNAKNTVYLQMNSLKSEDTAVYYCAIRIRDGVSPENPNEYGYWGQGTQVTVSS | 195. |
| DR906 | EVQLVESGGGLVQAGGSLRLSCAASGSTFSTYVMGWFRQAPGKEREFVAAISRSGGTTTYADSVKGRFDISRDNGKNTLFLQMNSLIPEDTAAYYCAARAGPAIGRTANDYHSWGQGTLVTVSS | 196. |
| DR907 | EVQLVESGGGLVQAGGSLRLSCAASGRTFSNYAMGWFRQAPGNEREFVAAINWNIGSTYYADSVKGRFTISRDNAKNTVYLQMNSLKPEDTAVYYCGAVWPTGRLRVDSEYDYWGQGTQVTVSS | 197. |
| DR908 | EVQLVESGGGLVQAGGSLRVTCAASGRTFTSLAMGWFRQAPGKEREFVAAISRSGGSTDYADSVKGRFFISRDNAKSTLYLQMSSLKPEDTAVYYCAARDYSTLQYYNEYEYSDWGQGTQVTVSS | 198. |
| DR909 | EVQLVESGGGLVQAGGSLRLSCAASGRTFGTSFGALSMGWFRQAPGKEREFVAAITRNTGRTFYADSVKDRFTISRDNAKNTASLQMNSLEPEDTAVYICAATNSYDDLRRSYAYNYWGQGTQVTVSS | 199. |

TABLE 4-continued anti-IFNGR1 sdAb VHH AMINO ACID SEQUENCE HUMAN

| Name | Sequence | SEQ ID NO: |
|---|---|---|
| DR910 | EVQLVESGGGLVQTGGSLRLSCAASGRTFSSYAMAWFRQAPGKEREFVAA<br>ISILGGSADYEDSVQGRFTISRDNAKNTMYLQMNSLKPEDTAVYYCAARR<br>PAPSDSYWSSTSYAYWGQGTLVTVSS | 200. |
| DR911 | EVQLVESGGALVQAGGSLRLSCTVSGRSFSTYAMAWFRRAPGKERELVSA<br>ITVGGGSTYYVDSVKGRFTISRENAKNTLYLQMNNLKPEDTAIYICAARD<br>YRRRSYAPEAEQYDYWGQGTQVTVSS | 201. |
| DR912 | EVQLVESGGGLVQAGGSLRLSCAPSGRTFSSYAMAWFRQPPGKEREFVAA<br>ITVSGASTYYADSVKGRFTISRDNAKNSMYLQMNSLKPEDTAVYYCAAGG<br>PGTIFPDYDYWGQGTQVTVSS | 202. |
| DR913 | EVQLVESGGGLVQAGGFLRLSCAASGRTFSSYAMGWFRQIPGKERELVAA<br>ISSWSGGSTYYADSVKGRFTISRDNAKNTVYLQMLSLKPEDTAVYYCTTG<br>DYYSDYFKYDNENWGKGTQVTVSS | 203. |
| DR914 | EVQLVESGGGLVQAGGSLTLSCVASGRAFSNSAMAWFRQTPGKEREFVSA<br>ISRGGGSTDYADSVKGRFTISKDNAKNTVYLQMNSLKPEDTAVYYCAMRY<br>YSGRYYESLEYDYWGQGTQVTVSS | 204. |
| DR915 | EVQLVESGGGLVQAGGSLRLSCAAARRTLHNFAMAWFRQAPGKEREFVAA<br>ISKGGGSADYADSVKGRFTISRDNAKNTVYLQMNSLKPEDTAVYYCAAND<br>LASYSDSSYTSTSRYDYWGQGTQVTVSS | 205. |
| DR916 | EVQLVESGGGLVQPGGSLRLSCTASGRPRTTYAMGWFRQAPGKEREIVAA<br>ISKAGGSTYVADSAKGRFAISKDNAKNTVYLQMNSLKPEDTAVYYCAARA<br>GFAAQIFEYDYWGQGTLVTVSS | 206. |
| DR917 | EVQLVESGGGLVQAGGSLRLSCAASGRTFSGYNMGWFRQAPGKEREFVAA<br>IAWAGSRTYYTDSVKGRFTISRDNAKNTMYLQMNTLRPEDTAVYYCAAHD<br>ETYYRLDRVDLYTHWGQGTLVTVSS | 207. |
| DR918 | EVQLVESGGGLVQAGGSLRLSCATSGLTDSTYGMAWFRQAPGKEREFVAA<br>ISRAGGSADHADSVKGRFTVSRDNAKKMVYLQMNSLKPEDTAVYYCASGR<br>SYSSPYDYFNALAYSYWGQGTQVTVSS | 208. |
| DR919 | EVQLVESGGGLVQPGGFLRLSCAASRRTLSTYAMGWFRQAPGKEREFVAA<br>ISWRSGNTYYADSVKGRFTISRDNAKNTMYLQMNSLKPEDTAVYYCAANE<br>VATMSGPHDHWGQGTLVTVSS | 209. |
| DR920 | EVQLVESGGGLVQAGGSLRLSCAASGRSFANYAMGWFRQAPGKERETVAA<br>ISRGGGSTWYADSVKGRFTISKDNAKNTVYLQMNSLKPEDTAIYYCAARS<br>YSGSYTYSFGEYDYWGQGTQVTVSS | 210. |
| DR921 | QVQLVESGGGLVQAGDSLRLSCAASGRTFTFSTHNMGWFRQAPGKEREFV<br>GGIMWTSRASYADSVKGRFTVSRDNAKNTVYLQMNSLKPEDTAVYYCAAA<br>WYGNSGASYDYWGQGTQVTVSS | 211. |
| DR922 | QVQLVESGGGLVRAGGSLRLSCAASGSITSINTMGWFRQAPGKQRELVAA<br>ITSGGSTNYADSVKGRFTISRDNARNTVYLQMYSLKPEDTAVYYCEADSM<br>YFRGQGTQVTVSS | 212. |
| DR923 | QVQLVESGGGLVQAGGSLRLSCAASRRTFMTYAMGWFRQAPGKEREFVAA<br>ISWSSGSTYYADSVKGRFTISRDNAKNTMYLQMNSLKPEDTAVYYCTASS<br>IATMYGPNDYAGQGTLVTVSS | 213. |
| DR924 | QVQLVESGGGLVQAGGSLRLSCTASGRTFSRYAMGWFRQAPGKEREFVAT<br>ISRSGGTTSYANSVKGRFTISRDNAKNTVYLQMNSLKTEDTAVYNCAARD<br>GPAMGVFGSDYDYWGQGTLVTVSS | 214. |
| DR925 | EVQLVESGGGLVQAGGSLVLSCAASGRTFSRYAMGWFRQAPGKEREFVAA<br>ISIGGGSADYADTVKGRFTISRNNAKNTMYLQMNSLKPEDTAVYYCAART<br>PRPSSSYFTPQDYEYWGQGTLVTVSS | 215. |
| DR926 | EVQLVESGGGLVQAGGSLRLSCAASGRTFSRYAMNWFRQAPGKEREFVAA<br>ISWSSGNTYVADSVKGRFTISRDNAKNTMYLQMNNLAPEDTAVYYCAATT<br>IATMSDENTYWGQGTQVTVSS | 216. |

TABLE 5 anti-IFNGR2 sdAb VHH AMINO ACID SEQUENCE HUMAN

| Name | Sequence | SEQ ID NO: |
|---|---|---|
| DR927 | QVQLVESGGGLVQAGGSLRLSCAASGRTFTSYAMNWFRQAPGKEREFVAAIS WSSGNTYVADSVKGRFAISRDKAKNTMYLQMNSLAPEDTAVYYCAATTIATM SDEYTYWGQGTQVTVSS | 217. |
| DR928 | QVQLVESGGGLVQAGGSLRLSCAASGRTFSNYRMGWFRQAPGKEREFVAAIS RGGGTTLYADSVKGRFTISRDNAKNTVDLQMNRLKPEDTAVYFCAAGDFSTT WDEYNYWGQGTQVTVSS | 218. |
| DR929 | QVQLVESGGGLVQAGGSLRLSCVASGRTFSSYAMGWFRQTPGKEREFVSAIS RGGGSTDYADSVKGRFTISRDNAKNTVYLQMNNLKSEDTAVYYCALRAYSGR YYQFLEYDYWGQGTQVTVSS | 219. |
| DR930 | EVQLVESGGGLVQAGGSLRLSCTVSGRTFSSYAVAWFRQAPGNVRELAAALS RGGGSAYYTDSVKGRFTISRDNAKNTVYLQMNSLKPEDTAVYYCAARNYDGT YYQENQYNYWGQGTQVTVSS | 220. |
| DR931 | QVQLVESGGGLVQAGGSLLLSCAASGRTFSTYAMGWFRQAPGKERMFVAAIS VNGGSTYYADSVTGRFTISRDNAKNTMYLQMNNLKPGDTAVYYCAARRPYPG SDFLTWASYDYRGQGTLVTVSS | 221. |
| DR932 | QVQLVESGGGLVQAGGFLRLSCAASGRTFSYTTIGWFRQAPGKEREFVAVIS AGGGSRDYADALKGRFTISRDNAKKMVYLQMNNLKPEDTAVYYCAVRRNTDT YTTTGDYDYWGQGTQVTVSS | 222. |
| DR933 | QVQLVESGGGLVQPGDSLRLSCVASGGTISSLAMGWFRQAPGKEREFVAAIS WSGRSTYYVDSVKGRFTISTDNAKNTVYLQMNSLKPEDTAVYYCVAGEDGHS EYDYWGQGTQVTVSS | 223. |
| DR934 | QVQLVESGGGLVQAGGSLRLSCAASGRSFANYAMGWFRQAPGKERETVAAIS RGGGSTWYADSVKGRFTISKDNAKNTVYLQMNSLKPEDTAIYYCAARSYSGS YTYSFGEYDYWGQGTQVTVSS | 224. |
| DR935 | QVQLVESGGGLVQAGGSLRLSCAASGRAFSTYALGWFRQAPGKEREFIAAIS RGGGSTDYADSVKGRFTISRDNAKSTVYLQMNSLKPEDTAVYYCAARSYSSS YYYSQYEYDYWGQGTQVTVSS | 225. |
| DR936 | EVQLVESGGGLVQAGGSLRLSCAASGRTFSSVAMAWFRQAPGKEREFVSAIS SGGGSTDYADSVKGRFTISKDNAKNTMYLQMDSLKPEDTAVYYCAARDYSSR RYYQSRYEYDLWGLGTQVTVSS | 226. |
| DR937 | QVQLVESGGGLVQPGGSLRLSCAASGRTFRSYSMGWFRQAPGKEREFVAAIS WYSGTTYYADPVKGRFTISRDDAKNTLYLQMNSLKPEDTAVYYCAANEIATM ESSNDYWGQGTQVTVSS | 227. |
| DR938 | QVQLVESGGGLVQPGGSLRLSCTASGRPRTTYAMGWFRQAPGKEREIVAAIS KAGGSTYVADSAKGRFAISKDNAKNTVYLQMNSLKPEDTAVYYCAARAGFAA QIFEYDYWGQGTLVTVSS | 228. |
| DR939 | EVQLVESGGGLVQAGGSMRLSCANSGRTFGTYAMGWFRQSPGKERERVASID RDGSMSYYADSVKGRFTISGDNAKNTVYLQMNSLKPEDTAVYYCAASRRAVI SLQTVDYWGQGTQVTVSS | 229. |
| DR940 | EVQLVESGGRLVQTGGSLRLSCAASGRTFSNYAMGWFRQAPGKEREFVAAIS WYSGNTYYADSVKGRFTISRDNAKNTMYLQMNSLKPEDTAVYYCAANQIATM ISVGDYWGQGTLVTVSS | 230. |
| DR941 | QVQLVESGGGLVEAGGSLRLACAASGSIFRLNLMGWYRQAPGKQRELVAHVG TTGNTAYADSVKGRFTISKDDAKNMVFLQMNSLKPEDTAVYYCYADRWGQFS WGQGTQVTVSS | 231. |
| DR942 | QVQLVESGGGLVQAGGSLRLSCVASGRTFTGYAMGWFRQAPGKEREFVAVIT WSGATTYYSASVKGRFTLSRDNAKNTVYLQMNSLKSEDTAVYYCAIRIRDGV SPENPNEYGYWGQGTQVTVSS | 232. |
| DR943 | QVQLVESGGGLVQAGGSLRLSCVASGRTVGYGMAWFRQAPGKQRDVVAAITW SGTSTYYPDSVKGRFTISRDNAKNTMYLQMSSLKPEDTAVYYCAAGSRRRVG VDVGGYDYWGQGTQVTVSS | 233. |
| DR944 | QVQLVESGGGLVQAGDSLRLSCAASGRTFTFSTHNMGWFRQAPGKEREFVGG IMWTSRASYADSVKGRFTVSRDNAKNTVYLQMNSLKPEDTAVYYCAAWYGN SGASYDYWGQGTQVTVSS | 234. |
| DR945 | QVQLVESGGGLVQLVQAGGSLRLSCAASGRTFSGYNMGWFRQAPGKEREFVA AIAWAGSRTYYTDSVKGRFTISRDNAKNTMYLQMNTLRPEDTAVYYCAAHDE TYYRLDRVDLYTHWGQGTQVTVSS | 235. |

TABLE 5-continued anti-IFNGR2 sdAb VHH AMINO ACID SEQUENCE HUMAN

| Name | Sequence | SEQ ID NO: |
|---|---|---|
| DR946 | QVQLVESGGGLVQPGESLRLSCAASGPFTRYAMGWFRQAPGKEREFVAAISW SSGNTYYVDSVKGRFTISRDNAKNTMYLQMNSLKPEDTAVYYCAANEVATMS GPDDYWGQGTQVTVSS | 236. |
| DR947 | QVQLVESGGGLVQAGGSLRLSCAASGGSFGRYTMGWYRQAPGKEREFVAVIS WSGTNTYYADSVKGRFTISRDNAKNTMYLQMNDLKPEDTAVYYCAARETYYS HWDERMEYDYWGQGTQVTVSS | 237. |
| DR948 | QVQLVESGGGLVQAGDSLRLSCVASGSIDSSYYVSWFRQAPGKERDLVAAIN WGDSRTAYADSVKGRFTISRDNAKNTVYLQMHSLRPNDTAVYYCASRIGLGG PVVAAPTRYPYWGQGTLVTVSS | 238. |
| DR949 | QVQLVESGGGLVQAGGSLRLSCAASESILRFNVMSWLRQAPGKQRELVAVIT SGGSTNYADSVKGRFTISRDNAKNTVYLQMNSLKPEDTAVYYCAADESGQYY WGQGTQVTVSS | 239. |
| DR950 | QVQLVESGGGLVQAGGSLRLSCAASGLTTSSAALAWFRQAPGKERELDPTIT SGGGSTYYADSVKGRFTISKDNAKNTLYLQMSSLKPEDTAVYYCAARFYSTT YYYREHEYSDWGQGTQVTVSS | 240. |
| DR951 | QVQLVESGGGLVQAGGSLRLSCAASGRTFGTSFGSLSMGWFRQAPGKEREFV AAISRNIGRTYYADSVKDRFTISRDNAKNTASLQMNSLEPEDTAVYNCAATN SYDDLRRSYAYDYWGQGTQVTVSS | 241. |
| DR952 | QVQLVESGGGLVQAGGFLRLSCAASGRTFSSLAMAWFRQAPGKEREFVAAIS RSGGSTDYADSVKGRFTISRDNAKSTLYLQMSSLKPEDTAVYYCAARDYSTL QYYNEYEYSDWGQGTLVTVSS | 242. |
| DR953 | QVQLVESGGGLVQAGDSLRLSCAASGPTFSTYAMAWFRQAPGKEREFVAAIT QSGRTTYYEDSVKGRFTISKDNAKNTLYLQMNSLQPEDTAVYYCAARDLWSD SPDDWRIYSFWGQGTQVTVSS | 243. |
| DR954 | QVQLVESGGGLVQAGGSLRLSCAAARRTLHNFAMAWFRQAPGKEREFVAAIS KGGGSADYADSVKGRFTISRDNAKNTVYLQMNSLKPEDTAVYYCAANDLASY SDSSYTSTSRYDYWGQGTQVTVSS | 244. |
| DR955 | QVQLVESGGGLVQTGGSLRLSCAASGRTFSSYAMAWFRQAPGKEREFVAAIS ILGGSADYEDSVQGRFTISRDNAKNTMYLQMNSLKPEDTAVYYCAARRPAPS DSYWSSTSYAYWGQGTLVTVSS | 245. |
| DR956 | EVQLVESGGGLVQAGGSLRLSCAASGRTFSSLAMAWFRQAPGKEREFVAATT ILGGSADYGDPVKGRFTISRDNAKNTVYLQMNSLKPEDTAVYYCTGRRPAPS DNYWSPASYAYWGQGTQVTVSS | 246. |
| DR957 | QVQLVESGGGLVQAGGSLRLSCAPSGRTFSSYAMAWFRQPPGKEREFVAAIT VSGASTYYADSVKGRFTISRDNAKNSMYLQMNSLKPEDTAVYYCAAGGPGTI FPDYDYWGQGTQVTVSS | 247. |
| DR958 | QVQLVESGGGLVQAGDSLTLSCTASGRTFSGYNMGWFRQAPGKERDFVAAIN WIGGATYYADSVKGRFTISRDNAKNTVYLQMNSLKPEDTAVYYCHRYSEKFY SGKDYYTRDYDYWGQGTQVTVSS | 248. |

TABLE 6 anti-IFNGR1 sdAb VHH DNA SEQUENCE HUMAN

| Name | Sequence | SEQ ID NO: |
|---|---|---|
| DR903 | GAAGTACAGCTGGTGGAGTCAGGAGGGGGTCTGGTCCAGGCCGGTGGGT CACTGAGGCTCTCCTGCGCTGCCAGCGGTCGCATTGCTTCCGACTACAC TAGAGGATGGTTTCGTCAGGCTCCAGGCAAGGAACGCGAGTTTGTTGCG GCTATTATCCGCAGTGTGGGCGACAGTTACTATGCCGACTCTGTGAAGG GCCGCTTCACTATCTCTATTGATAACGCAGAGAACACAGTGTACCTCCA AATGAACAGCCTCAAGCCCGAAGACACCGCTGTCTATTACTGCGCTGTG GGCGGACACCTGTATTACGGTAGTAGGTGGCGTTACCCGGCATCCTATG ATTACTGGGGGCAGGGCACCCAGGTGACCGTTTCTAGC | 249. |
| DR904 | GAAGTCCAGCTGGTGGAGAGTGGCGGTGGCCTGGTACAGGCCGGTGGCT CCTTGCGCCTCAGCTGTGAGGCTTCCGAGAGCATTCTGTCCATCAACAC TATGGGATGGTTCCGTCAGGCCCCTGGGAAACAGCGTGAACTTGTAGCA | 250. |

TABLE 6-continued anti-IFNGR1 sdAb VHH DNA SEQUENCE HUMAN

| Name | Sequence | SEQ ID NO: |
|---|---|---|
| | GCGATCTCCTCTGGGGGCTCCACTAACTATGCGGACTCTGTCAAGGGTC<br>GTTTCACTATCAGCGGGACAACGCTAAGAACACAGTCTACCTCCAGAT<br>GAACAGTCTCAAGCCTGAGGATACAGCCGTGTACTATTGTGACGCCGAC<br>CGCGCCTATTACAAGGGGCAGGGAACCCAGGTGACCGTCTCCTCC | |
| DR905 | GAGGTGCAGCTGGTGGAGTCTGGCGGAGGTCTTGTGCAGGCTGGAGGCT<br>CTTTTGCGCCTTAGCTGCGTGGCGAGTGGCCGCACCTTCACCGGGTACGC<br>TATGGGTTGGTTCCGCCAGGCCCCCGGCAAGGAGCGTGAGTTCGTGGCA<br>GTCATCACCTGGAGCGGAGCGACCACTTATTACTCCGCTTCCGTGAAGG<br>GTCGCTTTACACTCTCTAGGGACAATGCCAAGAACACCGTTTACCTCCA<br>GATGAACTCCCTGAAGTCCGAAGATACCGCTGTGTATTACTGCGCTATT<br>CGCATCAGGGATGGCGTTAGCCCTGAAAATCCTAACGAGTACGGATACT<br>GGGGGCAAGGCACCCAGGTGACGGTCTCTTCC | 251. |
| DR906 | GAGGTGCAGCTGGTGGAGTCCGGGGGCGGACTCGTGCAGGCCGGAGGCT<br>CCCTGCGTCTGTCCTGCGCGGCCAGCGGTAGCACCTTCTCTACTTACGT<br>CATGGGTTGGTTCAGACAAGCACCCGGAAAAGAGCGGGAGTTCGTCGCA<br>GCCATCTCCCGCTCAGGAGGCACGACCACTTACGCTGATTCTGTGAAAG<br>GCCGTTTTGACATCTCCAGGGACAACGGCAAGAACACCCTCTTCTTGCA<br>GATGAACAGTCTGATCCCCGAGGACACCGCAGCTTATTACTGTGCCGCG<br>CGGGCTGGCCCAGCTATTGGTAGAACTGCAAACGACTATCACTCTTGGG<br>GGCAGGGTACGCTGGTCACTGTTTCTTCC | 252. |
| DR907 | GAGGTCCAGCTCGTCGAGAGCGGTGGCGGATTGGTACAGGCTGGCGGGT<br>CCTTGAGACTGAGCTGTGCCGCTAGTGGGAGGACTTTCTCCAACTATGC<br>AATGGGTTGGTTTAGACAGGCCCCTGGAAACGAACGCGAGTTCGTGGCC<br>GCAATCAACTGGAACATCGGTTCCACTTACTATGCCGATTCTGTTAAGG<br>GCCGTTTCACCATTAGCCGCGATAATGCAAAGAATACTGTATACCTGCA<br>AATGAACTCCTTGAAACCTGAGGACACTGCTGTCTATTACTGTGGGGCC<br>GTCTGGCCCACCGGCAGACTGAGGGTGGATTCCGAGTACGATTACTGGG<br>GCCAGGGGACGCAAGTTACCGTGTCTAGC | 253. |
| DR908 | GAGGTGCAACTCGTCGAGTCCGGCGGTGGCCTGGTTCAGGCTGGTGGCT<br>CCCTGAGAGTGACCTGTGCCGCGTCTGGCCGTACTTTTACCAGCTTGGC<br>TATGGGCTGGTTCAGGCAGGCTCCGGGCAAAGAGCGGGAGTTCGTCGCT<br>GCAATCAGCCGCTCTGGTGGCTCTACCGATTATGCCGACTCTGTCAAGG<br>GTCGTTTTTTCATCAGCAGGGACAACGCGAAGAGTACCCTGTACCTGCA<br>AATGTCAAGCCTGAAGCGGAAGATACAGCGGTATATTACTGCGCGGCT<br>AGGGACTACAGCACTCTCCAATACTATAACGAATATGAATACTCCGATT<br>GGGGCCAAGGCACCCAGGTAACTGTGAGTTCC | 254. |
| DR909 | GAGGTGCAGCTCGTGGAGAGCGGCGGTGGCCTGGTCCAAGCGGGCGGTA<br>GCTTGCGTCTGAGCTGTGCGGCCTCTGGCCGTACCTTCGGCACCAGCTT<br>CGGCGCTCTGTCTATGGGATGGTTTAGGCAGGCTCCTGGCAAGGAGCGG<br>GAGTTCGTTGCCGCAATCACCCGGAACACAGGTAGGACGTTCTACGCCG<br>ATAGTGTCAAGGATCGGTTTACAATTTCCAGGGACAACGCTAAGAACAC<br>CGCGTCTCTTCAGATGAACTCCCTTGAACCCGAGGATACAGCCGTCTAT<br>ATCTGTGCAGCTACCAACTCTTACGATGACTTGAGGCGTTCCTACGCCT<br>ACAACTACTGGGGTCAAGGGACTCAGGTCACCGTCTCCAGC | 255. |
| DR910 | GAGGTGCAGCTTGTAGAGAGCGGCGGTGGCCTGGTCCAAACCGGAGGCA<br>GTCTGCGCCTGTCTTGCGCTGCCAGCGGGCGGACTTTTTCCAGCTATGC<br>AATGGCGTGGTTCCGTCAGGCCCCTGGGAAGGAGCGCGAGTTTGTGGCT<br>GCCATCTCCATCCTGGGAGGCTCCGCCGACTACGAGGATTCCGTGCAGG<br>GCCGCTTTACGATTTCCAGAGATAATGCGAAGAACACCATGTATTTGCA<br>GATGAACTCCCTCAAGCCCGAGGACACCGCCGTGTATTACTGTGCAGCT<br>AGACGCCCCGCCCCATCCGACAGCTACTGGAGCAGTACAAGTTACGCTT<br>ACTGGGGTCAGGGTACGCTGGTCACCGTGAGTTCT | 256. |
| DR911 | GAGGTGCAGTTGGTGGAGTCCGGGGGCGCACTGGTTCAAGCTGGCGGTT<br>CCCTCAGACTGTCCTGCACCGTGTCTGGCCGCTCTTTCTCTACTTACGC<br>GATGGCGTGGTTCAGGCGTGCGCCCGGCAAGGAGCGTGAGCTGGTGTCC<br>GCGATTACAGTCGGGGGTGGGTCCACTTACTATGTGGACAGCGTGAAGG<br>GACGTTTACCATCTCCCGCGAGAACGCTAAGAACACACTCTACCTTCA<br>GATGAATAACCTGAAGCCTGAAGACACTGCTATCTACATCTGTGCCGCT<br>CGCGATTATCGGCGCAGAAGCTATGCCCCTGAGGCTGAGCAGTACGACT<br>ACTGGGGCCAGGGCACCCAGGTGACCGTGTCCAGC | 257. |
| DR912 | GAGGTCCAACTGGTCGAGTCTGGTGGAGGCCTGGTTCAGGCTGGGGGCA<br>GTCTGCGTCTGAGTTGCGCTCCCAGCGGACGCACCTTCAGTTCCTACGC<br>TATGGCATGGTTCCGCCAACCTCCCGGTAAGGAAAGGGAGTTTGTCGCC<br>GCGATCACAGTTTCTGGAGCGTCAACCTATTACGCCGACTCCGTGAAGG<br>GTAGGTTCACCATCAGCCGGGACAATGCTAAGAACAGCATGTACCTCCA<br>GATGAATAGCCTGAAGCCTGAGGATACGGCTGTGTATTACTGTGCAGCC | 258. |

TABLE 6-continued anti-IFNGR1 sdAb VHH DNA SEQUENCE HUMAN

| Name | Sequence | SEQ ID NO: |
|---|---|---|
| | GGTGGCCCTGGCACTATTTTTCCCGATTACGATTACTGGGGACAAGGCA<br>CGCAGGTCACCGTAAGCAGT | |
| DR913 | GAAGTGCAACTGGTCGAGTCCGGTGGAGGGCTGGTGCAGGCTGGTGGAT<br>TTCTGCGCTTGTCTTGCGCGGCTAGTGGCCGGACCTTCTCCAGTTATGC<br>GATGGGGTGGTTCCGCCAAATCCCTGGCAAAGAACGCGAACTGGTTGCC<br>GCAATCTCCTCTTGGAGCGGCGAAGTACTTACTATGCGGACTCTGTGA<br>AGGGGAGGTTTACCATTTCTAGGGACAATGCTAAAAACACCGTGTACCT<br>CCAGATGCTGTCTCTGAAGCCTGAGGACACCGCCGTGTATTACTGCACC<br>ACGGGAGACTATTACAGCGACTACTTCAAATATGACAACGAGAATTGGG<br>GGAAAGGCACGCAGGTGACCGTCTCCAGT | 259. |
| DR914 | GAGGTGCAGCTGGTGGAGTCCGGGGGCGGGCTCGTACAGGCTGGAGGTT<br>CCCTTACTCTGTCTTGTGTTGCCAGTGGAAGAGCCTTCTCCAATTCAGC<br>TATGGCCTGGTTCCGTCAGACCCCAGGGAAGGAGAGGGAGTTCGTGTCA<br>GCAATTTCACGCGGGGGCGGATCTACCGACTACGCAGACAGCGTGAAAG<br>GGCGCTTCACTATCTCTAAGGACAACGCCAAAAACACAGTGTACCTCCA<br>GATGAACTCCCTCAAGCCCGAGGACACAGCCGTGTATTACTGTGCTATG<br>AGGTATTACTCTGGCCGCTATTACGAGAGCTTGGAGTACGATTATTGGG<br>GTCAGGGCACTCAGGTGACCGTTTCTTCC | 260. |
| DR915 | GAGGTACAGCTGGTCGAGAGTGGCGGGGGTCTGGTGCAGGCCGGAGGGT<br>CTCTGAGGCTGAGTTGTGCCGCTGCCCGGCGCACTCTGCACAACTTTGC<br>TATGGCATGGTTCCGGCAGGCTCCGGGCAAGGAGAGGGAGTTCGTGGCT<br>GCAATTTCAAAGGGTGGCGGTAGTGCTGATTACGCTGACAGCGTGAAGG<br>GTCGCTTTACCATCTCAAGAGATAATGCGAAAAACACCGTGTATCTCCA<br>GATGAATAGCCTGAAGCCCGAGGACACTGCTGTCTATTACTGCGCTGCC<br>AACGACCTGGCGTCCTACTCCGACTCCTCTTATACATCAACTTCCCGTT<br>ATGACTACTGGGGACAGGGTACACAGGTTACTGTTTCCTCC | 261. |
| DR916 | GAAGTGCAGCTGGTGGAGAGCGGTGGGGGACTGGTGCAGCCCGGAGGCT<br>CCCCTTAGGCTGAGTTGCACCGCCTCTGGCCGTCCACGTACCACTTACGC<br>GATGGGTTGGTTCCGTCAGGCCCCAGGCAAGGAACGTGAAATCGTGGCG<br>GCCATCTCTAAGGCAGGAGGCTCAACCTACGTGGCTGATTCTGCGAAGG<br>GAAGATTCGCAATCTCTAAGGATAACGCCAAGAACACCGTGTACCTGCA<br>AATGAACTCCCTCAAGCCGGAGGATACCGCTGTCTATTACTGCGCTGCC<br>CGCGCTGGCTTTGCCGCTCAAATCTTCGAGTACGACTACTGGGGTCAGG<br>GGACCCTGGTTACCGTTTCAAGT | 262. |
| DR917 | GAGGTGCAGCTGGTGGAGTCTGGAGGTGGACTCGTGCAGGCCGGTGGCA<br>GCCTGCGCCTGAGCTGTGCGGCCAGCGGCAGAACATTCTCTGGATACAA<br>CATGGGGTGGTTTAGACAGGCCCCCGGCAAGGAACGCGAATTTGTCGCA<br>GCTATCGCCTGGGCAGGCTCTCGGACCTATTACACTGACAGTGTGAAGG<br>GACGCTTCACCATCTCACGCGACAATGCGAAAAATACCATGTACCTCCA<br>GATGAACACTCTGCGCCCCGAGGACACCGCTGTGTATTACTGTGCAGCG<br>CATGACGAGACTTACTATCGCCTCGATAGAGTGGATCTCTACACCCACT<br>GGGGGCAGGGCACGCTTGTTACCGTGTCTTCC | 263. |
| DR918 | GAGGTCCAGCTCGTGGAATCTGGCGGGGGTCTGGTCCAGGCTGGCGGAT<br>CTCTGAGGCTGTCTTGCGCAACCAGTGGTTTGACCGACTCCACCTATGG<br>CATGGCATGGTTCCGCCAGGCACCCGGAAAGGAACGGGAGTTTGTGGCT<br>GCCATTTCTCGGGCTGGCGGATCAGCGGACCACGCCGATAGTGTCAAGG<br>GCAGGTTTACCGTGAGTCGCGACAACGCCAAAAAGATGGTTTACCTCCA<br>AATGAACTCTTTGAAGCCTGAGGATACTGCCGTCTATTACTGCGCCAGT<br>GGCAGATCCTATTCTAGTCCCTACGATTATTTCAATGCTTTGGCTTATA<br>GCTACTGGGGCCAAGGCACACAGGTTACCGTATCCTCT | 264. |
| DR919 | GAGGTCCAGCTGGTGGAGTCTGGCGGGGGCCTGGTTCAGCCCGGTGGGT<br>TCCTCCGTCTGTCCTGCGCTGCCAGCCGCAGGACTCTGAGCACATACGC<br>TATGGGATGGTTTCGTCAAGCGCCCGGTAAAGAGAGGGAATTTGTCGCT<br>GCGATTAGCTGGAGGTCAGGGAATACCTACTATGCAGATAGCGTGAAAG<br>GTCGTTTCACCATCTCTCGCGATAACGCCAAGAACACCATGTACCTCCA<br>GATGAACAGCCTGAAGCCCGAGGACACCGCAGTTTACTATTGTGCCGCT<br>AACGAGGTCGCCACTATGTCCGCCCTCACGATCATTGGGGACAGGGCA<br>CCCTGGTGACTGTTTCCTCA | 265. |
| DR920 | GAAGTTCAGCTCGTGGAGTCTGGTGGAGGGCTGGTCCAAGCTGGCGGAA<br>GCCTCCGCCTGAGCTGCGCCGCATCTGGGCGCTCTTTCGCCAATTACGC<br>AATGGGTTGGTTCAGACAAGCCCCCGGTAAGGAGAGGGAGACGGTCGCT<br>GCCATCAGTCGCGGCGGAGGCTCTACTTGGTACGCGGACAGCGTAAAAG<br>GAAGATTCACCATTTCTAAAGATAATGCCAAGAATACCGTGTATTTGCA<br>GATGAACTCCCTGAAACCAGAAGATACTGCTATCTATTACTGCGCCGCT<br>AGATCCTACTCTGGATCTTACACGTATTCCTTCGGTGAGTACGATTACT<br>GGGGACAGGGTACTCAGGTCACCGTGTCCAGC | 266. |

TABLE 6-continued anti-IFNGR1 sdAb VHH DNA SEQUENCE HUMAN

| Name | Sequence | SEQ ID NO: |
|---|---|---|
| DR921 | CAAGTGCAGCTGGTTGAGTCTGGTGGAGGCCTGGTGCAGGCCGGTGACA GTCTGCGCCTGTCCTGTGCTGCCAGCGGTCGCACATTCACCTTTTCCAC CCATAACATGGGTTGGTTCAGGCAAGCTCCCGGAAAGGAGCGCGAGTTC GTGGGCGGTATCATGTGGACTTCACGCGCCAGCTATGCTGACAGCGTTA AGGGTCGTTTCACCGTCTCCCGCGACAACGCCAAGAATACAGTGTACCT CCAGATGAATAGTCTGAAGCCCGAGGACACCGCAGTATATTACTGCGCC GCAGCCTGGTATGGCAACAGTGGGGCCTCTTATGACTATTGGGGTCAGG GAACGCAGGTGACAGTCTCCAGC | 267. |
| DR922 | CAGGTGCAACTGGTTGAGTCTGGTGGCGGGCTGGTGAGGGCCGGTGGCT CCCTGAGGCTGAGCTGCGCTGCCAGCGGCAGCATCACCTCCATTAACAC TATGGGGTGGTTTCGTCAGGCTCCGGGCAAGCAGCGTGAACTCGTGGCT GCCATTACTAGCGGCGGGAGCACCAACTACGCCGATTCAGTCAAGGGTA GATTCACAATTTCCCGCGACAACGCCCGGAACACCGTGTATCTCCAGAT GTATTCCCTGAAGCCGGAGGATACCGCTGTCTACTATTGCGAGGCAGAT AGCATGTACTTCCGGGGCCAGGGAACCCAAGTGACCGTTTCCAGC | 268. |
| DR923 | CAGGTACAGCTGGTTGAATCCGGCGGTGGCTTGGTGCAAGCCGGAGGCA GTCTCCGCCTGTCCTGCGCTGCGAGTCGGCGCACGTTTATGACCTACGC GATGGGATGGTTCCGCCAGGCTCCAGGTAAGGAGAGAGAGTTCGTCGCT GCCATCTCCTGGTCCTCTGGCAGCACTTACTATGCCGACTCTGTAAAAG GCCGTTTCACCATCAGCCGCGACAACGCTAAAAATACAATGTATCTCCA GATGAACTCCCTGAAGCCTGAGGATACAGCCGTGTATTACTGCACTGCA TCTTCCATCGCAACCATGTATGGTCCTAACGACTACGCTGGTCAGGGAA CCCTTGTAACAGTCTCCTCC | 269. |
| DR924 | CAGGTCCAGCTGGTTGAGAGTGGAGGCGGGCTGGTGCAAGCCGGAGGCT CCCTCAGACTGTCCTGCACGGCCAGCGGTCGCACTTTTTCCCGCTATGC TATGGGTTGGTTTCGGCAGGCACCAGGCAAAGAGAGAGAGTTCGTGGCG ACCATCAGCCGCAGCGGCGGGACGACCAGTTACGCTAATAGCGTCAAGG GGCGCTTCACGATTTCCCGCGACAACGCTAAGAACACGGTGTACCTCCA GATGAACTCCTTGAAAACAGAAGACACCGCCGTTTATAACTGTGCTGCG CGGGACGGCCCTGCTATGGGCGTGTTCGGGTCTGACTACGACTACTGGG GCCAGGGGACACTGGTGACCGTCTCTTCC | 270. |
| DR925 | GAGGTGCAGCTGGTGGAGAGTGGAGGTGGACTGGTGCAAGCGGGCGGTA GTCTCGTACTGAGCTGCGCTGCCTCAGGCCGCACTTTCAGCCGGTACGC GATGGGTTGGTTCAGGCAGGCCCCAGGCAAGGAACGCGAGTTTGTCGCT GCCATCTCCATCGGGGAGGCAGCGCTGACTACGCCGACACTGTAAAGG GTCGCTTCACCATCTCACGGAATAACGCTAAGAATACCATGTACCTTCA GATGAACTCACTGAAACCGGAAGACACTGCGGTGTACTATTGCGCCGCA CGTACCCCTCGCCCTAGCTCCAGCTACTTCACACCTCAGGACTACGAAT ACTGGGGCCAGGGCACACTGGTGACCGTTAGCAGT | 271. |
| DR926 | GAGGTGCAACTGGTGGAGTCTGGTGGCGGTTTGGTGCAGGCCGGTGGGT CTCTGCGCCTGAGTTGCGCTGCCTCTGGCCGGACATTCAGCCGTTACGC TATGAACTGGTTTCGTCAGGCTCCCGGCAAAGAGAGAGAGTTCGTGGCT GCAATCAGCTGGTCATCCGGCAACACCTATGTGGCTGACTCAGTGAAGG GCCGCTTCACTATTTCCAGAGACAACGCCAAGAATACGATGTATCTTCA GATGAATAACCTTGCGCCGGAGGACACCGCCGTGTACTATTGTGCTGCA ACAACCATCGCTACCATGAGTGACGAGAACACATATTGGGGACAGGGAA CCCAGGTGACTGTCTCCAGC | 272. |

TABLE 7 anti-IFNGR2 sdAb VHH DNA SEQUENCE HUMAN

| Name | Sequence | SEQ ID NO: |
|---|---|---|
| DR927 | CAGGTGCAGCTGGTGGAGAGCGGAGGCGGACTGGTACAAGCAGGGGGTT CTCTCAGGCTGAGCTGTGCGGCTTCCGGGAGGACTTTCACCTCTTATGC TATGAATTGGTTCCGCCAGGCCCCTGGGAAGGAAAGGGAGTTTGTGGCA GCCATCTCTTGGTCCAGCGGCAATACCTACGTGGCCGACTCCGTCAAGG GTAGGTTCGCCATCAGCCGGGACAAAGCTAAGAATACTATGTACTTGCA GATGAACAGCCTCGCGCCGGAAGATACTGCGGTGTATTACTGCGCCGCT ACTACCATCGCCACGATGTCCGACGAGTATACATATTGGGGACAGGGAA CTCAGGTTACAGTATCCTCC | 273. |
| DR928 | CAGGTCCAGCTGGTCGAATCCGGTGGCGGGTTGGTACAGGCGGGTGGCT CCCTGCGCCTGAGCTGCGCCGCGAGTGGGCGTACATTTTCTAACTACAG AATGGGCTGGTTCAGGCAGGCTCCGGGAAAGGAGCGTGAGTTCGTGGCT | 274. |

TABLE 7-continued anti-IFNGR2 sdAb VHH DNA SEQUENCE HUMAN

| Name | Sequence | SEQ ID NO: |
|---|---|---|
| | GCCATTTCACGCGGAGGTGGCACCACACTGTACGCCGACTCTGTCAAAG<br>GCCGCTTCACCATCTCTCGCGACAACGCTAAGAATACTGTTGATCTCCA<br>GATGAACCGCCTGAAGCCGGAAGACACCGCAGTTTACTTTTGTGCCGCA<br>GGCGATTTCTCTACCACTTGGGACGAGTATAACTACTGGGGGCAGGGAA<br>CACAAGTGACCGTGTCCAGT | |
| DR929 | CAGGTTCAACTGGTGGAGAGCGGTGGGGGCCTGGTGCAGGCAGGCGGGA<br>GCTTGCGGCTTTCATGTGTTGCATCTGGCCGCACCTTCTCAAGCTATGC<br>GATGGGCTGGTTCCGTCAGACTCCGGGGAAAGAGAGGGAGTTCGTGAGC<br>GCGATTTCTCGCGGTGGAGGCAGCACCGACTATGCCGATTCCGTGAAGG<br>GCAGGTTTACGATCTCCAGAGATAACGCCAAGAACACAGTTTATTTGCA<br>GATGAATAACCTGAAATCCGAGGACACCGCAGTGTATTACTGCGCCCTG<br>CGGGCCTATTCAGGCCGCTATTACCAGTTCCTGGAGTACGATTACTGGG<br>GCCAGGGCACACAGGTGACTGTGTCCTCC | 275. |
| DR930 | GAGGTTCAGTTGGTGGAGTCTGGGGGCGGTCTGGTCCAGGCTGGTGGAT<br>CATTGCGCCTGAGCTGTACCGTTTCAGGCAGGACTTTTTCTAGCTACGC<br>CGTAGCTTGGTTCCGCCAGGCACCTGGCAACGTCCGGGAGCTGGCGGCT<br>GCCCTGAGTCGCGGGGAGGCTCTGCTTACTATACAGACAGTGTCAAGG<br>GTCGCTTCACTATTAGCCGCGACAATGCGAAAAACACCGTCTACCTTCA<br>GATGAACAGTCTGAAGCCCGAAGACACTGCGGTGTATTACTGCGCGGCC<br>AGGAACTACGACGGCACCTATTACCAGGAAAACCAATACAATTACTGGG<br>GGCAGGGAACCCAGGTGACCGTCAGCAGC | 276. |
| DR931 | CAGGTCCAGCTGGTGGAATCAGGCGGAGGCTTGGTGCAGGCCGGGGGCA<br>GTCTGTTGCTGTCTTGCGCCGCGAGCGGACGCACATTCTCCACCTACGC<br>TATGGGGTGGTTCCGCCAGGCACCTGGAAAAGAACGCATGTTTGTCGCG<br>GCCATCTCCGTTAACGGAGGCAGTACCTACTATGCAGATTCTGTTACGG<br>GCCGTTTCACCATTAGCCGCGACAATGCGAAAAACACCATGTATTTGCA<br>AATGAATAACCTGAAGCCTGGTGACACAGCCGTGTATTACTGCGCAGCG<br>CGTCGCCCCTACCCCGGTTCCGACTTTCTCACATGGGCCTCCTACGATT<br>ACAGGGGCCAGGGCACCCTGGTGACCGTGTCTAGT | 277. |
| DR932 | CAGGTTCAGCTGGTCGAATCTGGCGGTGGACTGGTGCAAGCTGGTGGGT<br>TCCTGCGCCTCAGCTGTGCCGCTAGTGCCGTACCTTTAGCTATACAAC<br>CATCGGCTGGTTCCGCCAGGCTCCAGGGAAGGAACGCGAGTTCGTCGCC<br>GTGATCTCAGCAGGAGGCGGTTCCCGCGATTACGCGGACGCCCTCAAAG<br>GACGCTTTACAATCTCTCGCGATAACGCTAAAAAGATGGTTTATTTGCA<br>AATGAATAACTTGAAGCCCGAGGATACCGCCGTGTATTACTGCGCCGTG<br>AGGCGGAATACTGACACATATACCACAACCGGCGACTACGACTACTGGG<br>GTCAGGGCACCCAGGTTACCGTTTCATCC | 278. |
| DR933 | CAAGTTCAGCTTGTAGAGTCTGGCGGGGGCCTGGTGCAACCCGGTGACT<br>CACTGAGGCTGTCTTGTGTGGCCTCCGGGGGTACAATTTCCTCACTGGC<br>TATGGGTTGGTTCAGGCAGGCTCCGGGTAAGGAGAGGGAGTTTGTCGCA<br>GCCATCAGCTGGTCTGGCCGCTCAACATATTACGTGGATAGCGTGAAAG<br>GCCGCTTCACTATTTCTACTGATAACGCGAAGAATACCGTGTATCTCCA<br>AATGAACTCCCTGAAACCGGAGGACACAGCGGTGTACTATTGCGTCGCA<br>GGCGAGGATGGACACAGCGAGTATGACTATTGGGGCCAAGGCACCCAGG<br>TCACAGTGTCCTCA | 279. |
| DR934 | CAGGTGCAGCTTGTGGAGAGCGGAGGCGGGCTGGTGCAGGCCGGGGGTA<br>GCTTGCGCCTCAGCTGTGCTGCCTCTGGACGCTCATTTGCCAACTACGC<br>AATGGGCTGGTTCCGTCAGGCTCCTGGGAAAGAGCGCGAGACCGTGGCG<br>GCCATCAGTCGCGGGGAGGCAGCACGTGGTACGCGGACTCAGTCAAGG<br>GGAGGTTTACTATTTCCAAGGATAACGCTAAGAACACCGTGTATCTGCA<br>AATGAACAGCCTCAAGCCCGAGGACACAGCAATCTACTATTGCGCGGCC<br>CGCAGTTACTCCGGCTCCTACACTTATTCCTTCGGCGAGTACGACTACT<br>GGGGTCAGGGCACCCAAGTTACCGTGTCCTCC | 280. |
| DR935 | CAGGTGCAGCTGGTTGAGTCTGGAGGCGGTCTTGTCCAGGCTGGTGGCT<br>CCTTGCGCCTGAGCTGTGCCGCTTCCGGGAGAGCTTTCTCCACATACGC<br>TCTCGGCTGGTTCAGGCAGGCCCCCGGAAAGGAGCGCGAGTTCATCGCT<br>GCAATCAGCCGGGCGGTGGCAGCACTGATTATGCAGATTCTGTGAAGG<br>GACGCTTCACCATCTCTCGTGATAACGCCAAGTCTACCGTATATTTGCA<br>GATGAATAGTCTGAAGCCCGAAGACACCGCTGTGTATTACTGTGCAGCG<br>CGTAGCTACTCCTCAGTTACTATTACTCTCAGTACGAGTACGACTACT<br>GGGGACAGGGTACTCAGGTGACTGTGTCCAGC | 281. |
| DR936 | GAGGTCCAGCTCGTGGAGAGTGGCGGTGGCCTCGTGCAGGCCGGGGGCT<br>CCCTGAGACTGAGTTGTGCCGCTTCTGGCCGCACCTTCAGTTCAGTCGC<br>TATGGCTTGGTTTCGGCAGGCCCCTGGCAAGGAGCGCGAGTTCGTGTCC<br>GCTATCAGTTCTGGAGGCGGTTCCACGGATTACGCTGATAGCGTGAAGG<br>GCAGATTCACTATCAGCAAGGACAACGCTAAGAACACCATGTATCTCCA<br>GATGGACTCTCTTAAACCCGAGGATACCGCCGTGTATTACTGCGCCGCT | 282. |

TABLE 7-continued anti-IFNGR2 sdAb VHH DNA SEQUENCE HUMAN

| Name | Sequence | SEQ ID NO: |
|------|----------|------------|
| | CGCGACTATTCTAGCCGTCGCTATTACCAGTCCCGGTACGAGTACGACC<br>TCTGGGGCCTGGGAACCCAAGTCACAGTCTCCTCC | |
| DR937 | CAGGTGCAGTTGGTGGAGTCCGGTGGGGGCCTGGTGCAGCCAGGTGGAA<br>GCCTCCGCCTGTCCTGTGCTGCAAGTGGCCGCACCTTTAGGTCCTACTC<br>AATGGGCTGGTTTCGTCAGGCTCCAGGAAAGGAACGGGAGTTCGTTGCC<br>GCTATTTCCTGGTATTCCGGGACAACGTACTATGCCGACCCAGTCAAGG<br>GTAGATTCACTATCAGCCGGGACGATGCAAAGAACACTCTCTACTTGCA<br>GATGAACTCCCTGAAGCCCGAGGACACCGCCGTGTATTACTGCGCGGCT<br>AACGAGATCGCCACAATGGAATCCTCTAACGATTACTGGGGCCAGGGGA<br>CCCAGGTTACCGTCTCTAGC | 283. |
| DR938 | CAGGTGCAGCTGGTCGAGAGTGGAGGGGGATTGGTCCAGCCTGGTGGCT<br>CTCTGCGCCTGTCATGCACTGCTTCAGGCCGCCCCCGTACAACGTATGC<br>AATGGGCTGGTTCCGTCAGGCTCCCGGCAAGGAGCGCGAGATCGTGGCG<br>GCTATTTCCAAAGCCGGAGGCTCTACCTACGTGGCCGACTCTGCGAAAG<br>GCCGCTTTGCCATCTCTAAGGACAACGCCAAGAATACCGTCTATCTGCA<br>AATGAACAGCCTCAAGCCTGAGGATACCGCAGTTTATTACTGTGCAGCT<br>CGCGCAGGCTTCGCTGCCCAAATCTTCGAGTACGACTACTGGGGACAGG<br>GCACCCTGGTGACAGTGTCTAGC | 284. |
| DR939 | GAGGTTCAACTGGTCGAGTCCGGGGGCGGGCTCGTGCAGGCCGGAGGTT<br>CCATGCGCCTGTCCTGTGCCAATTCCGGTAGAACCTTTGGGACCTATGC<br>TATGGGCTGGTTCCGCCAGTCACCCGGCAAAGAGCGCGAGCGGGTCGCG<br>TCCATCGACCGTGACGGTTCTATGTCCTATTACGCCGACAGCGTGAAAG<br>GCAGGTTCACAATCAGCGGAGACAATGCGAAGAACACCGTGTATCTCCA<br>GATGAACTCCCTGAAACCTGAGGACACCGCCGTCTATTACTGCGCGGCT<br>TCAAGACGCGCCGTTATTTCTCTCCAGACAGTTGATTACTGGGGCCAGG<br>GAACCCAGGTGACTGTGTCCAGC | 285. |
| DR940 | GAAGTGCAGCTCGTGGAGTCTGGTGGCCGTTTGGTCCAGACCGGAGGCA<br>GCTTGAGGCTCTCATGCGCTGCCTCTGGCAGGACATTTTCCAATTATGC<br>AATGGGATGGTTTCGTCAGGCTCCTGGCAAGGAGAGGGAGTTCGTGGCT<br>GCAATCTCTTGGTACAGCGGCAACACATACTATGCCGACTCCGTGAAAG<br>GCAGGTTTACCATCAGCGGGATAACGCCAAAAACACTATGTATCTCCA<br>GATGAACTCCCTGAAGCCAGAGGATACGGCGGTCTATTACTGTGCAGCC<br>AATCAAATCGCCACTATGATTAGCGTGGGCGACTACTGGGGCCAAGGCA<br>CCCTGGTGACAGTGTCATCC | 286. |
| DR941 | CAGGTGCAGTTGGTCGAGTCAGGAGGGGGCCTGGTCGAGGCCGGGGGCT<br>CCCTGAGGCTCGCTTGCGCTGCGAGTGGATCAATCTTCCGTTTGAACCT<br>GATGGGATGGTATAGACAGGCTCCTGGCAAGCAGCGTGAACTGGTCGCA<br>CACGTGGGTACTACAGGAAACACCGCCTACGCCGACTCTGTCAAGGGGC<br>GCTTTACCATCTCAAAGGACGATGCTAAGAACATGGTGTTTCTCCAGAT<br>GAACTCCCTCAAGCCCGAGGATACTGCCGTCTATTACTGCTATGCGGAC<br>CGCTGGGGTCAGTTCTCCTGGGGCCAGGGAACACAGGTAACCGTTTCTT<br>CA | 287. |
| DR942 | CAGGTGCAGCTCGTGGAGTCTGGCGGTGGCCTGGTCCAGGCCGGAGGCA<br>GCTCCGGTTGAGCTGTGTAGCTAGTGGCCGTACCTTTACGGGCTACGC<br>GATGGGCTGGTTCAGACAAGCGCCTGGCAAGGAGAGGGAGTTCGTCGCC<br>GTGATTACTTGGTCCGGGGCCACTACCTATTACTCCGCTTCCGTGAAGG<br>GCCGTTTCACGCTGAGCCGGGATAACGCCAAAAACACAGTGTACCTCCA<br>GATGAACTCCCTGAAGTCCGAGGACACTGCCGTTTATTACTGCGCCATT<br>CGCATCCGGGACGGAGTGTCTCCTGAAAACCCTAACGAGTACGGTTACT<br>GGGGCCAGGGCACCCAGGTAACCGTGTCCTCA | 288. |
| DR943 | CAGGTCCAGCTCGTGGAGTCCGGCGGGGGCTTGGTTCAGGCTGGGGGAA<br>GCCTGCGTCTGTCATGCGTGGCGAGCGGGAGGACCGTCGGCTACGGCAT<br>GGCTTGGTTTAGGCAGGCTCCTGGCAAGCAACGCGATGTTGTGGCCGCG<br>ATCACTTGGTCCGGCACTTCCACCTATTACCCCGACTCAGTCAAGGGGC<br>GCTTCACCATCTCCAGAGATAACGCCAAGAACACTATGTATCTCCCAGAT<br>GTCATCTCTGAAGCCAGAAGATACCGCTGTATATTACTGCGCCGCTGGC<br>TCCCGTCGCCGGGTGGGCGTGGACGTGGGTGGATACGACTACTGGGGCC<br>AAGGCACTCAGGTGACCGTCTCCAGC | 289. |
| DR944 | CAGGTGCAGCTCGTCGAGAGCGGGGCGGACTGGTACAGGCTGGCGACT<br>CCTTGCGTCTGAGCTGCGCCGCGTCCGGCAGGACGTTCACCTTCTCAAC<br>TCACAATATGGGCTGGTTCCGTCAGGCACCGGGTAAGGAGAGAGAGTTC<br>GTCGGAGGCATCATGTGGACCAGCCGGGCAAGTTACGCCGATTCTGTGA<br>AGGGTCGTTTCACCGTAAGCCGTGATAACGCGAAGAACACTGTCTACTT<br>GCAGATGAACTCTCTGAAGCCCGAGGACACTGCGGTTACTATTGCGCT<br>GCCGCATGGTATGGTAACAGCGGAGCCTCCTACGACTACTGGGGTCAAG<br>GAACTCAGGTCACGGTCAGCTCC | 290. |

TABLE 7-continued anti-IFNGR2 sdAb VHH DNA SEQUENCE HUMAN

| Name | Sequence | SEQ ID NO: |
|---|---|---|
| DR945 | CAGGTCCAACTGGTCGAGTCTGGCGGAGGCCTCGTGCAACTTGTTCAAG CCGGGGGCAGCCTGCGCCTTTCTTGTGCTGCGAGTGGCCGCACCTTTTC CGGGTATAACATGGGTTGGTTTCGTCAGGCCCCAGGTAAGGAGCGCGAG TTCGTGGCTGCCATTGCTTGGGCAGGCAGCAGGACATATTACACCGATA GCGTCAAGGGGCGGTTTACTATCTCTCGCGACAATGCAAAAAACACTAT GTACCTCCAGATGAACACCCTGCGTCCTGAGGATACAGCCGTGTATTAC TGCGCAGCCCATGACGAGACCTATTACCGCCTTGACCGGTGGACCTCT ATACCCACTGGGGCCAGGGAACCCAGGTCACTGTGTCCTCC | 291. |
| DR946 | CAGGTGCAACTGGTTGAGTCCGGGGGCGGACTGGTGCAACCTGGCGAGA GTCTGCGCCTGTCCTGCGCGGCCTCCGGTCCTTTTACTAGATATGCGAT GGGTTGGTTCCGTCAAGCGCCTGGGAAGGAGCGTGAGTTCGTCGCGGCT ATCAGCTGGTCATCTGGAAATACGTATTACGTGGATTCCGTGAAGGGCA GGTTCACTATTTCCAGAGACAACGCTAAGAACACAATGTACTTGCAGAT GAACAGCCTGAAGCCAGAGGACACAGCGGTTTACTATTGTGCTGCAAAC GAGGTCGCCACCATGAGTGGACCCGATGACTATTGGGGACAAGGTACAC AAGTCACTGTGTCCTCT | 292. |
| DR947 | CAGGTGCAGCTGGTGGAGTCTGGAGGTGGGCTGGTGCAGGCGGGAGGCT CTCTGCGTCTGTCTTGTGCTGCCAGCGGCGGTTCCTTTGGCCGGTACAC AATGGGATGGTATCGTCAAGCGCCTGGTAAGGAGCGCGAGTTTGTTGCT GTGATCTCATGGAGCGGCACAAACACGTACTATGCGGACAGCGTGAAGG GTCGCTTTACCATTTCCCGTGATAACGCGAAGAATACCATGTACCTGCA AATGAACGATTTGAAACCCGAAGATACCGCAGTTTATTACTGTGCTGCG CGTGAGACTTATTACTCACACTGGGACGAAAGGATGGAGTATGACTATT GGGGCCAGGGCACCCAGGTTACAGTATCTTCC | 293. |
| DR948 | CAGGTCCAGCTCGTAGAAAGCGGAGGTGGCCTTGTCCAAGCTGGCGACA GCCTGCGCCTTTCCTGCGTTGCCAGCGGCTCCATCGACTCATCCTATTA CGTGTCTTGGTTCCGTCAGGCACCAGGCAAGGAACGTGATCTGGTAGCT GCCATCAACTGGGGCGATTCTCGCACCGCCTATGCTGACTCCGTTAAGG GCCGGTTCACGATCTCCCGTGATAACGCGAAAAATACTGTGTATCTCCA GATGCACTCCCTGCGCCCCAACGATACCGCAGTGTATTACTGTGCCAGC AGAATTGGGCTGGGCGGCCGGTGGTTGCGGCCCCCACCCGTTATCCCT ATTGGGGCCAGGGCACCCTGGTAACCGTGTCTTCC | 294. |
| DR949 | CAAGTGCAACTGGTAGAGTCAGGCGGTGGCCTTGTGCAGGCCGGTGGCT CTCTGCGCCTGTCTTGCGCTGCCTCTGAGTCTATCTTGCGGTTTAACGT GATGTCATGGTTGCGTCAGGCACCAGGGAAACAGCGTGAGCTGGTGGCA GTCATCACTAGCGGTGGCAGCACGAATTATGCAGACTCCGTGAAAGGCC GCTTCACGATCTCTCGTGACAACGCTAAAAACACCGTGATCTCCAGAT GAACAGCCTGAAGCCAGAAGACACTGCCGTGTATTACTGTGCTGCCGAC GAGAGCGGGCAGTATTACTGGGACAGGGCACTCAGGTGACAGTCAGCA GC | 295. |
| DR950 | CAGGTCCAGCTCGTGGAGTCTGGGGGCGGTCTCGTCCAGGCTGGGGGTT CCCTGCGGCTGAGCTGTGCCGCTTCTGGCTTGACGACCAGTAGCGCCGC TCTGGCCTGGTTTCGTCAGGCTCCTGGCAAGGAGCGTGAGCTTGATCCA ACTATTACCAGCGGCGGAGGCTCTACCTACTATGCCGACAGCGTTAAGG GTCGGTTTACCATCAGCAAAGACAACGCTAAGAACACTCTTTATCTCCA GATGTCAAGCCTCAAACCTGAGGACACCGCCGTCTACTATTGCGCCGCT CGCTTTTATAGCACCACTTACTATTACCGCGAACACGAGTATAGTGACT GGGGGCAGGGCACCCAAGTCACAGTGAGCAGC | 296. |
| DR951 | CAGGTGCAACTGGTGGAATCTGGGGGTGGCTTGGTGCAGGCTGGCGGGT CTCTGCGTCTGTCCTGTGCGGCTTCAGGACGCACTTTCGGCACCAGCTT TGGCAGCCTGAGCATGGGCTGGTTCAGACAAGCCCCCGGCAAAGAGCGT GAGTTCGTGGCTGCCATCTCTCGCAACATTGGCCGTACTTATTACGCAG ATTCCGTGAAAGACAGGTTTACGATCTCTCGCGACAACGCTAAGAATAC CGCCTCTCTTCAGATGAACTCTCTGGAGCCCGAAGACACTGCTGTCTAT AATTGTGCCGCGACAAACTCCTACGATGACCTTAGGCGCTCCTACGCCT ACGACTACTGGGGACAGGGCACCCAGGTGACAGTCAGCTCC | 297. |
| DR952 | CAGGTCCAGCTGGTGGAGAGCGGCGGTGGGCTGGTTCAGGCTGGAGGCT TCCTGCGCCTGTCTTGCGCTGCCTCAGGTCGTACTTTTTCCTCTTTGGC AATGGCTTGGTTCCGTCAAGCTCCCGGCAAGGAGCGCGAGTTCGTAGCC GCTATCTCCCGCTCTGGAGGCTCTACCGACTACGCTGACAGCGTCAAGG GACGCTTCACCATCTCTCGGGACAACGCCAAGTCCACCCTGTACTTGCA GATGTCTAGCCTGAAACCTGAGGATACAGCGGTGTATTACTGCGCTGCA CGTGACTACTCTCCAGTATTACAATGAGTATGAATACTCCGACT GGGGCCAAGGCACTCTGGTCACTGTGTCCTCA | 298. |
| DR953 | CAGGTGCAGCTCGTAGAGTCTGGCGGTGGCCTGGTCCAGGCTGGGGACT CACTGCGTCTGAGTTGTGCCGCGTCCGGCCCTACCTTCAGTACGTATGC AATGGCCTGGTTTCGCCAAGCTCCAGGTAAGGAACGCGAGTTCGTGGCT | 299. |

TABLE 7-continued anti-IFNGR2 sdAb VHH DNA SEQUENCE HUMAN

| Name | Sequence | SEQ ID NO: |
|---|---|---|
| | GCCATTACCCAGAGTGGTCGCACCACTTACTATGAAGATTCTGTGAAGG<br>GGCGGTTCACCATTAGCAAGGATAATGCCAAGAACACCCTCTATCTCCA<br>GATGAACAGCCTCCAGCCTGAAGATACGGCGGTGTATTACTGCGCGGCC<br>CGCGACTTGTGGTCTGATTCTCCCGATGACTGGAGAATTTACTCTTTCT<br>GGGGACAGGGGACCCAAGTAACAGTCAGTTCC | |
| DR954 | CAGGTTCAGCTTGTGGAGTCCGGTGGCGGTCTGGTCCAGGCAGGTGGCT<br>CCCTGCGGCTGTCTTGCGCAGCCGCTCGTCGCACACTGCACAACTTCGC<br>AATGGCGTGGTTTCGCCAGGCCCCTGGTAAGGAGAGGGAGTTTGTGGCT<br>GCCATTTCTAAGGGAGGCGGTTCCGCCGACTACGCCGATAGCGTTAAGG<br>GGCGCTTTACCATTAGTAGGGACAACGCTAAGAACACAGTGTACCTCCA<br>GATGAACAGCCTCAAGCCAGAGGATACCGCAGTTTACTATTGCGCTGCC<br>AACGATCTGGCTTCTTATAGCGACAGCTCTTACACATCCACAAGCCGCT<br>ACGACTACTGGGGTCAGGGCACCCAGGTTACAGTGTCCTCT | 300. |
| DR955 | CAGGTGCAGCTCGTCGAGTCTGGCGGGGACTGGTGCAGACTGGTGGCT<br>CCCTGCGCCTCTCTTGCGCGGCCTCTGGCCGCACCTTCTCATCCTATGC<br>TATGGCTTGGTTCCGTCAAGCGCCCGGTAAAGAGAGGGAGTTTGTGGCC<br>GCTATCTCTATCCTCGGTGGCAGCGCTGACTACGAGGATTCCGTTCAGG<br>GACGCTTCACTATCTCAAGAGATAACGCCAAGAACACTATGTACCTTCA<br>GATGAACTCCCTCAAGCCAGAGGACACCGCTGTGTATTACTGTGCCGCT<br>CGCAGACCGGCTCCCTCCGACAGCTACTGGAGCAGTACAAGTTACGCAT<br>ACTGGGGACAGGGGACCCTGGTGACAGTGTCCAGT | 301. |
| DR956 | GAGGTACAGCTGGTCGAATCCGGTGGCGGTCTGGTGCAGGCTGGCGGAA<br>GCCTGCGCTTGAGCTGTGCGGCCTCTGGCCGCACTTTCAGCTCTCTTGC<br>AATGGCGTGGTTCCGCCAGGCCCCTGGAAAGGAGCGCGAGTTCGTGGCC<br>GCGACCACAATCCTCGGAGGCTCCGCCGACTACGGCGACCCGGTCAAGG<br>GCCGCTTCACAATCTCCCGCGATAATGCTAAGAACACGGTGTATCTCCA<br>GATGAACTCACTGAAGCCAGAGGATACCGCCGTTTATTACTGCACTGGG<br>AGACGCCCCGCTCCATCCGACAACTACTGGTCCCCTGCCAGCTATGCTT<br>ACTGGGGACAAGGCACCCAAGTTACCGTGAGCAGT | 302. |
| DR957 | CAGGTGCAGTTGGTGGAAAGCGGCGGTGGCCTTGTGCAGGCTGGCGGTT<br>CACTGCGCCTCAGCTGCGCACCTTCCGGTCGCACCTTCTCCTCTTACGC<br>GATGGCGTGGTTTCGCCAGCCTCCAGGCAAGGAACGGGAGTTTGTGGCT<br>GCCATTACCGTTTCCGGCGCAAGTACCTATTACGCTGACTCTGTTAAGG<br>GCCGTTTCACCATCTCTCGCGATAATGCGAAAAACTCTATGTACCTTCA<br>GATGAACTCTTTGAAACCGGAGGATACCGCTGTGTACTATTGTGCAGCT<br>GGCGGTCCCGGAACCATCTTCCCAGACTATGATTACTGGGGTCAGGGTA<br>CTCAGGTCACCGTCTCCTCC | 303. |
| DR958 | CAAGTACAGCTCGTCGAATCCGGCGGTGGACTGGTGCAGGCCGGAGATT<br>CCCTTACCCTGTCTTGCACCGCTTCCGGTCGCACCTTTTCAGGTTACAA<br>TATGGGCTGGTTCAGGCAGGCCCCTGGTAAGGAGCGCGACTTCGTCGCT<br>GCCATCAACTGGATCGGAGGTGCTACCTATTACGCGGATAGCGTGAAAG<br>GCCGCTTTACCATTAGCAGGGATAATGCCAAGAACACTGTCTACCTGCA<br>AATGAACAGCCTGAAGCCCGAGGATACTGCCGTGTATTACTGCCATCGC<br>TATTCCGAGAAGTTCTACAGCGGGAAGGACTACTATACTCGTGACTACG<br>ACTACTGGGGTCAGGGTACACAGGTAACTGTGTCCTCA | 304. |

What is claimed is:

1. An IFNG receptor (IFNGR) binding molecule that specifically binds to IFNGR1 and IFNGR2,
   wherein the binding molecule causes the multimerization of IFNGR1 and IFNGR2 when bound to IFNGR1 and IFNGR2,
   wherein the binding molecule comprises a single-domain antibody (sdAb) that specifically binds to IFNGR1 (an anti-IFNGR1 sdAb) and a sdAb that specifically binds to IFNGR2 (an anti-IFNGR2 sdAb),
   wherein the anti-IFNGR1 sdAb comprising a CDR1, a CDR2, and a CDR3 in a single row of the following table:

| Name  | CDR1         | SEQ ID NO: |
|-------|--------------|------------|
| DR903 | RIASDYTRG    | 25         |
| DR904 | SILSINTMG    | 26         |
| DR905 | RTFTGYAMG    | 27         |
| DR906 | STFSTYVMG    | 28         |
| DR907 | RTFSNYAMG    | 29         |
| DR908 | RTFTSLAMG    | 30         |
| DR909 | RTFGTSFGALSMG| 31         |
| DR910 | RTFSSYAMA    | 32         |
| DR911 | RSFSTYAMA    | 33         |
| DR912 | RTFSSYAMA    | 34         |
| DR913 | RTFSSYAMG    | 35         |
| DR914 | RAFSNSAMA    | 36         |
| DR915 | RTLHNFAMA    | 37         |
| DR916 | RPRTTYAMG    | 38         |
| DR917 | RTFSGYNMG    | 39         |
| DR918 | LTDSTYGMA    | 40         |
| DR919 | RTLSTYAMG    | 41         |
| DR920 | RSFANYAMG    | 42         |
| DR921 | RTFTFSTHNMG  | 43         |
| DR922 | SITSINTMG    | 44         |
| DR923 | RTFMTYAMG    | 45         |
| DR924 | RTFSRYAMG    | 46         |
| DR925 | RTFSRYAMG    | 47         |
| DR926 | RTFSRYAMN    | 48         |

| Name  | CDR2              | SEQ ID NO: |
|-------|-------------------|------------|
| DR903 | AIIRSVGDSYYADSVKG | 49         |
| DR904 | AISSGGSTNYADSVKG  | 50         |
| DR905 | VITWSGATTYYSASVKG | 51         |
| DR906 | AISRSGGTTTYADSVKG | 52         |
| DR907 | AINWNIGSTYYADSVKG | 53         |
| DR908 | AISRSGGSTDYADSVKG | 54         |
| DR909 | AITRNTGRTFYADSVKD | 55         |

| Name | | SEQ ID NO: |
|---|---|---|
| DR910 | AISILGGSADYEDSVQG | 56 |
| DR911 | AITVGGGSTYYVDSVKG | 57 |
| DR912 | AITVSGASTYYADSVKG | 58 |
| DR913 | AISSWSGGSTYYADSVKG | 59 |
| DR914 | AISRGGGSTDYADSVKG | 60 |
| DR915 | AISKGGGSADYADSVKG | 61 |
| DR916 | AISKAGGSTYVADSAKG | 62 |
| DR917 | AIAWAGSRTYYTDSVKG | 63 |
| DR918 | AISRAGGSADHADSVKG | 64 |
| DR919 | AISWRSGNTYYADSVKG | 65 |
| DR920 | AISRGGGSTWYADSVKG | 66 |
| DR921 | GIMWTSRASYADSVKG | 67 |
| DR922 | AITSGGSTNYADSVKG | 68 |
| DR923 | AISWSSGSTYYADSVKG | 69 |
| DR924 | TISRSGGTTSYANSVKG | 70 |
| DR925 | AISIGGGSADYADTVKG | 71 |
| DR926 | AISWSSGNTYVADSVKG | 72 |

| Name | CDR3 | SEQ ID NO: |
|---|---|---|
| DR903 | GGHLYYGSRWRYPASYDY | 73 |
| DR904 | DRAYY | 74 |
| DR905 | RIRDGVSPENPNEYGY | 75 |
| DR906 | RAGPAIGRTANDYHS | 76 |
| DR907 | VWPTGRLRVDSEYDY | 77 |
| DR908 | RDYSTLQYYNEYEYSD | 78 |
| DR909 | TNSYDDLRRSYAYNY | 79 |
| DR910 | RRPAPSDSYWSSTSYAY | 80 |
| DR911 | RDYRRRSYAPEAEQYDY | 81 |
| DR912 | GGPGTIFPDYDY | 82 |
| DR913 | GDYYSDYFKYDNEN | 83 |
| DR914 | RYYSGRYYESLEYDY | 84 |
| DR915 | NDLASYSDSSYTSTSRYDY | 85 |
| DR916 | RAGFAAQIFEYDY | 86 |
| DR917 | HDETYYRLDRVDLYTH | 87 |
| DR918 | GRSYSSPYDYFNALAYSY | 88 |
| DR919 | NEVATMSGPHDH | 89 |
| DR920 | RSYSGSYTYSFGEYDY | 90 |
| DR921 | AWYGNSGASYDY | 91 |
| DR922 | DSMYF | 92 |
| DR923 | SSIATMYGPNDY | 93 |
| DR924 | RDGPAMGVFGSDYDY | 94 |
| DR925 | RTPRPSSSYFTPQDYEY | 95 |
| DR926 | TTIATMSDENTY | 96, | and
wherein the anti-IFNGR2 sdAb comprising a CDR1, a CDR2, and a CDR3 in a single row of the following table:

| Name | CDR1 | SEQ ID NO: |
|---|---|---|
| DR927 | RTFTSYAMN | 97 |
| DR928 | RTFSNYRMG | 98 |
| DR929 | RTFSSYAMG | 99 |
| DR930 | RTFSSYAVA | 100 |
| DR931 | RTFSTYAMG | 101 |
| DR932 | RTFSYTTIG | 102 |
| DR933 | GTISSLAMG | 103 |
| DR934 | RSFANYAMG | 104 |
| DR935 | RAFSTYALG | 105 |
| DR936 | RTFSSVAMA | 106 |
| DR937 | RTFRSYSMG | 107 |
| DR938 | RPRTTYAMG | 108 |
| DR939 | RTFGTYAMG | 109 |
| DR940 | RTFSNYAMG | 110 |
| DR941 | SIFRLNLMG | 111 |
| DR942 | RTFTGYAMG | 112 |
| DR943 | RTVGYGMA | 113 |
| DR944 | RTFTFSTHNMG | 114 |
| DR945 | RTFSGYNMG | 115 |
| DR946 | PFTRYAMG | 116 |
| DR947 | GSFGRYTMG | 117 |
| DR948 | SIDSSYYVS | 118 |
| DR949 | SILRFNVMS | 119 |
| DR950 | LTTSSAALA | 120 |
| DR951 | RTFGTSFGSLSMG | 121 |
| DR952 | RTFSSLAMA | 122 |
| DR953 | PTFSTYAMA | 123 |
| DR954 | RTLHNFAMA | 124 |
| DR955 | RTFSSYAMA | 125 |
| DR956 | RTFSSLAMA | 126 |
| DR957 | RTFSSYAMA | 127 |
| DR958 | RTFSGYNMG | 128 |

| Name | CDR2 | SEQ ID NO: |
| --- | --- | --- |
| DR927 | AISWSSGNTYVADSVKG | 129 |
| DR928 | AISRGGGTTLYADSVKG | 130 |
| DR929 | AISRGGGSTDYADSVKG | 131 |
| DR930 | ALSRGGGSAYYTDSVKG | 132 |
| DR931 | AISVNGGSTYYADSVTG | 133 |
| DR932 | VISAGGGSRDYADALKG | 134 |
| DR933 | AISWSGRSTYYVDSVKG | 135 |
| DR934 | AISRGGGSTWYADSVKG | 136 |
| DR935 | AISRGGGSTDYADSVKG | 137 |
| DR936 | AISSGGGSTDYADSVKG | 138 |
| DR937 | AISWYSGTTYYADPVKG | 139 |
| DR938 | AISKAGGSTYVADSAKG | 140 |
| DR939 | SIDRDGSMSYYADSVKG | 141 |
| DR940 | AISWYSGNTYYADSVKG | 142 |
| DR941 | HVGTTGNTAYADSVKG | 143 |
| DR942 | VITWSGATTYYSASVKG | 144 |
| DR943 | AITWSGTSTYYPDSVKG | 145 |
| DR944 | GIMWTSRASYADSVKG | 146 |
| DR945 | AIAWAGSRTYYTDSVKG | 147 |
| DR946 | AISWSSGNTYYVDSVKG | 148 |
| DR947 | VISWSGTNTYYADSVKG | 149 |
| DR948 | AINWGDSRTAYADSVKG | 150 |
| DR949 | VITSGGSTNYADSVKG | 151 |
| DR950 | TITSGGGSTYYADSVKG | 152 |
| DR951 | AISRNIGRTYYADSVKD | 153 |
| DR952 | AISRSGGSTDYADSVKG | 154 |
| DR953 | AITQSGRTTYYEDSVKG | 155 |
| DR954 | AISKGGGSADYADSVKG | 156 |
| DR955 | AISILGGSADYEDSVQG | 157 |
| DR956 | ATTILGGSADYGDPVKG | 158 |
| DR957 | AITVSGASTYYADSVKG | 159 |
| DR958 | AINWIGGATYYADSVKG | 160 |

| Name | CDR3 | SEQ ID NO: |
| --- | --- | --- |
| DR927 | TTIATMSDEYTY | 161 |
| DR928 | GDFSTTWDEYNY | 162 |
| DR929 | RAYSGRYYQFLEYDY | 163 |
| DR930 | RNYDGTYYQENQYNY | 164 |
| DR931 | RRPYPGSDFLTWASYDY | 165 |
| DR932 | RRNTDTYTTTGDYDY | 166 |
| DR933 | GEDGHSEYDY | 167 |
| DR934 | RSYSGSYTYSFGEYDY | 168 |
| DR935 | RSYSSSYYYSQYEYDY | 169 |
| DR936 | RDYSSRRYYQSRYEYDL | 170 |
| DR937 | NEIATMESSNDY | 171 |
| DR938 | RAGFAAQIFEYDY | 172 |
| DR939 | SRRAVISLQTVDY | 173 |
| DR940 | NQIATMISVGDY | 174 |
| DR941 | DRWGQFS | 175 |
| DR942 | RIRDGVSPENPNEYGY | 176 |
| DR943 | GSRRRVGVDVGGYDY | 177 |
| DR944 | AWYGNSGASYDY | 178 |
| DR945 | HDETYYRLDRVDLYTH | 179 |
| DR946 | NEVATMSGPDDY | 180 |
| DR947 | RETYYSHWDERMEYDY | 181 |
| DR948 | RIGLGGPVVAAPTRYPY | 182 |
| DR949 | DESGQYY | 183 |
| DR950 | RFYSTTYYYREHEYSD | 184 |
| DR951 | TNSYDDLRRSYAYDY | 185 |
| DR952 | RDYSTLQYYNEYEYSD | 186 |
| DR953 | RDLWSDSPDDWRIYSF | 187 |
| DR954 | NDLASYSDSSYTSTSRYDY | 188 |
| DR955 | RRPAPSDSYWSSTSYAY | 189 |
| DR956 | RRPAPSDNYWSPASYAY | 190 |
| DR957 | GGPGTIFPDYDY | 191 |
| DR958 | YSEKFYSGKDYYTRDYDY | 192. |

2. The IFNGR binding molecule of claim 1, wherein the anti-IFNGR1 sdAb is a VHH antibody and/or the anti-IFNGR2 sdAb is a $V_H$H antibody.

3. The IFNGR binding molecule of claim 1, wherein the anti-IFNGR1 sdAb and the anti-IFNGR2 sdAb are joined by a peptide linker.

4. The IFNGR binding molecule of claim 3, wherein the peptide linker comprises between 1 and 50 amino acids.

5. The IFNGR binding molecule of claim 4, wherein the peptide linker comprises a sequence of GGGS (SEQ ID NO:13).

6. The IFNGR binding molecule of claim 1, wherein the binding molecule comprises the anti-IFNGR1 sdAb linked to the N-terminus of a linker and the anti-IFNGR2 sdAb linked to the C-terminus of the linker.

7. The IFNGR binding molecule of claim 1, wherein the binding molecule comprises the anti-IFNGR2 sdAb linked to the N-terminus of a linker and the anti-IFNGR1 sdAb linked to the C-terminus of the linker.

8. The IFNGR binding molecule of claim 6, wherein the anti-IFNGR1 sdAb comprises a sequence having at least 90% sequence identity to a sequence of the following table:

| Name | Sequence | SEQ ID NO: |
|------|----------|------------|
| DR903 | EVQLVESGGGLVQAGGSLRLSCAASGRIASDYTRGWFRQAPGKEREFVAAI IRSVGDSYYADSVKGRFTISIDNAENTVYLQMNSLKPEDTAVYYCAVGGHL YYGSRWRYPASYDYWGQGTQVTVSS | 193 |
| DR904 | EVQLVESGGGLVQAGGSLRLSCEASESILSINTMGWFRQAPGKQRELVAAI SSGGSTNYADSVKGRFTISRDNAKNTVYLQMNSLKPEDTAVYYCDADRAYY KGQGTQVTVSS | 194 |
| DR905 | EVQLVESGGGLVQAGGSLRLSCVASGRTFTGYAMGWFRQAPGKEREFVAVI TWSGATTYYSASVKGRFTLSRDNAKNTVYLQMNSLKSEDTAVYYCAIRIRD GVSPENPNEYGYWGQGTQVTVSS | 195 |
| DR906 | EVQLVESGGGLVQAGGSLRLSCAASGSTFSTYVMGWFRQAPGKEREFVAAI SRSGGTTTYADSVKGREDISRDNGKNTLFLQMNSLIPEDTAAYYCAARAGP AIGRTANDYHSWGQGTLVTVSS | 196 |
| DR907 | EVQLVESGGGLVQAGGSLRLSCAASGRTFSNYAMGWFRQAPGNEREFVAAI NWNIGSTYYADSVKGRFTISRDNAKNTVYLQMNSLKPEDTAVYYCGAVWPT GRLRVDSEYDYWGQGTQVTVSS | 197 |
| DR908 | EVQLVESGGGLVQAGGSLRVTCAASGRTFTSLAMGWFRQAPGKEREFVAAI SRSGGSTDYADSVKGRFFISRDNAKSTLYLQMSSLKPEDTAVYYCAARDYS TLQYYNEYEYSDWGQGTQVTVSS | 198 |
| DR909 | EVQLVESGGGLVQAGGSLRLSCAASGRTFGTSFGALSMGWFRQAPGKEREF VAAITRNTGRTFYADSVKDRFTISRDNAKNTASLQMNSLEPEDTAVYICAA TNSYDDLRRSYAYNYWGQGTQVTVSS | 199 |
| DR910 | EVQLVESGGGLVQTGGSLRLSCAASGRTFSSYAMAWFRQAPGKEREFVAAI SILGGSADYEDSVQGRFTISRDNAKNTMYLQMNSLKPEDTAVYYCAARRPA PSDSYWSSTSYAYWGQGTLVTVSS | 200 |
| DR911 | EVQLVESGGALVQAGGSLRLSCTVSGRSFSTYAMAWFRRAPGKERELVSAI TVGGGSTYYVDSVKGRFTISRENAKNTLYLQMNNLKPEDTAIYICAARDYR RRSYAPEAEQYDYWGQGTQVTVSS | 201 |
| DR912 | EVQLVESGGGLVQAGGSLRLSCAPSGRTFSSYAMAWFRQPPGKEREFVAAI TVSGASTYYADSVKGRFTISRDNAKNSMYLQMNSLKPEDTAVYYCAAGGPG TIFPDYDYWGQGTQVTVSS | 202 |
| DR913 | EVQLVESGGGLVQAGGFLRLSCAASGRTFSSYAMGWFRQIPGKERELVAAI SSWSGGSTYYADSVKGRFTISRDNAKNTVYLQMLSLKPEDTAVYYCTTGDY YSDYFKYDNENWGKGTQVTVSS | 203 |
| DR914 | EVQLVESGGGLVQAGGSLTLSCVASGRAFSNSAMAWFRQTPGKEREFVSAI SRGGGSTDYADSVKGRFTISKDNAKNTVYLQMNSLKPEDTAVYYCAMRYYS GRYYESLEYDYWGQGTQVTVSS | 204 |
| DR915 | EVQLVESGGGLVQAGGSLRLSCAAARRTLHNFAMAWFRQAPGKEREFVAAI SKGGGSADYADSVKGRFTISRDNAKNTVYLQMNSLKPEDTAVYYCAANDLA SYSDSSYTSTSRYDYWGQGTQVTVSS | 205 |
| DR916 | EVQLVESGGGLVQPGGSLRLSCTASGRPRTTYAMGWFRQAPGKEREIVAAI SKAGGSTYVADSAKGRFAISKDNAKNTVYLQMNSLKPEDTAVYYCAARAGF AAQIFEYDYWGQGTLVTVSS | 206 |
| DR917 | EVQLVESGGGLVQAGGSLRLSCAASGRTFSGYNMGWFRQAPGKEREFVAAI AWAGSRTYYTDSVKGRFTISRDNAKNTMYLQMNTLRPEDTAVYYCAAHDET YYRLDRVDLYTHWGQGTLVTVSS | 207 |
| DR918 | EVQLVESGGGLVQAGGSLRLSCATSGLTDSTYGMAWFRQAPGKEREFVAAI SRAGGSADHADSVKGRFTVSRDNAKKMVYLQMNSLKPEDTAVYYCASGRSY SSPYDYFNALAYSYWGQGTQVTVSS | 208 |
| DR919 | EVQLVESGGGLVQPGGFLRLSCAASRRTLSTYAMGWFRQAPGKEREFVAAI SWRSGNTYYADSVKGRFTISRDNAKNTMYLQMNSLKPEDTAVYYCAANEVA TMSGPHDHWGQGTLVTVSS | 209 |
| DR920 | EVQLVESGGGLVQAGGSLRLSCAASGRSFANYAMGWFRQAPGKERETVAAI SRGGGSTWYADSVKGRFTISKDNAKNTVYLQMNSLKPEDTAIYYCAARSYS GSYTYSFGEYDYWGQGTQVTVSS | 210 |
| DR921 | QVQLVESGGGLVQAGDSLRLSCAASGRTFTFSTHNMGWFRQAPGKEREFVG GIMWTSRASYADSVKGRFTVSRDNAKNTVYLQMNSLKPEDTAVYYCAAAWY GNSGASYDYWGQGTQVTVSS | 211 |
| DR922 | QVQLVESGGGLVRAGGSLRLSCAASGSITSINTMGWFRQAPGKQRELVAAI TSGGSTNYADSVKGRFTISRDNARNTVYLQMYSLKPEDTAVYYCEADSMYF RGQGTQVTVSS | 212 |

-continued

| Name | Sequence | SEQ ID NO: |
|---|---|---|
| DR923 | QVQLVESGGGLVQAGGSLRLSCAASRRTFMTYAMGWFRQAPGKEREFVAAI SWSSGSTYYADSVKGRFTISRDNAKNTMYLQMNSLKPEDTAVYYCTASSIA TMYGPNDYAGQGTLVTVSS | 213 |
| DR924 | QVQLVESGGGLVQAGGSLRLSCTASGRTFSRYAMGWFRQAPGKEREFVATI SRSGGTTSYANSVKGRFTISRDNAKNTVYLQMNSLKTEDTAVYNCAARDGP AMGVFGSDYDYWGQGTLVTVSS | 214 |
| DR925 | EVQLVESGGGLVQAGGSLVLSCAASGRTFSRYAMGWFRQAPGKEREFVAAI SIGGGSADYADTVKGRFTISRNNAKNTMYLQMNSLKPEDTAVYYCAARTPR PSSSYFTPQDYEYWGQGTLVTVSS | 215 |
| DR926 | EVQLVESGGGLVQAGGSLRLSCAASGRTFSRYAMNWFRQAPGKEREFVAAI SWSSGNTYVADSVKGRFTISRDNAKNTMYLQMNNLAPEDTAVYYCAATTIA TMSDENTYWGQGTQVTVSS. | 216 |

9. The IFNGR binding molecule of claim 8, wherein the anti-IFNGR1 sdAb comprises a sequence of the table in claim 8.

10. The IFNGR binding molecule of claim 6, wherein the anti-IFNGR2 g comprises a sequence having at least 90% sequence identity to a sequence of the following table:

| Name | Sequence | SEQ ID NO: |
|---|---|---|
| DR927 | QVQLVESGGGLVQAGGSLRLSCAASGRTFTSYAMNWFRQAPGKEREFVAAISWS SGNTYVADSVKGRFAISRDKAKNTMYLQMNSLAPEDTAVYYCAATTIATMSDEY TYWGQGTQVTVSS | 217 |
| DR928 | QVQLVESGGGLVQAGGSLRLSCAASGRTFSNYRMGWFRQAPGKEREFVAAISRG GGTTLYADSVKGRFTISRDNAKNTVDLQMNRLKPEDTAVYFCAAGDESTTWDEY NYWGQGTQVTVSS | 218 |
| DR929 | QVQLVESGGGLVQAGGSLRLSCVASGRTFSSYAMGWFRQTPGKEREFVSAISRG GGSTDYADSVKGRFTISRDNAKNTVYLQMNNLKSEDTAVYYCALRAYSGRYYQF LEYDYWGQGTQVTVSS | 219 |
| DR930 | EVQLVESGGGLVQAGGSLRLSCTVSGRTFSSYAVAWFRQAPGNVRELAAALSRG GGSAYYTDSVKGRFTISRDNAKNTVYLQMNSLKPEDTAVYYCAARNYDGTYYQE NQYNYWGQGTQVTVSS | 220 |
| DR931 | QVQLVESGGGLVQAGGSLLLSCAASGRTFSTYAMGWFRQAPGKERMFVAAISVN GGSTYYADSVTGRFTISRDNAKNTMYLQMNNLKPGDTAVYYCAARRPYPGSDFL TWASYDYRGQGTLVTVSS | 221 |
| DR932 | QVQLVESGGGLVQAGGFLRLSCAASGRTFSYTTIGWFRQAPGKEREFVAVISAG GGSRDYADALKGRFTISRDNAKKMVYLQMNNLKPEDTAVYYCAVRRNTDTYTTT GDYDYWGQGTQVTVSS | 222 |
| DR933 | QVQLVESGGGLVQPGDSLRLSCVASGGTISSLAMGWFRQAPGKEREFVAAISWS GRSTYYVDSVKGRFTISTDNAKNTVYLQMNSLKPEDTAVYYCVAGEDGHSEYDY WGQGTQVTVSS | 223 |
| DR934 | QVQLVESGGGLVQAGGSLRLSCAASGRSFANYAMGWFRQAPGKERETVAAISRG GGSTWYADSVKGRFTISKDNAKNTVYLQMNSLKPEDTAIYYCAARSYSGSYTYS FGEYDYWGQGTQVTVSS | 224 |
| DR935 | QVQLVESGGGLVQAGGSLRLSCAASGRAFSTYALGWFRQAPGKEREFIAAISRG GGSTDYADSVKGRFTISRDNAKSTVYLQMNSLKPEDTAVYYCAARSYSSSYYYS QYEYDYWGQGTQVTVSS | 225 |
| DR936 | EVQLVESGGGLVQAGGSLRLSCAASGRTFSSVAMAWFRQAPGKEREFVSAISSG GGSTDYADSVKGRFTISKDNAKNTMYLQMDSLKPEDTAVYYCAARDYSSRRYYQ SRYEYDLWGLGTQVTVSS | 226 |
| DR937 | QVQLVESGGGLVQPGGSLRLSCAASGRTFRSYSMGWFRQAPGKEREFVAAISWY SGTTYYADPVKGRFTISRDDAKNTLYLQMNSLKPEDTAVYYCAANEIATMESSN DYWGQGTQVTVSS | 227 |
| DR938 | QVQLVESGGGLVQPGGSLRLSCTASGRPRTTYAMGWFRQAPGKEREIVAAISKA GGSTYVADSAKGRFAISKDNAKNTVYLQMNSLKPEDTAVYYCAARAGFAAQIFE YDYWGQGTLVTVSS | 228 |
| DR939 | EVQLVESGGGLVQAGGSMRLSCANSGRTFGTYAMGWFRQSPGKERERVASIDRD GSMSYYADSVKGRFTISGDNAKNTVYLQMNSLKPEDTAVYYCAASRRAVISLQT VDYWGQGTQVTVSS | 229 |

| Name | Sequence | SEQ ID NO: |
|---|---|---|
| DR940 | EVQLVESGGRLVQTGGSLRLSCAASGRTFSNYAMGWFRQAPGKEREFVAAISWYSGNTYYADSVKGRFTISRDNAKNTMYLQMNSLKPEDTAVYYCAANQIATMISVGDYWGQGTLVTVSS | 230 |
| DR941 | QVQLVESGGGLVEAGGSLRLACAASGSIFRLNLMGWYRQAPGKQRELVAHVGTTGNTAYADSVKGRFTISKDDAKNMVFLQMNSLKPEDTAVYYCYADRWGQFSWGQGTQVTVSS | 231 |
| DR942 | QVQLVESGGGLVQAGGSLRLSCVASGRTFTGYAMGWFRQAPGKEREFVAVITWSGATTYYSASVKGRFTLSRDNAKNTVYLQMNSLKSEDTAVYYCAIRIRDGVSPENPNEYGYWGQGTQVTVSS | 232 |
| DR943 | QVQLVESGGGLVQAGGSLRLSCVASGRTVGYGMAWFRQAPGKQRDVVAAITWSGTSTYYPDSVKGRFTISRDNKNTMYLQMSSLKPEDTAVYYCAAGSRRRVGVDVGGYDYWGQGTQVTVSS | 233 |
| DR944 | QVQLVESGGGLVQAGDSLRLSCAASGRTFTFSTHNMGWFRQAPGKEREFVGGIMWTSRASYADSVKGRFTVSRDNAKNTVYLQMNSLKPEDTAVYYCAAAWYGNSGASYDYWGQGTQVTVSS | 234 |
| DR945 | QVQLVESGGGLVQLVQAGGSLRLSCAASGRTFSGYNMGWFRQAPGKEREFVAAIAWAGSRTYYTDSVKGRFTISRDNAKNTMYLQMNTLRPEDTAVYYCAAHDETYYRLDRVDLYTHWGQGTQVTVSS | 235 |
| DR946 | QVQLVESGGGLVQPGESLRLSCAASGPFTRYAMGWFRQAPGKEREFVAAISWSSGNTYYVDSVKGRFTISRDNAKNTMYLQMNSLKPEDTAVYYCAANEVATMSGPDDYWGQGTQVTVSS | 236 |
| DR947 | QVQLVESGGGLVQAGGSLRLSCAASGGSFGRYTMGWYRQAPGKEREFVAVISWSGTNTYYADSVKGRFTISRDNAKNTMYLQMNDLKPEDTAVYYCAARETYYSHWDERMEYDYWGQGTQVTVSS | 237 |
| DR948 | QVQLVESGGGLVQAGDSLRLSCVASGSIDSSYYVSWFRQAPGKERDLVAAINWGDSRTAYADSVKGRFTISRDNAKNTVYLQMHSLRPNDTAVYYCASRIGLGGPVVAAPTRYPYWGQGTLVTVSS | 238 |
| DR949 | QVQLVESGGGLVQAGGSLRLSCAASESILRFNVMSWLRQAPGKQRELVAVITSGGSTNYADSVKGRFTISRDNAKNTVYLQMNSLKPEDTAVYYCAADESGQYYWGQGTQVTVSS | 239 |
| DR950 | QVQLVESGGGLVQAGGSLRLSCAASGLTTSSAALAWFRQAPGKERELDPTITSGGGSTYYADSVKGRFTISKDNAKNTLYLQMSSLKPEDTAVYYCAARFYSTTYYREHEYSDWGQGTQVTVSS | 240 |
| DR951 | QVQLVESGGGLVQAGGSLRLSCAASGRTFGTSFGSLSMGWFRQAPGKEREFVAAISRNIGRTYYADSVKDRFTISRDNAKNTASLQMNSLEPEDTAVYNCAATNSYDDLRRSYAYDYWGQGTQVTVSS | 241 |
| DR952 | QVQLVESGGGLVQAGGFLRLSCAASGRTFSSLAMAWFRQAPGKEREFVAAISRSGGSTDYADSVKGRFTISRDNAKSTLYLQMSSLKPEDTAVYYCAARDYSTLQYYNEYEYSDWGQGTLVTVSS | 242 |
| DR953 | QVQLVESGGGLVQAGDSLRLSCAASGPTFSTYAMAWFRQAPGKEREFVAAITQSGRTTYYEDSVKGRFTISKDNAKNTLYLQMNSLQPEDTAVYYCAARDLWSDSPDDWRIYSFWGQGTQVTVSS | 243 |
| DR954 | QVQLVESGGGLVQAGGSLRLSCAAARRTLHNFAMAWFRQAPGKEREFVAAISKGGGSADYADSVKGRFTISRDNAKNTVYLQMNSLKPEDTAVYYCAANDLASYSDSSYTSTSRYDYWGQGTQVTVSS | 244 |
| DR955 | QVQLVESGGGLVQTGGSLRLSCAASGRTFSSYAMAWFRQAPGKEREFVAAISILGGSADYEDSVQGRFTISRDNAKNTMYLQMNSLKPEDTAVYYCAARRPAPSDSYWSSTSYAYWGQGTLVTVSS | 245 |
| DR956 | EVQLVESGGGLVQAGGSLRLSCAASGRTFSSLAMAWFRQAPGKEREFVAATTILGGSADYGDPVKGRFTISRDNAKNTVYLQMNSLKPEDTAVYYCTGRRPAPSDNYWSPASYAYWGQGTQVTVSS | 246 |
| DR957 | QVQLVESGGGLVQAGGSLRLSCAPSGRTFSSYAMAWFRQPPGKEREFVAAITVSGASTYYADSVKGRFTISRDNAKNSMYLQMNSLKPEDTAVYYCAAGGPGTIFPDYDYWGQGTQVTVSS | 247 |
| DR958 | QVQLVESGGGLVQAGDSLTLSCTASGRTFSGYNMGWFRQAPGKERDFVAAINWIGGATYYADSVKGRFTISRDNAKNTVYLQMNSLKPEDTAVYYCHRYSEKFYSGKDYYTRDYDYWGQGTQVTVSS. | 248 |

11. The IFNGR binding molecule of claim 10, wherein the anti-IFNGR2 sdAb comprises a sequence of the table in claim 10.

12. The IFNGR binding molecule of claim 6, wherein each of the anti-IFNGR1 sdAb comprises a sequence having at least 90% sequence identity to a sequence of the following table:

| Name | Sequence | SEQ ID NO: |
|---|---|---|
| DR903 | EVQLVESGGGLVQAGGSLRLSCAASGRIASDYTRGWFRQAPGKEREFVAAI IRSVGDSYYADSVKGRFTISIDNAENTVYLQMNSLKPEDTAVYYCAVGGHL YYGSRWRYPASYDYWGQGTQVTVSS | 193 |
| DR904 | EVQLVESGGGLVQAGGSLRLSCEASESILSINTMGWFRQAPGKQRELVAAI SSGGSTNYADSVKGRFTISRDNAKNTVYLQMNSLKPEDTAVYYCDADRAYY KGQGTQVTVSS | 194 |
| DR905 | EVQLVESGGGLVQAGGSLRLSCVASGRTFTGYAMGWFRQAPGKEREFVAVI TWSGATTYYSASVKGRFTLSRDNAKNTVYLQMNSLKSEDTAVYYCAIRIRD GVSPENPNEYGYWGQGTQVTVSS | 195 |
| DR906 | EVQLVESGGGLVQAGGSLRLSCAASGSTFSTYVMGWFRQAPGKEREFVAAI SRSGGTTTYADSVKGRFDISRDNGKNTLFLQMNSLIPEDTAAYYCAARAGP AIGRTANDYHSWGQGTLVTVSS | 196 |
| DR907 | EVQLVESGGGLVQAGGSLRLSCAASGRTFSNYAMGWFRQAPGNEREFVAAI NWNIGSTYYADSVKGRFTISRDNAKNTVYLQMNSLKPEDTAVYYCGAVWPT GRLRVDSEYDYWGQGTQVTVSS | 197 |
| DR908 | EVQLVESGGGLVQAGGSLRVTCAASGRTFTSLAMGWFRQAPGKEREFVAAI SRSGGSTDYADSVKGRFFISRDNAKSTLYLQMSSLKPEDTAVYYCAARDYS TLQYYNEYEYSDWGQGTQVTVSS | 198 |
| DR909 | EVQLVESGGGLVQAGGSLRLSCAASGRTFGTSFGALSMGWFRQAPGKEREF VAAITRNTGRTFYADSVKDRFTISRDNAKNTASLQMNSLEPEDTAVYICAA TNSYDDLRRSYAYNYWGQGTQVTVSS | 199 |
| DR910 | EVQLVESGGGLVQTGGSLRLSCAASGRTFSSYAMAWFRQAPGKEREFVAAI SILGGSADYEDSVQGRFTISRDNAKNTMYLQMNSLKPEDTAVYYCAARRPA PSDSYWSSTSYAYWGQGTLVTVSS | 200 |
| DR911 | EVQLVESGGALVQAGGSLRLSCTVSGRSFSTYAMAWFRRAPGKERELVSAI TVGGGSTYYVDSVKGRFTISRENAKNTLYLQMNNLKPEDTAIYICAARDYR RRSYAPEAEQYDYWGQGTQVTVSS | 201 |
| DR912 | EVQLVESGGGLVQAGGSLRLSCAPSGRTFSSYAMAWFRQPPGKEREFVAAI TVSGASTYYADSVKGRFTISRDNAKNSMYLQMNSLKPEDTAVYYCAAGGPG TIFPDYDYWGQGTQVTVSS | 202 |
| DR913 | EVQLVESGGGLVQAGGFLRLSCAASGRTESSYAMGWFRQIPGKERELVAAI SSWSGGSTYYADSVKGRFTISRDNAKNTVYLQMLSLKPEDTAVYYCTTGDY YSDYFKYDNENWGKGTQVTVSS | 203 |
| DR914 | EVQLVESGGGLVQAGGSLTLSCVASGRAFSNSAMAWFRQTPGKEREFVSAI SRGGGSTDYADSVKGRFTISKDNAKNTVYLQMNSLKPEDTAVYYCAMRYYS GRYYESLEYDYWGQGTQVTVSS | 204 |
| DR915 | EVQLVESGGGLVQAGGSLRLSCAAARRTLHNFAMAWFRQAPGKEREFVAAI SKGGGSADYADSVKGRFTISRDNAKNTVYLQMNSLKPEDTAVYYCAANDLA SYSDSSYTSTSRYDYWGQGTQVTVSS | 205 |
| DR916 | EVQLVESGGGLVQPGGSLRLSCTASGRPRTTYAMGWFRQAPGKEREIVAAI SKAGGSTYVADSAKGRFAISKDNAKNTVYLQMNSLKPEDTAVYYCAARAGF AAQIFEYDYWGQGTLVTVSS | 206 |
| DR917 | EVQLVESGGGLVQAGGSLRLSCAASGRTFSGYNMGWFRQAPGKEREFVAAI AWAGSRTYYTDSVKGRFTISRDNAKNTMYLQMNTLRPEDTAVYYCAAHDET YYRLDRVDLYTHWGQGTLVTVSS | 207 |
| DR918 | EVQLVESGGGLVQAGGSLRLSCATSGLTDSTYGMAWFRQAPGKEREFVAAI SRAGGSADHADSVKGRFTVSRDNAKKMVYLQMNSLKPEDTAVYYCASGRSY SSPYDYFNALAYSYWGQGTQVTVSS | 208 |
| DR919 | EVQLVESGGGLVQPGGFLRLSCAASRRTLSTYAMGWFRQAPGKEREFVAAI SWRSGNTYYADSVKGRFTISRDNAKNTMYLQMNSLKPEDTAVYYCAANEVA TMSGPHDHWGQGTLVTVSS | 209 |
| DR920 | EVQLVESGGGLVQAGGSLRLSCAASGRSFANYAMGWFRQAPGKERETVAAI SRGGGSTWYADSVKGRFTISKDNAKNTVYLQMNSLKPEDTAIYYCAARSYS | 210 |

| Name | Sequence | SEQ ID NO: |
|---|---|---|
| | GSYTYSFGEYDYWGQGTQVTVSS | |
| DR921 | QVQLVESGGGLVQAGDSLRLSCAASGRTFTFSTHNMGWFRQAPGKEREFVG<br>GIMWTSRASYADSVKGRFTVSRDNAKNTVYLQMNSLKPEDTAVYYCAAAWY<br>GNSGASYDYWGQGTQVTVSS | 211 |
| DR922 | QVQLVESGGGLVRAGGSLRLSCAASGSITSINTMGWFRQAPGKQRELVAAI<br>TSGGSTNYADSVKGRFTISRDNARNTVYLQMYSLKPEDTAVYYCEADSMYF<br>RGQGTQVTVSS | 212 |
| DR923 | QVQLVESGGGLVQAGGSLRLSCAASRRTFMTYAMGWFRQAPGKEREFVAAI<br>SWSSGSTYYADSVKGRFTISRDNAKNTMYLQMNSLKPEDTAVYYCTASSIA<br>TMYGPNDYAGQGTLVTVSS | 213 |
| DR924 | QVQLVESGGGLVQAGGSLRLSCTASGRTFSRYAMGWFRQAPGKEREFVATI<br>SRSGGTTSYANSVKGRFTISRDNAKNTVYLQMNSLKTEDTAVYNCAARDGP<br>AMGVFGSDYDYWGQGTLVTVSS | 214 |
| DR925 | EVQLVESGGGLVQAGGSLVLSCAASGRTFSRYAMGWFRQAPGKEREFVAAI<br>SIGGGSADYADTVKGRFTISRNNAKNTMYLQMNSLKPEDTAVYYCAARTPR<br>PSSSYFTPQDYEYWGQGTLVTVSS | 215 |
| DR926 | EVQLVESGGGLVQAGGSLRLSCAASGRTFSRYAMNWFRQAPGKEREFVAAI<br>SWSSGNTYVADSVKGRFTISRDNAKNTMYLQMNNLAPEDTAVYYCAATTIA<br>TMSDENTYWGQGTQVTVSS, | 216 | and the anti-IFNGR2 sdAb comprises a sequence having at least 90% sequence identity to a sequence of the following table:

| Name | Sequence | SEQ ID NO: |
|---|---|---|
| DR927 | QVQLVESGGGLVQAGGSLRLSCAASGRTFTSYAMNWFRQAPGKEREFVAAISWS<br>SGNTYVADSVKGRFAISRDKAKNTMYLQMNSLAPEDTAVYYCAATTIATMSDEY<br>TYWGQGTQVTVSS | 217 |
| DR928 | QVQLVESGGGLVQAGGSLRLSCAASGRTFSNYRMGWFRQAPGKEREFVAAISRG<br>GGTTLYADSVKGRFTISRDNAKNTVDLQMNRLKPEDTAVYFCAAGDESTTWDEY<br>NYWGQGTQVTVSS | 218 |
| DR929 | QVQLVESGGGLVQAGGSLRLSCVASGRTFSSYAMGWFRQTPGKEREFVSAISRG<br>GGSTDYADSVKGRFTISRDNAKNTVYLQMNNLKSEDTAVYYCALRAYSGRYYQF<br>LEYDYWGQGTQVTVSS | 219 |
| DR930 | EVQLVESGGGLVQAGGSLRLSCTVSGRTFSSYAVAWFRQAPGNVRELAAALSRG<br>GGSAYYTDSVKGRFTISRDNAKNTVYLQMNSLKPEDTAVYYCAARNYDGTYYQE<br>NQYNYWGQGTQVTVSS | 220 |
| DR931 | QVQLVESGGGLVQAGGSLLLSCAASGRTFSTYAMGWFRQAPGKERMFVAAISVN<br>GGSTYYADSVTGRFTISRDNAKNTMYLQMNNLKPGDTAVYYCAARRPYPGSDFL<br>TWASYDYRGQGTLVTVSS | 221 |
| DR932 | QVQLVESGGGLVQAGGFLRLSCAASGRTFSYTTIGWFRQAPGKEREFVAVISAG<br>GGSRDYADALKGRFTISRDNAKKMVYLQMNNLKPEDTAVYYCAVRRNTDTYTTT<br>GDYDYWGQGTQVTVSS | 222 |
| DR933 | QVQLVESGGGLVQPGDSLRLSCVASGGTISSLAMGWFRQAPGKEREFVAAISWS<br>GRSTYYVDSVKGRFTISTDNAKNTVYLQMNSLKPEDTAVYYCVAGEDGHSEYDY<br>WGQGTQVTVSS | 223 |
| DR934 | QVQLVESGGGLVQAGGSLRLSCAASGRSFANYAMGWFRQAPGKERETVAAISRG<br>GGSTWYADSVKGRFTISKDNAKNTVYLQMNSLKPEDTAIYYCAARSYSGSYTYS<br>FGEYDYWGQGTQVTVSS | 224 |
| DR935 | QVQLVESGGGLVQAGGSLRLSCAASGRAFSTYALGWFRQAPGKEREFIAAISRG<br>GGSTDYADSVKGRETISRDNAKSTVYLQMNSLKPEDTAVYYCAARSYSSSYYYS<br>QYEYDYWGQGTQVTVSS | 225 |
| DR936 | EVQLVESGGGLVQAGGSLRLSCAASGRTFSSVAMAWFRQAPGKEREFVSAISSG<br>GGSTDYADSVKGRFTISKDNAKNTMYLQMDSLKPEDTAVYYCAARDYSSRRYYQ<br>SRYEYDLWGLGTQVTVSS | 226 |
| DR937 | QVQLVESGGGLVQPGGSLRLSCAASGRTFRSYSMGWFRQAPGKEREFVAAISWY<br>SGTTYYADPVKGRFTISRDDAKNTLYLQMNSLKPEDTAVYYCAANEIATMESSN | 227 |

-continued

| Name | Sequence | SEQ ID NO: |
|---|---|---|
| | DYWGQGTQVTVSS | |
| DR938 | QVQLVESGGGLVQPGGSLRLSCTASGRPRTTYAMGWFRQAPGKEREIVAAISKA GGSTYVADSAKGRFAISKDNAKNTVYLQMNSLKPEDTAVYYCAARAGFAAQIFE YDYWGQGTLVTVSS | 228 |
| DR939 | EVQLVESGGGLVQAGGSMRLSCANSGRTFGTYAMGWFRQSPGKERERVASIDRD GSMSYYADSVKGRFTISGDNAKNTVYLQMNSLKPEDTAVYYCAASRRAVISLQT VDYWGQGTQVTVSS | 229 |
| DR940 | EVQLVESGGRLVQTGGSLRLSCAASGRTFSNYAMGWFRQAPGKEREFVAAISWY SGNTYYADSVKGRFTISRDNAKNTMYLQMNSLKPEDTAVYYCAANQIATMISVG DYWGQGTLVTVSS | 230 |
| DR941 | QVQLVESGGGLVEAGGSLRLACAASGSIFRLNLMGWYRQAPGKQRELVAHVGTT GNTAYADSVKGRFTISKDDAKNMVFLQMNSLKPEDTAVYYCYADRWGQFSWGQG TQVTVSS | 231 |
| DR942 | QVQLVESGGGLVQAGGSLRLSCVASGRTFTGYAMGWFRQAPGKEREFVAVITWS GATTYYSASVKGRFTLSRDNAKNTVYLQMNSLKSEDTAVYYCAIRIRDGVSPEN PNEYGYWGQGTQVTVSS | 232 |
| DR943 | QVQLVESGGGLVQAGGSLRLSCVASGRTVGYGMAWFRQAPGKQRDVVAAITWSG TSTYYPDSVKGRFTISRDNAKNTMYLQMSSLKPEDTAVYYCAAGSRRRVGVDVG GYDYWGQGTQVTVSS | 233 |
| DR944 | QVQLVESGGGLVQAGDSLRLSCAASGRTFTFSTHNMGWFRQAPGKEREFVGGIM WTSRASYADSVKGRFTVSRDNAKNTVYLQMNSLKPEDTAVYYCAAAWYGNSGAS YDYWGQGTQVTVSS | 234 |
| DR945 | QVQLVESGGGLVQLVQAGGSLRLSCAASGRTFSGYNMGWFRQAPGKEREFVAAI AWAGSRTYYTDSVKGRFTISRDNAKNTMYLQMNTLRPEDTAVYYCAAHDETYYR LDRVDLYTHWGQGTQVTVSS | 235 |
| DR946 | QVQLVESGGGLVQPGESLRLSCAASGPFTRYAMGWFRQAPGKEREFVAAISWSS GNTYYVDSVKGRFTISRDNAKNTMYLQMNSLKPEDTAVYYCAANEVATMSGPDD YWGQGTQVTVSS | 236 |
| DR947 | QVQLVESGGGLVQAGGSLRLSCAASGGSFGRYTMGWYRQAPGKEREFVAVISWS GTNTYYADSVKGRFTISRDNAKNTMYLQMNDLKPEDTAVYYCAARETYYSHWDE RMEYDYWGQGTQVTVSS | 237 |
| DR948 | QVQLVESGGGLVQAGDSLRLSCVASGSIDSSYYVSWFRQAPGKERDLVAAINWG DSRTAYADSVKGRFTISRDNAKNTVYLQMHSLRPNDTAVYYCASRIGLGGPVVA APTRYPYWGQGTLVTVSS | 238 |
| DR949 | QVQLVESGGGLVQAGGSLRLSCAASESILRFNVMSWLRQAPGKQRELVAVITSG GSTNYADSVKGRFTISRDNAKNTVYLQMNSLKPEDTAVYYCAADESGQYYWGQG TQVTVSS | 239 |
| DR950 | QVQLVESGGGLVQAGGSLRLSCAASGLTTSSAALAWFRQAPGKERELDPTITSG GGSTYYADSVKGRFTISKDNAKNTLYLQMSSLKPEDTAVYYCAARFYSTTYYYR EHEYSDWGQGTQVTVSS | 240 |
| DR951 | QVQLVESGGGLVQAGGSLRLSCAASGRTFGTSFGSLSMGWFRQAPGKEREFVAA ISRNIGRTYYADSVKDRFTISRDNAKNTASLQMNSLEPEDTAVYNCAATNSYDD LRRSYAYDYWGQGTQVTVSS | 241 |
| DR952 | QVQLVESGGGLVQAGGFLRLSCAASGRTFSSLAMAWFRQAPGKEREFVAAISRS GGSTDYADSVKGRFTISRDNAKSTLYLQMSSLKPEDTAVYYCAARDYSTLQYYN EYEYSDWGQGTLVTVSS | 242 |
| DR953 | QVQLVESGGGLVQAGDSLRLSCAASGPTFSTYAMAWFRQAPGKEREFVAAITQS GRTTYYEDSVKGRFTISKDNAKNTLYLQMNSLQPEDTAVYYCAARDLWSDSPDD WRIYSFWGQGTQVTVSS | 243 |
| DR954 | QVQLVESGGGLVQAGGSLRLSCAAARRTLHNFAMAWFRQAPGKEREFVAAISKG GGSADYADSVKGRFTISRDNAKNTVYLQMNSLKPEDTAVYYCAANDLASYSDSS YTSTSRYDYWGQGTQVTVSS | 244 |
| DR955 | QVQLVESGGGLVQTGGSLRLSCAASGRTFSSYAMAWFRQAPGKEREFVAAISIL GGSADYEDSVQGRFTISRDNAKNTMYLQMNSLKPEDTAVYYCAARRPAPSDSYW SSTSYAYWGQGTLVTVSS | 245 |
| DR956 | EVQLVESGGGLVQAGGSLRLSCAASGRTFSSLAMAWFRQAPGKEREFVAATTIL GGSADYGDPVKGRFTISRDNAKNTVYLQMNSLKPEDTAVYYCTGRRPAPSDNYW SPASYAYWGQGTQVTVSS | 246 |

-continued

| Name | Sequence | SEQ ID NO: |
|---|---|---|
| DR957 | QVQLVESGGGLVQAGGSLRLSCAPSGRTFSSYAMAWFRQPPGKEREFVAAITVS GASTYYADSVKGRFTISRDNAKNSMYLQMNSLKPEDTAVYYCAAGGPGTIFPDY DYWGQGTQVTVSS | 247 |
| DR958 | QVQLVESGGGLVQAGDSLTLSCTASGRTFSGYNMGWFRQAPGKERDFVAAINWI GGATYYADSVKGRFTISRDNAKNTVYLQMNSLKPEDTAVYYCHRYSEKFYSGKD YYTRDYDYWGQGTQVTVSS. | 248 |

13. The IFNGR binding molecule of claim 12, wherein each of the anti-IFNGR1 sdAb comprises a sequence of the first table in claim 12 and the anti-IFNGR2 sdAb comprises a sequence of the second table in claim 12.

14. A pharmaceutically acceptable formulation comprising the IFNGR binding molecule of claim 1 and a pharmaceutically acceptable carrier.

* * * * *

SEQUENCE LISTING

<160> NUMBER OF SEQ ID NOS: 317

<210> SEQ ID NO 1
<211> LENGTH: 489
<212> TYPE: PRT
<213> ORGANISM: Homo sapiens

<400> SEQUENCE: 1

Met Ala Leu Leu Phe Leu Leu Pro Leu Val Met Gln Gly Val Ser Arg
1               5                   10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

-continued

```
Glu Tyr Gln Ile Met Pro Gln Val Pro Val Phe Thr Val Glu Val Lys
 50                  55                  60
Asn Tyr Gly Val Lys Asn Ser Glu Trp Ile Asp Ala Cys Ile Asn Ile
 65                  70                  75                  80
Ser His His Tyr Cys Asn Ile Ser Asp His Val Gly Asp Pro Ser Asn
                     85                  90                  95
Ser Leu Trp Val Arg Val Lys Ala Arg Val Gly Gln Lys Glu Ser Ala
                    100                 105                 110
Tyr Ala Lys Ser Glu Glu Phe Ala Val Cys Arg Asp Gly Lys Ile Gly
                115                 120                 125
Pro Pro Lys Leu Asp Ile Arg Lys Glu Lys Gln Ile Met Ile Asp
        130                 135                 140
Ile Phe His Pro Ser Val Phe Val Asn Gly Asp Glu Gln Val Asp
145                 150                 155                 160
Tyr Asp Pro Glu Thr Thr Cys Tyr Ile Arg Val Tyr Asn Val Tyr Val
                    165                 170                 175
Arg Met Asn Gly Ser Glu Ile Gln Tyr Lys Ile Leu Thr Gln Lys Glu
                180                 185                 190
Asp Asp Cys Asp Glu Ile Gln Cys Gln Leu Ala Ile Pro Val Ser Ser
            195                 200                 205
Leu Asn Ser Gln Tyr Cys Val Ser Ala Glu Gly Val Leu His Val Trp
210                 215                 220
Gly Val Thr Thr Glu Lys Ser Lys Glu Val Cys Ile Thr Ile Phe Asn
225                 230                 235                 240
Ser Ser Ile Lys Gly Ser Leu Trp Ile Pro Val Ala Ala Leu Leu
                245                 250                 255
Leu Phe Leu Val Leu Ser Leu Val Phe Ile Cys Phe Tyr Ile Lys Lys
                260                 265                 270
Ile Asn Pro Leu Lys Glu Lys Ser Ile Ile Leu Pro Lys Ser Leu Ile
            275                 280                 285
Ser Val Val Arg Ser Ala Thr Leu Glu Thr Lys Pro Glu Ser Lys Tyr
    290                 295                 300
Val Ser Leu Ile Thr Ser Tyr Gln Pro Phe Ser Leu Glu Lys Glu Val
305                 310                 315                 320
Val Cys Glu Glu Pro Leu Ser Pro Ala Thr Val Pro Gly Met His Thr
                325                 330                 335
Glu Asp Asn Pro Gly Lys Val Glu His Thr Glu Glu Leu Ser Ser Ile
            340                 345                 350
Thr Glu Val Val Thr Thr Glu Glu Asn Ile Pro Asp Val Val Pro Gly
    355                 360                 365
Ser His Leu Thr Pro Ile Glu Arg Glu Ser Ser Ser Pro Leu Ser Ser
    370                 375                 380
Asn Gln Ser Glu Pro Gly Ser Ile Ala Leu Asn Ser Tyr His Ser Arg
385                 390                 395                 400
Asn Cys Ser Glu Ser Asp His Ser Arg Asn Gly Phe Asp Thr Asp Ser
                405                 410                 415
Ser Cys Leu Glu Ser His Ser Ser Leu Ser Asp Ser Glu Phe Pro Pro
            420                 425                 430
Asn Asn Lys Gly Glu Ile Lys Thr Glu Gly Gln Glu Leu Ile Thr Val
        435                 440                 445
Ile Lys Ala Pro Thr Ser Phe Gly Tyr Asp Lys Pro His Val Leu Val
450                 455                 460
```

Asp Leu Leu Val Asp Asp Ser Gly Lys Glu Ser Leu Ile Gly Tyr Arg
465                 470                 475                 480

Pro Thr Glu Asp Ser Lys Glu Phe Ser
                485

<210> SEQ ID NO 2
<211> LENGTH: 228
<212> TYPE: PRT
<213> ORGANISM: Homo sapiens

<400> SEQUENCE: 2

Glu Met Gly Thr Ala Asp Leu Gly Pro Ser Ser Val Pro Thr Pro Thr
1               5                   10                  15

Asn Val Thr Ile Glu Ser Tyr Asn Met Asn Pro Ile Val Tyr Trp Glu
            20                  25                  30

Tyr Gln Ile Met Pro Gln Val Pro Val Phe Thr Val Glu Val Lys Asn
        35                  40                  45

Tyr Gly Val Lys Asn Ser Glu Trp Ile Asp Ala Cys Ile Asn Ile Ser
    50                  55                  60

His His Tyr Cys Asn Ile Ser Asp His Val Gly Asp Pro Ser Asn Ser
65                  70                  75                  80

Leu Trp Val Arg Val Lys Ala Arg Val Gly Gln Lys Glu Ser Ala Tyr
                85                  90                  95

Ala Lys Ser Glu Glu Phe Ala Val Cys Arg Asp Gly Lys Ile Gly Pro
            100                 105                 110

Pro Lys Leu Asp Ile Arg Lys Glu Lys Gln Ile Met Ile Asp Ile
        115                 120                 125

Phe His Pro Ser Val Phe Val Asn Gly Asp Glu Gln Glu Val Asp Tyr
    130                 135                 140

Asp Pro Glu Thr Thr Cys Tyr Ile Arg Val Tyr Asn Val Tyr Val Arg
145                 150                 155                 160

Met Asn Gly Ser Glu Ile Gln Tyr Lys Ile Leu Thr Gln Lys Glu Asp
                165                 170                 175

Asp Cys Asp Glu Ile Gln Cys Gln Leu Ala Ile Pro Val Ser Ser Leu
            180                 185                 190

Asn Ser Gln Tyr Cys Val Ser Ala Glu Gly Val Leu His Val Trp Gly
        195                 200                 205

Val Thr Thr Glu Lys Ser Lys Glu Val Cys Ile Thr Ile Phe Asn Ser
    210                 215                 220

Ser Ile Lys Gly
225

<210> SEQ ID NO 3
<211> LENGTH: 477
<212> TYPE: PRT
<213> ORGANISM: Mus musculus

<400> SEQUENCE: 3

Met Gly Pro Gln Ala Ala Ala Gly Arg Met Ile Leu Leu Val Val Leu
1               5                   10                  15

Met Leu Ser Ala Lys Val Gly Ser Gly Ala Leu Thr Ser Thr Glu Asp
            20                  25                  30

Pro Glu Pro Pro Ser Val Pro Val Pro Thr Asn Val Leu Ile Lys Ser
        35                  40                  45

Tyr Asn Leu Asn Pro Val Val Cys Trp Glu Tyr Gln Asn Met Ser Gln
    50                  55                  60

-continued

```
Thr Pro Ile Phe Thr Val Gln Val Lys Val Tyr Ser Gly Ser Trp Thr
 65                  70                  75                  80

Asp Ser Cys Thr Asn Ile Ser Asp His Cys Cys Asn Ile Tyr Glu Gln
                 85                  90                  95

Ile Met Tyr Pro Asp Val Ser Ala Trp Ala Arg Val Lys Ala Lys Val
            100                 105                 110

Gly Gln Lys Glu Ser Asp Tyr Ala Arg Ser Lys Glu Phe Leu Met Cys
        115                 120                 125

Leu Lys Gly Lys Val Gly Pro Pro Gly Leu Glu Ile Arg Arg Lys Lys
    130                 135                 140

Glu Glu Gln Leu Ser Val Leu Val Phe His Pro Glu Val Val Asn
145                 150                 155                 160

Gly Glu Ser Gln Gly Thr Met Phe Gly Asp Gly Ser Thr Cys Tyr Thr
                165                 170                 175

Phe Asp Tyr Thr Val Tyr Val Glu His Asn Arg Ser Gly Glu Ile Leu
            180                 185                 190

His Thr Lys His Thr Val Glu Lys Glu Cys Asn Glu Thr Leu Cys
        195                 200                 205

Glu Leu Asn Ile Ser Val Ser Thr Leu Asp Ser Arg Tyr Cys Ile Ser
    210                 215                 220

Val Asp Gly Ile Ser Ser Phe Trp Gln Val Arg Thr Glu Lys Ser Lys
225                 230                 235                 240

Asp Val Cys Ile Pro Pro Phe His Asp Asp Arg Lys Asp Ser Ile Trp
                245                 250                 255

Ile Leu Val Val Ala Pro Leu Thr Val Phe Thr Val Val Ile Leu Val
            260                 265                 270

Phe Ala Tyr Trp Tyr Thr Lys Lys Asn Ser Phe Lys Arg Lys Ser Ile
        275                 280                 285

Met Leu Pro Lys Ser Leu Leu Ser Val Val Lys Ser Ala Thr Leu Glu
    290                 295                 300

Thr Lys Pro Glu Ser Lys Tyr Ser Leu Val Thr Pro His Gln Pro Ala
305                 310                 315                 320

Val Leu Glu Ser Glu Thr Val Ile Cys Glu Glu Pro Leu Ser Thr Val
                325                 330                 335

Thr Ala Pro Asp Ser Pro Glu Ala Ala Glu Gln Glu Glu Leu Ser Lys
            340                 345                 350

Glu Thr Lys Ala Leu Glu Ala Gly Gly Ser Thr Ser Ala Met Thr Pro
        355                 360                 365

Asp Ser Pro Pro Thr Pro Thr Gln Arg Arg Ser Phe Ser Leu Leu Ser
    370                 375                 380

Ser Asn Gln Ser Gly Pro Cys Ser Leu Thr Ala Tyr His Ser Arg Asn
385                 390                 395                 400

Gly Ser Asp Ser Gly Leu Val Gly Ser Gly Ser Ser Ile Ser Asp Leu
                405                 410                 415

Glu Ser Leu Pro Asn Asn Asn Ser Glu Thr Lys Met Ala Glu His Asp
            420                 425                 430

Pro Pro Pro Val Arg Lys Ala Pro Met Ala Ser Gly Tyr Asp Lys Pro
        435                 440                 445

His Met Leu Val Asp Val Leu Val Asp Val Gly Gly Lys Glu Ser Leu
    450                 455                 460

Met Gly Tyr Arg Leu Thr Gly Glu Ala Gln Glu Leu Ser
465                 470                 475
```

<210> SEQ ID NO 4
<211> LENGTH: 229
<212> TYPE: PRT
<213> ORGANISM: Mus musculus

<400> SEQUENCE: 4

```
Ala Leu Thr Ser Thr Glu Asp Pro Glu Pro Ser Val Pro Val Pro
1               5                   10                  15

Thr Asn Val Leu Ile Lys Ser Tyr Asn Leu Asn Pro Val Val Cys Trp
            20                  25                  30

Glu Tyr Gln Asn Met Ser Gln Thr Pro Ile Phe Thr Val Gln Val Lys
            35                  40                  45

Val Tyr Ser Gly Ser Trp Thr Asp Ser Cys Thr Asn Ile Ser Asp His
    50                  55                  60

Cys Cys Asn Ile Tyr Glu Gln Ile Met Tyr Pro Asp Val Ser Ala Trp
65                  70                  75                  80

Ala Arg Val Lys Ala Lys Val Gly Gln Lys Glu Ser Asp Tyr Ala Arg
                85                  90                  95

Ser Lys Glu Phe Leu Met Cys Leu Lys Gly Lys Val Gly Pro Pro Gly
            100                 105                 110

Leu Glu Ile Arg Arg Lys Lys Glu Glu Gln Leu Ser Val Leu Val Phe
        115                 120                 125

His Pro Glu Val Val Val Asn Gly Glu Ser Gln Gly Thr Met Phe Gly
130                 135                 140

Asp Gly Ser Thr Cys Tyr Thr Phe Asp Tyr Thr Val Tyr Val Glu His
145                 150                 155                 160

Asn Arg Ser Gly Glu Ile Leu His Thr Lys His Thr Val Glu Lys Glu
                165                 170                 175

Glu Cys Asn Glu Thr Leu Cys Glu Leu Asn Ile Ser Val Ser Thr Leu
            180                 185                 190

Asp Ser Arg Tyr Cys Ile Ser Val Asp Gly Ile Ser Ser Phe Trp Gln
        195                 200                 205

Val Arg Thr Glu Lys Ser Lys Asp Val Cys Ile Pro Pro Phe His Asp
    210                 215                 220

Asp Arg Lys Asp Ser
225
```

<210> SEQ ID NO 5
<211> LENGTH: 337
<212> TYPE: PRT
<213> ORGANISM: Homo sapiens

<400> SEQUENCE: 5

```
Met Arg Pro Thr Leu Leu Trp Ser Leu Leu Leu Leu Leu Gly Val Phe
1               5                   10                  15

Ala Ala Ala Ala Ala Ala Pro Pro Asp Pro Leu Ser Gln Leu Pro Ala
            20                  25                  30

Pro Gln His Pro Lys Ile Arg Leu Tyr Asn Ala Glu Gln Val Leu Ser
        35                  40                  45

Trp Glu Pro Val Ala Leu Ser Asn Ser Thr Arg Pro Val Val Tyr Gln
    50                  55                  60

Val Gln Phe Lys Tyr Thr Asp Ser Lys Trp Phe Thr Ala Asp Ile Met
65                  70                  75                  80

Ser Ile Gly Val Asn Cys Thr Gln Ile Thr Ala Thr Glu Cys Asp Phe
                85                  90                  95

Thr Ala Ala Ser Pro Ser Ala Gly Phe Pro Met Asp Phe Asn Val Thr
```

```
            100                 105                 110
Leu Arg Leu Arg Ala Glu Leu Gly Ala Leu His Ser Ala Trp Val Thr
            115                 120                 125

Met Pro Trp Phe Gln His Tyr Arg Asn Val Thr Val Gly Pro Pro Glu
            130                 135             140

Asn Ile Glu Val Thr Pro Gly Glu Gly Ser Leu Ile Ile Arg Phe Ser
145                 150                 155                 160

Ser Pro Phe Asp Ile Ala Asp Thr Ser Thr Ala Phe Phe Cys Tyr Tyr
                165                 170                 175

Val His Tyr Trp Glu Lys Gly Ile Gln Gln Val Lys Gly Pro Phe
                180                 185                 190

Arg Ser Asn Ser Ile Ser Leu Asp Asn Leu Lys Pro Ser Arg Val Tyr
            195                 200                 205

Cys Leu Gln Val Gln Ala Gln Leu Leu Trp Asn Lys Ser Asn Ile Phe
            210                 215                 220

Arg Val Gly His Leu Ser Asn Ile Ser Cys Tyr Glu Thr Met Ala Asp
225                 230                 235                 240

Ala Ser Thr Glu Leu Gln Gln Val Ile Leu Ile Ser Val Gly Thr Phe
                245                 250                 255

Ser Leu Leu Ser Val Leu Ala Gly Ala Cys Phe Phe Leu Val Leu Lys
                260                 265                 270

Tyr Arg Gly Leu Ile Lys Tyr Trp Phe His Thr Pro Pro Ser Ile Pro
            275                 280                 285

Leu Gln Ile Glu Glu Tyr Leu Lys Asp Pro Thr Gln Pro Ile Leu Glu
            290                 295                 300

Ala Leu Asp Lys Asp Ser Ser Pro Lys Asp Asp Val Trp Asp Ser Val
305                 310                 315                 320

Ser Ile Ile Ser Phe Pro Glu Lys Glu Gln Asp Val Leu Gln Thr
                325                 330                 335

Leu

<210> SEQ ID NO 6
<211> LENGTH: 220
<212> TYPE: PRT
<213> ORGANISM: Homo sapiens

<400> SEQUENCE: 6

Ser Gln Leu Pro Ala Pro Gln His Pro Lys Ile Arg Leu Tyr Asn Ala
1               5                   10                  15

Glu Gln Val Leu Ser Trp Glu Pro Val Ala Leu Ser Asn Ser Thr Arg
            20                  25                  30

Pro Val Val Tyr Gln Val Gln Phe Lys Tyr Thr Asp Ser Lys Trp Phe
            35                  40                  45

Thr Ala Asp Ile Met Ser Ile Gly Val Asn Cys Thr Gln Ile Thr Ala
50              55                  60

Thr Glu Cys Asp Phe Thr Ala Ala Ser Pro Ser Ala Gly Phe Pro Met
65                  70                  75                  80

Asp Phe Asn Val Thr Leu Arg Leu Arg Ala Glu Leu Gly Ala Leu His
                85                  90                  95

Ser Ala Trp Val Thr Met Pro Trp Phe Gln His Tyr Arg Asn Val Thr
                100                 105                 110

Val Gly Pro Pro Glu Asn Ile Glu Val Thr Pro Gly Glu Gly Ser Leu
            115                 120                 125

Ile Ile Arg Phe Ser Ser Pro Phe Asp Ile Ala Asp Thr Ser Thr Ala
```

```
            130                 135                 140
Phe Phe Cys Tyr Tyr Val His Tyr Trp Glu Lys Gly Ile Gln Gln
145                 150                 155                 160

Val Lys Gly Pro Phe Arg Ser Asn Ser Ile Ser Leu Asp Asn Leu Lys
                165                 170                 175

Pro Ser Arg Val Tyr Cys Leu Gln Val Gln Ala Gln Leu Leu Trp Asn
                180                 185                 190

Lys Ser Asn Ile Phe Arg Val Gly His Leu Ser Asn Ile Ser Cys Tyr
                195                 200                 205

Glu Thr Met Ala Asp Ala Ser Thr Glu Leu Gln Gln
210                 215                 220

<210> SEQ ID NO 7
<211> LENGTH: 332
<212> TYPE: PRT
<213> ORGANISM: Mus musculus

<400> SEQUENCE: 7

Met Arg Pro Leu Pro Leu Trp Leu Pro Ser Leu Leu Leu Cys Gly Leu
1               5                   10                  15

Gly Ala Ala Ser Ser Pro Asp Ser Phe Ser Gln Leu Ala Ala Pro
                20                  25                  30

Leu Asn Pro Arg Leu His Leu Tyr Asn Asp Glu Gln Ile Leu Thr Trp
            35                  40                  45

Glu Pro Ser Pro Ser Ser Asn Asp Pro Arg Pro Val Val Tyr Gln Val
        50                  55                  60

Glu Tyr Ser Phe Ile Asp Gly Ser Trp His Arg Leu Leu Glu Pro Asn
65                  70                  75                  80

Cys Thr Asp Ile Thr Glu Thr Lys Cys Asp Leu Thr Gly Gly Gly Arg
                85                  90                  95

Leu Lys Leu Phe Pro His Pro Phe Thr Val Phe Leu Arg Val Arg Ala
                100                 105                 110

Lys Arg Gly Asn Leu Thr Ser Lys Trp Val Gly Leu Glu Pro Phe Gln
            115                 120                 125

His Tyr Glu Asn Val Thr Val Gly Pro Pro Lys Asn Ile Ser Val Thr
        130                 135                 140

Pro Gly Lys Gly Ser Leu Val Ile His Phe Ser Pro Pro Phe Asp Val
145                 150                 155                 160

Phe His Gly Ala Thr Phe Gln Tyr Leu Val His Tyr Trp Glu Lys Ser
                165                 170                 175

Glu Thr Gln Gln Glu Gln Val Glu Gly Pro Phe Lys Ser Asn Ser Ile
                180                 185                 190

Val Leu Gly Asn Leu Lys Pro Tyr Arg Val Tyr Cys Leu Gln Thr Glu
            195                 200                 205

Ala Gln Leu Ile Leu Lys Asn Lys Lys Ile Arg Pro His Gly Leu Leu
        210                 215                 220

Ser Asn Val Ser Cys His Glu Thr Thr Ala Asn Ala Ser Ala Arg Leu
225                 230                 235                 240

Gln Gln Val Ile Leu Ile Pro Leu Gly Ile Phe Ala Leu Leu Leu Gly
                245                 250                 255

Leu Thr Gly Ala Cys Phe Thr Leu Phe Leu Lys Tyr Gln Ser Arg Val
                260                 265                 270

Lys Tyr Trp Phe Gln Ala Pro Pro Asn Ile Pro Glu Gln Ile Glu Glu
            275                 280                 285
```

```
Tyr Leu Lys Asp Pro Asp Gln Phe Ile Leu Glu Val Leu Asp Lys Asp
    290                 295                 300

Gly Ser Pro Lys Glu Asp Ser Trp Asp Ser Val Ser Ile Ile Ser Ser
305                 310                 315                 320

Pro Glu Lys Glu Arg Asp Asp Val Leu Gln Thr Pro
                325                 330

<210> SEQ ID NO 8
<211> LENGTH: 224
<212> TYPE: PRT
<213> ORGANISM: Mus musculus

<400> SEQUENCE: 8

Ala Ser Ser Pro Asp Ser Phe Ser Gln Leu Ala Ala Pro Leu Asn Pro
1               5                   10                  15

Arg Leu His Leu Tyr Asn Asp Glu Gln Ile Leu Thr Trp Glu Pro Ser
                20                  25                  30

Pro Ser Ser Asn Asp Pro Arg Pro Val Val Tyr Gln Val Glu Tyr Ser
            35                  40                  45

Phe Ile Asp Gly Ser Trp His Arg Leu Leu Glu Pro Asn Cys Thr Asp
50                  55                  60

Ile Thr Glu Thr Lys Cys Asp Leu Thr Gly Gly Arg Leu Lys Leu
65                  70                  75                  80

Phe Pro His Pro Phe Thr Val Phe Leu Arg Val Arg Ala Lys Arg Gly
                85                  90                  95

Asn Leu Thr Ser Lys Trp Val Gly Leu Glu Pro Phe Gln His Tyr Glu
            100                 105                 110

Asn Val Thr Val Gly Pro Pro Lys Asn Ile Ser Val Thr Pro Gly Lys
        115                 120                 125

Gly Ser Leu Val Ile His Phe Ser Pro Pro Phe Asp Val Phe His Gly
130                 135                 140

Ala Thr Phe Gln Tyr Leu Val His Tyr Trp Glu Lys Ser Glu Thr Gln
145                 150                 155                 160

Gln Glu Gln Val Glu Gly Pro Phe Lys Ser Asn Ser Ile Val Leu Gly
                165                 170                 175

Asn Leu Lys Pro Tyr Arg Val Tyr Cys Leu Gln Thr Glu Ala Gln Leu
            180                 185                 190

Ile Leu Lys Asn Lys Lys Ile Arg Pro His Gly Leu Leu Ser Asn Val
        195                 200                 205

Ser Cys His Glu Thr Thr Ala Asn Ala Ser Ala Arg Leu Gln Gln Val
210                 215                 220

<210> SEQ ID NO 9
<211> LENGTH: 166
<212> TYPE: PRT
<213> ORGANISM: Homo sapiens

<400> SEQUENCE: 9

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
                20                  25                  30

Asn Leu Lys Lys Tyr Phe Asn Ala Gly His Ser Asp Val Ala Asp Asn
            35                  40                  45

Gly Thr Leu Phe Leu Gly Ile Leu Lys Asn Trp Lys Glu Glu Ser Asp
50                  55                  60
```

```
Arg Lys Ile Met Gln Ser Gln Ile Val Ser Phe Tyr Phe Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Lys Arg
                100                 105                 110

Asp Asp Phe Glu Lys Leu Thr Asn Tyr Ser Val Thr Asp Leu Asn Val
            115                 120                 125

Gln Arg Lys Ala Ile His Glu Leu Ile Gln Val Met Ala Glu Leu Ser
        130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 10
<211> LENGTH: 155
<212> TYPE: PRT
<213> ORGANISM: Mus musculus

<400> SEQUENCE: 10

Met Asn Ala Thr His Cys Ile Leu Ala Leu Gln Leu Phe Leu Met Ala
 1               5                  10                  15

Val Ser Gly Cys Tyr Cys His Gly Thr Val Ile Glu Ser Leu Glu Ser
                20                  25                  30

Leu Asn Asn Tyr Phe Asn Ser Ser Gly Ile Asp Val Glu Glu Lys Ser
                35                  40                  45

Leu Phe Leu Asp Ile Trp Arg Asn Trp Gln Lys Asp Gly Asp Met Lys
 50                  55                  60

Ile Leu Gln Ser Gln Ile Ile Ser Phe Tyr Leu Arg Leu Phe Glu Val
 65                  70                  75                  80

Leu Lys Asp Asn Gln Ala Ile Ser Asn Asn Ile Ser Val Ile Glu Ser
                 85                  90                  95

His Leu Ile Thr Thr Phe Phe Ser Asn Ser Lys Ala Lys Lys Asp Ala
                100                 105                 110

Phe Met Ser Ile Ala Lys Phe Glu Val Asn Asn Pro Gln Val Gln Arg
            115                 120                 125

Gln Ala Phe Asn Glu Leu Ile Arg Val Val His Gln Leu Leu Pro Glu
        130                 135                 140

Ser Ser Leu Arg Lys Arg Lys Arg Ser Arg Cys
145                 150                 155

<210> SEQ ID NO 11

<400> SEQUENCE: 11

000

<210> SEQ ID NO 12

<400> SEQUENCE: 12

000

<210> SEQ ID NO 13
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 13

Gly Gly Gly Ser
1

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Gly Ser
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Ser Gly
1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Ser Gly Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ser Gly Ser Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ser Gly Gly Gly
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Ser Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ser Ser Ser Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Ser Gly Gly Gly Ser Gly
1               5

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Ser Gly Gly Gly Ser Gly Gly Gly Ser Gly
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Ser Gly Gly Gly Ser Gly Gly Gly Ser Gly Gly Gly Ser Gly
1               5                   10                  15

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Gly Gly Ser Gly Gly Gly Ser Gly Gly Gly Ser Gly Gly Gly Ser Gly
1               5                   10                  15

Gly Gly Ser Gly
            20

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ile Ala Ser Asp Tyr Thr Arg Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ile Leu Ser Ile Asn Thr Met Gly
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Thr Phe Thr Gly Tyr Ala Met Gly
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Thr Phe Ser Thr Tyr Val Met Gly
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Thr Phe Ser Asn Tyr Ala Met Gly
1               5

<210> SEQ ID NO 30
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Thr Phe Thr Ser Leu Ala Met Gly
1               5

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Thr Phe Gly Thr Ser Phe Gly Ala Leu Ser Met Gly
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Thr Phe Ser Ser Tyr Ala Met Ala
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Phe Ser Thr Tyr Ala Met Ala
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Thr Phe Ser Ser Tyr Ala Met Ala
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35
```

```
Arg Thr Phe Ser Ser Tyr Ala Met Gly
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Phe Ser Asn Ser Ala Met Ala
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Thr Leu His Asn Phe Ala Met Ala
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Pro Arg Thr Thr Tyr Ala Met Gly
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Thr Phe Ser Gly Tyr Asn Met Gly
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Thr Asp Ser Thr Tyr Gly Met Ala
1               5

<210> SEQ ID NO 41
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 41

Arg Thr Leu Ser Thr Tyr Ala Met Gly
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ser Phe Ala Asn Tyr Ala Met Gly
1               5

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Thr Phe Thr Phe Ser Thr His Asn Met Gly
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Ile Thr Ser Ile Asn Thr Met Gly
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Thr Phe Met Thr Tyr Ala Met Gly
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Thr Phe Ser Arg Tyr Ala Met Gly
1               5
```

```
<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Thr Phe Ser Arg Tyr Ala Met Gly
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Thr Phe Ser Arg Tyr Ala Met Asn
1               5

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ile Ile Arg Ser Val Gly Asp Ser Tyr Tyr Ala Asp Ser Val Lys
1               5                   10                  15

Gly

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Ile Ser Ser Gly Gly Ser Thr Asn Tyr Ala Asp Ser Val Lys Gly
1               5                   10                  15

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Ile Thr Trp Ser Gly Ala Thr Thr Tyr Tyr Ser Ala Ser Val Lys
1               5                   10                  15

Gly

<210> SEQ ID NO 52
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 52

Ala Ile Ser Arg Ser Gly Gly Thr Thr Thr Tyr Ala Asp Ser Val Lys
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ile Asn Trp Asn Ile Gly Ser Thr Tyr Tyr Ala Asp Ser Val Lys
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Ile Ser Arg Ser Gly Gly Ser Thr Asp Tyr Ala Asp Ser Val Lys
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Ile Thr Arg Asn Thr Gly Arg Thr Phe Tyr Ala Asp Ser Val Lys
1               5                   10                  15

Asp

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Ile Ser Ile Leu Gly Gly Ser Ala Asp Tyr Glu Asp Ser Val Gln
1               5                   10                  15

Gly

<210> SEQ ID NO 57
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 57

Ala Ile Thr Val Gly Gly Ser Thr Tyr Tyr Val Asp Ser Val Lys
1               5                   10                  15

Gly

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ile Thr Val Ser Gly Ala Ser Thr Tyr Tyr Ala Asp Ser Val Lys
1               5                   10                  15

Gly

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Ile Ser Ser Trp Ser Gly Gly Ser Thr Tyr Tyr Ala Asp Ser Val
1               5                   10                  15

Lys Gly

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Ile Ser Arg Gly Gly Gly Ser Thr Asp Tyr Ala Asp Ser Val Lys
1               5                   10                  15

Gly

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ile Ser Lys Gly Gly Gly Ser Ala Asp Tyr Ala Asp Ser Val Lys
1               5                   10                  15

Gly

<210> SEQ ID NO 62
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 62

Ala Ile Ser Lys Ala Gly Gly Ser Thr Tyr Val Ala Asp Ser Ala Lys
1               5                   10                  15

Gly

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Ile Ala Trp Ala Gly Ser Arg Thr Tyr Tyr Thr Asp Ser Val Lys
1               5                   10                  15

Gly

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Ile Ser Arg Ala Gly Gly Ser Ala Asp His Ala Asp Ser Val Lys
1               5                   10                  15

Gly

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ile Ser Trp Arg Ser Gly Asn Thr Tyr Tyr Ala Asp Ser Val Lys
1               5                   10                  15

Gly

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Ile Ser Arg Gly Gly Gly Ser Thr Trp Tyr Ala Asp Ser Val Lys
1               5                   10                  15

Gly

<210> SEQ ID NO 67
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ile Met Trp Thr Ser Arg Ala Ser Tyr Ala Asp Ser Val Lys Gly
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Ile Thr Ser Gly Gly Ser Thr Asn Tyr Ala Asp Ser Val Lys Gly
1               5                   10                  15

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Ile Ser Trp Ser Ser Gly Ser Thr Tyr Tyr Ala Asp Ser Val Lys
1               5                   10                  15

Gly

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Ile Ser Arg Ser Gly Gly Thr Thr Ser Tyr Ala Asn Ser Val Lys
1               5                   10                  15

Gly

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Ile Ser Ile Gly Gly Gly Ser Ala Asp Tyr Ala Asp Thr Val Lys
1               5                   10                  15

Gly

<210> SEQ ID NO 72
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 72

Ala Ile Ser Trp Ser Ser Gly Asn Thr Tyr Val Ala Asp Ser Val Lys
1               5                   10                  15
Gly

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Gly His Leu Tyr Tyr Gly Ser Arg Trp Arg Tyr Pro Ala Ser Tyr
1               5                   10                  15
Asp Tyr

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Arg Ala Tyr Tyr
1               5

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ile Arg Asp Gly Val Ser Pro Glu Asn Pro Asn Glu Tyr Gly Tyr
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ala Gly Pro Ala Ile Gly Arg Thr Ala Asn Asp Tyr His Ser
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

```
Val Trp Pro Thr Gly Arg Leu Arg Val Asp Ser Glu Tyr Asp Tyr
1               5                   10                  15
```

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Arg Asp Tyr Ser Thr Leu Gln Tyr Tyr Asn Glu Tyr Glu Tyr Ser Asp
1               5                   10                  15
```

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Thr Asn Ser Tyr Asp Asp Leu Arg Arg Ser Tyr Ala Tyr Asn Tyr
1               5                   10                  15
```

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Arg Arg Pro Ala Pro Ser Asp Ser Tyr Trp Ser Ser Thr Ser Tyr Ala
1               5                   10                  15

Tyr
```

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Arg Asp Tyr Arg Arg Arg Ser Tyr Ala Pro Glu Ala Glu Gln Tyr Asp
1               5                   10                  15

Tyr
```

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

```
Gly Gly Pro Gly Thr Ile Phe Pro Asp Tyr Asp Tyr
1               5                   10
```

<210> SEQ ID NO 83

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Asp Tyr Tyr Ser Asp Tyr Phe Lys Tyr Asp Asn Glu Asn
1               5                   10

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Tyr Tyr Ser Gly Arg Tyr Tyr Glu Ser Leu Glu Tyr Asp Tyr
1               5                   10                  15

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asn Asp Leu Ala Ser Tyr Ser Asp Ser Ser Tyr Thr Ser Thr Ser Arg
1               5                   10                  15

Tyr Asp Tyr

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ala Gly Phe Ala Ala Gln Ile Phe Glu Tyr Asp Tyr
1               5                   10

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

His Asp Glu Thr Tyr Tyr Arg Leu Asp Arg Val Asp Leu Tyr Thr His
1               5                   10                  15

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 88

Gly Arg Ser Tyr Ser Ser Pro Tyr Asp Tyr Phe Asn Ala Leu Ala Tyr
1               5                   10                  15

Ser Tyr

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asn Glu Val Ala Thr Met Ser Gly Pro His Asp His
1               5                   10

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Ser Tyr Ser Gly Ser Tyr Thr Tyr Ser Phe Gly Glu Tyr Asp Tyr
1               5                   10                  15

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Trp Tyr Gly Asn Ser Gly Ala Ser Tyr Asp Tyr
1               5                   10

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Ser Met Tyr Phe
1               5

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Ser Ile Ala Thr Met Tyr Gly Pro Asn Asp Tyr
1               5                   10

<210> SEQ ID NO 94
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Asp Gly Pro Ala Met Gly Val Phe Gly Ser Asp Tyr Asp Tyr
1               5                   10                  15

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Thr Pro Arg Pro Ser Ser Ser Tyr Phe Thr Pro Gln Asp Tyr Glu
1               5                   10                  15

Tyr

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Thr Ile Ala Thr Met Ser Asp Glu Asn Thr Tyr
1               5                   10

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Thr Phe Thr Ser Tyr Ala Met Asn
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Thr Phe Ser Asn Tyr Arg Met Gly
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 99

Arg Thr Phe Ser Ser Tyr Ala Met Gly
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Thr Phe Ser Ser Tyr Ala Val Ala
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Thr Phe Ser Thr Tyr Ala Met Gly
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Thr Phe Ser Tyr Thr Thr Ile Gly
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Thr Ile Ser Ser Leu Ala Met Gly
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ser Phe Ala Asn Tyr Ala Met Gly
1               5

<210> SEQ ID NO 105
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 105

Arg Ala Phe Ser Thr Tyr Ala Leu Gly
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Thr Phe Ser Ser Val Ala Met Ala
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Thr Phe Arg Ser Tyr Ser Met Gly
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Pro Arg Thr Thr Tyr Ala Met Gly
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Thr Phe Gly Thr Tyr Ala Met Gly
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Thr Phe Ser Asn Tyr Ala Met Gly
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ser Ile Phe Arg Leu Asn Leu Met Gly
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Thr Phe Thr Gly Tyr Ala Met Gly
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Thr Val Gly Tyr Gly Met Ala
1               5

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Thr Phe Thr Phe Ser Thr His Asn Met Gly
1               5                   10

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Thr Phe Ser Gly Tyr Asn Met Gly
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Pro Phe Thr Arg Tyr Ala Met Gly
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Ser Phe Gly Arg Tyr Thr Met Gly
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ser Ile Asp Ser Ser Tyr Tyr Val Ser
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Ile Leu Arg Phe Asn Val Met Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Leu Thr Thr Ser Ser Ala Ala Leu Ala
1               5

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Thr Phe Gly Thr Ser Phe Gly Ser Leu Ser Met Gly
1               5                   10

<210> SEQ ID NO 122
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Thr Phe Ser Ser Leu Ala Met Ala
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Pro Thr Phe Ser Thr Tyr Ala Met Ala
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Thr Leu His Asn Phe Ala Met Ala
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Thr Phe Ser Ser Tyr Ala Met Ala
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Thr Phe Ser Ser Leu Ala Met Ala
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Thr Phe Ser Ser Tyr Ala Met Ala
```

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Thr Phe Ser Gly Tyr Asn Met Gly
1               5

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Ile Ser Trp Ser Ser Gly Asn Thr Tyr Val Ala Asp Ser Val Lys
1               5                   10                  15

Gly

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Ile Ser Arg Gly Gly Gly Thr Thr Leu Tyr Ala Asp Ser Val Lys
1               5                   10                  15

Gly

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Ile Ser Arg Gly Gly Gly Ser Thr Asp Tyr Ala Asp Ser Val Lys
1               5                   10                  15

Gly

<210> SEQ ID NO 132
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Leu Ser Arg Gly Gly Gly Ser Ala Tyr Tyr Thr Asp Ser Val Lys
1               5                   10                  15

Gly

```
<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Ile Ser Val Asn Gly Gly Ser Thr Tyr Tyr Ala Asp Ser Val Thr
1               5                   10                  15

Gly

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Val Ile Ser Ala Gly Gly Gly Ser Arg Asp Tyr Ala Asp Ala Leu Lys
1               5                   10                  15

Gly

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Ile Ser Trp Ser Gly Arg Ser Thr Tyr Tyr Val Asp Ser Val Lys
1               5                   10                  15

Gly

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Ile Ser Arg Gly Gly Gly Ser Thr Trp Tyr Ala Asp Ser Val Lys
1               5                   10                  15

Gly

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Ile Ser Arg Gly Gly Gly Ser Thr Asp Tyr Ala Asp Ser Val Lys
1               5                   10                  15
```

Gly

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Ile Ser Ser Gly Gly Gly Ser Thr Asp Tyr Ala Asp Ser Val Lys
1               5                   10                  15

Gly

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ala Ile Ser Trp Tyr Ser Gly Thr Thr Tyr Tyr Ala Asp Pro Val Lys
1               5                   10                  15

Gly

<210> SEQ ID NO 140
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Ile Ser Lys Ala Gly Gly Ser Thr Tyr Val Ala Asp Ser Ala Lys
1               5                   10                  15

Gly

<210> SEQ ID NO 141
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Ile Asp Arg Asp Gly Ser Met Ser Tyr Tyr Ala Asp Ser Val Lys
1               5                   10                  15

Gly

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Ile Ser Trp Tyr Ser Gly Asn Thr Tyr Tyr Ala Asp Ser Val Lys
1               5                   10                  15

Gly

<210> SEQ ID NO 143
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

His Val Gly Thr Thr Gly Asn Thr Ala Tyr Ala Asp Ser Val Lys Gly
1               5                   10                  15

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Val Ile Thr Trp Ser Gly Ala Thr Thr Tyr Tyr Ser Ala Ser Val Lys
1               5                   10                  15

Gly

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Ile Thr Trp Ser Gly Thr Ser Thr Tyr Tyr Pro Asp Ser Val Lys
1               5                   10                  15

Gly

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Ile Met Trp Thr Ser Arg Ala Ser Tyr Ala Asp Ser Val Lys Gly
1               5                   10                  15

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Ile Ala Trp Ala Gly Ser Arg Thr Tyr Tyr Thr Asp Ser Val Lys
1               5                   10                  15

Gly

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Ile Ser Trp Ser Ser Gly Asn Thr Tyr Tyr Val Asp Ser Val Lys
1               5                   10                  15

Gly

<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Val Ile Ser Trp Ser Gly Thr Asn Thr Tyr Tyr Ala Asp Ser Val Lys
1               5                   10                  15

Gly

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Ile Asn Trp Gly Asp Ser Arg Thr Ala Tyr Ala Asp Ser Val Lys
1               5                   10                  15

Gly

<210> SEQ ID NO 151
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Val Ile Thr Ser Gly Gly Ser Thr Asn Tyr Ala Asp Ser Val Lys Gly
1               5                   10                  15

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Thr Ile Thr Ser Gly Gly Gly Ser Thr Tyr Tyr Ala Asp Ser Val Lys
1               5                   10                  15

Gly

```
<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Ile Ser Arg Asn Ile Gly Arg Thr Tyr Tyr Ala Asp Ser Val Lys
1               5                   10                  15
Asp

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Ile Ser Arg Ser Gly Gly Ser Thr Asp Tyr Ala Asp Ser Val Lys
1               5                   10                  15
Gly

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Ile Thr Gln Ser Gly Arg Thr Thr Tyr Tyr Glu Asp Ser Val Lys
1               5                   10                  15
Gly

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Ile Ser Lys Gly Gly Gly Ser Ala Asp Tyr Ala Asp Ser Val Lys
1               5                   10                  15
Gly

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Ile Ser Ile Leu Gly Gly Ser Ala Asp Tyr Glu Asp Ser Val Gln
1               5                   10                  15
Gly
```

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Thr Thr Ile Leu Gly Gly Ser Ala Asp Tyr Gly Asp Pro Val Lys
1               5                   10                  15

Gly

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Ile Thr Val Ser Gly Ala Ser Thr Tyr Tyr Ala Asp Ser Val Lys
1               5                   10                  15

Gly

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Ile Asn Trp Ile Gly Gly Ala Thr Tyr Tyr Ala Asp Ser Val Lys
1               5                   10                  15

Gly

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Thr Ile Ala Thr Met Ser Asp Glu Tyr Thr Tyr
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Asp Phe Ser Thr Thr Trp Asp Glu Tyr Asn Tyr
1               5                   10

<210> SEQ ID NO 163
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Arg Ala Tyr Ser Gly Arg Tyr Tyr Gln Phe Leu Glu Tyr Asp Tyr
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Arg Asn Tyr Asp Gly Thr Tyr Tyr Gln Glu Asn Gln Tyr Asn Tyr
1               5                   10                  15

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Arg Pro Tyr Pro Gly Ser Asp Phe Leu Thr Trp Ala Ser Tyr Asp
1               5                   10                  15

Tyr

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Arg Asn Thr Asp Thr Tyr Thr Thr Thr Gly Asp Tyr Asp Tyr
1               5                   10                  15

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Glu Asp Gly His Ser Glu Tyr Asp Tyr
1               5                   10

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168
```

```
Arg Ser Tyr Ser Gly Ser Tyr Thr Tyr Ser Phe Gly Glu Tyr Asp Tyr
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Arg Ser Tyr Ser Ser Ser Tyr Tyr Tyr Ser Gln Tyr Glu Tyr Asp Tyr
1               5                   10                  15

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Arg Asp Tyr Ser Ser Arg Arg Tyr Tyr Gln Ser Arg Tyr Glu Tyr Asp
1               5                   10                  15

Leu

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asn Glu Ile Ala Thr Met Glu Ser Ser Asn Asp Tyr
1               5                   10

<210> SEQ ID NO 172
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Arg Ala Gly Phe Ala Ala Gln Ile Phe Glu Tyr Asp Tyr
1               5                   10

<210> SEQ ID NO 173
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Arg Arg Ala Val Ile Ser Leu Gln Thr Val Asp Tyr
1               5                   10

<210> SEQ ID NO 174
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asn Gln Ile Ala Thr Met Ile Ser Val Gly Asp Tyr
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asp Arg Trp Gly Gln Phe Ser
1               5

<210> SEQ ID NO 176
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Arg Ile Arg Asp Gly Val Ser Pro Glu Asn Pro Asn Glu Tyr Gly Tyr
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Ser Arg Arg Arg Val Gly Val Asp Val Gly Gly Tyr Asp Tyr
1               5                   10                  15

<210> SEQ ID NO 178
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Trp Tyr Gly Asn Ser Gly Ala Ser Tyr Asp Tyr
1               5                   10

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

His Asp Glu Thr Tyr Tyr Arg Leu Asp Arg Val Asp Leu Tyr Thr His
```

```
                1               5                  10                 15
```

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Asn Glu Val Ala Thr Met Ser Gly Pro Asp Asp Tyr
1               5                   10
```

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

```
Arg Glu Thr Tyr Tyr Ser His Trp Asp Glu Arg Met Glu Tyr Asp Tyr
1               5                   10                  15
```

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

```
Arg Ile Gly Leu Gly Gly Pro Val Val Ala Ala Pro Thr Arg Tyr Pro
1               5                   10                  15

Tyr
```

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

```
Asp Glu Ser Gly Gln Tyr Tyr
1               5
```

<210> SEQ ID NO 184
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Arg Phe Tyr Ser Thr Thr Tyr Tyr Tyr Arg Glu His Glu Tyr Ser Asp
1               5                   10                  15
```

<210> SEQ ID NO 185
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 185

Thr Asn Ser Tyr Asp Asp Leu Arg Arg Ser Tyr Ala Tyr Asp Tyr
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Asp Tyr Ser Thr Leu Gln Tyr Tyr Asn Glu Tyr Glu Tyr Ser Asp
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Arg Asp Leu Trp Ser Asp Ser Pro Asp Asp Trp Arg Ile Tyr Ser Phe
1               5                   10                  15

<210> SEQ ID NO 188
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asn Asp Leu Ala Ser Tyr Ser Asp Ser Ser Tyr Thr Ser Thr Ser Arg
1               5                   10                  15

Tyr Asp Tyr

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Arg Arg Pro Ala Pro Ser Asp Ser Tyr Trp Ser Ser Thr Ser Tyr Ala
1               5                   10                  15

Tyr

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190
```

```
Arg Arg Pro Ala Pro Ser Asp Asn Tyr Trp Ser Pro Ala Ser Tyr Ala
1               5                   10                  15

Tyr

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Gly Pro Gly Thr Ile Phe Pro Asp Tyr Asp Tyr
1               5                   10

<210> SEQ ID NO 192
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Tyr Ser Glu Lys Phe Tyr Ser Gly Lys Asp Tyr Tyr Thr Arg Asp Tyr
1               5                   10                  15

Asp Tyr

<210> SEQ ID NO 193
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Ala Ser Asp Tyr
            20                  25                  30

Thr Arg Gly Trp Phe Arg Gln Ala Pro Gly Lys Glu Arg Glu Phe Val
        35                  40                  45

Ala Ala Ile Ile Arg Ser Val Gly Asp Ser Tyr Tyr Ala Asp Ser Val
    50                  55                  60

Lys Gly Arg Phe Thr Ile Ser Ile Asp Asn Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Val Gly Gly His Leu Tyr Tyr Gly Ser Arg Trp Arg Tyr Pro Ala
            100                 105                 110

Ser Tyr Asp Tyr Trp Gly Gln Gly Thr Gln Val Thr Val Ser Ser
        115                 120                 125

<210> SEQ ID NO 194
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 194

Glu Val Gln Leu Val Glu Ser Gly Gly Gly Leu Val Gln Ala Gly Gly
1               5                   10                  15

Ser Leu Arg Leu Ser Cys Glu Ala Ser Glu Ser Ile Leu Ser Ile Asn
            20                  25                  30

Thr Met Gly Trp Phe Arg Gln Ala Pro Gly Lys Gln Arg Glu Leu Val
        35                  40                  45

Ala Ala Ile Ser Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asp
                85                  90                  95

Ala Asp Arg Ala Tyr Tyr Lys Gly Gln Gly Thr Gln Val Thr Val Ser
            100                 105                 110

Ser

<210> SEQ ID NO 195
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Thr Gly Tyr
            20                  25                  30

Ala Met Gly Trp Phe Arg Gln Ala Pro Gly Lys Glu Arg Glu Phe Val
        35                  40                  45

Ala Val Ile Thr Trp Ser Gly Ala Thr Thr Tyr Tyr Ser Ala Ser Val
    50                  55                  60

Lys Gly Arg Phe Thr Leu Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ile Arg Ile Arg Asp Gly Val Ser Pro Glu Asn Pro Asn Glu Tyr
            100                 105                 110

Gly Tyr Trp Gly Gln Gly Thr Gln Val Thr Val Ser Ser
        115                 120                 125

<210> SEQ ID NO 196
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ser Thr Tyr
            20                  25                  30

Val Met Gly Trp Phe Arg Gln Ala Pro Gly Lys Glu Arg Glu Phe Val

```
            35                  40                  45

Ala Ala Ile Ser Arg Ser Gly Gly Thr Thr Thr Tyr Ala Asp Ser Val
        50                  55                  60

Lys Gly Arg Phe Asp Ile Ser Arg Asp Asn Gly Lys Asn Thr Leu Phe
 65                  70                  75                  80

Leu Gln Met Asn Ser Leu Ile Pro Glu Asp Thr Ala Ala Tyr Tyr Cys
                85                  90                  95

Ala Ala Arg Ala Gly Pro Ala Ile Gly Arg Thr Ala Asn Asp Tyr His
                100                 105                 110

Ser Trp Gly Gln Gly Thr Leu Val Thr Val Ser Ser
                115                 120

<210> SEQ ID NO 197
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Asn Tyr
                20                  25                  30

Ala Met Gly Trp Phe Arg Gln Ala Pro Gly Asn Glu Arg Glu Phe Val
            35                  40                  45

Ala Ala Ile Asn Trp Asn Ile Gly Ser Thr Tyr Tyr Ala Asp Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Gly Ala Val Trp Pro Thr Gly Arg Leu Arg Val Asp Ser Glu Tyr Asp
                100                 105                 110

Tyr Trp Gly Gln Gly Thr Gln Val Thr Val Ser Ser
                115                 120

<210> SEQ ID NO 198
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Val Gln Leu Val Glu Ser Gly Gly Gly Leu Val Gln Ala Gly Gly
 1               5                  10                  15

Ser Leu Arg Val Thr Cys Ala Ala Ser Gly Arg Thr Phe Thr Ser Leu
                20                  25                  30

Ala Met Gly Trp Phe Arg Gln Ala Pro Gly Lys Glu Arg Glu Phe Val
            35                  40                  45

Ala Ala Ile Ser Arg Ser Gly Gly Ser Thr Asp Tyr Ala Asp Ser Val
        50                  55                  60

Lys Gly Arg Phe Phe Ile Ser Arg Asp Asn Ala Lys Ser Thr Leu Tyr
 65                  70                  75                  80

Leu Gln Met Ser Ser Leu Lys Pro Glu Asp Thr Ala Val Tyr Tyr Cys
```

```
                    85                  90                  95

Ala Ala Arg Asp Tyr Ser Thr Leu Gln Tyr Tyr Asn Glu Tyr Glu Tyr
                100                 105                 110

Ser Asp Trp Gly Gln Gly Thr Gln Val Thr Val Ser Ser
            115                 120                 125

<210> SEQ ID NO 199
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Thr Ser
            20                  25                  30

Phe Gly Ala Leu Ser Met Gly Trp Phe Arg Gln Ala Pro Gly Lys Glu
        35                  40                  45

Arg Glu Phe Val Ala Ala Ile Thr Arg Asn Thr Gly Arg Thr Phe Tyr
    50                  55                  60

Ala Asp Ser Val Lys Asp Arg Phe Thr Ile Ser Arg Asp Asn Ala Lys
65                  70                  75                  80

Asn Thr Ala Ser Leu Gln Met Asn Ser Leu Glu Pro Glu Asp Thr Ala
                85                  90                  95

Val Tyr Ile Cys Ala Ala Thr Asn Ser Tyr Asp Asp Leu Arg Arg Ser
                100                 105                 110

Tyr Ala Tyr Asn Tyr Trp Gly Gln Gly Thr Gln Val Thr Val Ser Ser
            115                 120                 125

<210> SEQ ID NO 200
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Val Gln Leu Val Glu Ser Gly Gly Gly Leu Val Gln Thr Gly Gly
1               5                   10                  15

Ser Leu Arg Leu Ser Cys Ala Ala Ser Gly Arg Thr Phe Ser Ser Tyr
            20                  25                  30

Ala Met Ala Trp Phe Arg Gln Ala Pro Gly Lys Glu Arg Glu Phe Val
        35                  40                  45

Ala Ala Ile Ser Ile Leu Gly Gly Ser Ala Asp Tyr Glu Asp Ser Val
    50                  55                  60

Gln Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Arg Arg Pro Ala Pro Ser Asp Ser Tyr Trp Ser Thr Ser
                100                 105                 110

Tyr Ala Tyr Trp Gly Gln Gly Thr Leu Val Thr Val Ser Ser
            115                 120                 125
```

```
<210> SEQ ID NO 201
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Val Glu Ser Gly Gly Ala Leu Val Gln Ala Gly Gly
1               5                   10                  15

Ser Leu Arg Leu Ser Cys Thr Val Ser Gly Arg Ser Phe Ser Thr Tyr
            20                  25                  30

Ala Met Ala Trp Phe Arg Arg Ala Pro Gly Lys Glu Arg Glu Leu Val
        35                  40                  45

Ser Ala Ile Thr Val Gly Gly Gly Ser Thr Tyr Tyr Val Asp Ser Val
    50                  55                  60

Lys Gly Arg Phe Thr Ile Ser Arg Glu Asn Ala Lys Asn Thr Leu Tyr
65                  70                  75                  80

Leu Gln Met Asn Asn Leu Lys Pro Glu Asp Thr Ala Ile Tyr Ile Cys
                85                  90                  95

Ala Ala Arg Asp Tyr Arg Arg Ser Tyr Ala Pro Glu Ala Glu Gln
            100                 105                 110

Tyr Asp Tyr Trp Gly Gln Gly Thr Gln Val Thr Val Ser Ser
        115                 120                 125

<210> SEQ ID NO 202
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Glu Val Gln Leu Val Glu Ser Gly Gly Gly Leu Val Gln Ala Gly Gly
1               5                   10                  15

Ser Leu Arg Leu Ser Cys Ala Pro Ser Gly Arg Thr Phe Ser Ser Tyr
            20                  25                  30

Ala Met Ala Trp Phe Arg Gln Pro Pro Gly Lys Glu Arg Glu Phe Val
        35                  40                  45

Ala Ala Ile Thr Val Ser Gly Ala Ser Thr Tyr Tyr Ala Asp Ser Val
    50                  55                  60

Lys Gly Arg Phe Thr Ile Ser Arg Asp Asn Ala Lys Asn Ser Met Tyr
65                  70                  75                  80

Leu Gln Met Asn Ser Leu Lys Pro Glu Asp Thr Ala Val Tyr Tyr Cys
                85                  90                  95

Ala Ala Gly Gly Pro Gly Thr Ile Phe Pro Asp Tyr Asp Tyr Trp Gly
            100                 105                 110

Gln Gly Thr Gln Val Thr Val Ser Ser
        115                 120

<210> SEQ ID NO 203
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203
```

Glu Val Gln Leu Val Glu Ser Gly Gly Gly Leu Val Gln Ala Gly Gly
1               5                   10                  15

Phe Leu Arg Leu Ser Cys Ala Ala Ser Gly Arg Thr Phe Ser Ser Tyr
                20                  25                  30

Ala Met Gly Trp Phe Arg Gln Ile Pro Gly Lys Glu Arg Glu Leu Val
            35                  40                  45

Ala Ala Ile Ser Ser Trp Ser Gly Ser Thr Tyr Tyr Ala Asp Ser
50                      55                  60

Val Lys Gly Arg Phe Thr Ile Ser Arg Asp Asn Ala Lys Asn Thr Val
65                  70                  75                  80

Tyr Leu Gln Met Leu Ser Leu Lys Pro Glu Asp Thr Ala Val Tyr Tyr
                85                  90                  95

Cys Thr Thr Gly Asp Tyr Tyr Ser Asp Tyr Phe Lys Tyr Asp Asn Glu
                100                 105                 110

Asn Trp Gly Lys Gly Thr Gln Val Thr Val Ser Ser
            115                 120

<210> SEQ ID NO 204
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Glu Val Gln Leu Val Glu Ser Gly Gly Gly Leu Val Gln Ala Gly Gly
1               5                   10                  15

Ser Leu Thr Leu Ser Cys Val Ala Ser Gly Arg Ala Phe Ser Asn Ser
                20                  25                  30

Ala Met Ala Trp Phe Arg Gln Thr Pro Gly Lys Glu Arg Glu Phe Val
            35                  40                  45

Ser Ala Ile Ser Arg Gly Gly Gly Ser Thr Asp Tyr Ala Asp Ser Val
50                      55                  60

Lys Gly Arg Phe Thr Ile Ser Lys Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Met Arg Tyr Tyr Ser Gly Arg Tyr Tyr Glu Ser Leu Glu Tyr Asp
                100                 105                 110

Tyr Trp Gly Gln Gly Thr Gln Val Thr Val Ser Ser
            115                 120

<210> SEQ ID NO 205
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Val Gln Leu Val Glu Ser Gly Gly Gly Leu Val Gln Ala Gly Gly
1               5                   10                  15

Ser Leu Arg Leu Ser Cys Ala Ala Ala Arg Arg Thr Leu His Asn Phe
                20                  25                  30

Ala Met Ala Trp Phe Arg Gln Ala Pro Gly Lys Glu Arg Glu Phe Val
            35                  40                  45

```
Ala Ala Ile Ser Lys Gly Gly Ser Ala Asp Tyr Ala Asp Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Asn Asp Leu Ala Ser Tyr Ser Asp Ser Ser Tyr Thr Ser Thr
            100                 105                 110

Ser Arg Tyr Asp Tyr Trp Gly Gln Gly Thr Gln Val Thr Val Ser Ser
            115                 120                 125

<210> SEQ ID NO 206
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Glu Val Gln Leu Val Glu Ser Gly Gly Gly Leu Val Gln Pro Gly Gly
 1               5                  10                  15

Ser Leu Arg Leu Ser Cys Thr Ala Ser Gly Arg Pro Arg Thr Thr Tyr
             20                  25                  30

Ala Met Gly Trp Phe Arg Gln Ala Pro Gly Lys Glu Arg Glu Ile Val
         35                  40                  45

Ala Ala Ile Ser Lys Ala Gly Gly Ser Thr Tyr Val Ala Asp Ser Ala
    50                  55                  60

Lys Gly Arg Phe Ala Ile Ser Lys Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Arg Ala Gly Phe Ala Ala Gln Ile Phe Glu Tyr Asp Tyr Trp
            100                 105                 110

Gly Gln Gly Thr Leu Val Thr Val Ser Ser
            115                 120

<210> SEQ ID NO 207
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Gly Tyr
             20                  25                  30

Asn Met Gly Trp Phe Arg Gln Ala Pro Gly Lys Glu Arg Glu Phe Val
         35                  40                  45

Ala Ala Ile Ala Trp Ala Gly Ser Arg Thr Tyr Tyr Thr Asp Ser Val
    50                  55                  60

Lys Gly Arg Phe Thr Ile Ser Arg Asp Asn Ala Lys Asn Thr Met Tyr
 65                  70                  75                  80

Leu Gln Met Asn Thr Leu Arg Pro Glu Asp Thr Ala Val Tyr Tyr Cys
                 85                  90                  95
```

```
Ala Ala His Asp Glu Thr Tyr Tyr Arg Leu Asp Arg Val Asp Leu Tyr
            100                 105                 110

Thr His Trp Gly Gln Gly Thr Leu Val Thr Val Ser Ser
        115                 120                 125

<210> SEQ ID NO 208
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Glu Val Gln Leu Val Glu Ser Gly Gly Gly Leu Val Gln Ala Gly Gly
1               5                   10                  15

Ser Leu Arg Leu Ser Cys Ala Thr Ser Gly Leu Thr Asp Ser Thr Tyr
            20                  25                  30

Gly Met Ala Trp Phe Arg Gln Ala Pro Gly Lys Glu Arg Glu Phe Val
        35                  40                  45

Ala Ala Ile Ser Arg Ala Gly Gly Ser Ala Asp His Ala Asp Ser Val
    50                  55                  60

Lys Gly Arg Phe Thr Val Ser Arg Asp Asn Ala Lys Lys Met Val Tyr
65                  70                  75                  80

Leu Gln Met Asn Ser Leu Lys Pro Glu Asp Thr Ala Val Tyr Tyr Cys
                85                  90                  95

Ala Ser Gly Arg Ser Tyr Ser Ser Pro Tyr Asp Tyr Phe Asn Ala Leu
            100                 105                 110

Ala Tyr Ser Tyr Trp Gly Gln Gly Thr Gln Val Thr Val Ser Ser
        115                 120                 125

<210> SEQ ID NO 209
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Glu Val Gln Leu Val Glu Ser Gly Gly Gly Leu Val Gln Pro Gly Gly
1               5                   10                  15

Phe Leu Arg Leu Ser Cys Ala Ala Ser Arg Arg Thr Leu Ser Thr Tyr
            20                  25                  30

Ala Met Gly Trp Phe Arg Gln Ala Pro Gly Lys Glu Arg Glu Phe Val
        35                  40                  45

Ala Ala Ile Ser Trp Arg Ser Gly Asn Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Asn Glu Val Ala Thr Met Ser Gly Pro His Asp His Trp Gly
            100                 105                 110

Gln Gly Thr Leu Val Thr Val Ser Ser
        115                 120

<210> SEQ ID NO 210
```

```
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ala Asn Tyr
            20                  25                  30

Ala Met Gly Trp Phe Arg Gln Ala Pro Gly Lys Glu Arg Glu Thr Val
        35                  40                  45

Ala Ala Ile Ser Arg Gly Gly Gly Ser Thr Trp Tyr Ala Asp Ser Val
    50                  55                  60

Lys Gly Arg Phe Thr Ile Ser Lys Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Arg Ser Tyr Ser Gly Ser Tyr Thr Tyr Ser Phe Gly Glu Tyr
            100                 105                 110

Asp Tyr Trp Gly Gln Gly Thr Gln Val Thr Val Ser Ser
        115                 120                 125

<210> SEQ ID NO 211
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Thr Phe Ser
            20                  25                  30

Thr His Asn Met Gly Trp Phe Arg Gln Ala Pro Gly Lys Glu Arg Glu
        35                  40                  45

Phe Val Gly Gly Ile Met Trp Thr Ser Arg Ala Ser Tyr Ala Asp Ser
    50                  55                  60

Val Lys Gly Arg Phe Thr Val Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Ala Trp Tyr Gly Asn Ser Gly Ala Ser Tyr Asp Tyr Trp
            100                 105                 110

Gly Gln Gly Thr Gln Val Thr Val Ser Ser
        115                 120

<210> SEQ ID NO 212
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212
```

-continued

Gln Val Gln Leu Val Glu Ser Gly Gly Gly Leu Val Arg Ala Gly Gly
1               5                   10                  15

Ser Leu Arg Leu Ser Cys Ala Ala Ser Gly Ser Ile Thr Ser Ile Asn
            20                  25                  30

Thr Met Gly Trp Phe Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Arg Asn Thr Val Tyr Leu
65                  70                  75                  80

Gln Met Tyr Ser Leu Lys Pro Glu Asp Thr Ala Val Tyr Tyr Cys Glu
                85                  90                  95

Ala Asp Ser Met Tyr Phe Arg Gly Gln Gly Thr Gln Val Thr Val Ser
            100                 105                 110

Ser

<210> SEQ ID NO 213
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gln Val Gln Leu Val Glu Ser Gly Gly Gly Leu Val Gln Ala Gly Gly
1               5                   10                  15

Ser Leu Arg Leu Ser Cys Ala Ala Ser Arg Arg Thr Phe Met Thr Tyr
            20                  25                  30

Ala Met Gly Trp Phe Arg Gln Ala Pro Gly Lys Glu Arg Glu Phe Val
        35                  40                  45

Ala Ala Ile Ser Trp Ser Ser Gly Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Thr Ala Ser Ser Ile Ala Thr Met Tyr Gly Pro Asn Asp Tyr Ala Gly
            100                 105                 110

Gln Gly Thr Leu Val Thr Val Ser Ser
        115                 120

<210> SEQ ID NO 214
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gln Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Phe Ser Arg Tyr
            20                  25                  30

Ala Met Gly Trp Phe Arg Gln Ala Pro Gly Lys Glu Arg Glu Phe Val
        35                  40                  45

Ala Thr Ile Ser Arg Ser Gly Gly Thr Thr Ser Tyr Ala Asn Ser Val

```
                50             55              60
Lys Gly Arg Phe Thr Ile Ser Arg Asp Asn Ala Lys Asn Thr Val Tyr
 65                  70                  75                  80

Leu Gln Met Asn Ser Leu Lys Thr Glu Asp Thr Ala Val Tyr Asn Cys
                 85                  90                  95

Ala Ala Arg Asp Gly Pro Ala Met Gly Val Phe Gly Ser Asp Tyr Asp
                100                 105                 110

Tyr Trp Gly Gln Gly Thr Leu Val Thr Val Ser Ser
            115                 120
```

<210> SEQ ID NO 215
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

```
Glu Val Gln Leu Val Glu Ser Gly Gly Gly Leu Val Gln Ala Gly Gly
 1               5                  10                  15

Ser Leu Val Leu Ser Cys Ala Ala Ser Gly Arg Thr Phe Ser Arg Tyr
             20                  25                  30

Ala Met Gly Trp Phe Arg Gln Ala Pro Gly Lys Glu Arg Glu Phe Val
         35                  40                  45

Ala Ala Ile Ser Ile Gly Gly Ser Ala Asp Tyr Ala Asp Thr Val
     50                  55                  60

Lys Gly Arg Phe Thr Ile Ser Arg Asn Asn Ala Lys Asn Thr Met Tyr
 65                  70                  75                  80

Leu Gln Met Asn Ser Leu Lys Pro Glu Asp Thr Ala Val Tyr Tyr Cys
                 85                  90                  95

Ala Ala Arg Thr Pro Arg Pro Ser Ser Ser Tyr Phe Thr Pro Gln Asp
                100                 105                 110

Tyr Glu Tyr Trp Gly Gln Gly Thr Leu Val Thr Val Ser Ser
            115                 120                 125
```

<210> SEQ ID NO 216
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

```
Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Arg Tyr
             20                  25                  30

Ala Met Asn Trp Phe Arg Gln Ala Pro Gly Lys Glu Arg Glu Phe Val
         35                  40                  45

Ala Ala Ile Ser Trp Ser Ser Gly Asn Thr Tyr Val Ala Asp Ser Val
     50                  55                  60

Lys Gly Arg Phe Thr Ile Ser Arg Asp Asn Ala Lys Asn Thr Met Tyr
 65                  70                  75                  80

Leu Gln Met Asn Asn Leu Ala Pro Glu Asp Thr Ala Val Tyr Tyr Cys
                 85                  90                  95

Ala Ala Thr Thr Ile Ala Thr Met Ser Asp Glu Asn Thr Tyr Trp Gly
```

```
                    100                 105                 110
Gln Gly Thr Gln Val Thr Val Ser Ser
        115                 120

<210> SEQ ID NO 217
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Ser Tyr
            20                  25                  30

Ala Met Asn Trp Phe Arg Gln Ala Pro Gly Lys Glu Arg Glu Phe Val
        35                  40                  45

Ala Ala Ile Ser Trp Ser Ser Gly Asn Thr Tyr Val Ala Asp Ser Val
    50                  55                  60

Lys Gly Arg Phe Ala Ile Ser Arg Asp Lys Ala Lys Asn Thr Met Tyr
65                  70                  75                  80

Leu Gln Met Asn Ser Leu Ala Pro Glu Asp Thr Ala Val Tyr Tyr Cys
                85                  90                  95

Ala Ala Thr Thr Ile Ala Thr Met Ser Asp Glu Tyr Thr Tyr Trp Gly
            100                 105                 110

Gln Gly Thr Gln Val Thr Val Ser Ser
        115                 120

<210> SEQ ID NO 218
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Arg Met Gly Trp Phe Arg Gln Ala Pro Gly Lys Glu Arg Glu Phe Val
        35                  40                  45

Ala Ala Ile Ser Arg Gly Gly Gly Thr Thr Leu Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Arg Leu Lys Pro Glu Asp Thr Ala Val Tyr Phe Cys
                85                  90                  95

Ala Ala Gly Asp Phe Ser Thr Thr Trp Asp Glu Tyr Asn Tyr Trp Gly
            100                 105                 110

Gln Gly Thr Gln Val Thr Val Ser Ser
        115                 120

<210> SEQ ID NO 219
<211> LENGTH: 124
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 219

Gln Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Thr Pro Gly Lys Glu Arg Glu Phe Val
        35                  40                  45

Ser Ala Ile Ser Arg Gly Gly Ser Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Ser Glu Asp Thr Ala Val Tyr Tyr Cys
                85                  90                  95

Ala Leu Arg Ala Tyr Ser Gly Arg Tyr Tyr Gln Phe Leu Glu Tyr Asp
            100                 105                 110

Tyr Trp Gly Gln Gly Thr Gln Val Thr Val Ser Ser
        115                 120

<210> SEQ ID NO 220
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Glu Val Gln Leu Val Glu Ser Gly Gly Gly Leu Val Gln Ala Gly Gly
1               5                   10                  15

Ser Leu Arg Leu Ser Cys Thr Val Ser Gly Arg Thr Phe Ser Ser Tyr
            20                  25                  30

Ala Val Ala Trp Phe Arg Gln Ala Pro Gly Asn Val Arg Glu Leu Ala
        35                  40                  45

Ala Ala Leu Ser Arg Gly Gly Ser Ala Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Asn Tyr Asp Gly Thr Tyr Tyr Gln Glu Asn Gln Tyr Asn
            100                 105                 110

Tyr Trp Gly Gln Gly Thr Gln Val Thr Val Ser Ser
        115                 120

<210> SEQ ID NO 221
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Val Gln Leu Val Glu Ser Gly Gly Gly Leu Val Gln Ala Gly Gly
1               5                   10                  15

```
Ser Leu Leu Leu Ser Cys Ala Ala Ser Gly Arg Thr Phe Ser Thr Tyr
            20                  25                  30

Ala Met Gly Trp Phe Arg Gln Ala Pro Gly Lys Glu Arg Met Phe Val
        35                  40                  45

Ala Ala Ile Ser Val Asn Gly Ser Thr Tyr Tyr Ala Asp Ser Val
50                  55                  60

Thr Gly Arg Phe Thr Ile Ser Arg Asp Asn Ala Lys Asn Thr Met Tyr
65                  70                  75                  80

Leu Gln Met Asn Asn Leu Lys Pro Gly Asp Thr Ala Val Tyr Tyr Cys
                85                  90                  95

Ala Ala Arg Arg Pro Tyr Pro Gly Ser Asp Phe Leu Thr Trp Ala Ser
                100                 105                 110

Tyr Asp Tyr Arg Gly Gln Gly Thr Leu Val Thr Val Ser Ser
            115                 120                 125

<210> SEQ ID NO 222
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gln Val Gln Leu Val Glu Ser Gly Gly Gly Leu Val Gln Ala Gly Gly
1               5                   10                  15

Phe Leu Arg Leu Ser Cys Ala Ala Ser Gly Arg Thr Phe Ser Tyr Thr
            20                  25                  30

Thr Ile Gly Trp Phe Arg Gln Ala Pro Gly Lys Glu Arg Glu Phe Val
        35                  40                  45

Ala Val Ile Ser Ala Gly Gly Ser Arg Asp Tyr Ala Asp Ala Leu
50                  55                  60

Lys Gly Arg Phe Thr Ile Ser Arg Asp Asn Ala Lys Lys Met Val Tyr
65                  70                  75                  80

Leu Gln Met Asn Asn Leu Lys Pro Glu Asp Thr Ala Val Tyr Tyr Cys
                85                  90                  95

Ala Val Arg Arg Asn Thr Asp Thr Tyr Thr Thr Thr Gly Asp Tyr Asp
                100                 105                 110

Tyr Trp Gly Gln Gly Thr Gln Val Thr Val Ser Ser
            115                 120

<210> SEQ ID NO 223
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gln Val Gln Leu Val Glu Ser Gly Gly Gly Leu Val Gln Pro Gly Asp
1               5                   10                  15

Ser Leu Arg Leu Ser Cys Val Ala Ser Gly Thr Ile Ser Ser Leu
            20                  25                  30

Ala Met Gly Trp Phe Arg Gln Ala Pro Gly Lys Glu Arg Glu Phe Val
        35                  40                  45

Ala Ala Ile Ser Trp Ser Gly Arg Ser Thr Tyr Tyr Val Asp Ser Val
50                  55                  60
```

Lys Gly Arg Phe Thr Ile Ser Thr Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Val Ala Gly Glu Asp Gly His Ser Glu Tyr Asp Tyr Trp Gly Gln Gly
            100                 105                 110

Thr Gln Val Thr Val Ser Ser
        115

<210> SEQ ID NO 224
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ala Asn Tyr
            20                  25                  30

Ala Met Gly Trp Phe Arg Gln Ala Pro Gly Lys Glu Arg Glu Thr Val
        35                  40                  45

Ala Ala Ile Ser Arg Gly Gly Gly Ser Thr Trp Tyr Ala Asp Ser Val
    50                  55                  60

Lys Gly Arg Phe Thr Ile Ser Lys Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Arg Ser Tyr Ser Gly Ser Tyr Thr Tyr Ser Phe Gly Glu Tyr
            100                 105                 110

Asp Tyr Trp Gly Gln Gly Thr Gln Val Thr Val Ser Ser
        115                 120                 125

<210> SEQ ID NO 225
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Ser Thr Tyr
            20                  25                  30

Ala Leu Gly Trp Phe Arg Gln Ala Pro Gly Lys Glu Arg Glu Phe Ile
        35                  40                  45

Ala Ala Ile Ser Arg Gly Gly Gly Ser Thr Asp Tyr Ala Asp Ser Val
    50                  55                  60

Lys Gly Arg Phe Thr Ile Ser Arg Asp Asn Ala Lys Ser Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ser Tyr Ser Ser Ser Tyr Tyr Tyr Ser Gln Tyr Glu Tyr
            100                 105                 110

Asp Tyr Trp Gly Gln Gly Thr Gln Val Thr Val Ser Ser
            115                 120                 125

<210> SEQ ID NO 226
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Val
            20                  25                  30

Ala Met Ala Trp Phe Arg Gln Ala Pro Gly Lys Glu Arg Glu Phe Val
        35                  40                  45

Ser Ala Ile Ser Ser Gly Gly Ser Thr Asp Tyr Ala Asp Ser Val
    50                  55                  60

Lys Gly Arg Phe Thr Ile Ser Lys Asp Asn Ala Lys Asn Thr Met Tyr
65                  70                  75                  80

Leu Gln Met Asp Ser Leu Lys Pro Glu Asp Thr Ala Val Tyr Tyr Cys
                85                  90                  95

Ala Ala Arg Asp Tyr Ser Ser Arg Arg Tyr Tyr Gln Ser Arg Tyr Glu
            100                 105                 110

Tyr Asp Leu Trp Gly Leu Gly Thr Gln Val Thr Val Ser Ser
            115                 120                 125

<210> SEQ ID NO 227
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg Ser Tyr
            20                  25                  30

Ser Met Gly Trp Phe Arg Gln Ala Pro Gly Lys Glu Arg Glu Phe Val
        35                  40                  45

Ala Ala Ile Ser Trp Tyr Ser Gly Thr Thr Tyr Tyr Ala Asp Pro Val
    50                  55                  60

Lys Gly Arg Phe Thr Ile Ser Arg Asp Asp Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Asn Glu Ile Ala Thr Met Glu Ser Ser Asn Asp Tyr Trp Gly
            100                 105                 110

Gln Gly Thr Gln Val Thr Val Ser Ser
            115                 120

<210> SEQ ID NO 228
<211> LENGTH: 122
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 228

Gln Val Gln Leu Val Glu Ser Gly Gly Gly Leu Val Gln Pro Gly Gly
1               5                   10                  15

Ser Leu Arg Leu Ser Cys Thr Ala Ser Gly Arg Pro Arg Thr Thr Tyr
            20                  25                  30

Ala Met Gly Trp Phe Arg Gln Ala Pro Gly Lys Glu Arg Glu Ile Val
        35                  40                  45

Ala Ala Ile Ser Lys Ala Gly Gly Ser Thr Tyr Val Ala Asp Ser Ala
    50                  55                  60

Lys Gly Arg Phe Ala Ile Ser Lys Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ala Gly Phe Ala Ala Gln Ile Phe Glu Tyr Asp Tyr Trp
            100                 105                 110

Gly Gln Gly Thr Leu Val Thr Val Ser Ser
        115                 120

<210> SEQ ID NO 229
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Glu Val Gln Leu Val Glu Ser Gly Gly Gly Leu Val Gln Ala Gly Gly
1               5                   10                  15

Ser Met Arg Leu Ser Cys Ala Asn Ser Gly Arg Thr Phe Gly Thr Tyr
            20                  25                  30

Ala Met Gly Trp Phe Arg Gln Ser Pro Gly Lys Glu Arg Glu Arg Val
        35                  40                  45

Ala Ser Ile Asp Arg Asp Gly Ser Met Ser Tyr Tyr Ala Asp Ser Val
    50                  55                  60

Lys Gly Arg Phe Thr Ile Ser Gly Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Arg Arg Ala Val Ile Ser Leu Gln Thr Val Asp Tyr Trp
            100                 105                 110

Gly Gln Gly Thr Gln Val Thr Val Ser Ser
        115                 120

<210> SEQ ID NO 230
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Glu Val Gln Leu Val Glu Ser Gly Gly Arg Leu Val Gln Thr Gly Gly
1               5                   10                  15
```

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Tyr Ser Gly Asn Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Asn Gln Ile Ala Thr Met Ile Ser Val Gly Asp Tyr Trp Gly
            100                 105                 110

Gln Gly Thr Leu Val Thr Val Ser Ser
        115                 120

<210> SEQ ID NO 231
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Val Gln Leu Val Glu Ser Gly Gly Gly Leu Val Glu Ala Gly Gly
1               5                   10                  15

Ser Leu Arg Leu Ala Cys Ala Ala Ser Gly Ser Ile Phe Arg Leu Asn
            20                  25                  30

Leu Met Gly Trp Tyr Arg Gln Ala Pro Gly Lys Gln Arg Glu Leu Val
        35                  40                  45

Ala His Val Gly Thr Thr Gly Asn Thr Ala Tyr Ala Asp Ser Val Lys
    50                  55                  60

Gly Arg Phe Thr Ile Ser Lys Asp Asp Ala Lys Asn Met Val Phe Leu
65                  70                  75                  80

Gln Met Asn Ser Leu Lys Pro Glu Asp Thr Ala Val Tyr Tyr Cys Tyr
                85                  90                  95

Ala Asp Arg Trp Gly Gln Phe Ser Trp Gly Gln Gly Thr Gln Val Thr
            100                 105                 110

Val Ser Ser
        115

<210> SEQ ID NO 232
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Thr Gly Tyr
            20                  25                  30

Ala Met Gly Trp Phe Arg Gln Ala Pro Gly Lys Glu Arg Glu Phe Val
        35                  40                  45

Ala Val Ile Thr Trp Ser Gly Ala Thr Thr Tyr Tyr Ser Ala Ser Val
    50                  55                  60

Lys Gly Arg Phe Thr Leu Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ile Arg Ile Arg Asp Gly Val Ser Pro Glu Asn Pro Asn Glu Tyr
            100                 105                 110

Gly Tyr Trp Gly Gln Gly Thr Gln Val Thr Val Ser Ser
            115                 120                 125

<210> SEQ ID NO 233
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gln Val Gln Leu Val Glu Ser Gly Gly Gly Leu Val Gln Ala Gly Gly
1               5                   10                  15

Ser Leu Arg Leu Ser Cys Val Ala Ser Gly Arg Thr Val Gly Tyr Gly
            20                  25                  30

Met Ala Trp Phe Arg Gln Ala Pro Gly Lys Gln Arg Asp Val Val Ala
        35                  40                  45

Ala Ile Thr Trp Ser Gly Thr Ser Thr Tyr Tyr Pro Asp Ser Val Lys
50                  55                  60

Gly Arg Phe Thr Ile Ser Arg Asp Asn Ala Lys Asn Thr Met Tyr Leu
65                  70                  75                  80

Gln Met Ser Ser Leu Lys Pro Glu Asp Thr Ala Val Tyr Tyr Cys Ala
                85                  90                  95

Ala Gly Ser Arg Arg Val Gly Val Asp Val Gly Tyr Asp Tyr
            100                 105                 110

Trp Gly Gln Gly Thr Gln Val Thr Val Ser Ser
            115                 120

<210> SEQ ID NO 234
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Thr Phe Ser
            20                  25                  30

Thr His Asn Met Gly Trp Phe Arg Gln Ala Pro Gly Lys Glu Arg Glu
        35                  40                  45

Phe Val Gly Gly Ile Met Trp Thr Ser Arg Ala Ser Tyr Ala Asp Ser
50                  55                  60

Val Lys Gly Arg Phe Thr Val Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Ala Trp Tyr Gly Asn Ser Gly Ala Ser Tyr Asp Tyr Trp
            100                 105                 110

```
Gly Gln Gly Thr Gln Val Thr Val Ser Ser
        115                 120
```

<210> SEQ ID NO 235
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

```
Gln Val Gln Leu Val Glu Ser Gly Gly Gly Leu Val Gln Leu Val Gln
1               5                   10                  15

Ala Gly Gly Ser Leu Arg Leu Ser Cys Ala Ala Ser Gly Arg Thr Phe
            20                  25                  30

Ser Gly Tyr Asn Met Gly Trp Phe Arg Gln Ala Pro Gly Lys Glu Arg
        35                  40                  45

Glu Phe Val Ala Ala Ile Ala Trp Ala Gly Ser Arg Thr Tyr Tyr Thr
50                  55                  60

Asp Ser Val Lys Gly Arg Phe Thr Ile Ser Arg Asp Asn Ala Lys Asn
65                  70                  75                  80

Thr Met Tyr Leu Gln Met Asn Thr Leu Arg Pro Glu Asp Thr Ala Val
                85                  90                  95

Tyr Tyr Cys Ala Ala His Asp Glu Thr Tyr Tyr Arg Leu Asp Arg Val
            100                 105                 110

Asp Leu Tyr Thr His Trp Gly Gln Gly Thr Gln Val Thr Val Ser Ser
        115                 120                 125
```

<210> SEQ ID NO 236
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

```
Gln Val Gln Leu Val Glu Ser Gly Gly Gly Leu Val Gln Pro Gly Glu
1               5                   10                  15

Ser Leu Arg Leu Ser Cys Ala Ala Ser Gly Pro Phe Thr Arg Tyr Ala
            20                  25                  30

Met Gly Trp Phe Arg Gln Ala Pro Gly Lys Glu Arg Glu Phe Val Ala
        35                  40                  45

Ala Ile Ser Trp Ser Ser Gly Asn Thr Tyr Tyr Val Asp Ser Val Lys
50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Ala
                85                  90                  95

Ala Asn Glu Val Ala Thr Met Ser Gly Pro Asp Asp Tyr Trp Gly Gln
            100                 105                 110

Gly Thr Gln Val Thr Val Ser Ser
        115                 120
```

<210> SEQ ID NO 237
<211> LENGTH: 125
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 237

Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Ser Phe Gly Arg Tyr
            20                  25                  30

Thr Met Gly Trp Tyr Arg Gln Ala Pro Gly Lys Glu Arg Glu Phe Val
        35                  40                  45

Ala Val Ile Ser Trp Ser Gly Thr Asn Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Asp Leu Lys Pro Glu Asp Thr Ala Val Tyr Tyr Cys
                85                  90                  95

Ala Ala Arg Glu Thr Tyr Tyr Ser His Trp Asp Glu Arg Met Glu Tyr
            100                 105                 110

Asp Tyr Trp Gly Gln Gly Thr Gln Val Thr Val Ser Ser
        115                 120                 125

<210> SEQ ID NO 238
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gln Val Gln Leu Val Glu Ser Gly Gly Gly Leu Val Gln Ala Gly Asp
1               5                   10                  15

Ser Leu Arg Leu Ser Cys Val Ala Ser Gly Ser Ile Asp Ser Ser Tyr
            20                  25                  30

Tyr Val Ser Trp Phe Arg Gln Ala Pro Gly Lys Glu Arg Asp Leu Val
        35                  40                  45

Ala Ala Ile Asn Trp Gly Asp Ser Arg Thr Ala Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met His Ser Leu Arg Pro Asn Asp Thr Ala Val Tyr Tyr Cys
                85                  90                  95

Ala Ser Arg Ile Gly Leu Gly Pro Val Val Ala Ala Pro Thr Arg
            100                 105                 110

Tyr Pro Tyr Trp Gly Gln Gly Thr Leu Val Thr Val Ser Ser
        115                 120                 125

<210> SEQ ID NO 239
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gln Val Gln Leu Val Glu Ser Gly Gly Gly Leu Val Gln Ala Gly Gly
1               5                   10                  15

Ser Leu Arg Leu Ser Cys Ala Ala Ser Glu Ser Ile Leu Arg Phe Asn

```
                    20                  25                  30

Val Met Ser Trp Leu Arg Gln Ala Pro Gly Lys Gln Arg Glu Leu Val
            35                  40                  45

Ala Val Ile Thr Ser Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                85                  90                  95

Ala Asp Glu Ser Gly Gln Tyr Tyr Trp Gly Gln Gly Thr Gln Val Thr
                100                 105                 110

Val Ser Ser
        115

<210> SEQ ID NO 240
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gln Val Gln Leu Val Glu Ser Gly Gly Gly Leu Val Gln Ala Gly Gly
 1               5                  10                  15

Ser Leu Arg Leu Ser Cys Ala Ala Ser Gly Leu Thr Thr Ser Ser Ala
                20                  25                  30

Ala Leu Ala Trp Phe Arg Gln Ala Pro Gly Lys Glu Arg Glu Leu Asp
            35                  40                  45

Pro Thr Ile Thr Ser Gly Gly Gly Ser Thr Tyr Tyr Ala Asp Ser Val
 50                  55                  60

Lys Gly Arg Phe Thr Ile Ser Lys Asp Asn Ala Lys Asn Thr Leu Tyr
 65                  70                  75                  80

Leu Gln Met Ser Ser Leu Lys Pro Glu Asp Thr Ala Val Tyr Tyr Cys
                85                  90                  95

Ala Ala Arg Phe Tyr Ser Thr Thr Tyr Tyr Tyr Arg Glu His Glu Tyr
                100                 105                 110

Ser Asp Trp Gly Gln Gly Thr Gln Val Thr Val Ser Ser
        115                 120                 125

<210> SEQ ID NO 241
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Gly Thr Ser
                20                  25                  30

Phe Gly Ser Leu Ser Met Gly Trp Phe Arg Gln Ala Pro Gly Lys Glu
            35                  40                  45

Arg Glu Phe Val Ala Ala Ile Ser Arg Asn Ile Gly Arg Thr Tyr Tyr
 50                  55                  60

Ala Asp Ser Val Lys Asp Arg Phe Thr Ile Ser Arg Asp Asn Ala Lys
```

```
                65                  70                  75                  80
Asn Thr Ala Ser Leu Gln Met Asn Ser Leu Glu Pro Glu Asp Thr Ala
                    85                  90                  95

Val Tyr Asn Cys Ala Ala Thr Asn Ser Tyr Asp Asp Leu Arg Arg Ser
                100                 105                 110

Tyr Ala Tyr Asp Tyr Trp Gly Gln Gly Thr Gln Val Thr Val Ser Ser
            115                 120                 125

<210> SEQ ID NO 242
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Gln Val Gln Leu Val Glu Ser Gly Gly Gly Leu Val Gln Ala Gly Gly
1               5                   10                  15

Phe Leu Arg Leu Ser Cys Ala Ala Ser Gly Arg Thr Phe Ser Ser Leu
                20                  25                  30

Ala Met Ala Trp Phe Arg Gln Ala Pro Gly Lys Glu Arg Glu Phe Val
            35                  40                  45

Ala Ala Ile Ser Arg Ser Gly Gly Ser Thr Asp Tyr Ala Asp Ser Val
        50                  55                  60

Lys Gly Arg Phe Thr Ile Ser Arg Asp Asn Ala Lys Ser Thr Leu Tyr
65                  70                  75                  80

Leu Gln Met Ser Ser Leu Lys Pro Glu Asp Thr Ala Val Tyr Tyr Cys
                85                  90                  95

Ala Ala Arg Asp Tyr Ser Thr Leu Gln Tyr Tyr Asn Glu Tyr Glu Tyr
                100                 105                 110

Ser Asp Trp Gly Gln Gly Thr Leu Val Thr Val Ser Ser
            115                 120                 125

<210> SEQ ID NO 243
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Gln Val Gln Leu Val Glu Ser Gly Gly Gly Leu Val Gln Ala Gly Asp
1               5                   10                  15

Ser Leu Arg Leu Ser Cys Ala Ala Ser Gly Pro Thr Phe Ser Thr Tyr
                20                  25                  30

Ala Met Ala Trp Phe Arg Gln Ala Pro Gly Lys Glu Arg Glu Phe Val
            35                  40                  45

Ala Ala Ile Thr Gln Ser Gly Arg Thr Thr Tyr Tyr Glu Asp Ser Val
        50                  55                  60

Lys Gly Arg Phe Thr Ile Ser Lys Asp Asn Ala Lys Asn Thr Leu Tyr
65                  70                  75                  80

Leu Gln Met Asn Ser Leu Gln Pro Glu Asp Thr Ala Val Tyr Tyr Cys
                85                  90                  95

Ala Ala Arg Asp Leu Trp Ser Asp Ser Pro Asp Asp Trp Arg Ile Tyr
                100                 105                 110

Ser Phe Trp Gly Gln Gly Thr Gln Val Thr Val Ser Ser
```

115                 120                 125

<210> SEQ ID NO 244
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gln Val Gln Leu Val Glu Ser Gly Gly Gly Leu Val Gln Ala Gly Gly
1               5                   10                  15

Ser Leu Arg Leu Ser Cys Ala Ala Ala Arg Arg Thr Leu His Asn Phe
            20                  25                  30

Ala Met Ala Trp Phe Arg Gln Ala Pro Gly Lys Glu Arg Glu Phe Val
        35                  40                  45

Ala Ala Ile Ser Lys Gly Gly Gly Ser Ala Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asn Asp Leu Ala Ser Tyr Ser Asp Ser Ser Tyr Thr Ser Thr
            100                 105                 110

Ser Arg Tyr Asp Tyr Trp Gly Gln Gly Thr Gln Val Thr Val Ser Ser
        115                 120                 125

<210> SEQ ID NO 245
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gln Val Gln Leu Val Glu Ser Gly Gly Gly Leu Val Gln Thr Gly Gly
1               5                   10                  15

Ser Leu Arg Leu Ser Cys Ala Ala Ser Gly Arg Thr Phe Ser Ser Tyr
            20                  25                  30

Ala Met Ala Trp Phe Arg Gln Ala Pro Gly Lys Glu Arg Glu Phe Val
        35                  40                  45

Ala Ala Ile Ser Ile Leu Gly Gly Ser Ala Asp Tyr Glu Asp Ser Val
    50                  55                  60

Gln Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Arg Arg Pro Ala Pro Ser Asp Ser Tyr Trp Ser Ser Thr Ser
            100                 105                 110

Tyr Ala Tyr Trp Gly Gln Gly Thr Leu Val Thr Val Ser Ser
        115                 120                 125

<210> SEQ ID NO 246
<211> LENGTH: 126
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 246

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Leu
            20                  25                  30

Ala Met Ala Trp Phe Arg Gln Ala Pro Gly Lys Glu Arg Glu Phe Val
        35                  40                  45

Ala Ala Thr Thr Ile Leu Gly Gly Ser Ala Asp Tyr Gly Asp Pro Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Thr Gly Arg Arg Pro Ala Pro Ser Asp Asn Tyr Trp Ser Pro Ala Ser
            100                 105                 110

Tyr Ala Tyr Trp Gly Gln Gly Thr Gln Val Thr Val Ser Ser
        115                 120                 125

<210> SEQ ID NO 247
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gln Val Gln Leu Val Glu Ser Gly Gly Gly Leu Val Gln Ala Gly Gly
1               5                   10                  15

Ser Leu Arg Leu Ser Cys Ala Pro Ser Gly Arg Thr Phe Ser Ser Tyr
            20                  25                  30

Ala Met Ala Trp Phe Arg Gln Pro Pro Gly Lys Glu Arg Glu Phe Val
        35                  40                  45

Ala Ala Ile Thr Val Ser Gly Ala Ser Thr Tyr Tyr Ala Asp Ser Val
    50                  55                  60

Lys Gly Arg Phe Thr Ile Ser Arg Asp Asn Ala Lys Asn Ser Met Tyr
65                  70                  75                  80

Leu Gln Met Asn Ser Leu Lys Pro Glu Asp Thr Ala Val Tyr Tyr Cys
                85                  90                  95

Ala Ala Gly Gly Pro Gly Thr Ile Phe Pro Asp Tyr Asp Tyr Trp Gly
            100                 105                 110

Gln Gly Thr Gln Val Thr Val Ser Ser
        115                 120

<210> SEQ ID NO 248
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Val Gln Leu Val Glu Ser Gly Gly Gly Leu Val Gln Ala Gly Asp
1               5                   10                  15

Ser Leu Thr Leu Ser Cys Thr Ala Ser Gly Arg Thr Phe Ser Gly Tyr
            20                  25                  30

```
Asn Met Gly Trp Phe Arg Gln Ala Pro Gly Lys Glu Arg Asp Phe Val
         35                  40                  45

Ala Ala Ile Asn Trp Ile Gly Gly Ala Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

His Arg Tyr Ser Glu Lys Phe Tyr Ser Gly Lys Asp Tyr Tyr Thr Arg
             100                 105                 110

Asp Tyr Asp Tyr Trp Gly Gln Gly Thr Gln Val Thr Val Ser Ser
             115                 120                 125

<210> SEQ ID NO 249
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
gaagtacagc tggtggagtc aggagggggt ctggtccagg ccggtgggtc actgaggctc      60
tcctgcgctg ccagcggtcg cattgcttcc gactacacta gaggatggtt tcgtcaggct     120
ccaggcaagg aacgcgagtt tgttgcggct attatccgca gtgtgggcga cagttactat     180
gccgactctg tgaagggccg cttcactatc tctattgata cgcagagaaa cacagtgtac     240
ctccaaatga acagcctcaa gcccgaagac accgctgtct attactgcgc tgtgggcgga     300
cacctgtatt acggtagtag gtggcgttac ccggcatcct atgattactg ggggcagggc     360
acccaggtga ccgtttctag c                                                381

<210> SEQ ID NO 250
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250
gaagtccagc tggtggagag tggcggtggc ctggtacagg ccggtggctc cttgcgcctc      60
agctgtgagg cttccgagag cattctgtcc atcaacacta tgggatggtt ccgtcaggcc     120
cctgggaaac agcgtgaact tgtagcagcg atctcctctg ggggctccac taactatgcg     180
gactctgtca agggtcgttt cactatcagc cgggacaacg ctaagaacac agtctacctc     240
cagatgaaca gtctcaagcc tgaggataca gccgtgtact attgtgacgc cgaccgcgcc     300
tattacaagg ggcagggaac ccaggtgacc gtctcctcc                            339

<210> SEQ ID NO 251
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251
gaggtgcagc tggtggagtc tggcggaggt cttgtgcagg ctggaggctc tttgcgcctt      60
```

```
agctgcgtgg cgagtggccg caccttcacc gggtacgcta tgggttggtt ccgccaggcc    120
cccggcaagg agcgtgagtt cgtggcagtc atcacctgga gcggagcgac cacttattac    180
tccgcttccg tgaagggtcg ctttacactc tctagggaca atgccaagaa caccgtttac    240
ctccagatga actccctgaa gtccgaagat accgctgtgt attactgcgc tattcgcatc    300
agggatggcg ttagccctga aaatcctaac gagtacggat actggggca aggcacccag    360 gtgacggtct cttcc                                                    375

<210> SEQ ID NO 252
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252
gaggtgcagc tggtggagtc cggggggcgga ctcgtgcagg ccggaggctc cctgcgtctg    60
tcctgcgcgg ccagcggtag caccttctct acttacgtca tgggttggtt cagacaagca   120
cccggaaaag agcgggagtt cgtcgcagcc atctcccgct caggaggcac gaccacttac   180
gctgattctg tgaaaggccg ttttgacatc tccagggaca acggcaagaa caccctcttc   240
ttgcagatga acagtctgat ccccgaggac accgcagctt attactgtgc cgcgcgggct   300
ggcccagcta ttggtagaac tgcaaacgac tatcactctt gggggcaggg tacgctggtc   360
actgtttctt cc                                                      372

<210> SEQ ID NO 253
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253
gaggtccagc tcgtcgagag cggtggcgga ttggtacagg ctggcgggtc cttgagactg    60
agctgtgccg ctagtgggag gactttctcc aactatgcaa tgggttggtt tagacaggcc   120
cctggaaacg aacgcgagtt cgtggccgca atcaactgga acatcggttc cacttactat   180
gccgattctg ttaagggccg tttcaccatt agccgcgata tgcaaagaa tactgtatac    240 ctgcaaatga actccttgaa acctgaggac actgctgtct attactgtgg ggccgtctgg   300
cccaccggca gactgagggt ggattccgag tacgattact ggggccaggg gacgcaagtt   360
accgtgtcta gc                                                      372

<210> SEQ ID NO 254
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254
gaggtgcaac tcgtcgagtc cggcggtggc ctggttcagg ctggtggctc cctgagagtg    60
acctgtgccg cgtctggccg tactttttacc agcttggcta tgggctggtt caggcaggct   120
ccgggcaaag agcgggagtt cgtcgctgca atcagccgct ctggtggctc taccgattat   180
```

```
gccgactctg tcaagggtcg ttttttcatc agcagggaca acgcgaagag taccctgtac      240
ctgcaaatgt caagcctgaa gccggaagat acagcggtat attactgcgc ggctagggac      300
tacagcactc tccaatacta taacgaatat gaatactccg attggggcca aggcacccag      360
gtaactgtga gttcc                                                        375

<210> SEQ ID NO 255
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255
gaggtgcagc tcgtggagag cggcggtggc ctggtccaag cgggcggtag cttgcgtctg      60
agctgtgcgg cctctggccg taccttcggc accagcttcg gcgctctgtc tatgggatgg     120
tttaggcagg ctcctggcaa ggagcgggag ttcgttgccg caatcacccg gaacacaggt     180
aggacgttct acgccgatag tgtcaaggat cggtttacaa tttccaggga caacgctaag     240
aacaccgcgt ctcttcagat gaactccctt gaacccgagg atacagccgt ctatatctgt     300
gcagctacca actcttacga tgacttgagg cgttcctacg cctacaacta ctggggtcaa     360
gggactcagg tcaccgtctc cagc                                             384

<210> SEQ ID NO 256
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256
gaggtgcagc ttgtagagag cggcggtggc ctggtccaaa ccggaggcag tctgcgcctg      60
tcttgcgctg ccagcgggcg gacttttttcc agctatgcaa tggcgtggtt ccgtcaggcc    120
cctgggaagg agcgcgagtt tgtggctgcc atctccatcc tgggaggctc cgccgactac     180
gaggattccg tgcagggccg ctttacgatt tccagagata tgcgaagaa caccatgtat      240 ttgcagatga actccctcaa gcccgaggac accgccgtgt attactgtgc agctagacgc     300
cccgccccat ccgacagcta ctggagcagt acaagttacg cttactgggg tcagggtacg     360
ctggtcaccg tgagttct                                                    378

<210> SEQ ID NO 257
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
gaggtgcagt tggtggagtc cgggggcgca ctggttcaag ctggcggttc cctcagactg      60
tcctgcaccg tgtctggccg ctctttctct acttacgcga tggcgtggtt caggcgtgcg    120
cccggcaagg agcgtgagct ggtgtccgcg attacagtcg ggggtgggtc cacttactat     180
gtggacagcg tgaagggacg ttttaccatc tcccgcgaga acgctaagaa cacactctac     240
cttcagatga ataacctgaa gcctgaagac actgctatct acatctgtgc cgctcgcgat     300
```

```
tatcggcgca gaagctatgc ccctgaggct gagcagtacg actactgggg ccagggcacc    360
caggtgaccg tgtccagc                                                  378

<210> SEQ ID NO 258
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258
gaggtccaac tggtcgagtc tgtggaggc ctggttcagg ctgggggcag tctgcgtctg     60
agttgcgctc ccagcggacg caccttcagt tcctacgcta tggcatggtt ccgccaacct   120
cccggtaagg aaagggagtt tgtcgccgcg atcacagttt ctggagcgtc aacctattac   180
gccgactccg tgaagggtag gttcaccatc agccgggaca atgctaagaa cagcatgtac   240
ctccagatga atagcctgaa gcctgaggat acggctgtgt attactgtgc agccggtggc   300
cctggcacta ttttcccga ttacgattac tggggacaag gcacgcaggt caccgtaagc    360
agt                                                                 363

<210> SEQ ID NO 259
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259
gaagtgcaac tggtcgagtc cggtggaggg ctggtgcagg ctggtggatt tctgcgcttg    60
tcttgcgcgg ctagtggccg gaccttctcc agttatgcga tggggtggtt ccgccaaatc   120
cctggcaaag aacgcgaact ggttgccgca atctcctctt ggagcggcgg aagtacttac   180
tatgcggact ctgtgaaggg gaggtttacc atttctaggg acaatgctaa aaacaccgtg   240
tacctccaga tgctgtctct gaagcctgag gacaccgccg tgtattactg caccacggga   300
gactattaca gcgactactt caaatatgac aacgagaatt ggggaaagg cacgcaggtg    360 accgtctcca gt                                                       372

<210> SEQ ID NO 260
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260
gaggtgcagc tggtggagtc cggggcggg ctcgtacagg ctggaggttc ccttactctg     60
tcttgtgttg ccagtggaag agccttctcc aattcagcta tggcctggtt ccgtcagacc   120
ccagggaagg agagggagtt cgtgtcagca atttcacgcg gggcggatc taccgactac    180 gcagacagcg tgaaagggcg cttcactatc tctaaggaca cgccaaaaa cacagtgtac    240 ctccagatga actccctcaa gcccgaggac acagccgtgt attactgtgc tatgaggtat   300
tactctggcc gctattacga gagcttggag tacgattatt ggggtcaggg cactcaggtg   360
accgtttctt cc                                                       372
```

<210> SEQ ID NO 261
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261
gaggtacagc tggtcgagag tggcgggggt ctggtgcagg ccggagggtc tctgaggctg      60
agttgtgccg ctgcccggcg cactctgcac aactttgcta tggcatggtt ccggcaggct     120
ccgggcaagg agagggagtt cgtggctgca atttcaaagg gtggcggtag tgctgattac     180
gctgacagcg tgaagggtcg ctttaccatc tcaagagata atgcgaaaaa caccgtgtat     240
ctccagatga atagcctgaa gcccgaggac actgctgtct attactgcgc tgccaacgac     300
ctggcgtcct actccgactc ctcttataca tcaacttccc gttatgacta ctggggacag     360
ggtacacagg ttactgtttc ctcc                                            384

<210> SEQ ID NO 262
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 262
gaagtgcagc tggtggagag cggtggggga ctggtgcagc ccggaggctc ccttaggctg      60
agttgcaccg cctctggccg tccacgtacc acttacgcga tgggttggtt ccgtcaggcc     120
ccaggcaagg aacgtgaaat cgtggcggcc atctctaagg caggaggctc aacctacgtg     180
gctgattctg cgaagggaag attcgcaatc tctaaggata cgccaagaa caccgtgtac      240 ctgcaaatga actccctcaa gccggaggat accgctgtct attactgcgc tgcccgcgct     300
ggctttgccg ctcaaatctt cgagtacgac tactggggtc aggggaccct ggttaccgtt     360
tcaagt                                                                366

<210> SEQ ID NO 263
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263
gaggtgcagc tggtggagtc tggaggtgga ctcgtgcagg ccggtggcag cctgcgcctg      60
agctgtgcgg ccagcggcag aacattctct ggatacaaca tggggtggtt tagacaggcc     120
cccggcaagg aacgcgaatt tgtcgcagct atcgcctggg caggctctcg gacctattac     180
actgacagtg tgaagggacg cttcaccatc tcacgcgaca atgcgaaaaa taccatgtac     240
ctccagatga acactctgcg ccccgaggac accgctgtgt attactgtgc agcgcatgac     300
gagacttact atcgcctcga tagagtggat ctctacaccc actgggggca gggcacgctt     360
gttaccgtgt cttcc                                                      375

<210> SEQ ID NO 264
<211> LENGTH: 381

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264
gaggtccagc tcgtggaatc tggcggggt ctggtccagg ctggcggatc tctgaggctg      60
tcttgcgcaa ccagtggttt gaccgactcc acctatggca tggcatggtt ccgccaggca    120
cccggaaagg aacgggagtt tgtggctgcc atttctcggg ctggcggatc agcggaccac    180
gccgatagtg tcaagggcag gtttaccgtg agtcgcgaca acgccaaaaa gatggtttac    240
ctccaaatga actctttgaa gcctgaggat actgccgtct attactgcgc cagtggcaga    300
tcctattcta gtccctacga ttatttcaat gctttggctt atagctactg gggccaaggc    360
acacaggtta ccgtatcctc t                                              381

<210> SEQ ID NO 265
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
gaggtccagc tggtggagtc tggcgggggc ctggttcagc ccggtgggtt cctccgtctg      60
tcctgcgctg ccagccgcag gactctgagc acatacgcta tgggatggtt tcgtcaagcg    120
cccggtaaag agagggaatt tgtcgctgcg attagctgga ggtcagggaa tacctactat    180
gcagatagcg tgaaaggtcg tttcaccatc tctcgcgata acgccaagaa caccatgtac    240
ctccagatga acagcctgaa gcccgaggac accgcagttt actattgtgc cgctaacgag    300
gtcgccacta tgtccggccc tcacgatcat tggggacagg gcaccctggt gactgtttcc    360
tca                                                                   363

<210> SEQ ID NO 266
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 266
gaagttcagc tcgtggagtc tggtggaggg ctggtccaag ctggcggaag cctccgcctg      60
agctgcgccg catctgggcg ctctttcgcc aattacgcaa tgggttggtt cagacaagcc    120
cccggtaagg agagggagac ggtcgctgcc atcagtcgcg gcggaggctc tacttggtac    180
gcggacagcg taaaggaag attcaccatt tctaaagata atgccaagaa taccgtgtat    240
ttgcagatga actccctgaa accagaagat actgctatct attactgcgc cgctagatcc    300
tactctggat cttacacgta ttccttcggt gagtacgatt actggggaca gggtactcag    360
gtcaccgtgt ccagc                                                     375

<210> SEQ ID NO 267
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 267

| caagtgcagc tggttgagtc tggtggaggc ctggtgcagg ccggtgacag tctgcgcctg | 60 |
| tcctgtgctg ccagcggtcg cacattcacc ttttccaccc ataacatggg ttggttcagg | 120 |
| caagctcccg gaaaggagcg cgagttcgtg ggcggtatca tgtggacttc acgcgccagc | 180 |
| tatgctgaca gcgttaaggg tcgtttcacc gtctcccgcg acaacgccaa gaatacagtg | 240 |
| tacctccaga tgaatagtct gaagcccgag gacaccgcag tatattactg cgccgcagcc | 300 |
| tggtatggca acagtggggc ctcttatgac tattggggtc agggaacgca ggtgacagtc | 360 |
| tccagc | 366 |

<210> SEQ ID NO 268
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 268

| caggtgcaac tggttgagtc tggtggcggg ctggtgaggg ccggtggctc cctgaggctg | 60 |
| agctgcgctg ccagcggcag catcacctcc attaacacta tggggtggtt tcgtcaggct | 120 |
| ccgggcaagc agcgtgaact cgtggctgcc attactagcg gcgggagcac caactacgcc | 180 |
| gattcagtca agggtagatt cacaatttcc cgcgacaacg cccggaacac cgtgtatctc | 240 |
| cagatgtatt ccctgaagcc ggaggatacc gctgtctact attgcgaggc agatagcatg | 300 |
| tacttccggg gccagggaac ccaagtgacc gtttccagc | 339 |

<210> SEQ ID NO 269
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 269

| caggtacagc tggttgaatc cggcggtggc ttggtgcaag ccggaggcag tctccgcctg | 60 |
| tcctgcgctg cgagtcggcg cacgtttatg acctacgcga tgggatggtt ccgccaggct | 120 |
| ccaggtaagg agagagagtt cgtcgctgcc atctcctggt cctctggcag cacttactat | 180 |
| gccgactctg taaaggccg tttcaccatc agccgcgaca acgctaaaaa tacaatgtat | 240 |
| ctccagatga actccctgaa gcctgaggat acagccgtgt attactgcac tgcatcttcc | 300 |
| atcgcaacca tgtatggtcc taacgactac gctggtcagg aacccttgt aacagtctcc | 360 |
| tcc | 363 |

<210> SEQ ID NO 270
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 270

| caggtccagc tggttgagag tggaggcggg ctggtgcaag ccggaggctc cctcagactg | 60 |

```
tcctgcacgg ccagcggtcg cactttttcc cgctatgcta tgggttggtt tcggcaggca    120
ccaggcaaag agagagagtt cgtggcgacc atcagccgca gcggcgggac gaccagttac    180
gctaatagcg tcaaggggcg cttcacgatt tcccgcgaca acgctaagaa cacggtgtac    240
ctccagatga actccttgaa aacagaagac accgccgttt ataactgtgc tgcgcgggac    300
ggccctgcta tgggcgtgtt cgggtctgac tacgactact ggggccaggg gacactggtg    360
accgtctctt cc                                                        372

<210> SEQ ID NO 271
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271
gaggtgcagc tggtggagag tggaggtgga ctggtgcaag cgggcggtag tctcgtactg     60
agctgcgctg cctcaggccg cactttcagc cggtacgcga tgggttggtt caggcaggcc    120
ccaggcaagg aacgcgagtt tgtcgctgcc atctccatcg ggggaggcag cgctgactac    180
gccgacactg taagggtcg cttcaccatc tcacggaata acgctaagaa taccatgtac    240
cttcagatga actcactgaa accggaagac actgcggtgt actattgcgc cgcacgtacc    300
cctcgcccta gctccagcta cttcacacct caggactacg aatactgggg ccagggcaca    360
ctggtgaccg ttagcagt                                                  378

<210> SEQ ID NO 272
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 272
gaggtgcaac tggtggagtc tgtggcggt ttggtgcagg ccggtgggtc tctgcgcctg     60
agttgcgctg cctctggccg gacattcagc cgttacgcta tgaactggtt tcgtcaggct    120
cccggcaaag agagagagtt cgtggctgca atcagctggt catccggcaa cacctatgtg    180
gctgactcag tgaagggccg cttcactatt tccagagaca acgccaagaa tacgatgtat    240
cttcagatga ataaccttgc gccggaggac accgccgtgt actattgtgc tgcaacaacc    300
atcgctacca tgagtgacga gaacacatat tggggacagg gaacccaggt gactgtctcc    360
agc                                                                  363

<210> SEQ ID NO 273
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273
caggtgcagc tggtggagag cggaggcgga ctggtacaag caggggttc tctcaggctg     60 agctgtgcgg cttccgggag gactttcacc tcttatgcta tgaattggtt ccgccaggcc    120
cctgggaagg aaagggagtt tgtggcagcc atctcttggt ccagcggcaa tacctacgtg    180
```

```
gccgactccg tcaagggtag gttcgccatc agccgggaca aagctaagaa tactatgtac    240
ttgcagatga acagcctcgc gccggaagat actgcggtgt attactgcgc cgctactacc    300
atcgccacga tgtccgacga gtatacatat tggggacagg gaactcaggt tacagtatcc    360
tcc                                                                  363

<210> SEQ ID NO 274
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 274
caggtccagc tggtcgaatc cggtggcggg ttggtacagg cgggtggctc cctgcgcctg    60
agctgcgccg cgagtgggcg tacattttct aactacagaa tgggctggtt caggcaggct    120
ccgggaaagg agcgtgagtt cgtggctgcc atttcacgcg gaggtggcac cacactgtac    180
gccgactctg tcaaaggccg cttcaccatc tctcgcgaca cgctaagaa tactgttgat     240 ctccagatga accgcctgaa gccggaagac accgcagttt acttttgtgc cgcaggcgat    300
ttctctacca cttgggacga gtataactac tggggggcagg gaacacaagt gaccgtgtcc   360
agt                                                                  363

<210> SEQ ID NO 275
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 275
caggttcaac tggtggagag cggtgggggc ctggtgcagg caggcgggag cttgcggctt    60
tcatgtgttg catctggccg caccttctca agctatgcga tgggctggtt ccgtcagact    120
ccggggaaag agagggagtt cgtgagcgcg atttctcgcg gtggaggcag caccgactat    180
gccgattccg tgaagggcag gtttacgatc tccagagata cgccaagaa cacagtttat     240 ttgcagatga ataacctgaa atccgaggac accgcagtgt attactgcgc cctgcgggcc    300
tattcaggcc gctattacca gttcctggag tacgattact ggggccaggg cacacaggtg    360
actgtgtcct cc                                                        372

<210> SEQ ID NO 276
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276
gaggttcagt tggtggagtc tgggggcggt ctggtccagg ctggtggatc attgcgcctg    60
agctgtaccg tttcaggcag gacttttcct agctacgccg tagcttggtt ccgccaggca    120
cctggcaacg tccgggagct ggcggctgcc ctgagtcgcg ggggaggctc tgcttactat    180
acagacagtg tcaagggtcg cttcactatt agccgcgaca tgcgaaaaa caccgtctac     240 cttcagatga acagtctgaa gcccgaagac actgcggtgt attactgcgc ggccaggaac    300
```

```
tacgacggca cctattacca ggaaaaccaa tacaattact gggggcaggg aacccaggtg    360
accgtcagca gc                                                       372

<210> SEQ ID NO 277
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277
caggtccagc tggtggaatc aggcggaggc ttggtgcagg ccggggggcag tctgttgctg    60 tcttgcgccg cgagcggacg cacattctcc acctacgcta tggggtggtt ccgccaggca   120
cctggaaaag aacgcatgtt tgtcgcggcc atctccgtta acggaggcag tacctactat   180
gcagattctg ttacgggccg tttcaccatt agccgcgaca atgcgaaaaa caccatgtat   240
ttgcaaatga ataacctgaa gcctggtgac acagccgtgt attactgcgc agcgcgtcgc   300
ccctaccccg gttccgactt tctcacatgg gcctcctacg attacagggg ccagggcacc   360
ctggtgaccg tgtctagt                                                378

<210> SEQ ID NO 278
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278
caggttcagc tggtcgaatc tggcggtgga ctggtgcaag ctggtggggtt cctgcgcctc    60 agctgtgccg ctagtggccg tacctttagc tatacaacca tcggctggtt ccgccaggct   120
ccagggaagg aacgcgagtt cgtcgccgtg atctcagcag gaggcggttc ccgcgattac   180
gcggacgccc tcaaaggacg ctttacaatc tctcgcgata cgctaaaaa gatggtttat    240 ttgcaaatga ataacttgaa gcccgaggat ccgccgtgt attactgcgc cgtgaggcgg    300
aatactgaca catataccac aaccggcgac tacgactact ggggtcaggg cacccaggtt   360
accgtttcat cc                                                       372

<210> SEQ ID NO 279
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279
caagttcagc ttgtagagtc tggcggggggc ctggtgcaac ccggtgactc actgaggctg    60
tcttgtgtgg cctccggggg tacaatttcc tcactggcta tgggttggtt caggcaggct   120
ccgggtaagg agagggagtt tgtcgcagcc atcagctggt ctggccgctc aacatattac   180
gtggatagcg tgaaaggccg cttcactatt tctactgata cgcgaagaa taccgtgtat    240 ctccaaatga actccctgaa accggaggac acagcggtgt actattgcgt cgcaggcgag   300
gatggacaca gcgagtatga ctattggggc caaggcaccc aggtcacagt gtcctca      357

<210> SEQ ID NO 280
```

```
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 280
caggtgcagc ttgtggagag cggaggcggg ctggtgcagg ccgggggtag cttgcgcctc      60
agctgtgctg cctctggacg ctcatttgcc aactacgcaa tgggctggtt ccgtcaggct     120
cctgggaaag agcgcgagac cgtggcggcc atcagtcgcg ggggaggcag cacgtggtac     180
gcggactcag tcaaggggag gtttactatt tccaaggata cgctaagaa caccgtgtat      240 ctgcaaatga acagcctcaa gcccgaggac acagcaatct actattgcgc ggcccgcagt    300
tactccggct cctacactta ttccttcggc gagtacgact actggggtca gggcacccaa    360
gttaccgtgt cctcc                                                     375

<210> SEQ ID NO 281
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
caggtgcagc tggttgagtc tggaggcggt cttgtccagg ctggtggctc cttgcgcctg     60
agctgtgccg cttccgggag agctttctcc acatacgctc tcggctggtt caggcaggcc    120
cccggaaagg agcgcgagtt catcgctgca atcagccggg gcggtggcag cactgattat    180
gcagattctg tgaagggacg cttcaccatc tctcgtgata cgccaagtc taccgtatat     240 ttgcagatga atagtctgaa gcccgaagac accgctgtgt attactgtgc agcgcgtagc    300
tactcctcta gttactatta ctctcagtac gagtacgact actggggaca gggtactcag    360
gtgactgtgt ccagc                                                     375

<210> SEQ ID NO 282
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 282
gaggtccagc tcgtggagag tggcggtggc ctcgtgcagg ccgggggctc cctgagactg     60
agttgtgccg cttctggccg caccttcagt tcagtcgcta tggcttggtt tcggcaggcc    120
cctggcaagg agcgcgagtt cgtgtccgct atcagttctg gaggcggttc cacggattac    180
gctgatagcg tgaagggcag attcactatc agcaaggaca cgctaagaa ccatgtgtat     240 ctccagatgg actctcttaa acccgaggat accgccgtgt attactgcgc cgctcgcgac   300
tattctagcc gtcgctatta ccagtcccgg tacgagtacg acctctgggg cctgggaacc   360
caagtcacag tctcctcc                                                 378

<210> SEQ ID NO 283
<211> LENGTH: 363
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 283

```
caggtgcagt tggtggagtc cggtgggggc ctggtgcagc caggtggaag cctccgcctg      60
tcctgtgctg caagtggccg cacctttagg tcctactcaa tgggctggtt tcgtcaggct     120
ccaggaaagg aacgggagtt cgttgccgct atttcctggt attccgggac aacgtactat     180
gccgacccag tcaagggtag attcactatc agccgggacg atgcaaagaa cactctctac     240
ttgcagatga actccctgaa gcccgaggac accgccgtgt attactgcgc ggctaacgag     300
atcgccacaa tggaatcctc taacgattac tggggccagg ggacccaggt taccgtctct     360
agc                                                                   363
```

<210> SEQ ID NO 284
<211> LENGTH: 366
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 284

```
caggtgcagc tggtcgagag tggagggggga ttggtccagc ctggtggctc tctgcgcctg     60
tcatgcactg cttcaggccg cccccgtaca acgtatgcaa tgggctggtt ccgtcaggct    120
cccggcaagg agcgcgagat cgtggcggct atttccaaag ccggaggctc tacctacgtg    180
gccgactctg cgaaaggccg ctttgccatc tctaaggaca cgccaagaa taccgtctat    240
ctgcaaatga acagcctcaa gcctgaggat accgcagttt attactgtgc agctcgcgca    300
ggcttcgctg cccaaatctt cgagtacgac tactggggac agggcaccct ggtgacagtg    360
tctagc                                                               366
```

<210> SEQ ID NO 285
<211> LENGTH: 366
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 285

```
gaggttcaac tggtcgagtc cggggggcggg ctcgtgcagg ccggaggttc catgcgcctg     60
tcctgtgcca attccggtag aacctttggg acctatgcta tgggctggtt ccgccagtca    120
cccggcaaag agcgcgagcg ggtcgcgtcc atcgaccgtg acggttctat gtcctattac    180
gccgacagcg tgaaaggcag gttcacaatc agcggagaca atgcgaagaa caccgtgtat    240
ctccagatga actccctgaa acctgaggac accgccgtct attactgcgc ggcttcaaga    300
cgcgccgtta tttctctcca gacagttgat tactggggcc agggaacccca ggtgactgtg    360
tccagc                                                               366
```

<210> SEQ ID NO 286
<211> LENGTH: 363
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 286

```
gaagtgcagc tcgtggagtc tggtggccgt ttggtccaga ccggaggcag cttgaggctc    60
tcatgcgctg cctctggcag gacatttttcc aattatgcaa tgggatggtt tcgtcaggct   120
cctggcaagg agagggagtt cgtggctgca atctcttggt acagcggcaa cacatactat   180
gccgactccg tgaaaggcag gtttaccatc agccgggata cgccaaaaa cactatgtat   240 ctccagatga actccctgaa gccagaggat acggcggtct attactgtgc agccaatcaa   300
atcgccacta tgattagcgt gggcgactac tggggccaag gcaccctggt gacagtgtca   360
tcc                                                                 363
```

```
<210> SEQ ID NO 287
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 287
caggtgcagt tggtcgagtc aggagggggc ctggtcgagg ccgggggctc cctgaggctc    60
gcttgcgctg cgagtggatc aatcttccgt ttgaacctga tgggatggta tagacaggct   120
cctggcaagc agcgtgaact ggtcgcacac gtgggtacta caggaaacac cgcctacgcc   180
gactctgtca aggggcgctt taccatctca aggacgatg ctaagaacat ggtgtttctc    240
cagatgaact ccctcaagcc cgaggatact gccgtctatt actgctatgc ggaccgctgg    300
ggtcagttct cctggggcca gggaacacag gtaaccgttt cttca                   345
```

```
<210> SEQ ID NO 288
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 288
caggtgcagc tcgtggagtc tggcggtggc ctggtccagg ccggaggcag cctccggttg    60
agctgtgtag ctagtggccg tacctttacg ggctacgcga tgggctggtt cagacaagcg   120
cctggcaagg agagggagtt cgtcgccgtg attacttggt ccggggccac tacctattac   180
tccgcttccg tgaagggccg tttcacgctg agccgggata cgccaaaaa cacagtgtac    240 ctccagatga actccctgaa gtccgaggac actgccgttt attactgcgc cattcgcatc    300
cgggacggag tgtctcctga aaaccctaac gagtacggtt actggggcca gggcacccag    360
gtaaccgtgt cctca                                                    375
```

```
<210> SEQ ID NO 289
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 289
caggtccagc tcgtggagtc cggcgggggc ttggttcagg ctgggggaag cctgcgtctg    60
tcatgcgtgg cgagcgggag gaccgtcggc tacggcatgg cttggtttag gcaggctcct   120
ggcaagcaac gcgatgttgt ggccgcgatc acttggtccg gcacttccac ctattacccc   180
```

```
gactcagtca aggggcgctt caccatctcc agagataacg ccaagaacac tatgtatctc    240
cagatgtcat ctctgaagcc agaagatacc gctgtatatt actgcgccgc tggctcccgt    300
cgccgggtgg gcgtggacgt gggtggatac gactactggg gccaaggcac tcaggtgacc    360
gtctccagc                                                            369
```

<210> SEQ ID NO 290
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 290

```
caggtgcagc tcgtcgagag cggggggcgga ctggtacagg ctggcgactc cttgcgtctg    60
agctgcgccg cgtccggcag gacgttcacc ttctcaactc acaatatggg ctggttccgt    120
caggcaccgg gtaaggagag agagttcgtc ggaggcatca tgtggaccag ccgggcaagt    180
tacgccgatt ctgtgaaggg tcgtttcacc gtaagccgtg ataacgcgaa gaacactgtc    240
tacttgcaga tgaactctct gaagcccgag gacactgcgg tttactattg cgctgccgca    300
tggtatggta acagcggagc ctcctacgac tactggggtc aaggaactca ggtcacggtc    360
agctcc                                                                366
```

<210> SEQ ID NO 291
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 291

```
caggtccaac tggtcgagtc tggcggaggc ctcgtgcaac ttgttcaagc cggggggcagc    60 ctgcgccttt cttgtgctgc gagtggccgc accttttccg ggtataacat gggttggttt    120
cgtcaggccc caggtaagga gcgcgagttc gtggctgcca ttgcttgggc aggcagcagg    180
acatattaca ccgatagcgt caaggggcgg tttactatct ctcgcgacaa tgcaaaaaac    240
actatgtacc tccagatgaa caccctgcgt cctgaggata cagccgtgta ttactgcgca    300
gcccatgacg agacctatta ccgccttgac cgggtggacc tctatacccca ctggggccag    360 ggaacccagg tcactgtgtc ctcc                                            384
```

<210> SEQ ID NO 292
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 292

```
caggtgcaac tggttgagtc cggggggcgga ctggtgcaac tggcgagag tctgcgcctg    60 tcctgcgcgg cctccggtcc tttttactaga tatgcgatgg gttggttccg tcaagcgcct    120 ggaaggagc gtgagttcgt cgcggctatc agctggtcat ctggaaatac gtattacgtg    180
gattccgtga agggcaggtt cactatttcc agagacaacg ctaagaacac aatgtacttg    240
cagatgaaca gcctgaagcc agaggacaca gcggtttact attgtgctgc aaacgaggtc    300
```

```
gccaccatga gtggacccga tgactattgg ggacaaggta cacaagtcac tgtgtcctct    360
```

<210> SEQ ID NO 293
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 293

```
caggtgcagc tggtggagtc tggaggtggg ctggtgcagg cgggaggctc tctgcgtctg    60
tcttgtgctg ccagcggcgg ttcctttggc cggtacacaa tgggatggta tcgtcaagcg    120
cctggtaagg agcgcgagtt tgttgctgtg atctcatgga gcggcacaaa cacgtactat    180
gcggacagcg tgaagggtcg ctttaccatt tcccgtgata acgcgaagaa taccatgtac    240
ctgcaaatga acgatttgaa acccgaagat accgcagttt attactgtgc tgcgcgtgag    300
acttattact cacactggga cgaaaggatg gagtatgact attggggcca gggcacccag    360
gttacagtat cttcc                                                      375
```

<210> SEQ ID NO 294
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 294

```
caggtccagc tcgtagaaag cggaggtggc cttgtccaag ctggcgacag cctgcgcctt    60
tcctgcgttg ccagcggctc catcgactca tcctattacg tgtcttggtt ccgtcaggca    120
ccaggcaagg aacgtgatct ggtagctgcc atcaactggg gcgattctcg caccgcctat    180
gctgactccg ttaagggccg gttcacgatc tcccgtgata acgcgaaaaa tactgtgtat    240
ctccagatgc actccctgcg ccccaacgat accgcagtgt attactgtgc cagcagaatt    300
gggctgggcg ggccggtggt tgcggccccc acccgttatc cctattgggg ccagggcacc    360
ctggtaaccg tgtcttcc                                                   378
```

<210> SEQ ID NO 295
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 295

```
caagtgcaac tggtagagtc aggcggtggc cttgtgcagg ccggtggctc tctgcgcctg    60
tcttgcgctg cctctgagtc tatcttgcgg tttaacgtga tgtcatggtt gcgtcaggca    120
ccagggaaac agcgtgagct ggtggcagtc atcactagcg gtggcagcac gaattatgca    180
gactccgtga aggccgcttc acgatctctc gtgacaacg ctaaaaacac cgtgtatctc    240
cagatgaaca gcctgaagcc agaagacact gccgtgtatt actgtgctgc cgacgagagc    300
gggcagtatt actggggaca gggcactcag gtgacagtca gcagc                    345
```

<210> SEQ ID NO 296
<211> LENGTH: 375

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 296
caggtccagc tcgtggagtc tgggggcggt ctcgtccagg ctggggttc  cctgcggctg     60 agctgtgccg cttctggctt gacgaccagt agcgccgctc tggcctggtt tcgtcaggct    120
cctggcaagg agcgtgagct tgatccaact attaccagcg gcggaggctc tacctactat    180
gccgacagcg ttaagggtcg gtttaccatc agcaaagaca acgctaagaa cactctttat    240
ctccagatgt caagcctcaa acctgaggac accgccgtct actattgcgc cgctcgcttt    300
tatagcacca cttactatta ccgcgaacac gagtatagtg actgggggca gggcacccaa    360
gtcacagtga gcagc                                                     375

<210> SEQ ID NO 297
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297
caggtgcaac tggtggaatc tgggggtggc ttggtgcagg ctggcgggtc tctgcgtctg     60
tcctgtgcgg cttcaggacg cactttcggc accagctttg gcagcctgag catgggctgg    120
ttcagacaag cccccggcaa agagcgtgag ttcgtggctg ccatctctcg caacattggc    180
cgtacttatt acgcagattc cgtgaaagac aggtttacga tctctcgcga caacgctaag    240
aataccgcct ctcttcagat gaactctctg gagcccgaag acactgctgt ctataattgt    300
gccgcgacaa actcctacga tgaccttagg cgctcctacg cctacgacta ctggggacag    360
ggcacccagg tgacagtcag ctcc                                           384

<210> SEQ ID NO 298
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 298
caggtccagc tggtggagag cggcggtggg ctggttcagg ctggaggctt cctgcgcctg     60
tcttgcgctg cctcaggtcg tacttttcc  tctttggcaa tggcttggtt ccgtcaagct    120
cccggcaagg agcgcgagtt cgtagccgct atctcccgct ctggaggctc taccgactac    180
gctgacagcg tcaagggacg cttcaccatc tctcgggaca acgccaagtc caccctgtac    240
ttgcagatgt ctagcctgaa acctgaggat acagcggtgt attactgcgc tgcacgtgac    300
tactctactc tccagtatta caatgagtat gaatactccg actggggcca aggcactctg    360
gtcactgtgt cctca                                                     375

<210> SEQ ID NO 299
<211> LENGTH: 375
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 299

```
caggtgcagc tcgtagagtc tggcggtggc ctggtccagg ctggggactc actgcgtctg      60
agttgtgccg cgtccggccc taccttcagt acgtatgcaa tggcctggtt tcgccaagct     120
ccaggtaagg aacgcgagtt cgtggctgcc attacccaga gtggtcgcac cacttactat     180
gaagattctg tgaaggggcg gttcaccatt agcaaggata atgccaagaa caccctctat     240
ctccagatga acagcctcca gcctgaagat acggcggtgt attactgcgc ggcccgcgac     300
ttgtggtctg attctcccga tgactggaga atttactctt tctggggaca ggggacccaa     360
gtaacagtca gttcc                                                      375
```

<210> SEQ ID NO 300
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 300

```
caggttcagc ttgtggagtc cggtggcggt ctggtccagg caggtggctc cctgcggctg      60
tcttgcgcag ccgctcgtcg cacactgcac aacttcgcaa tggcgtggtt tcgccaggcc     120
cctggtaagg agagggagtt tgtggctgcc atttctaagg gaggcggttc cgccgactac     180
gccgatagcg ttaaggggcg ctttaccatt agtagggaca cgctaagaa cacagtgtac      240
ctccagatga acagcctcaa gccagaggat accgcagttt actattgcgc tgccaacgat     300
ctggcttctt atagcgacag ctcttacaca tccacaagcc gctacgacta ctggggtcag     360
ggcacccagg ttacagtgtc ctct                                            384
```

<210> SEQ ID NO 301
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 301

```
caggtgcagc tcgtcgagtc tggcgggga ctggtgcaga ctggtggctc cctgcgcctc       60
tcttgcgcgg cctctggccg caccttctca tcctatgcta tggcttggtt ccgtcaagcg     120
cccggtaaag agagggagtt tgtggccgct atctctatcc tcggtggcag cgctgactac     180
gaggattccg ttcagggacg cttcactatc tcaagagata cgccaagaa cactatgtac      240
cttcagatga actccctcaa gccagaggac accgctgtgt attactgtgc cgctcgcaga     300
ccggctccct ccgacagcta ctggagcagt acaagttacg catactgggg acaggggacc     360
ctggtgacag tgtccagt                                                   378
```

<210> SEQ ID NO 302
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 302

```
gaggtacagc tggtcgaatc cggtggcggt ctggtgcagg ctggcggaag cctgcgcttg    60
agctgtgcgg cctctggccg cactttcagc tctcttgcaa tggcgtggtt ccgccaggcc   120
cctggaaagg agcgcgagtt cgtggccgcg accacaatcc tcggaggctc cgccgactac   180
ggcgacccgg tcaagggccg cttcacaatc tcccgcgata atgctaagaa cacggtgtat   240
ctccagatga actcactgaa gccagaggat accgccgttt attactgcac tgggagacgc   300
cccgctccat ccgacaacta ctggtcccct gccagctatg cttactgggg acaaggcacc   360
caagttaccg tgagcagt                                                 378
```

<210> SEQ ID NO 303  
<211> LENGTH: 363  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 303

```
caggtgcagt tggtggaaag cggcggtggc cttgtgcagg ctggcggttc actgcgcctc    60
agctgcgcac cttccggtcg caccttctcc tcttacgcga tggcgtggtt tcgccagcct   120
ccaggcaagg aacgggagtt tgtggctgcc attaccgttt ccggcgcaag tacctattac   180
gctgactctg ttaagggccg tttcaccatc tctcgcgata atgcgaaaaa ctctatgtac   240
cttcagatga actctttgaa accggaggat accgctgtgt actattgtgc agctggcggt   300
cccggaacca tcttcccaga ctatgattac tggggtcagg gtactcaggt caccgtctcc   360
tcc                                                                363
```

<210> SEQ ID NO 304  
<211> LENGTH: 381  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 304

```
caagtacagc tcgtcgaatc cggcggtgga ctggtgcagg ccggagattc ccttaccctg    60
tcttgcaccg cttccggtcg cacctttca ggttacaata tgggctggtt caggcaggcc   120
cctggtaagg agcgcgactt cgtcgctgcc atcaactgga tcggaggtgc tacctattac   180
gcggatagcg tgaaaggccg ctttaccatt agcagggata atgccaagaa cactgtctac   240
ctgcaaatga acagcctgaa gcccgaggat actgccgtgt attactgcca tcgctattcc   300
gagaagttct acagcgggaa ggactactat actcgtgact acgactactg gggtcagggt   360
acacaggtaa ctgtgtcctc a                                            381
```

<210> SEQ ID NO 305  
<211> LENGTH: 8  
<212> TYPE: PRT  
<213> ORGANISM: Artificial Sequence  
<220> FEATURE:  
<223> OTHER INFORMATION: Description of Artificial Sequence: Synthetic peptide

<400> SEQUENCE: 305

Ala Ser His His His His His His  
1               5

```
<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gly Ser His His His His His His His His
1               5                   10

<210> SEQ ID NO 307
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 307

His His His His His His
1               5

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 308

His His His His His His His His
1               5

<210> SEQ ID NO 309
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
```

```
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
```

```
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (1)..(800)
<223> OTHER INFORMATION: This sequence may encompass 1-20
      "(Gly)m(Ser)o" repeating units,
      wherein m = 1 to 20, o = 1 to 20
<220> FEATURE:
<223> OTHER INFORMATION: See specification as filed for detailed
      description of substitutions and preferred embodiments

<400> SEQUENCE: 309

Gly Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser Ser
            20                  25                  30

Ser Ser Ser Ser Ser Ser Ser Gly Gly Gly Gly Gly Gly Gly Gly Gly
        35                  40                  45

Gly Gly Gly Gly Gly Gly Gly Gly Gly Gly Gly Gly Ser Ser Ser Ser
    50                  55                  60

Ser Ser Ser Ser Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly Gly
```

```
                    85                  90                  95
Gly Gly Gly Gly Ser Ser Ser Ser Ser Ser Ser Ser Ser Ser
                100                 105                 110
Ser Ser Ser Ser Ser Ser Ser Gly Gly Gly Gly Gly Gly Gly
                115                 120                 125
Gly Gly Gly Gly Gly Gly Gly Gly Gly Gly Ser Ser Ser Ser
                130                 135                 140
Ser Ser Ser Ser Ser Ser Ser Ser Ser Ser Ser Ser
145                 150                 155                 160
Gly Gly Gly Gly Gly Gly Gly Gly Gly Gly Gly Gly Gly
                165                 170                 175
Gly Gly Gly Gly Ser Ser Ser Ser Ser Ser Ser Ser Ser
                180                 185                 190
Ser Ser Ser Ser Ser Ser Ser Gly Gly Gly Gly Gly Gly Gly
                195                 200                 205
Gly Gly Gly Gly Gly Gly Gly Gly Gly Gly Ser Ser Ser Ser
                210                 215                 220
Ser Ser Ser Ser Ser Ser Ser Ser Ser Ser Ser Ser
225                 230                 235                 240
Gly Gly Gly Gly Gly Gly Gly Gly Gly Gly Gly Gly Gly Gly
                245                 250                 255
Gly Gly Gly Gly Ser Ser Ser Ser Ser Ser Ser Ser Ser Ser
                260                 265                 270
Ser Ser Ser Ser Ser Ser Gly Gly Gly Gly Gly Gly Gly
                275                 280                 285
Gly Gly Gly Gly Gly Gly Gly Gly Gly Gly Ser Ser Ser Ser
                290                 295                 300
Ser Ser Ser Ser Ser Ser Ser Ser Ser Ser Ser Ser Ser Ser
305                 310                 315                 320
Gly Gly Gly Gly Gly Gly Gly Gly Gly Gly Gly Gly Gly
                325                 330                 335
Gly Gly Gly Gly Ser Ser Ser Ser Ser Ser Ser Ser Ser Ser
                340                 345                 350
Ser Ser Ser Ser Ser Ser Gly Gly Gly Gly Gly Gly Gly
                355                 360                 365
Gly Gly Gly Gly Gly Gly Gly Gly Gly Gly Ser Ser Ser Ser
                370                 375                 380
Ser Ser Ser Ser Ser Ser Ser Ser Ser Ser Ser Ser
385                 390                 395                 400
Gly Gly Gly Gly Gly Gly Gly Gly Gly Gly Gly Gly Gly Gly
                405                 410                 415
Gly Gly Gly Gly Ser Ser Ser Ser Ser Ser Ser Ser Ser
                420                 425                 430
Ser Ser Ser Ser Ser Ser Ser Gly Gly Gly Gly Gly Gly
                435                 440                 445
Gly Gly Gly Gly Gly Gly Gly Gly Gly Gly Ser Ser Ser
                450                 455                 460
Ser Ser Ser Ser Ser Ser Ser Ser Ser Ser Ser Ser Ser Ser
465                 470                 475                 480
Gly Gly Gly Gly Gly Gly Gly Gly Gly Gly Gly Gly Gly
                485                 490                 495
Gly Gly Gly Gly Ser Ser Ser Ser Ser Ser Ser Ser Ser Ser
                500                 505                 510
```

Ser Ser Ser Ser Ser Ser Ser Gly Gly Gly Gly Gly Gly Gly
        515                 520                 525

Gly Gly Gly Gly Gly Gly Gly Gly Gly Gly Ser Ser Ser Ser
        530                 535                 540

Ser Ser Ser Ser Ser Ser Ser Ser Ser Ser Ser Ser Ser Ser
545                 550                 555                 560

Gly Gly Gly Gly Gly Gly Gly Gly Gly Gly Gly Gly Gly Gly
                565                 570                 575

Gly Gly Gly Gly Ser Ser Ser Ser Ser Ser Ser Ser Ser Ser
        580                 585                 590

Ser Ser Ser Ser Ser Ser Ser Gly Gly Gly Gly Gly Gly Gly
        595                 600                 605

Gly Gly Gly Gly Gly Gly Gly Gly Gly Gly Ser Ser Ser Ser
        610                 615                 620

Ser Ser Ser Ser Ser Ser Ser Ser Ser Ser Ser Ser Ser Ser
625                 630                 635                 640

Gly Gly Gly Gly Gly Gly Gly Gly Gly Gly Gly Gly Gly Gly
                645                 650                 655

Gly Gly Gly Gly Ser Ser Ser Ser Ser Ser Ser Ser Ser Ser
        660                 665                 670

Ser Ser Ser Ser Ser Ser Ser Gly Gly Gly Gly Gly Gly Gly
        675                 680                 685

Gly Gly Gly Gly Gly Gly Gly Gly Gly Gly Ser Ser Ser Ser
        690                 695                 700

Ser Ser Ser Ser Ser Ser Ser Ser Ser Ser Ser Ser Ser Ser
705                 710                 715                 720

Gly Gly Gly Gly Gly Gly Gly Gly Gly Gly Gly Gly Gly Gly
                725                 730                 735

Gly Gly Gly Gly Ser Ser Ser Ser Ser Ser Ser Ser Ser Ser
        740                 745                 750

Ser Ser Ser Ser Ser Ser Ser Gly Gly Gly Gly Gly Gly Gly
        755                 760                 765

Gly Gly Gly Gly Gly Gly Gly Gly Gly Gly Ser Ser Ser Ser
        770                 775                 780

Ser Ser Ser Ser Ser Ser Ser Ser Ser Ser Ser Ser Ser Ser
785                 790                 795                 800

<210> SEQ ID NO 310
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(100)
<223> OTHER INFORMATION: This sequence may encompass 1-20
      "Gly Ser Gly Gly Ser" repeating units
<220> FEATURE:
<223> OTHER INFORMATION: See specification as filed for detailed
      description of substitutions and preferred embodiments

<400> SEQUENCE: 310

Gly Ser Gly Gly Ser Gly Ser Gly Gly Ser Gly Ser Gly Gly Ser Gly
1               5                   10                  15

Ser Gly Gly Ser Gly Ser Gly Gly Ser Gly Ser Gly Gly Ser Gly Ser
                20                  25                  30

```
Gly Gly Ser Gly Ser Gly Gly Ser Gly Ser Gly Gly Ser Gly Ser Gly
        35                  40                  45

Gly Ser Gly Ser Gly Gly Ser Gly Ser Gly Gly Ser Gly Ser Gly Gly
    50                  55                  60

Ser Gly Ser Gly Gly Ser Gly Ser Gly Gly Ser Gly Ser Gly Gly Ser
65                  70                  75                  80

Gly Ser Gly Gly Ser Gly Ser Gly Gly Ser Gly Ser Gly Gly Ser Gly
            85                  90                  95

Ser Gly Gly Ser
            100

<210> SEQ ID NO 311
<211> LENGTH: 1200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
```

```
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
```

```
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (801)..(820)
<223> OTHER INFORMATION: This region may encompass 1-20 residues
<220> FEATURE:
<221> NAME/KEY: SITE
<222> LOCATION: (821)..(840)
<223> OTHER INFORMATION: This region may encompass 1-20 residues
<220> FEATURE:
<221> NAME/KEY: SITE
<222> LOCATION: (841)..(860)
<223> OTHER INFORMATION: This region may encompass 1-20 residues
<220> FEATURE:
<221> NAME/KEY: SITE
<222> LOCATION: (861)..(880)
<223> OTHER INFORMATION: This region may encompass 1-20 residues
<220> FEATURE:
<221> NAME/KEY: SITE
<222> LOCATION: (881)..(900)
<223> OTHER INFORMATION: This region may encompass 1-20 residues
<220> FEATURE:
<221> NAME/KEY: SITE
<222> LOCATION: (901)..(920)
<223> OTHER INFORMATION: This region may encompass 1-20 residues
<220> FEATURE:
<221> NAME/KEY: SITE
<222> LOCATION: (921)..(940)
<223> OTHER INFORMATION: This region may encompass 1-20 residues
<220> FEATURE:
<221> NAME/KEY: SITE
<222> LOCATION: (941)..(960)
<223> OTHER INFORMATION: This region may encompass 1-20 residues
<220> FEATURE:
<221> NAME/KEY: SITE
<222> LOCATION: (961)..(980)
<223> OTHER INFORMATION: This region may encompass 1-20 residues
<220> FEATURE:
<221> NAME/KEY: SITE
<222> LOCATION: (981)..(1000)
<223> OTHER INFORMATION: This region may encompass 1-20 residues
<220> FEATURE:
<221> NAME/KEY: SITE
<222> LOCATION: (1001)..(1020)
<223> OTHER INFORMATION: This region may encompass 1-20 residues
<220> FEATURE:
<221> NAME/KEY: SITE
<222> LOCATION: (1021)..(1040)
<223> OTHER INFORMATION: This region may encompass 1-20 residues
<220> FEATURE:
<221> NAME/KEY: SITE
<222> LOCATION: (1041)..(1060)
<223> OTHER INFORMATION: This region may encompass 1-20 residues
<220> FEATURE:
```

```
<221> NAME/KEY: SITE
<222> LOCATION: (1061)..(1080)
<223> OTHER INFORMATION: This region may encompass 1-20 residues
<220> FEATURE:
<221> NAME/KEY: SITE
<222> LOCATION: (1081)..(1100)
<223> OTHER INFORMATION: This region may encompass 1-20 residues
<220> FEATURE:
<221> NAME/KEY: SITE
<222> LOCATION: (1101)..(1120)
<223> OTHER INFORMATION: This region may encompass 1-20 residues
<220> FEATURE:
<221> NAME/KEY: SITE
<222> LOCATION: (1121)..(1140)
<223> OTHER INFORMATION: This region may encompass 1-20 residues
<220> FEATURE:
<221> NAME/KEY: SITE
<222> LOCATION: (1141)..(1160)
<223> OTHER INFORMATION: This region may encompass 1-20 residues
<220> FEATURE:
<221> NAME/KEY: SITE
<222> LOCATION: (1161)..(1180)
<223> OTHER INFORMATION: This region may encompass 1-20 residues
<220> FEATURE:
<221> NAME/KEY: SITE
<222> LOCATION: (1181)..(1200)
<223> OTHER INFORMATION: This region may encompass 1-20 residues
<220> FEATURE:
<221> NAME/KEY: SITE
<222> LOCATION: (1)..(1200)
<223> OTHER INFORMATION: This sequence may encompass 1-20
      "(Gly)m(Ser)o(Gly)m" repeating units,
      wherein m = 1 to 20, o = 1 to 20
<220> FEATURE:
<223> OTHER INFORMATION: See specification as filed for detailed
      description of substitutions and preferred embodiments

<400> SEQUENCE: 311

Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser
                20                  25                  30

Ser Ser Ser Ser Ser Ser Ser Ser Gly Gly Gly Gly Gly Gly Gly
            35                  40                  45

Gly Gly Gly Gly Gly Gly Gly Gly Gly Gly Gly Gly Gly Gly Gly
        50                  55                  60

Gly Gly Gly Gly Gly Gly Gly Gly Gly Gly Gly Gly Gly Gly Gly
65                  70                  75                  80

Ser Ser Ser Ser Ser Ser Ser Ser Ser Ser Ser Ser Ser Ser Ser
                85                  90                  95

Ser Ser Ser Ser Gly Gly Gly Gly Gly Gly Gly Gly Gly Gly Gly
                100                 105                 110

Gly Gly Gly Gly Gly Gly Gly Gly Gly Gly Gly Gly Gly Gly Gly
            115                 120                 125

Gly Gly Gly Gly Gly Gly Gly Gly Gly Gly Gly Ser Ser Ser Ser
        130                 135                 140

Ser Ser Ser Ser Ser Ser Ser Ser Ser Ser Ser Ser Ser Ser Ser
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190

Gly Gly Gly Gly Gly Gly Gly Ser Ser Ser Ser Ser Ser Ser Ser
        195                 200                 205

Ser Ser Ser Ser Ser Ser Ser Ser Ser Ser Ser Gly Gly Gly Gly
```

```
                    210                 215                 220
Gly Gly Gly Gly Gly Gly Gly Gly Gly Gly Gly Gly Gly Gly Gly Gly
225                 230                 235                 240

Gly Gly Gly Gly Gly Gly Gly Gly Gly Gly Gly Gly Gly Gly Gly Gly
                245                 250                 255

Gly Gly Gly Gly Ser Ser Ser Ser Ser Ser Ser Ser Ser Ser Ser Ser
                260                 265                 270

Ser Ser Ser Ser Ser Ser Ser Ser Gly Gly Gly Gly Gly Gly Gly Gly
            275                 280                 285

Gly Gly Gly Gly Gly Gly Gly Gly Gly Gly Gly Gly Gly Gly Gly Gly
290                 295                 300

Gly Gly Gly Gly Gly Gly Gly Gly Gly Gly Gly Gly Gly Gly Gly Gly
305                 310                 315                 320

Ser Ser Ser Ser Ser Ser Ser Ser Ser Ser Ser Ser Ser Ser Ser Ser
                325                 330                 335

Ser Ser Ser Ser Gly Gly Gly Gly Gly Gly Gly Gly Gly Gly Gly Gly
            340                 345                 350

Gly Gly Gly Gly Gly Gly Gly Gly Gly Gly Gly Gly Gly Gly Gly Gly
                355                 360                 365

Gly Gly Gly Gly Gly Gly Gly Gly Gly Gly Gly Ser Ser Ser Ser Ser
            370                 375                 380

Ser Ser Ser Ser Ser Ser Ser Ser Ser Ser Ser Ser Ser Ser Ser Ser
385                 390                 395                 400

Gly Gly Gly Gly Gly Gly Gly Gly Gly Gly Gly Gly Gly Gly Gly Gly
                405                 410                 415

Gly Gly Gly Gly Gly Gly Gly Gly Gly Gly Gly Gly Gly Gly Gly Gly
                420                 425                 430

Gly Gly Gly Gly Gly Gly Gly Gly Ser Ser Ser Ser Ser Ser Ser Ser
            435                 440                 445

Ser Ser Ser Ser Ser Ser Ser Ser Ser Ser Ser Gly Gly Gly Gly Gly
450                 455                 460

Gly Gly Gly Gly Gly Gly Gly Gly Gly Gly Gly Gly Gly Gly Gly Gly
465                 470                 475                 480

Gly Gly Gly Gly Gly Gly Gly Gly Gly Gly Gly Gly Gly Gly Gly Gly
                485                 490                 495

Gly Gly Gly Gly Ser Ser Ser Ser Ser Ser Ser Ser Ser Ser Ser Ser
            500                 505                 510

Ser Ser Ser Ser Ser Ser Ser Gly Gly Gly Gly Gly Gly Gly Gly Gly
            515                 520                 525

Gly Gly Gly Gly Gly Gly Gly Gly Gly Gly Gly Gly Gly Gly Gly Gly
            530                 535                 540

Gly Gly Gly Gly Gly Gly Gly Gly Gly Gly Gly Gly Gly Gly Gly Gly
545                 550                 555                 560

Ser Ser Ser Ser Ser Ser Ser Ser Ser Ser Ser Ser Ser Ser Ser Ser
                565                 570                 575

Ser Ser Ser Ser Gly Gly Gly Gly Gly Gly Gly Gly Gly Gly Gly Gly
            580                 585                 590

Gly Gly Gly Gly Gly Gly Gly Gly Gly Gly Gly Gly Gly Gly Gly Gly
            595                 600                 605

Gly Gly Gly Gly Gly Gly Gly Gly Gly Gly Gly Gly Ser Ser Ser Ser
            610                 615                 620

Ser Ser Ser Ser Ser Ser Ser Ser Ser Ser Ser Ser Ser Ser Ser Ser
625                 630                 635                 640
```

Gly Gly Gly Gly Gly Gly Gly Gly Gly Gly Gly Gly Gly Gly
            645                 650                 655
Gly Gly Gly Gly Gly Gly Gly Gly Gly Gly Gly Gly Gly Gly
            660                 665                 670
Gly Gly Gly Gly Gly Gly Gly Ser Ser Ser Ser Ser Ser Ser
            675                 680                 685
Ser Ser Ser Ser Ser Ser Ser Ser Ser Ser Gly Gly Gly Gly
            690                 695                 700
Gly Gly Gly Gly Gly Gly Gly Gly Gly Gly Gly Gly Gly Gly
705                 710                 715                 720
Gly Gly Gly Gly Gly Gly Gly Gly Gly Gly Gly Gly Gly Gly
            725                 730                 735
Gly Gly Gly Gly Ser Ser Ser Ser Ser Ser Ser Ser Ser Ser
            740                 745                 750
Ser Ser Ser Ser Ser Ser Ser Gly Gly Gly Gly Gly Gly Gly
            755                 760                 765
Gly Gly Gly Gly Gly Gly Gly Gly Gly Gly Gly Gly Gly Gly
            770                 775                 780
Gly Gly Gly Gly Gly Gly Gly Gly Gly Gly Gly Gly Gly Gly
785                 790                 795                 800
Ser Ser Ser Ser Ser Ser Ser Ser Ser Ser Ser Ser Ser Ser
            805                 810                 815
Ser Ser Ser Ser Gly Gly Gly Gly Gly Gly Gly Gly Gly Gly
            820                 825                 830
Gly Gly Gly Gly Gly Gly Gly Gly Gly Gly Gly Gly Gly Gly
            835                 840                 845
Gly Gly Gly Gly Gly Gly Gly Gly Gly Gly Ser Ser Ser Ser
            850                 855                 860
Ser Ser Ser Ser Ser Ser Ser Ser Ser Ser Ser Ser Ser Ser
865                 870                 875                 880
Gly Gly Gly Gly Gly Gly Gly Gly Gly Gly Gly Gly Gly Gly
            885                 890                 895
Gly Gly Gly Gly Gly Gly Gly Gly Gly Gly Gly Gly Gly Gly
            900                 905                 910
Gly Gly Gly Gly Gly Gly Gly Ser Ser Ser Ser Ser Ser Ser
            915                 920                 925
Ser Ser Ser Ser Ser Ser Ser Ser Ser Ser Gly Gly Gly Gly
            930                 935                 940
Gly Gly Gly Gly Gly Gly Gly Gly Gly Gly Gly Gly Gly Gly
945                 950                 955                 960
Gly Gly Gly Gly Gly Gly Gly Gly Gly Gly Gly Gly Gly Gly
            965                 970                 975
Gly Gly Gly Gly Ser Ser Ser Ser Ser Ser Ser Ser Ser Ser
            980                 985                 990
Ser Ser Ser Ser Ser Ser Ser Gly Gly Gly Gly Gly Gly Gly
            995                 1000                1005
Gly Gly Gly Gly Gly Gly Gly Gly Gly Gly Gly Gly Gly Gly
            1010                1015                1020
Gly Gly Gly Gly Gly Gly Gly Gly Gly Gly Gly Gly Gly Gly
            1025                1030                1035
Gly Gly Ser Ser Ser Ser Ser Ser Ser Ser Ser Ser Ser Ser
            1040                1045                1050

```
Ser  Ser  Ser  Ser  Ser  Ser  Ser  Gly  Gly  Gly  Gly  Gly  Gly  Gly  Gly
     1055                1060                     1065

Gly  Gly  Gly  Gly  Gly  Gly  Gly  Gly  Gly  Gly  Gly  Gly  Gly  Gly  Gly
     1070                1075                     1080

Gly  Gly  Gly  Gly  Gly  Gly  Gly  Gly  Gly  Gly  Gly  Gly  Gly  Gly  Gly
     1085                1090                     1095

Gly  Gly  Ser  Ser  Ser  Ser  Ser  Ser  Ser  Ser  Ser  Ser  Ser  Ser
     1100                1105                     1110

Ser  Ser  Ser  Ser  Ser  Ser  Gly  Gly  Gly  Gly  Gly  Gly  Gly  Gly
     1115                1120                     1125

Gly  Gly  Gly  Gly  Gly  Gly  Gly  Gly  Gly  Gly  Gly  Gly  Gly  Gly  Gly
     1130                1135                     1140

Gly  Gly  Gly  Gly  Gly  Gly  Gly  Gly  Gly  Gly  Gly  Gly  Gly  Gly  Gly
     1145                1150                     1155

Gly  Gly  Ser  Ser  Ser  Ser  Ser  Ser  Ser  Ser  Ser  Ser  Ser  Ser
     1160                1165                     1170

Ser  Ser  Ser  Ser  Ser  Ser  Gly  Gly  Gly  Gly  Gly  Gly  Gly  Gly
     1175                1180                     1185

Gly  Gly  Gly  Gly  Gly  Gly  Gly  Gly  Gly  Gly  Gly
     1190                1195                     1200

<210> SEQ ID NO 312
<211> LENGTH: 2000
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
```

```
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
```

```
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (801)..(820)
<223> OTHER INFORMATION: This region may encompass 1-20 residues
<220> FEATURE:
<221> NAME/KEY: SITE
<222> LOCATION: (821)..(840)
<223> OTHER INFORMATION: This region may encompass 1-20 residues
<220> FEATURE:
<221> NAME/KEY: SITE
<222> LOCATION: (841)..(860)
<223> OTHER INFORMATION: This region may encompass 1-20 residues
<220> FEATURE:
<221> NAME/KEY: SITE
<222> LOCATION: (861)..(880)
<223> OTHER INFORMATION: This region may encompass 1-20 residues
<220> FEATURE:
<221> NAME/KEY: SITE
<222> LOCATION: (881)..(900)
<223> OTHER INFORMATION: This region may encompass 1-20 residues
<220> FEATURE:
<221> NAME/KEY: SITE
<222> LOCATION: (901)..(920)
<223> OTHER INFORMATION: This region may encompass 1-20 residues
<220> FEATURE:
<221> NAME/KEY: SITE
<222> LOCATION: (921)..(940)
<223> OTHER INFORMATION: This region may encompass 1-20 residues
<220> FEATURE:
<221> NAME/KEY: SITE
<222> LOCATION: (941)..(960)
<223> OTHER INFORMATION: This region may encompass 1-20 residues
<220> FEATURE:
<221> NAME/KEY: SITE
<222> LOCATION: (961)..(980)
<223> OTHER INFORMATION: This region may encompass 1-20 residues
<220> FEATURE:
<221> NAME/KEY: SITE
<222> LOCATION: (981)..(1000)
```

```
<223> OTHER INFORMATION: This region may encompass 1-20 residues
<220> FEATURE:
<221> NAME/KEY: SITE
<222> LOCATION: (1001)..(1020)
<223> OTHER INFORMATION: This region may encompass 1-20 residues
<220> FEATURE:
<221> NAME/KEY: SITE
<222> LOCATION: (1021)..(1040)
<223> OTHER INFORMATION: This region may encompass 1-20 residues
<220> FEATURE:
<221> NAME/KEY: SITE
<222> LOCATION: (1041)..(1060)
<223> OTHER INFORMATION: This region may encompass 1-20 residues
<220> FEATURE:
<221> NAME/KEY: SITE
<222> LOCATION: (1061)..(1080)
<223> OTHER INFORMATION: This region may encompass 1-20 residues
<220> FEATURE:
<221> NAME/KEY: SITE
<222> LOCATION: (1081)..(1100)
<223> OTHER INFORMATION: This region may encompass 1-20 residues
<220> FEATURE:
<221> NAME/KEY: SITE
<222> LOCATION: (1101)..(1120)
<223> OTHER INFORMATION: This region may encompass 1-20 residues
<220> FEATURE:
<221> NAME/KEY: SITE
<222> LOCATION: (1121)..(1140)
<223> OTHER INFORMATION: This region may encompass 1-20 residues
<220> FEATURE:
<221> NAME/KEY: SITE
<222> LOCATION: (1141)..(1160)
<223> OTHER INFORMATION: This region may encompass 1-20 residues
<220> FEATURE:
<221> NAME/KEY: SITE
<222> LOCATION: (1161)..(1180)
<223> OTHER INFORMATION: This region may encompass 1-20 residues
<220> FEATURE:
<221> NAME/KEY: SITE
<222> LOCATION: (1181)..(1200)
<223> OTHER INFORMATION: This region may encompass 1-20 residues
<220> FEATURE:
<221> NAME/KEY: SITE
<222> LOCATION: (1201)..(1220)
<223> OTHER INFORMATION: This region may encompass 1-20 residues
<220> FEATURE:
<221> NAME/KEY: SITE
<222> LOCATION: (1221)..(1240)
<223> OTHER INFORMATION: This region may encompass 1-20 residues
<220> FEATURE:
<221> NAME/KEY: SITE
<222> LOCATION: (1241)..(1260)
<223> OTHER INFORMATION: This region may encompass 1-20 residues
<220> FEATURE:
<221> NAME/KEY: SITE
<222> LOCATION: (1261)..(1280)
<223> OTHER INFORMATION: This region may encompass 1-20 residues
<220> FEATURE:
<221> NAME/KEY: SITE
<222> LOCATION: (1281)..(1300)
<223> OTHER INFORMATION: This region may encompass 1-20 residues
<220> FEATURE:
<221> NAME/KEY: SITE
<222> LOCATION: (1301)..(1320)
<223> OTHER INFORMATION: This region may encompass 1-20 residues
<220> FEATURE:
<221> NAME/KEY: SITE
<222> LOCATION: (1321)..(1340)
<223> OTHER INFORMATION: This region may encompass 1-20 residues
<220> FEATURE:
<221> NAME/KEY: SITE
<222> LOCATION: (1341)..(1360)
<223> OTHER INFORMATION: This region may encompass 1-20 residues
<220> FEATURE:
<221> NAME/KEY: SITE
<222> LOCATION: (1361)..(1380)
<223> OTHER INFORMATION: This region may encompass 1-20 residues
<220> FEATURE:
<221> NAME/KEY: SITE
```

```
<222> LOCATION: (1381)..(1400)
<223> OTHER INFORMATION: This region may encompass 1-20 residues
<220> FEATURE:
<221> NAME/KEY: SITE
<222> LOCATION: (1401)..(1420)
<223> OTHER INFORMATION: This region may encompass 1-20 residues
<220> FEATURE:
<221> NAME/KEY: SITE
<222> LOCATION: (1421)..(1440)
<223> OTHER INFORMATION: This region may encompass 1-20 residues
<220> FEATURE:
<221> NAME/KEY: SITE
<222> LOCATION: (1441)..(1460)
<223> OTHER INFORMATION: This region may encompass 1-20 residues
<220> FEATURE:
<221> NAME/KEY: SITE
<222> LOCATION: (1461)..(1480)
<223> OTHER INFORMATION: This region may encompass 1-20 residues
<220> FEATURE:
<221> NAME/KEY: SITE
<222> LOCATION: (1481)..(1500)
<223> OTHER INFORMATION: This region may encompass 1-20 residues
<220> FEATURE:
<221> NAME/KEY: SITE
<222> LOCATION: (1501)..(1520)
<223> OTHER INFORMATION: This region may encompass 1-20 residues
<220> FEATURE:
<221> NAME/KEY: SITE
<222> LOCATION: (1521)..(1540)
<223> OTHER INFORMATION: This region may encompass 1-20 residues
<220> FEATURE:
<221> NAME/KEY: SITE
<222> LOCATION: (1541)..(1560)
<223> OTHER INFORMATION: This region may encompass 1-20 residues
<220> FEATURE:
<221> NAME/KEY: SITE
<222> LOCATION: (1561)..(1580)
<223> OTHER INFORMATION: This region may encompass 1-20 residues
<220> FEATURE:
<221> NAME/KEY: SITE
<222> LOCATION: (1581)..(1600)
<223> OTHER INFORMATION: This region may encompass 1-20 residues
<220> FEATURE:
<221> NAME/KEY: SITE
<222> LOCATION: (1601)..(1620)
<223> OTHER INFORMATION: This region may encompass 1-20 residues
<220> FEATURE:
<221> NAME/KEY: SITE
<222> LOCATION: (1621)..(1640)
<223> OTHER INFORMATION: This region may encompass 1-20 residues
<220> FEATURE:
<221> NAME/KEY: SITE
<222> LOCATION: (1641)..(1660)
<223> OTHER INFORMATION: This region may encompass 1-20 residues
<220> FEATURE:
<221> NAME/KEY: SITE
<222> LOCATION: (1661)..(1680)
<223> OTHER INFORMATION: This region may encompass 1-20 residues
<220> FEATURE:
<221> NAME/KEY: SITE
<222> LOCATION: (1681)..(1700)
<223> OTHER INFORMATION: This region may encompass 1-20 residues
<220> FEATURE:
<221> NAME/KEY: SITE
<222> LOCATION: (1701)..(1720)
<223> OTHER INFORMATION: This region may encompass 1-20 residues
<220> FEATURE:
<221> NAME/KEY: SITE
<222> LOCATION: (1721)..(1740)
<223> OTHER INFORMATION: This region may encompass 1-20 residues
<220> FEATURE:
<221> NAME/KEY: SITE
<222> LOCATION: (1741)..(1760)
<223> OTHER INFORMATION: This region may encompass 1-20 residues
<220> FEATURE:
<221> NAME/KEY: SITE
<222> LOCATION: (1761)..(1780)
<223> OTHER INFORMATION: This region may encompass 1-20 residues
<220> FEATURE:
```

```
<221> NAME/KEY: SITE
<222> LOCATION: (1781)..(1800)
<223> OTHER INFORMATION: This region may encompass 1-20 residues
<220> FEATURE:
<221> NAME/KEY: SITE
<222> LOCATION: (1801)..(1820)
<223> OTHER INFORMATION: This region may encompass 1-20 residues
<220> FEATURE:
<221> NAME/KEY: SITE
<222> LOCATION: (1821)..(1840)
<223> OTHER INFORMATION: This region may encompass 1-20 residues
<220> FEATURE:
<221> NAME/KEY: SITE
<222> LOCATION: (1841)..(1860)
<223> OTHER INFORMATION: This region may encompass 1-20 residues
<220> FEATURE:
<221> NAME/KEY: SITE
<222> LOCATION: (1861)..(1880)
<223> OTHER INFORMATION: This region may encompass 1-20 residues
<220> FEATURE:
<221> NAME/KEY: SITE
<222> LOCATION: (1881)..(1900)
<223> OTHER INFORMATION: This region may encompass 1-20 residues
<220> FEATURE:
<221> NAME/KEY: SITE
<222> LOCATION: (1901)..(1920)
<223> OTHER INFORMATION: This region may encompass 1-20 residues
<220> FEATURE:
<221> NAME/KEY: SITE
<222> LOCATION: (1921)..(1940)
<223> OTHER INFORMATION: This region may encompass 1-20 residues
<220> FEATURE:
<221> NAME/KEY: SITE
<222> LOCATION: (1941)..(1960)
<223> OTHER INFORMATION: This region may encompass 1-20 residues
<220> FEATURE:
<221> NAME/KEY: SITE
<222> LOCATION: (1961)..(1980)
<223> OTHER INFORMATION: This region may encompass 1-20 residues
<220> FEATURE:
<221> NAME/KEY: SITE
<222> LOCATION: (1981)..(2000)
<223> OTHER INFORMATION: This region may encompass 1-20 residues
<220> FEATURE:
<221> NAME/KEY: SITE
<222> LOCATION: (1)..(2000)
<223> OTHER INFORMATION: This sequence may encompass 1-20
      "(Gly)m(Ser)o(Gly)m(Ser)o(Gly)m" repeating units,
      wherein m = 1 to 20, o = 1 to 20
<220> FEATURE:
<223> OTHER INFORMATION: See specification as filed for detailed
      description of substitutions and preferred embodiments

<400> SEQUENCE: 312

Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser
                20                  25                  30

Ser Ser Ser Ser Ser Ser Ser Gly Gly Gly Gly Gly Gly Gly Gly
            35                  40                  45

Gly Gly Gly Gly Gly Gly Gly Gly Gly Gly Gly Ser Ser Ser Ser
        50                  55                  60

Ser Ser Ser Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly
            100                 105                 110

Gly Gly Gly Gly Gly Gly Gly Gly Ser Ser Ser Ser Ser Ser Ser
        115                 120                 125
```

```
Ser Ser Ser Ser Ser Ser Ser Ser Ser Ser Gly Gly Gly
    130                 135                 140

Gly Gly Gly Gly Gly Gly Gly Gly Gly Gly Gly Gly Gly Gly Gly Gly
145                 150                 155                 160

Ser Ser Ser Ser Ser Ser Ser Ser Ser Ser Ser Ser
            165                 170                 175

Ser Ser Ser Ser Gly Gly Gly Gly Gly Gly Gly Gly Gly
            180                 185                 190

Gly Gly Gly Gly Gly Gly Gly Gly Gly Gly Gly Gly Gly Gly Gly Gly
            195                 200                 205

Gly Gly Gly Gly Gly Gly Gly Gly Gly Ser Ser Ser Ser
    210                 215                 220

Ser Ser Ser Ser Ser Ser Ser Ser Ser Ser Ser Ser Ser
225                 230                 235                 240

Gly Gly Gly Gly Gly Gly Gly Gly Gly Gly Gly Gly Gly
            245                 250                 255

Gly Gly Gly Gly Ser Ser Ser Ser Ser Ser Ser Ser Ser Ser
            260                 265                 270

Ser Ser Ser Ser Ser Ser Ser Gly Gly Gly Gly Gly Gly Gly
    275                 280                 285

Gly Gly Gly Gly Gly Gly Gly Gly Gly Gly Gly Gly Gly Gly Gly Gly
    290                 295                 300

Gly Gly Gly Gly Gly Gly Gly Gly Gly Gly Gly Gly Gly Gly Gly Gly
305                 310                 315                 320

Ser Ser Ser Ser Ser Ser Ser Ser Ser Ser Ser Ser Ser Ser Ser
            325                 330                 335

Ser Ser Ser Ser Gly Gly Gly Gly Gly Gly Gly Gly Gly Gly
    340                 345                 350

Gly Gly Gly Gly Gly Gly Gly Ser Ser Ser Ser Ser Ser Ser
            355                 360                 365

Ser Ser Ser Ser Ser Ser Ser Ser Ser Gly Gly Gly Gly
    370                 375                 380

Gly Gly Gly Gly Gly Gly Gly Gly Gly Gly Gly Gly Gly Gly Gly
385                 390                 395                 400

Gly Gly Gly Gly Gly Gly Gly Gly Gly Gly Gly Gly Gly Gly Gly
            405                 410                 415

Gly Gly Gly Gly Ser Ser Ser Ser Ser Ser Ser Ser Ser Ser
            420                 425                 430

Ser Ser Ser Ser Ser Ser Ser Gly Gly Gly Gly Gly Gly Gly
    435                 440                 445

Gly Gly Gly Gly Gly Gly Gly Gly Gly Gly Gly Ser Ser Ser Ser
    450                 455                 460

Ser Ser Ser Ser Ser Ser Ser Ser Ser Ser Ser Ser Ser Ser Ser
465                 470                 475                 480

Gly Gly Gly Gly Gly Gly Gly Gly Gly Gly Gly Gly Gly Gly
            485                 490                 495

Gly Gly Gly Gly Gly Gly Gly Gly Gly Gly Gly Gly Gly Gly Gly
            500                 505                 510

Gly Gly Gly Gly Gly Gly Gly Ser Ser Ser Ser Ser Ser Ser
            515                 520                 525

Ser Ser Ser Ser Ser Ser Ser Ser Ser Ser Gly Gly Gly Gly
    530                 535                 540

Gly Gly Gly Gly Gly Gly Gly Gly Gly Gly Gly Gly Gly Gly Gly
```

-continued

```
            545                 550                 555                 560
Ser Ser Ser Ser Ser Ser Ser Ser Ser Ser Ser Ser Ser Ser Ser Ser
                565                 570                 575
Ser Ser Ser Ser Gly Gly Gly Gly Gly Gly Gly Gly Gly Gly Gly Gly
                580                 585                 590
Gly Gly Gly Gly Gly Gly Gly Gly Gly Gly Gly Gly Gly Gly Gly Gly
                595                 600                 605
Gly Gly Gly Gly Gly Gly Gly Gly Gly Gly Gly Ser Ser Ser Ser
        610                 615                 620
Ser Ser Ser Ser Ser Ser Ser Ser Ser Ser Ser Ser Ser Ser Ser Ser
625                 630                 635                 640
Gly Gly Gly Gly Gly Gly Gly Gly Gly Gly Gly Gly Gly Gly Gly Gly
                645                 650                 655
Gly Gly Gly Gly Ser Ser Ser Ser Ser Ser Ser Ser Ser Ser Ser Ser
        660                 665                 670
Ser Ser Ser Ser Ser Ser Ser Gly Gly Gly Gly Gly Gly Gly Gly
        675                 680                 685
Gly Gly Gly Gly Gly Gly Gly Gly Gly Gly Gly Gly Gly Gly Gly Gly
    690                 695                 700
Gly Gly Gly Gly Gly Gly Gly Gly Gly Gly Gly Gly Gly Gly Gly Gly
705                 710                 715                 720
Ser Ser Ser Ser Ser Ser Ser Ser Ser Ser Ser Ser Ser Ser Ser Ser
                725                 730                 735
Ser Ser Ser Ser Gly Gly Gly Gly Gly Gly Gly Gly Gly Gly Gly Gly
                740                 745                 750
Gly Gly Gly Gly Gly Gly Gly Gly Ser Ser Ser Ser Ser Ser Ser Ser
        755                 760                 765
Ser Ser Ser Ser Ser Ser Ser Ser Ser Gly Gly Gly Gly
        770                 775                 780
Gly Gly Gly Gly Gly Gly Gly Gly Gly Gly Gly Gly Gly Gly Gly Gly
785                 790                 795                 800
Gly Gly Gly Gly Gly Gly Gly Gly Gly Gly Gly Gly Gly Gly Gly Gly
                805                 810                 815
Gly Gly Gly Gly Ser Ser Ser Ser Ser Ser Ser Ser Ser Ser Ser Ser
        820                 825                 830
Ser Ser Ser Ser Ser Ser Ser Gly Gly Gly Gly Gly Gly Gly
        835                 840                 845
Gly Gly Gly Gly Gly Gly Gly Gly Gly Gly Gly Ser Ser Ser Ser
    850                 855                 860
Ser Ser Ser Ser Ser Ser Ser Ser Ser Ser Ser Ser Ser Ser Ser Ser
865                 870                 875                 880
Gly Gly Gly Gly Gly Gly Gly Gly Gly Gly Gly Gly Gly Gly Gly Gly
                885                 890                 895
Gly Gly Gly Gly Gly Gly Gly Gly Gly Gly Gly Gly Gly Gly Gly Gly
            900                 905                 910
Gly Gly Gly Gly Gly Gly Gly Ser Ser Ser Ser Ser Ser Ser
        915                 920                 925
Ser Ser Ser Ser Ser Ser Ser Ser Ser Ser Gly Gly Gly Gly
        930                 935                 940
Gly Gly Gly Gly Gly Gly Gly Gly Gly Gly Gly Gly Gly Gly Gly Gly
945                 950                 955                 960
Ser Ser Ser Ser Ser Ser Ser Ser Ser Ser Ser Ser Ser Ser Ser Ser
                965                 970                 975
```

-continued

```
Ser Ser Ser Ser Gly Gly Gly Gly Gly Gly Gly Gly Gly Gly Gly
            980                 985                 990
Gly Gly Gly Gly Gly Gly Gly Gly  Gly Gly Gly Gly  Gly Gly Gly
            995                1000                1005
Gly Gly  Gly Gly Gly Gly Gly  Gly Gly Gly Gly  Ser Ser Ser
       1010                1015                1020
Ser Ser  Ser Ser Ser Ser Ser  Ser Ser Ser Ser  Ser Ser Ser
       1025                1030                1035
Ser Ser  Gly Gly Gly Gly Gly  Gly Gly Gly Gly  Gly Gly Gly
       1040                1045                1050
Gly Gly  Gly Gly Gly Gly Gly  Ser Ser Ser Ser  Ser Ser Ser
       1055                1060                1065
Ser Ser  Ser Ser Ser Ser Ser  Ser Ser Ser Ser  Gly Gly Gly
       1070                1075                1080
Gly Gly  Gly Gly Gly Gly Gly  Gly Gly Gly Gly  Gly Gly Gly
       1085                1090                1095
Gly Gly  Gly Gly Gly Gly Gly  Gly Gly Gly Gly  Gly Gly Gly
       1100                1105                1110
Gly Gly  Gly Gly Gly Gly Gly  Ser Ser Ser Ser  Ser Ser Ser
       1115                1120                1125
Ser Ser  Ser Ser Ser Ser Ser  Ser Ser Ser Ser  Gly Gly Gly
       1130                1135                1140
Gly Gly  Gly Gly Gly Gly Gly  Gly Gly Gly Gly  Gly Gly Gly
       1145                1150                1155
Gly Gly  Ser Ser Ser Ser Ser  Ser Ser Ser Ser  Ser Ser Ser
       1160                1165                1170
Ser Ser  Ser Ser Ser Ser Ser  Gly Gly Gly Gly  Gly Gly Gly
       1175                1180                1185
Gly Gly  Gly Gly Gly Gly Gly  Gly Gly Gly Gly  Gly Gly Gly
       1190                1195                1200
Gly Gly  Gly Gly Gly Gly Gly  Gly Gly Gly Gly  Gly Gly Gly
       1205                1210                1215
Gly Gly  Ser Ser Ser Ser Ser  Ser Ser Ser Ser  Ser Ser Ser
       1220                1225                1230
Ser Ser  Ser Ser Ser Ser Ser  Gly Gly Gly Gly  Gly Gly Gly
       1235                1240                1245
Gly Gly  Gly Gly Gly Gly Gly  Gly Gly Gly Gly  Ser Ser Ser
       1250                1255                1260
Ser Ser  Ser Ser Ser Ser Ser  Ser Ser Ser Ser  Ser Ser Ser
       1265                1270                1275
Ser Ser  Gly Gly Gly Gly Gly  Gly Gly Gly Gly  Gly Gly Gly
       1280                1285                1290
Gly Gly  Gly Gly Gly Gly Gly  Gly Gly Gly Gly  Gly Gly Gly
       1295                1300                1305
Gly Gly  Gly Gly Gly Gly Gly  Gly Gly Gly Gly  Ser Ser Ser
       1310                1315                1320
Ser Ser  Ser Ser Ser Ser Ser  Ser Ser Ser Ser  Ser Ser Ser
       1325                1330                1335
Ser Ser  Gly Gly Gly Gly Gly  Gly Gly Gly Gly  Gly Gly Gly
       1340                1345                1350
Gly Gly  Gly Gly Gly Gly Gly  Ser Ser Ser Ser  Ser Ser Ser
       1355                1360                1365
```

```
Ser Ser Ser Ser Ser Ser Ser  Ser Ser Ser Ser Ser  Gly Gly Gly
    1370            1375                  1380

Gly Gly Gly Gly Gly Gly Gly  Gly Gly Gly Gly Gly  Gly Gly Gly
    1385            1390                  1395

Gly Gly Gly Gly Gly Gly Gly  Gly Gly Gly Gly Gly  Gly Gly Gly
    1400            1405                  1410

Gly Gly Gly Gly Gly Gly Gly  Ser Ser Ser Ser Ser  Ser Ser Ser
    1415            1420                  1425

Ser Ser Ser Ser Ser Ser Ser  Ser Ser Ser Ser Ser  Gly Gly Gly
    1430            1435                  1440

Gly Gly Gly Gly Gly Gly Gly  Gly Gly Gly Gly Gly  Gly Gly Gly
    1445            1450                  1455

Gly Gly Ser Ser Ser Ser Ser  Ser Ser Ser Ser Ser  Ser Ser Ser
    1460            1465                  1470

Ser Ser Ser Ser Ser Ser Ser  Gly Gly Gly Gly Gly  Gly Gly Gly
    1475            1480                  1485

Gly Gly Gly Gly Gly Gly Gly  Gly Gly Gly Gly Gly  Gly Gly Gly
    1490            1495                  1500

Gly Gly Gly Gly Gly Gly Gly  Gly Gly Gly Gly Gly  Gly Gly Gly
    1505            1510                  1515

Gly Gly Ser Ser Ser Ser Ser  Ser Ser Ser Ser Ser  Ser Ser Ser
    1520            1525                  1530

Ser Ser Ser Ser Ser Ser Ser  Gly Gly Gly Gly Gly  Gly Gly Gly
    1535            1540                  1545

Gly Gly Gly Gly Gly Gly Gly  Gly Gly Gly Gly Gly  Ser Ser Ser
    1550            1555                  1560

Ser Ser Ser Ser Ser Ser Ser  Ser Ser Ser Ser Ser  Ser Ser Ser
    1565            1570                  1575

Ser Ser Gly Gly Gly Gly Gly  Gly Gly Gly Gly Gly  Gly Gly Gly
    1580            1585                  1590

Gly Gly Gly Gly Gly Gly Gly  Gly Gly Gly Gly Gly  Gly Gly Gly
    1595            1600                  1605

Gly Gly Gly Gly Gly Gly Gly  Gly Gly Gly Gly Gly  Ser Ser Ser
    1610            1615                  1620

Ser Ser Ser Ser Ser Ser Ser  Ser Ser Ser Ser Ser  Ser Ser Ser
    1625            1630                  1635

Ser Ser Gly Gly Gly Gly Gly  Gly Gly Gly Gly Gly  Gly Gly Gly
    1640            1645                  1650

Gly Gly Gly Gly Gly Gly Gly  Ser Ser Ser Ser Ser  Ser Ser Ser
    1655            1660                  1665

Ser Ser Ser Ser Ser Ser Ser  Ser Ser Ser Ser Ser  Gly Gly Gly
    1670            1675                  1680

Gly Gly Gly Gly Gly Gly Gly  Gly Gly Gly Gly Gly  Gly Gly Gly
    1685            1690                  1695

Gly Gly Gly Gly Gly Gly Gly  Gly Gly Gly Gly Gly  Gly Gly Gly
    1700            1705                  1710

Gly Gly Gly Gly Gly Gly Gly  Ser Ser Ser Ser Ser  Ser Ser Ser
    1715            1720                  1725

Ser Ser Ser Ser Ser Ser Ser  Ser Ser Ser Ser Ser  Gly Gly Gly
    1730            1735                  1740

Gly Gly Gly Gly Gly Gly Gly  Gly Gly Gly Gly Gly  Gly Gly Gly
    1745            1750                  1755

Gly Gly Ser Ser Ser Ser Ser  Ser Ser Ser Ser Ser  Ser Ser Ser
```

```
                        1760                1765                1770

Ser  Ser  Ser  Ser  Ser  Ser  Ser  Gly  Gly  Gly  Gly  Gly  Gly  Gly  Gly
        1775                1780                1785

Gly  Gly  Gly  Gly  Gly  Gly  Gly  Gly  Gly  Gly  Gly  Gly  Gly  Gly  Gly
        1790                1795                1800

Gly  Gly  Gly  Gly  Gly  Gly  Gly  Gly  Gly  Gly  Gly  Gly  Gly  Gly  Gly
        1805                1810                1815

Gly  Gly  Ser  Ser  Ser  Ser  Ser  Ser  Ser  Ser  Ser  Ser  Ser  Ser  Ser
        1820                1825                1830

Ser  Ser  Ser  Ser  Ser  Ser  Ser  Gly  Gly  Gly  Gly  Gly  Gly  Gly  Gly
        1835                1840                1845

Gly  Gly  Gly  Gly  Gly  Gly  Gly  Gly  Gly  Gly  Gly  Ser  Ser  Ser  Ser
        1850                1855                1860

Ser  Ser  Ser  Ser  Ser  Ser  Ser  Ser  Ser  Ser  Ser  Ser  Ser  Ser  Ser
        1865                1870                1875

Ser  Ser  Gly  Gly  Gly  Gly  Gly  Gly  Gly  Gly  Gly  Gly  Gly  Gly  Gly
        1880                1885                1890

Gly  Gly  Gly  Gly  Gly  Gly  Gly  Gly  Gly  Gly  Gly  Gly  Gly  Gly  Gly
        1895                1900                1905

Gly  Gly  Gly  Gly  Gly  Gly  Gly  Gly  Gly  Gly  Gly  Ser  Ser  Ser  Ser
        1910                1915                1920

Ser  Ser  Ser  Ser  Ser  Ser  Ser  Ser  Ser  Ser  Ser  Ser  Ser  Ser  Ser
        1925                1930                1935

Ser  Ser  Gly  Gly  Gly  Gly  Gly  Gly  Gly  Gly  Gly  Gly  Gly  Gly  Gly
        1940                1945                1950

Gly  Gly  Gly  Gly  Gly  Gly  Gly  Ser  Ser  Ser  Ser  Ser  Ser  Ser  Ser
        1955                1960                1965

Ser  Ser  Ser  Ser  Ser  Ser  Ser  Ser  Ser  Ser  Ser  Gly  Gly  Gly  Gly
        1970                1975                1980

Gly  Gly  Gly  Gly  Gly  Gly  Gly  Gly  Gly  Gly  Gly  Gly  Gly  Gly  Gly
        1985                1990                1995

Gly  Gly
    2000

<210> SEQ ID NO 313
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (5)..(24)
<223> OTHER INFORMATION: This region may encompass 1-20 residues
<220> FEATURE:
<221> NAME/KEY: SITE
<222> LOCATION: (29)..(48)
<223> OTHER INFORMATION: This region may encompass 1-20 residues
<220> FEATURE:
<221> NAME/KEY: SITE
<222> LOCATION: (53)..(72)
<223> OTHER INFORMATION: This region may encompass 1-20 residues
<220> FEATURE:
<221> NAME/KEY: SITE
<222> LOCATION: (77)..(96)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
```

```
<221> NAME/KEY: SITE
<222> LOCATION: (125)..(144)
<223> OTHER INFORMATION: This region may encompass 1-20 residues
<220> FEATURE:
<221> NAME/KEY: SITE
<222> LOCATION: (149)..(168)
<223> OTHER INFORMATION: This region may encompass 1-20 residues
<220> FEATURE:
<221> NAME/KEY: SITE
<222> LOCATION: (173)..(192)
<223> OTHER INFORMATION: This region may encompass 1-20 residues
<220> FEATURE:
<221> NAME/KEY: SITE
<222> LOCATION: (197)..(216)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (245)..(264)
<223> OTHER INFORMATION: This region may encompass 1-20 residues
<220> FEATURE:
<221> NAME/KEY: SITE
<222> LOCATION: (269)..(288)
<223> OTHER INFORMATION: This region may encompass 1-20 residues
<220> FEATURE:
<221> NAME/KEY: SITE
<222> LOCATION: (293)..(312)
<223> OTHER INFORMATION: This region may encompass 1-20 residues
<220> FEATURE:
<221> NAME/KEY: SITE
<222> LOCATION: (317)..(336)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (365)..(384)
<223> OTHER INFORMATION: This region may encompass 1-20 residues
<220> FEATURE:
<221> NAME/KEY: SITE
<222> LOCATION: (389)..(408)
<223> OTHER INFORMATION: This region may encompass 1-20 residues
<220> FEATURE:
<221> NAME/KEY: SITE
<222> LOCATION: (413)..(432)
<223> OTHER INFORMATION: This region may encompass 1-20 residues
<220> FEATURE:
<221> NAME/KEY: SITE
<222> LOCATION: (437)..(456)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (1)..(480)
<223> OTHER INFORMATION: This sequence may encompass 1-20
      "(Gly)(Ser)(Gly)(Gly)(Ser)m" repeating units,
      wherein m = 1 to 20
<220> FEATURE:
<223> OTHER INFORMATION: See specification as filed for detailed
      description of substitutions and preferred embodiments

<400> SEQUENCE: 313

Gly Ser Gly Gly Ser Ser Ser Ser Ser Ser Ser Ser Ser Ser Ser Ser
1               5                   10                  15

Ser Ser Ser Ser Ser Ser Ser Ser Gly Ser Gly Gly Ser Ser Ser Ser
                20                  25                  30

Ser Ser Ser Ser Ser Ser Ser Ser Ser Ser Ser Ser Ser Ser Ser Ser
            35                  40                  45
```

Gly Ser Gly Gly Ser Ser Ser Ser Ser Ser Ser Ser Ser Ser
            50                      55                      60

Ser Ser Ser Ser Ser Ser Ser Ser Gly Ser Gly Gly Ser Ser Ser Ser
65                      70                      75                      80

Ser Ser Ser Ser Ser Ser Ser Ser Ser Ser Ser Ser Ser
            85                      90                      95

Gly Ser Gly Gly Ser Ser Ser Ser Ser Ser Ser Ser Ser Ser
            100                     105                     110

Ser Ser Ser Ser Ser Ser Ser Gly Ser Gly Gly Ser Ser Ser
            115                     120                     125

Ser Ser Ser Ser Ser Ser Ser Ser Ser Ser Ser Ser Ser
            130                     135                     140

Gly Ser Gly Gly Ser Ser Ser Ser Ser Ser Ser Ser Ser Ser
145                     150                     155                     160

Ser Ser Ser Ser Ser Ser Ser Gly Ser Gly Gly Ser Ser Ser
            165                     170                     175

Ser Ser Ser Ser Ser Ser Ser Ser Ser Ser Ser Ser Ser
            180                     185                     190

Gly Ser Gly Gly Ser Ser Ser Ser Ser Ser Ser Ser Ser Ser
            195                     200                     205

Ser Ser Ser Ser Ser Ser Ser Gly Ser Gly Gly Ser Ser Ser
210                     215                     220

Ser Ser Ser Ser Ser Ser Ser Ser Ser Ser Ser Ser Ser
225                     230                     235                     240

Gly Ser Gly Gly Ser Ser Ser Ser Ser Ser Ser Ser Ser Ser
            245                     250                     255

Ser Ser Ser Ser Ser Ser Ser Gly Ser Gly Gly Ser Ser Ser
            260                     265                     270

Ser Ser Ser Ser Ser Ser Ser Ser Ser Ser Ser Ser Ser
            275                     280                     285

Gly Ser Gly Gly Ser Ser Ser Ser Ser Ser Ser Ser Ser Ser
            290                     295                     300

Ser Ser Ser Ser Ser Ser Ser Gly Ser Gly Gly Ser Ser Ser Ser
305                     310                     315                     320

Ser Ser Ser Ser Ser Ser Ser Ser Ser Ser Ser Ser Ser
            325                     330                     335

Gly Ser Gly Gly Ser Ser Ser Ser Ser Ser Ser Ser Ser Ser
            340                     345                     350

Ser Ser Ser Ser Ser Ser Ser Gly Ser Gly Gly Ser Ser Ser
            355                     360                     365

Ser Ser Ser Ser Ser Ser Ser Ser Ser Ser Ser Ser Ser
            370                     375                     380

Gly Ser Gly Gly Ser Ser Ser Ser Ser Ser Ser Ser Ser Ser
385                     390                     395                     400

Ser Ser Ser Ser Ser Ser Ser Gly Ser Gly Gly Ser Ser Ser
            405                     410                     415

Ser Ser Ser Ser Ser Ser Ser Ser Ser Ser Ser Ser Ser
            420                     425                     430

Gly Ser Gly Gly Ser Ser Ser Ser Ser Ser Ser Ser Ser Ser
            435                     440                     445

Ser Ser Ser Ser Ser Ser Ser Gly Ser Gly Gly Ser Ser Ser Ser
            450                     455                     460

```
Ser Ser Ser Ser Ser Ser Ser Ser Ser Ser Ser Ser Ser Ser Ser Ser
465                 470                 475                 480

<210> SEQ ID NO 314
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (4)..(23)
<223> OTHER INFORMATION: This region may encompass 1-20 residues
<220> FEATURE:
<221> NAME/KEY: SITE
<222> LOCATION: (28)..(47)
<223> OTHER INFORMATION: This region may encompass 1-20 residues
<220> FEATURE:
<221> NAME/KEY: SITE
<222> LOCATION: (52)..(71)
<223> OTHER INFORMATION: This region may encompass 1-20 residues
<220> FEATURE:
<221> NAME/KEY: SITE
<222> LOCATION: (76)..(95)
<223> OTHER INFORMATION: This region may encompass 1-20 residues
<220> FEATURE:
<221> NAME/KEY: SITE
<222> LOCATION: (100)..(119)
<223> OTHER INFORMATION: This region may encompass 1-20 residues
<220> FEATURE:
<221> NAME/KEY: SITE
<222> LOCATION: (124)..(143)
<223> OTHER INFORMATION: This region may encompass 1-20 residues
<220> FEATURE:
<221> NAME/KEY: SITE
<222> LOCATION: (148)..(167)
<223> OTHER INFORMATION: This region may encompass 1-20 residues
<220> FEATURE:
<221> NAME/KEY: SITE
<222> LOCATION: (172)..(191)
<223> OTHER INFORMATION: This region may encompass 1-20 residues
<220> FEATURE:
<221> NAME/KEY: SITE
<222> LOCATION: (196)..(215)
<223> OTHER INFORMATION: This region may encompass 1-20 residues
<220> FEATURE:
<221> NAME/KEY: SITE
<222> LOCATION: (220)..(239)
<223> OTHER INFORMATION: This region may encompass 1-20 residues
<220> FEATURE:
<221> NAME/KEY: SITE
<222> LOCATION: (244)..(263)
<223> OTHER INFORMATION: This region may encompass 1-20 residues
<220> FEATURE:
<221> NAME/KEY: SITE
<222> LOCATION: (268)..(287)
<223> OTHER INFORMATION: This region may encompass 1-20 residues
<220> FEATURE:
<221> NAME/KEY: SITE
<222> LOCATION: (292)..(311)
<223> OTHER INFORMATION: This region may encompass 1-20 residues
<220> FEATURE:
<221> NAME/KEY: SITE
<222> LOCATION: (316)..(335)
<223> OTHER INFORMATION: This region may encompass 1-20 residues
<220> FEATURE:
<221> NAME/KEY: SITE
<222> LOCATION: (340)..(359)
<223> OTHER INFORMATION: This region may encompass 1-20 residues
<220> FEATURE:
<221> NAME/KEY: SITE
<222> LOCATION: (364)..(383)
<223> OTHER INFORMATION: This region may encompass 1-20 residues
<220> FEATURE:
<221> NAME/KEY: SITE
<222> LOCATION: (388)..(407)
<223> OTHER INFORMATION: This region may encompass 1-20 residues
```

```
<220> FEATURE:
<221> NAME/KEY: SITE
<222> LOCATION: (412)..(431)
<223> OTHER INFORMATION: This region may encompass 1-20 residues
<220> FEATURE:
<221> NAME/KEY: SITE
<222> LOCATION: (436)..(455)
<223> OTHER INFORMATION: This region may encompass 1-20 residues
<220> FEATURE:
<221> NAME/KEY: SITE
<222> LOCATION: (460)..(479)
<223> OTHER INFORMATION: This region may encompass 1-20 residues
<220> FEATURE:
<221> NAME/KEY: SITE
<222> LOCATION: (1)..(480)
<223> OTHER INFORMATION: This sequence may encompass 1-20
      "(Gly)(Ser)(Gly)(Ser)m(Gly)" repeating units,
      wherein m = 1 to 20
<220> FEATURE:
<223> OTHER INFORMATION: See specification as filed for detailed
      description of substitutions and preferred embodiments

<400> SEQUENCE: 314

Gly Ser Gly Ser Ser Ser Ser Ser Ser Ser Ser Ser Ser Ser Ser
1               5                   10                  15

Ser Ser Ser Ser Ser Ser Ser Gly Gly Ser Gly Ser Ser Ser Ser
                20                  25                  30

Ser Ser Ser Ser Ser Ser Ser Ser Ser Ser Ser Ser Ser Ser Gly
            35                  40                  45

Gly Ser Gly Ser Ser Ser Ser Ser Ser Ser Ser Ser Ser Ser Ser
    50                  55                  60

Ser Ser Ser Ser Ser Ser Gly Gly Ser Gly Ser Ser Ser Ser Ser
65                  70                  75                  80

Ser Ser Ser Ser Ser Ser Ser Ser Ser Ser Ser Ser Ser Ser Gly
                85                  90                  95

Gly Ser Gly Ser Ser Ser Ser Ser Ser Ser Ser Ser Ser Ser Ser
                100                 105                 110

Ser Ser Ser Ser Ser Ser Gly Gly Ser Gly Ser Ser Ser Ser Ser
            115                 120                 125

Ser Ser Ser Ser Ser Ser Ser Ser Ser Ser Ser Ser Ser Ser Gly
        130                 135                 140

Gly Ser Gly Ser Ser Ser Ser Ser Ser Ser Ser Ser Ser Ser Ser
145                 150                 155                 160

Ser Ser Ser Ser Ser Ser Gly Gly Ser Gly Ser Ser Ser Ser Ser
                165                 170                 175

Ser Ser Ser Ser Ser Ser Ser Ser Ser Ser Ser Ser Ser Ser Gly
                180                 185                 190

Gly Ser Gly Ser Ser Ser Ser Ser Ser Ser Ser Ser Ser Ser Ser
            195                 200                 205

Ser Ser Ser Ser Ser Ser Gly Gly Ser Gly Ser Ser Ser Ser Ser
        210                 215                 220

Ser Ser Ser Ser Ser Ser Ser Ser Ser Ser Ser Ser Ser Ser Gly
225                 230                 235                 240

Gly Ser Gly Ser Ser Ser Ser Ser Ser Ser Ser Ser Ser Ser Ser
                245                 250                 255

Ser Ser Ser Ser Ser Ser Gly Gly Ser Gly Ser Ser Ser Ser Ser
                260                 265                 270

Ser Ser Ser Ser Ser Ser Ser Ser Ser Ser Ser Ser Ser Ser Gly
            275                 280                 285

Gly Ser Gly Ser Ser Ser Ser Ser Ser Ser Ser Ser Ser Ser Ser
```

```
                290             295             300
Ser Ser Ser Ser Ser Ser Gly Gly Ser Gly Ser Ser Ser Ser Ser
305                 310             315                 320

Ser Ser Ser Ser Ser Ser Ser Ser Ser Ser Ser Ser Ser Ser Gly
            325             330             335

Gly Ser Gly Ser Ser Ser Ser Ser Ser Ser Ser Ser Ser Ser Ser
            340             345             350

Ser Ser Ser Ser Ser Ser Gly Gly Ser Gly Ser Ser Ser Ser Ser
        355             360             365

Ser Ser Ser Ser Ser Ser Ser Ser Ser Ser Ser Ser Ser Ser Gly
        370             375             380

Gly Ser Gly Ser Ser Ser Ser Ser Ser Ser Ser Ser Ser Ser Ser
385             390             395             400

Ser Ser Ser Ser Ser Ser Gly Gly Ser Gly Ser Ser Ser Ser Ser
            405             410             415

Ser Ser Ser Ser Ser Ser Ser Ser Ser Ser Ser Ser Ser Ser Gly
            420             425             430

Gly Ser Gly Ser Ser Ser Ser Ser Ser Ser Ser Ser Ser Ser Ser
            435             440             445

Ser Ser Ser Ser Ser Ser Gly Gly Ser Gly Ser Ser Ser Ser Ser
450                 455             460

Ser Ser Ser Ser Ser Ser Ser Ser Ser Ser Ser Ser Ser Ser Gly
465                 470             475             480

<210> SEQ ID NO 315
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (4)..(23)
<223> OTHER INFORMATION: This region may encompass 1-20 residues
<220> FEATURE:
<221> NAME/KEY: SITE
<222> LOCATION: (27)..(46)
<223> OTHER INFORMATION: This region may encompass 1-20 residues
<220> FEATURE:
<221> NAME/KEY: SITE
<222> LOCATION: (50)..(69)
<223> OTHER INFORMATION: This region may encompass 1-20 residues
<220> FEATURE:
<221> NAME/KEY: SITE
<222> LOCATION: (73)..(92)
<223> OTHER INFORMATION: This region may encompass 1-20 residues
<220> FEATURE:
<221> NAME/KEY: SITE
<222> LOCATION: (96)..(115)
<223> OTHER INFORMATION: This region may encompass 1-20 residues
<220> FEATURE:
<221> NAME/KEY: SITE
<222> LOCATION: (119)..(138)
<223> OTHER INFORMATION: This region may encompass 1-20 residues
<220> FEATURE:
<221> NAME/KEY: SITE
<222> LOCATION: (142)..(161)
<223> OTHER INFORMATION: This region may encompass 1-20 residues
<220> FEATURE:
<221> NAME/KEY: SITE
<222> LOCATION: (165)..(184)
<223> OTHER INFORMATION: This region may encompass 1-20 residues
<220> FEATURE:
<221> NAME/KEY: SITE
<222> LOCATION: (188)..(207)
<223> OTHER INFORMATION: This region may encompass 1-20 residues
```

```
<220> FEATURE:
<221> NAME/KEY: SITE
<222> LOCATION: (211)..(230)
<223> OTHER INFORMATION: This region may encompass 1-20 residues
<220> FEATURE:
<221> NAME/KEY: SITE
<222> LOCATION: (234)..(253)
<223> OTHER INFORMATION: This region may encompass 1-20 residues
<220> FEATURE:
<221> NAME/KEY: SITE
<222> LOCATION: (257)..(276)
<223> OTHER INFORMATION: This region may encompass 1-20 residues
<220> FEATURE:
<221> NAME/KEY: SITE
<222> LOCATION: (280)..(299)
<223> OTHER INFORMATION: This region may encompass 1-20 residues
<220> FEATURE:
<221> NAME/KEY: SITE
<222> LOCATION: (303)..(322)
<223> OTHER INFORMATION: This region may encompass 1-20 residues
<220> FEATURE:
<221> NAME/KEY: SITE
<222> LOCATION: (326)..(345)
<223> OTHER INFORMATION: This region may encompass 1-20 residues
<220> FEATURE:
<221> NAME/KEY: SITE
<222> LOCATION: (349)..(368)
<223> OTHER INFORMATION: This region may encompass 1-20 residues
<220> FEATURE:
<221> NAME/KEY: SITE
<222> LOCATION: (372)..(391)
<223> OTHER INFORMATION: This region may encompass 1-20 residues
<220> FEATURE:
<221> NAME/KEY: SITE
<222> LOCATION: (395)..(414)
<223> OTHER INFORMATION: This region may encompass 1-20 residues
<220> FEATURE:
<221> NAME/KEY: SITE
<222> LOCATION: (418)..(437)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (1)..(460)
<223> OTHER INFORMATION: This sequence may encompass 1-20
      "(Gly)(Gly)(Gly)(Ser)m" repeating units,
      wherein m = 1 to 20
<220> FEATURE:
<223> OTHER INFORMATION: See specification as filed for detailed
      description of substitutions and preferred embodiments

<400> SEQUENCE: 315

Gly Gly Gly Ser Ser Ser Ser Ser Ser Ser Ser Ser Ser Ser Ser
1               5                   10                  15

Ser Ser Ser Ser Ser Ser Ser Gly Gly Gly Ser Ser Ser Ser Ser
                20                  25                  30

Ser Ser Ser Ser Ser Ser Ser Ser Ser Ser Ser Ser Ser Gly Gly
            35                  40                  45

Gly Ser Ser Ser Ser Ser Ser Ser Ser Ser Ser Ser Ser Ser Ser
        50                  55                  60

Ser Ser Ser Ser Ser Gly Gly Gly Ser Ser Ser Ser Ser Ser Ser
65                  70                  75                  80

Ser Ser Ser Ser Ser Ser Ser Ser Ser Ser Ser Gly Gly Gly Ser
                85                  90                  95

Ser Ser Ser Ser Ser Ser Ser Ser Ser Ser Ser Ser Ser Ser Ser
            100                 105                 110

Ser Ser Ser Gly Gly Gly Ser Ser Ser Ser Ser Ser Ser Ser Ser
        115                 120                 125
```

Ser Ser Ser Ser Ser Ser Ser Ser Ser Gly Gly Gly Ser Ser Ser
        130                 135                 140

Ser Ser Ser Ser Ser Ser Ser Ser Ser Ser Ser Ser Ser Ser Ser Ser
145                 150                 155                 160

Ser Gly Gly Gly Ser Ser Ser Ser Ser Ser Ser Ser Ser Ser
                165                 170                 175

Ser Ser Ser Ser Ser Ser Ser Gly Gly Gly Ser Ser Ser Ser
        180                 185                 190

Ser Ser Ser Ser Ser Ser Ser Ser Ser Ser Ser Ser Ser Gly
        195                 200                 205

Gly Gly Ser Ser Ser Ser Ser Ser Ser Ser Ser Ser Ser Ser
        210                 215                 220

Ser Ser Ser Ser Ser Gly Gly Gly Ser Ser Ser Ser Ser Ser Ser Ser
225                 230                 235                 240

Ser Ser Ser Ser Ser Ser Ser Ser Ser Ser Gly Gly Gly
                245                 250                 255

Ser Ser Ser Ser Ser Ser Ser Ser Ser Ser Ser Ser Ser
        260                 265                 270

Ser Ser Ser Ser Gly Gly Gly Ser Ser Ser Ser Ser Ser Ser
        275                 280                 285

Ser Ser Ser Ser Ser Ser Ser Ser Ser Gly Gly Gly Ser Ser
        290                 295                 300

Ser Ser Ser Ser Ser Ser Ser Ser Ser Ser Ser Ser Ser Ser Ser Ser
305                 310                 315                 320

Ser Ser Gly Gly Gly Ser Ser Ser Ser Ser Ser Ser Ser Ser
                325                 330                 335

Ser Ser Ser Ser Ser Ser Ser Ser Gly Gly Gly Ser Ser Ser Ser
        340                 345                 350

Ser Ser Ser Ser Ser Ser Ser Ser Ser Ser Ser Ser Ser Ser
        355                 360                 365

Gly Gly Gly Ser Ser Ser Ser Ser Ser Ser Ser Ser Ser Ser
        370                 375                 380

Ser Ser Ser Ser Ser Ser Gly Gly Gly Ser Ser Ser Ser Ser Ser
385                 390                 395                 400

Ser Ser Ser Ser Ser Ser Ser Ser Ser Ser Ser Ser Ser Gly Gly
                405                 410                 415

Gly Ser Ser Ser Ser Ser Ser Ser Ser Ser Ser Ser Ser
        420                 425                 430

Ser Ser Ser Ser Ser Gly Gly Gly Ser Ser Ser Ser Ser Ser
        435                 440                 445

Ser Ser Ser Ser Ser Ser Ser Ser Ser Ser Ser
        450                 455                 460

<210> SEQ ID NO 316
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(60)
<223> OTHER INFORMATION: This sequence may encompass 1-20
      "Gly Gly Ser" repeating units
<220> FEATURE:
<223> OTHER INFORMATION: See specification as filed for detailed -continued

```
description of substitutions and preferred embodiments

<400> SEQUENCE: 316

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly
    50                  55                  60

<210> SEQ ID NO 317
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(6)
<223> OTHER INFORMATION: This sequence may encompass 3-6 residues

<400> SEQUENCE: 317

His His His His His His
1               5
```